(12) United States Patent
Eastwood et al.

(10) Patent No.: US 8,772,288 B2
(45) Date of Patent: Jul. 8, 2014

(54) SUBSTITUTED SPIRO[CYCLOALKYL-1,3'-INDO]-2'(1'H)-ONE DERIVATIVES AND THEIR USE AS P38 MITOGEN-ACTIVATED KINASE INHIBITORS

(75) Inventors: Paul Robert Eastwood, Rubi (ES); Jacob Gonzalez Rodriguez, Molins de Rei (ES); Bernet Vidal Juan, St. Cebrià de Vallalta (ES); Nuria Aguilar Izquierdo, Barcelona (ES)

(73) Assignee: Almirall, S.A., Barcelona (ES)

( * ) Notice: Subject to any disclaimer, the term of this patent is extended or adjusted under 35 U.S.C. 154(b) by 489 days.

(21) Appl. No.: 12/936,784

(22) PCT Filed: Apr. 3, 2009

(86) PCT No.: PCT/EP2009/002458
§ 371 (c)(1),
(2), (4) Date: Oct. 26, 2010

(87) PCT Pub. No.: WO2009/124692
PCT Pub. Date: Oct. 15, 2009

(65) Prior Publication Data
US 2011/0053936 A1   Mar. 3, 2011

(30) Foreign Application Priority Data

Apr. 11, 2008  (EP) .................................. 08382013

(51) Int. Cl.
| | | |
|---|---|---|
| *A61K 31/403* | (2006.01) | |
| *A61K 31/4178* | (2006.01) | |
| *A61K 31/4196* | (2006.01) | |
| *A61K 31/4245* | (2006.01) | |
| *A61K 31/438* | (2006.01) | |
| *A61K 31/519* | (2006.01) | |
| *A61K 31/5377* | (2006.01) | |
| *A61K 31/4439* | (2006.01) | |
| *A61K 31/437* | (2006.01) | |
| *A61P 29/00* | (2006.01) | |
| *A61P 1/00* | (2006.01) | |
| *A61P 9/00* | (2006.01) | |
| *A61P 17/06* | (2006.01) | |
| *C07D 403/10* | (2006.01) | |
| *C07D 209/96* | (2006.01) | |
| *C07D 413/10* | (2006.01) | |
| *C07D 413/14* | (2006.01) | |
| *C07D 471/10* | (2006.01) | |
| *C07D 487/04* | (2006.01) | |
| *C07D 491/20* | (2006.01) | |
| *C07D 491/107* | (2006.01) | |
| *C07D 495/10* | (2006.01) | |
| *C07D 487/10* | (2006.01) | |

(52) U.S. Cl.
USPC .................... 514/235.2; 514/265.1; 514/278; 514/364; 514/383; 514/397; 514/409; 514/234.5; 514/300; 514/380; 514/418; 544/70; 544/230; 546/15; 546/17; 546/113; 548/131; 548/143; 548/266.4; 548/301.1; 548/411; 548/246; 548/265.4; 548/486

(58) Field of Classification Search
CPC ............ A61K 31/403; A61K 31/4178; A61K 31/4196; A61K 31/4245; A61K 31/438; A61K 31/519; A61K 31/5377; A61K 31/4439; A61K 31/437; A61P 29/00; A61P 1/00; A61P 9/00; A61P 17/06; C07D 209/96; C07D 403/10; C07D 413/10; C07D 413/14; C07D 471/10; C07D 487/04; C07D 491/107; C07D 491/20; C07D 495/10; C07D 487/10
USPC .......... 514/235.2, 410, 265.1, 278, 364, 383, 514/397, 409, 234.5, 300, 380, 418; 548/452, 131, 143, 266.4, 301.1, 411, 548/246, 265.4, 486; 544/70, 230; 546/15, 546/17, 113
See application file for complete search history.

(56) References Cited

U.S. PATENT DOCUMENTS

| | | | |
|---|---|---|---|
| 4,550,166 A | 10/1985 | Moran et al. | |
| 4,959,368 A | 9/1990 | Awaya et al. | |
| 5,414,088 A | 5/1995 | Von Der Saal et al. | |
| 6,586,447 B1 | 7/2003 | Lyssikatos et al. | |
| 8,106,190 B2 | 1/2012 | Kuramochi et al. | |
| 2003/0166724 A1 | 9/2003 | Hangeland | |
| 2005/0131014 A1 | 6/2005 | Collini et al. | |
| 2006/0106048 A1 | 5/2006 | Inoue et al. | |
| 2007/0213341 A1 | 9/2007 | Chen et al. | |
| 2008/0009486 A1 | 1/2008 | Chen et al. | |
| 2010/0120731 A1 | 5/2010 | Juan et al. | |
| 2010/0130517 A1 | 5/2010 | Amador et al. | |
| 2010/0227881 A1 | 9/2010 | Javaloyes et al. | |
| 2011/0046097 A1 | 2/2011 | Eastwood et al. | |

FOREIGN PATENT DOCUMENTS

| | | |
|---|---|---|
| CN | 1502608 A | 6/2004 |
| EP | 0 549 892 A1 | 7/1993 |

(Continued)

OTHER PUBLICATIONS

International Search Report for PCT/EP2009/002783 (WO 2009/132774) dated May 28, 2009 (2 pages).
International Search Report for PCT/EP2009/002458 (WO 2009/124692) dated Jun. 3, 2009 (3 pages).
U.S. Appl. No. 12/376,499, filed Apr. 1, 2009, Javaloyes et al.
U.S. Appl. No. 12/529,490, filed Sep. 1, 2009, Juan et al.
U.S. Appl. No. 12/597,187, filed Jan. 7, 2010, Amador et al.
U.S. Appl. No. 13/509,076, filed May 10, 2012, Bosch et al.
U.S. Appl. No. 12/989,696, filed Oct. 26, 2010, Eastwood et al.

(Continued)

*Primary Examiner* — Kendra D Carter
*Assistant Examiner* — Jason A Deck
(74) *Attorney, Agent, or Firm* — Finnegan, Henderson, Farabow, Garrett & Dunner, LLP

(57) ABSTRACT

The present disclosure is directed to new inhibitors of the p38 mitogen-activated protein kinase having the general formula (I), processes for preparation thereof, pharmaceutical compositions thereof, and methods of use thereof.

21 Claims, No Drawings

(56) References Cited

FOREIGN PATENT DOCUMENTS

| | | |
|---|---|---|
| EP | 0 743 066 A2 | 11/1996 |
| JP | 57-203068 | 12/1982 |
| JP | 10-79183 | 3/1989 |
| JP | 1996-005887 | 1/1996 |
| JP | 9-104638 | 4/1997 |
| WO | WO 87/04928 | 8/1987 |
| WO | WO 91/04974 | 4/1991 |
| WO | WO 91/06545 | 5/1991 |
| WO | WO 99/01449 | 1/1999 |
| WO | WO 99/64400 | 12/1999 |
| WO | WO 00/63204 | 10/2000 |
| WO | WO 00/66583 | 11/2000 |
| WO | WO 01/01986 A1 | 1/2001 |
| WO | WO 01/29042 A1 | 4/2001 |
| WO | WO 02/02549 A1 | 1/2002 |
| WO | WO 02/46184 A1 | 6/2002 |
| WO | WO 02/058695 A1 | 8/2002 |
| WO | WO 02/072576 A1 | 9/2002 |
| WO | WO 02/072579 A1 | 9/2002 |
| WO | WO 03/008413 A1 | 1/2003 |
| WO | WO 03/033502 A1 | 4/2003 |
| WO | WO 03/043998 A1 | 5/2003 |
| WO | WO 03/087087 A2 | 10/2003 |
| WO | WO 03/097062 A1 | 11/2003 |
| WO | WO 03/103590 A2 | 12/2003 |
| WO | WO 2004/010995 A1 | 2/2004 |
| WO | WO 2004/011470 A1 | 2/2004 |
| WO | WO 2004/014900 A1 | 2/2004 |
| WO | WO 2004/020438 A2 | 3/2004 |
| WO | WO 2004/020440 A1 | 3/2004 |
| WO | WO 2004/074290 A1 | 9/2004 |
| WO | WO 2005/000232 A2 | 1/2005 |
| WO | WO 2005/018624 A2 | 3/2005 |
| WO | WO 2005/032551 A1 | 4/2005 |
| WO | WO 2005/070929 A1 | 8/2005 |
| WO | WO 2005/073219 A1 | 8/2005 |
| WO | WO 2005104711 A2 * | 11/2005 |
| WO | WO 2005/121142 A1 | 12/2005 |
| WO | WO 2007/063925 A1 | 6/2007 |
| WO | WO 2007/096214 A1 | 8/2007 |
| WO | WO 2007/104664 A1 | 9/2007 |
| WO | WO 2008/017461 A1 | 2/2008 |
| WO | WO 2008/045393 A1 | 4/2008 |
| WO | WO 2008/107125 A1 | 9/2008 |
| WO | WO 2008/131922 A1 | 11/2008 |
| WO | WO 2009/132774 A1 | 11/2009 |
| WO | WO 2011/057757 A1 | 5/2011 |

OTHER PUBLICATIONS

Adams, R. H., et al., "Essential role of p38α MAP kinase in placental but not embryonic cardiovascular development," Molecular Cell, 6:109-116 (2000).
Allen, M., et al., "Deficiency of the stress kinase p38a results in embryonic lethality: characterization of the kinase dependance of stress responses of enzyme-deficient embryonic stem cells," J. Exp. Med. 191(5): 859-869 (2000).
Amato, J.S., et al., "Synthesis of 1-tert-Butyl-4-chlorpiperidine: generation of an N-tert-Butyl group by the reaction of a dimethyliminium salt with methylmagnesium chloride," The Journal of Organic Chemistry, 70(5):1930-1933 (2005).
Balaban, A. T., "Aminyloxides (nitroxides) from 1-hydroxy-2-indolinones," Tetrahedron, 30:739-744 (1974).
Bao, J. et al., "p38 MAP kinase inhibitors: metabolically stabilized piperidine-substituted quinolinones and naphthyridinones," Bioorganic & Medicinal Chemistry Letters, 16: 64-68 (2006).
Baxter, I. et al., "The oxidation of 5-arylsulphonamido-3,3-dimethyloxindoles and related compounds," Journal of the Chemical Society (C), pp. 952-955 (1971).
Beardmore, V. A., et al., "Generation and characterization of p38β (MAPK11) gene targeted mice," Molecular and Cellular Biology, 25(23):10454-10464 (2005).
Brancho, D., et al., "Mechanism of p38 MAP kinase activation in vivo," Genes & Development, 17:1969-1978 (2003).
Cheng, C., et al., "The friedlander synthesis of quinolines," Org. React., Chapter 2:37-201 (1982).
Dopp, D., "Substituenteneinflüsse auf die photocyclisierung von 1-*tert*-Butyl-2- nitrobenzolen," Liebigs Annalen der Chemie, pp. 554-563 (1979).
English Language Abstract for CN 1502608.
English Language Abstract for JP-203068 from esp@cenet, dated Dec. 13, 1982.
English Language Abstract for JP 1996-005887.
English Language Abstract for JP 10-79183.
English Language Abstract for JP 09-104638.
English Language Abstract for WO 1987/04928.
English Language Abstract for WO 1991/04974.
English Language Abstract for WO 1991/06545.
English Language Abstract for WO 2004/011470.
English Language Abstract for WO 2007/063925.
Fang, Cheng-Lin, et al., "Dimerization of a 3-substituted oxidindole at C-3 and its application to the synthesis of (±)-folicanthine," Journal of the American Chemical Society, 116: 9480-9486 (1994).
Gavrin, L. K., et al., "Inhibition of Tp12 kinase and TNF-α production with 1,7-naphthyridine-3-carbonitriles: synthesis and structure-activity relationship," Bioorganic & Medicinal Chemistry Letters, 15: 5288-5292 (2005).
Gilman, H., et al., "Some substituted isoquinolines," Journal of American Chemical Society, 69(8):1946-1948 (1947).
Hale, K. K., et al., "Differential expression and activation of p38 mitogen-activated protein kinase α, β, γ, and δ in inflammatory cell lineages," The Journal of Immunology, 162: 4246-4252 (1999).
Hideshima, T., et al., "Targeting p38 MAPK inhibits multiple myeloma cell growth in the bone marrow milieu," Blood, 101(2):703-705 (2003).
Hildesheim, J., et al., "p38 Mitogen-activated protein kinase inhibitor protects the epidermis against the acute damaging effects of ultraviolet Irradiation by blocking apoptosis and inflammatory responses," The Journal of Investigative Dermatology, 122:497-502 (2004).
Hollenbach, E., et al., "Inhibition of RICK/Nuclear factor-κB and p38 signaling attenuates the inflammatory response in a murine model of crohn disease," The Journal of Biological Chemistry, 280(15):14981-14988 (2005).
International Search Report, PCT/EP2007/006981, mailed Oct. 18, 2007.
International Search Report, PCT/EP2008/001616, mailed May 28, 2008.
International Search Report, PCT/EP2008003357, mailed Oct. 18, 2007.
International Search Report, PCT/EP2010/006817, mailed May 2, 2011.
Jin, Shan-Xue, et al., "p38 Mitogen-activated protein kinase is activated after a spinal nerve ligation in spinal cord microglia and dorsal root ganglion neurons and contributes to thegeneration of neuropathic pain," The Journal of Neuroscience, 23(10):4017-4022 (2003).
Karp, G., et al., "Preparation and alkylation of regioisomeric tetrahydrophthalimide-substituted Indolin-2(3H)-ones," Journal of Heterocyclic Chemistry, 31:1513-1520 (1994).
Katsoulidis, E., et al., "Role of the p38 mitogen-activated protein kinase pathway in cytokine-mediated hematopoietic suppression in myelodysplastic syndromes," Cancer Research, 65(19):9029-9037 (2005).
Kotlyarov, A., et al., "MAPKAP Kinase 2 is essential for LPS-induced TNF-α biosynthesis," Nature Cell Biology, 1:94-97 (1999).
Kumar, S., et al., "p38 Map kinases: key signaling molecules as therapeutic targets for inflammatory diseases," Nature Reviews Drug Discovery,2:717-726 (2003).
Kyriakis, J. M., et al., "Mammalian mitogen-activated protein kinase signal transduction pathways activated by stress and inflammation," Physiological Reviews; 81(2):807-869 (2001).
Lee, H. J., et al., "Biochemical and physiological effects of benzheterocycles and related compounds," Journal of Agricultural and Food Chemistry, 43: 2722-2727 (1995).
Lee, J. C., et al., "A protein kinase involved in the regulation of inflammatory cytokine biosynthesis," Nature. 372(22/29):739-746 (1994).

(56) References Cited

OTHER PUBLICATIONS

Lyga, J., et al., "Structural replacements for the benzoxazinone protox Inhibitors," Pesticide Science. 55: 281-287 (1999).
Miyaura, N., et al., "Palladium-catalyzed cross-coupling reactions of organoboron compounds," Chem. Rev., 95(7): 2457-2483 (1995).
Moran, D. B., et al., "Synthesis of (pyridinyl)-1,2,4-triazolo[4,3-a]pyridines," J. Heterocyclic Chem., 23:1071-1077 (1986).
Müller, C., et al., "Chiral Pyrrolo[2,3-d]pyrimidine and Pyrimido[4,5-b]indole derivatives: structure-activity relationships of potent, highly stereoselective $A_1$-adenosine receptor antagonists," Journal of Medicinal Chemistry, 39:2482-2491 (1996).
Negishi, E., et al., "Novel stereoselective alkenyl-aryl coupling via nickel-catalysed reaction of alkenylalanes with aryl halides," J.C.S. Chem. Comm.,pp. 596-597 (1976).
Nick, J. A., et al., "Selective suppression of neutrophil accumulation in ongoing pulmonary inflammation by systemic Inhibition of p38 mitogen-activated protein kinase," The Journal of Immunology, 169:5260-5269 (2002).
Notice of Allowance dated Nov. 8, 2010 for U.S. Appl. No. 12/376,499.
Office Action dated Aug. 2, 2010 for U.S. Appl. No. 12/376,499.
Office Action dated Oct. 28, 2011 for U.S. Appl. No. 12/529,490.
Notice of Allowance dated May 10, 2012 for U.S. Appl. No. 12/529,490.
Office Action dated Feb. 8, 2012 for U.S. Appl. No. 12/597,187.
Notice of Allowance dated Aug. 3, 2012 for U.S. Appl. No. 12/597,187.
Notice of allowance dated Oct. 4, 2012 for U.S. Appl. No. 12/989,696.
Pargellis, C., et al., "Inhibitors of p38 mitogen-activated protein kinase for the treatment of rheumatoid arthritis," Current Opinion in Investigational Drugs, 4(5): 566-571 (2003).
Patani, G. A., et al., "Bioisosterism: a rational approach in drug design," Chemical Reviews, ACS, 96(8):3147-3176 (1996).
Sabio, G., et al., "p38γ regulates the localisation of SAP97 in the cytoskeleton by modulating its interaction with GKAP," The EMBO Journal, 24(6):1134-1145 (2005).
Saccani, S., et al., "p38-dependent marking of inflammatory genes for increased NF-κB recruitment,"Nature Immunology, 3(1): 69-75 (2002).
Santilli, A. A., et al., "7-Deazapurines v. synthesis and reactions of 7-amino-5,7-dihydro-4-methyl-2-phenyl-6H-pyrrolo[2,3-d]pyrimidin-6-one," Journal of Heterocyclic Chemistry, 12:1291-1293 (1975).
Schäfers, M., et al., "Tumor necrosis factor-α induces mechanical allodynia after spinal nerve ligation by activation of p38 MAPK in primary sensory neurons," The Journal of Neuroscience, 23(7): 2517-2521 (2003).
See, F., et al., "p38 MAP kinase as a therapeutic target in cardiovascular disease," Drug Discovery Today: Therapeutic Strategies, 1(2):149-154 (2004).
Shi, Y., et al., "In the cellular garden of forking paths: how p38 MAPKs signal for downstream assistance," Biol. Chem., 383(10):1519-1536 (2002).
Tamura, K., et al., "Requirement for P38α in erythropoietin expression: a role for stress kinases in erythropoiesis," Cell, 102:221-231 (2000).
Tsuda, M., et al., "Activation of p38 mitogen-activated protein kinase in spinal hyperactive microglia contributes to pain hypersensitivity following peripheral nerve injury," GLIA, 89:89-95 (2004).
Underwood, D. C., "SB 239063, a p38 MAPK inhibitor, reduces neutrophilia, inflammatory cytokines, MMP-9, and fibrosis in lung," Am. J. Physiol. Lung Cell Mol. Physiol., 279:L895-L902 (2000).
Waetzig, G. H., et al., "p38 Mitogen-activated protein kinase is activated and linked to TNF-α signaling in inflammatory bowel disease," The Journal of Immunology, 168:5342-5351 (2002).
Wang, X. S., et al., "Molecular cloning and characterization of a novel p38 mitogen-activated protein kinase," The Journal of Biological Chemistry, 272(38):23668-23674 (1997).
Zhou, Z., et al., "TNFR-induced the NF-κB, but not the ERK, p38MAPK or JNK activation, mediates TNF-induced ICAM-1 and VCAM-1 expression on endothelial cells," Cellular Signalling, 19:1238-1248 (2007).

\* cited by examiner

SUBSTITUTED SPIRO[CYCLOALKYL-1,3'-INDO]-2'(1'H)-ONE DERIVATIVES AND THEIR USE AS P38 MITOGEN-ACTIVATED KINASE INHIBITORS

This application is a national stage filing under 35 U.S.C. §371 of International Application No. PCT/EP2009/002458 filed on Apr. 3, 2009, which claims priority to European Application No. 08382013.4 filed on Apr. 11, 2008, the disclosures of which are incorporated herein by reference in their entireties.

The present invention relates to new inhibitors of the p38 mitogen-activated protein kinase.

MAP kinases are evolutionary conserved enzymes translating membrane signals into gene expression responses. In mammals, four MAPK families can be distinguished: extracellular signal-related kinases (ERK1/2), Jun amino terminal kinases (JNK1/2/3), p38 proteins (alpha, beta, gamma and delta) and ERK5. The regulation of these proteins is exerted by a three-tier cascade composed of MAPK, MAPK kinase, and MAPK kinase kinase.

p38 MAPK was originally identified as the target of CSAIDs (cytokine suppressive anti-inflammatory drugs), having a central role in the signal transduction pathway leading to the production of TNF-alpha and other cytokines (Lee et al, 1984). p38 is activated by phosphorylation of Thr and Tyr by either MKK3, MKK4, or MKK6 (Kyriakis and Avruch, 2001) in response to stress and pro-inflammatory stimuli. In turn, p38 phosphorylates its effectors in Ser and Thr residues, namely protein kinase phosphatases and transcription factors, such as ATF-2, MEF2, MAPKAPK2, MSK1/2 or MNK1/2. Altogether this activation cascade results in control of gene expression through four different mechanisms: transcription factor activation; mRNA stabilization; mRNA translation; and histone phosphorylation at NF-kB binding sites in chromatin (Shi and Gaestel, 2002; Sacanni et al, 2001).

There are four different p38 isoforms encoded by separate genes: p38 alpha, beta, gamma and delta, each one showing a distinct tissue expression pattern. As assessed by mRNA and protein levels (Beardmore et al, 2005; Wang et al, 1997), p38 alpha and beta are ubiquitously expressed, with p38 beta expression being more relevant in CNS tissues (brain, cortex, cerebellum, hippocampus, etc). The expression of p38 gamma is more prominent in skeletal muscle while p38 delta is localized mainly in the heart, kidney, lung and adrenal gland. At the cellular level, p38 alpha and delta seem to be the most relevant isoforms in immune cells (monocytes, macrophages, neutrophils and T cells) (Hale et al, 1999). Pharmacological inhibition with specific p38alpha/beta inhibitors as well as gene targeting studies have indicated that p38alpha is the isoform regulating inflammatory responses most probably through its downstream substrate MAPKAP-K2 (Kotlyarov et al, 1999). Likewise, this isoform is necessary in early embryonic development as p38alpha KO (knock-out) mice die in embryonic day 12.5 due to placental insufficiency and vascular defects (Allen et al, 2000; Tamura et al, 2000; Adams et al, 2000), a phenotype that is also reproduced in the MKK3/MKK6 double KO mice (Brancho et al, 2003). In contrast, p38 beta, gamma and delta knock-out mice do not show any developmental deficiencies (Beardmore et al, 2005; Sabio et al, 2005). p38 beta KO mice appear to respond similarly to pro-inflammatory stimuli (LPS) as wild type controls, indicating that this isoform does not have a role in inflammation (Beardmore et al 2005).

The contribution of the p38MAPK pathway to inflammation has been studied both in vitro and in vivo by employing different chemical series of p38 inhibitors (Pargellis and Regan, 2003; Kumar et al, 2003). The most widely used inhibitor molecule, SB203580, is, in fact, a dual p38alpha/beta inhibitor. Inhibition of p38 abrogates the release of TNF-alpha as well as other pro-inflammatory cytokines like IL-1, IL-6, and IL-8, in PBMC, whole blood, or the human monocytic cell line THP-1.

By virtue of the involvement of p38 in TNF-alpha production, inhibitors of p38 have been tested in animal models of diseases in which TNF-alpha has a pathophysiological role. p38 inhibition decreases murine collagen-induced arthritis and rat adjuvant-induced arthritis severity (Pargellis and Regan, 2003). Furthermore, p38 inhibitors also improve bone resorption in animal models of arthritis, probably due to the implication of p38 MAPK in the differentiation of osteoclasts. p38 inhibition attenuates the inflammatory response in a murine model of Crohn's disease and diminishes TNF-alpha production in human Crohn's disease patient biopsies (Hollenbach et al 2005; Waetzig et al, 2002). Due to the exclusive usage of the p38 pathway by neutrophils, p38 has also been considered a target for chronic obstructive pulmonary disease (COPD) (Nick et al, 2002). p38 inhibition reduces neutrophilia, inflammatory cytokines, MMP-9 and fibrosis in lung (Underwood et al, 2000). In skin models of irradiation, inhibition of p38 protects the epidermis against acute ultraviolet radiation exposure by blocking apoptosis and inflammatory responses (Hildesheim et al, 2004). p38 inhibition also reverses hematopoietic defects in bone marrow from patients with myelodysplastic syndromes, in which TNF-alpha overproduction has a pathophysiological role (Katsoulidis et al, 2005).

In hematopoietic malignancies, a study has shown that p38 inhibitors can block the proliferation of multiple myeloma cells by inhibiting the production of IL-6 and VEGF in bone marrow stromal cells (Hideshima et al, 2002).

p38 is involved in key cellular mechanisms such as apoptosis, fibrosis and cellular hypertrophy, which are common to cardiac and vascular pathologies. Pharmacological inhibition of p38 has proven useful in improving ischemia-reperfusion injury, cerebral focal ischemia, acute coronary syndrome, chronic heart failure and post-myocardial infarction remodelling (See et al, 2004).

Experimental inhibition of p38 has been reported effective in reducing pain in animal models of neuropathy that rely on COX-2 expression and TNF-alpha production by glial cells (Schafers et al, 2003; Jin et al, 2003; Tsuda et al, 2004).

Therefore, the compounds of the invention may be useful in the prophylaxis or treatment of any disease or disorder in which p38 kinase plays a role including conditions caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further, the invention extends to the administration to a human an effective amount of a p38 inhibitor for treating any such disease or disorder.

Diseases or disorders in which p38 kinase plays a role either directly or via pro-inflammatory cytokines including the cytokines TNF, IL-1, IL-6 and IL-8 include without limitation autoimmune diseases, immune and inflammatory diseases, destructive bone disorders, neoplastic disorders, neurodegenerative disorders, viral diseases, infectious diseases, cardiovascular diseases, angiogenesis-related disorders, and pain-related disorders.

Autoimmune diseases which may be prevented or treated include but are not limited to rheumatoid arthritis, psoriatic arthritis, ankylosing spondilytis, Reiter's syndrome, fibromyalgia, inflammatory bowel disease such as ulcerative colitis and Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, autoimmune chronic active hepatitis, myasthenia gravis, or Addison's disease.

Immune and inflammatory diseases which may be prevented or treated include, but are not limited to, asthma, COPD, respiratory distress syndrome, acute or chronic pancreatitis, graft versus-host disease, Behcet syndrome, inflammatory eye conditions such as conjunctivitis and uveitis, psoriasis, contact dermatitis, atopic dermatitis, sarcoidosis, gout, pyresis, transplant rejection, allergic rhinitis and allergic conjunctivitis.

Cardiovascular diseases which may be prevented or treated include, but are not limited to, ischemia-reperfusion injury, cerebral focal ischemia, acute coronary syndrome, congestive heart failure, cardiomyopathy, myocarditis, atherosclerosis, vasculitis and restenosis.

Destructive bone disorders which may be prevented or treated include, but are not limited to, osteoporosis, osteoarthritis and multiple myeloma-related bone disorder.

Neoplastic disorders which may be prevented or treated include, but are not limited to, solid tumors such as Kaposi's sarcoma, metastatic melanoma, and hematopoietic malignancies such as acute or chronic myelogenous leukemia and multiple myeloma.

Neurodegenerative diseases which may be prevented or treated include, but are not limited to, Parkinson's disease, Alzheimer's disease, neurodegenerative disease caused by traumatic injury, or Huntington's disease.

Viral diseases which may be prevented or treated include, but are not limited to, acute hepatitis infection (including hepatitis A, hepatitis B and hepatitis C), HIV infection, Epstein-Barr infection, CMV retinitis, SARS or avian influenza A infection.

Infectious diseases which may be prevented or treated include, but are not limited to, sepsis, septic shock, endotoxic shock, Gram negative sepsis, toxic shock syndrome, Shigellosis, or cerebral malaria.

Angiogenesis-related disorders which may be prevented or treated include, but are not limited to, hemangiomas, ocular neovascularization, macular degeneration or diabetic retinopathy.

Pain-related disorders which may be prevented or treated include, but are not limited to, neuropathic pain (such as diabetic neuropathy, post-herpetic or trigeminal neuralgia), cancer-related pain, chronic pain (such as lower back pain syndrome), and inflammatory pain.

Other miscellaneous diseases or disorders which may be prevented or treated include, but are not limited to, myelodysplastic syndrome, cachexia, endometriosis, acute skin injuries such as sunburn, and wound healing.

In view of the physiological effects mediated by inhibition of the p38 mitogen-activated protein kinase, several compounds have been recently disclosed for the treatment or prevention of rheumatoid arthritis, ischemia-reperfusion injury, cerebral focal ischemia, acute coronary syndrome, COPD, Crohn's disease, irritable bowel syndrome, adult respiratory distress syndrome, osteoporosis, neurodegenerative diseases such as Alzheimer's disease, rheumatoid spondylitis, psoriasis, atherosclerosis, osteoarthritis and multiple myeloma. See for example WO 99/01449, WO 00/63204, WO 01/01986, WO 01/29042, WO 02/046184, WO 02/058695, WO 02/072576, WO 02/072579, WO 03/008413, WO 03/033502, WO 03/087087, WO 03/097062, WO 03/103590, WO 2004/010995, WO 2004/014900, WO 2004/020438, WO 2004/020440, WO 2005/018624, WO 2005/032551, WO 2005/073219.

It has now been found that certain substituted spiro[cycloalkyl-1,3'-indol]-2'(1'H)-one derivatives are novel potent inhibitors of the p38 mitogen-activated protein kinase and can therefore be used in the treatment or prevention of these diseases.

Further objectives of the present invention are to provide a method for preparing said compounds; pharmaceutical compositions comprising an effective amount of said compounds; the use of the compounds in the manufacture of a medicament for the treatment of pathological conditions or diseases susceptible of being improved by inhibition of the p38 mitogen-activated protein kinase; and methods of treatment of pathological conditions or diseases susceptible to amelioration by inhibition of the p38 mitogen-activated protein kinase comprising the administration of the compounds of the invention to a subject in need of treatment.

Thus, the present invention is directed to new substituted derivatives represented by formula (I):

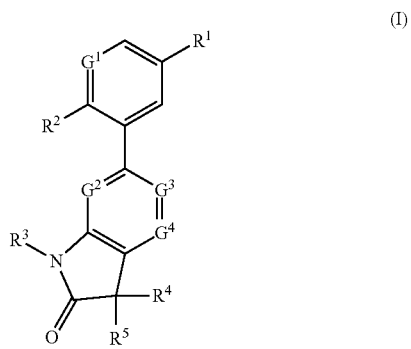

wherein $R^1$ represents a 5-membered heteroaromatic ring having 1, 2 or 3 heteroatoms selected from nitrogen, oxygen and sulphur atoms which heteroaromatic ring may be optionally substituted by one or two groups selected from linear or branched $C_{1-4}$ alkyl and —$(CH_2)_p$—$C_{3-6}$cycloalkyl groups wherein the alkyl and cycloalkyl groups are optionally substituted by one, two or three groups selected from fluorine atoms, —OR and —NRR' groups wherein R and R' each are independently selected from hydrogen atoms, linear or branched $C_{1-4}$ alkyl and $C_{3-6}$ cycloalkyl groups, p represents an integer from 0 to 3 or $R^1$ represents a group of formula —CO—$NHR^6$, wherein $R^6$ represents a hydrogen atom, a linear or branched $C_{1-4}$ alkyl, a $C_{3-6}$ cycloalkyl group, a $C_{3-6}$ cycloalkyl-$C_{1-2}$alkylene group or a 5 to 6 membered heteroaromatic group having 1, 2 or 3 heteroatoms selected from nitrogen, oxygen and sulphur atoms, wherein the heteroaromatic group is optionally substituted by 1 or 2 linear or branched $C_{1-4}$ alkyl and $C_{3-6}$ cycloalkyl groups.

R² is selected from the group consisting of hydrogen atoms, chlorine atoms and methyl groups R³ is selected from the group consisting of hydrogen atoms and $C_{1-4}$ alkyl groups, R⁴ and R⁵ each independently represent a $C_{1-3}$ alkyl group optionally substituted by hydroxy group, or R⁴ and R⁵ form together with the carbon atom to which they are attached a cyclic group of formula

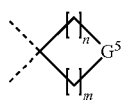

wherein n and m each independently represent an integer from 1 to 2 and G⁵ is selected from —O—, —S—, —SO—, —SO₂—, —C(R⁷R⁸)— and —N(LR⁹)—, wherein R⁷ is selected from the group consisting of hydrogen atom, halogen atom, hydroxyl group, $C_{1-4}$ alkyl group, morpholine and morpholino-ethoxy group, R⁸ is selected from the group consisting of hydrogen and halogen atoms and $C_{1-4}$ alkyl groups, L represents a direct bond, —SO₂—, —CO—, —(CO)O—, —(CO)NH—, —(SO₂)NH—, and R⁹ represents a hydrogen atom, a linear or branched $C_{1-4}$ alkyl group, —(CH₂)$_q$—$C_{3-6}$ cycloalkyl group, an $C_5$-$C_{10}$ aryl group or a 5 to 10-membered heteroaryl group containing at least one heteroatom selected from N, S and O, wherein the alkyl and cycloalkyl groups are optionally substituted by one or two groups selected from halogen atoms, —OR" and —NR"R'" groups, and the aryl and heteroaryl groups are optionally substituted by one or two groups selected from linear or branched $C_1$-$C_4$ alkyl groups, halogen atoms, —OR" and —NR"R'" groups, wherein R" and R'" each are independently selected from hydrogen atoms, $C_{1-4}$ alkyl groups and $C_{3-6}$ cycloalkyl groups, or R" and R'" together with the nitrogen atom to which they are attached form a 5-6 membered saturated heterocyclic ring optionally containing one further heteroatom selected from N, O or S, and q represents an integer from 0 to 3

G¹ is selected from a nitrogen atom or a group —CH= or —CF=

G² is selected from a nitrogen atom or a group —CH= or —CF=

G³ is selected from a nitrogen atom or a group —CH=, —CCl= or —CF=, and

G⁴ is selected from a nitrogen atom or a group —CH= or —CF= and pharmaceutically acceptable salts thereof.

As used herein the term $C_{1-4}$ alkyl embraces optionally substituted, linear or branched hydrocarbon radicals having 1 to 4 carbon atoms, for example 1 to 3 carbon atoms. Thus, the alkyl radical may be unsubstituted or substituted with one or more, for example 1, 2 or 3 substituents. When an alkyl radical carries 2 or more substituents, the substituents may be the same or different. Preferably, unless otherwise specified, an alkyl radical is unsubstituted.

Examples include methyl, ethyl, n-propyl, i-propyl, n-butyl, sec-butyl and tert-butyl radicals.

As used herein, the term cycloalkyl embraces saturated carbocyclic radicals and, unless otherwise specified, a cycloalkyl radical typically has from 3 to 7 carbon atoms, preferably from 3 to 6 carbon atoms, more preferably from 3 to 5 carbon atoms and most preferably from 3 to 4 carbon atoms.

Examples include cyclopropyl, cyclobutyl, cyclopentyl, cyclohexyl and cycloheptyl. When a cycloalkyl radical carries 2 or more substituents, the substituents may be the same or different. Preferred substituents on the cycloalkyl groups are halogen atoms and methyl groups. Preferably, unless otherwise specified, a cycloalkyl radical is unsubstituted.

As used herein, the term $C_5$-$C_{14}$ aryl radical embraces typically a monocyclic or polycyclic aryl radical such as phenyl or naphthyl, anthranyl or phenanthryl, and is preferably a $C_5$-$C_{10}$ aryl radical such as phenyl or naphthyl. Phenyl is preferred. When an aryl radical carries 2 or more substituents, the substituents may be the same or different. Preferably, unless otherwise specified, an aryl radical is unsubstituted.

As used herein, the term heteroaryl radical embraces typically a 5 to 14 membered ring system, preferably a 5 to 10 membered ring system, more preferably a 5 to 6 membered ring system, comprising at least one heteroaromatic ring and containing at least one heteroatom selected from O, S and N. A heteroaryl radical may be a single ring or two or more fused rings wherein at least one ring contains a heteroatom.

Examples include pyridyl, pyrazinyl, pyrimidinyl, pyridazinyl, furyl, oxadiazolyl, oxazolyl, imidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl and pyrazolyl radicals. Pyridyl, thienyl, furanyl, pyridazinyl, pyrimidinyl and quinolyl radicals are preferred.

When a heteroaryl radical carries 2 or more substituents, the substituents may be the same or different. Preferably, unless otherwise specified, a heteroaryl radical is unsubstituted.

As used herein, the term heterocyclic group embraces typically a saturated or unsaturated $C_3$-$C_7$ carbocyclic ring, such as a 5, 6 or 7 membered radical, preferably a 5 or 7 membered radical, in which one or more, for example 1, 2, or 3 of the carbon atoms preferably 1 or 2 of the carbon atoms are replaced by a heteroatom selected from N, O and S. Saturated heterocyclic radicals are preferred. A heterocyclic radical may be a single ring or two or more fused rings wherein at least one ring contains a heteroatom.

Examples of heterocyclic radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, cromanyl, isocromanyl, imidazolidinyl, imidazolyl, oxiranyl, azaridinyl, 4,5-dihydro-oxazolyl and 3-aza-tetrahydrofuranyl. Where a heterocyclic radical carries 2 or more substituents, the substituents may be the same or different. Preferably a heterocyclic radical is unsubstituted.

As used herein, the term halogen atom embraces chlorine, fluorine, bromine or iodine atoms typically a fluorine, chlorine or bromine atom, most preferably chlorine or fluorine. The term halo when used as a prefix has the same meaning.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X–) is associated with the positive charge of the N atom. X– may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X– is preferably an anion selected from chloride, bromide, iodide, sulphate, nitrate, acetate, maleate, oxalate, succinate or trifluoroacetate. More preferably X– is chloride, bromide, trifluoroacetate or methanesulphonate.

As used herein, an N-oxide is formed from the tertiary basic amines or imines present in the molecule, using a convenient oxidising agent.

When $R^1$ represents a 5-membered heteroaromatic ring substituted by one or two groups selected from linear or branched $C_{1-4}$ alkyl and —$(CH_2)_p$—$C_{3-6}$ cycloalkyl groups, if the alkyl and cycloalkyl groups are substituted by —OR or —NRR', they are preferably substituted by either one —OR group or one —NRR' group Typically, $R^1$ is selected from triazolyl, oxadiazolyl and imidazolyl groups all of which may be optionally substituted by one group selected from linear or branched $C_{1-4}$ alkyl, $C_{3-6}$ cycloalkyl and —$CF_3$, or $R^1$ represents a group of formula —CO—$NHR^6$, wherein $R^6$ represents a hydrogen atom, a linear or branched $C_{1-4}$ alkyl, a $C_{3-6}$ cycloalkyl group, a $C_{3-6}$ cycloalkyl-$C_{1-2}$alkylene group, an isoxazolyl group, a triazolyl group or a pyridyl group. More preferably, $R^1$ represents a triazolyl group which may be optionally substituted by one methyl group or $R^1$ represents a group of formula —CO—$NHR^6$, wherein $R^6$ represents a hydrogen atom, a methyl group, a cyclopropyl group, a cyclopropylmethyl group, a cyclobutyl group or an isoxazolyl group. Most preferably, $R^1$ represents a triazolyl group which may be optionally substituted by one methyl group or $R^1$ represents a group of formula —CO—$NHR^6$, wherein $R^6$ represents a cyclopropyl group or an isoxazolyl group.

Typically, $R^2$ is selected from the group consisting of a chlorine atom and a methyl group. $R^2$ is preferably a methyl group.

Typically, $R^3$ is selected from the group consisting of a hydrogen atom and a methyl group. Preferably, $R^3$ represents a hydrogen atom.

Typically, $R^4$ and $R^5$ each independently represent a methyl group or a 2-hydroxyethyl group, or $R^4$ and $R^5$ form together with the carbon atom to which they are attached a cyclic group of formula

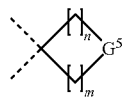

wherein n and m each independently represent an integer from 1 to 2 and $G^5$ is selected from —O—, —S—, —SO—, $SO_2$—, —$C(R^7R^8)$— and —$N(LR^9)$—, wherein $R^7$ is selected from the group consisting of a hydrogen atom, a fluorine atom, a hydroxyl group, a methyl group, morpholine and morpholino-ethoxy groups, $R^8$ is selected from a hydrogen atom, a fluorine atom or a methyl group, L is selected from the group consisting of a direct bond, —$SO_2$—, —CO—, —(CO)O— and —C(O)NH—, $R^9$ represents a linear or branched $C_{1-4}$ alkyl group, a $C_{3-6}$ cycloalkyl group, a phenyl or a pyridyl group, wherein the alkyl and cycloalkyl groups are optionally substituted with one group selected from a chlorine atom, piperazine and morpholine groups, and the phenyl and pyridyl groups are optionally substituted with one group selected from a chlorine atom, methyl, piperazine and morpholine groups.

Preferably $R^4$ and $R^5$ form together with the carbon atom to which they are attached a cyclic group of formula

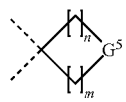

wherein n and m each independently represent an integer from 1 to 2 and $G^5$ is selected from —O—, —S—, —SO—, $SO_2$—, —$C(R^7R^8)$— and —$N(LR^9)$—, wherein $R^7$ is selected from the group consisting of a hydrogen atom, a fluorine atom, a hydroxyl group, a methyl group, morpholine and morpholino-ethoxy groups, $R^8$ is selected from a hydrogen atom, a fluorine atom or a methyl group, L is selected from the group consisting of a direct bond, —$SO_2$—, —CO—, (CO)O— and —C(O)NH—

$R^9$ represents a linear or branched $C_{1-4}$ alkyl group, a $C_{3-6}$ cycloalkyl group, a phenyl or a pyridyl group, wherein the alkyl and cycloalkyl groups are optionally substituted with one group selected from a chlorine atom, piperazine and morpholine groups, and the phenyl and pyridyl groups are optionally substituted with one group selected from a chlorine atom, methyl, piperazine and morpholine groups.

More preferably, $G^5$ is selected from —O—, —S—, —$C(R^7R^8)$— and —$N(LR^9)$—, wherein $R^7$ is selected from the group consisting of a hydrogen atom, a fluorine atom, a hydroxyl group, a morpholine group and a morpholino-ethoxy group, $R^8$ is selected from a hydrogen atom, a fluorine atom or a methyl group, L is selected from the group consisting of a direct bond, —$SO_2$—(CO)O— and —C(O)NH—, and $R^9$ represents a methyl, a tert-butyl, a cyclopropyl, a phenyl group, wherein the phenyl group is optionally substituted by a chlorine atom, a methyl, a piperazine or a morpholine group. Most preferably, L is selected from the group consisting of a direct bond and —$SO_2$—, and $R^9$ represents a methyl group.

Typically, $G^1$ is selected from the groups —CH═ and —CF═

Typically, $G^2$ is selected from a nitrogen atom or a group —CH═.

Typically, $G^3$ is selected from the groups consisting of a nitrogen atom, —CH═ and —CCl═ groups. $G^3$ is preferably selected from the groups consisting of a nitrogen atom and a —CH═ group.

Typically, G⁴ is selected from a nitrogen atom or a —CH═ group

In a preferred embodiment of the invention, R¹ represents a triazolyl group which may be optionally substituted by one methyl group or R¹ represents a group of formula —CO—NHR⁶, wherein R⁶ represents a cyclopropyl group or an isoxazolyl group, R² represents a methyl group, R³ represents a hydrogen atom, R⁴ and R⁵ form together with the carbon atom to which they are attached a cyclic group of formula

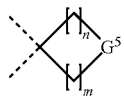

wherein n and m each independently represent an integer from 1 to 2 and G⁵ is selected from —O—, —S—, —C(R⁷R⁸)— and —N(LR⁹)—, wherein R⁷ is selected from the group consisting of a hydrogen atom, a fluorine atom, a hydroxyl group, a morpholine group and a morpholinoethoxy group, R⁸ is selected from a hydrogen atom, a fluorine atom and a methyl group, L is selected from the group consisting of a direct bond or —SO₂—, and R⁹ represents a methyl group, G¹ is selected from the groups —CH═ and —CF═, G², G³ and G⁴ independently are selected from a nitrogen atom or a group —CH═.

Particular individual compounds of the invention include:
N-Cyclopropyl-4-methyl-3-(2'-oxospiro[cyclopentane-1,3'-indoline]-6'-yl)benzamide
N-Cyclopropyl-3-(4,4,5,5-tetramethyl-1,3,2-dioxaborolan-2-yl)benzamide
N-Cyclopropyl-4-methyl-3-(2'-oxo-1',2'-dihydrospiro[cyclobutane-1,3'-indol]-6'-yl)benzamide
N-Isopropyl-4-methyl-3-(2'-oxospiro[cyclopentane-1,3'-indoline]-6'-yl)benzamide
N-4-Dimethyl-3-(2'-oxospiro[cyclopentane-1,3'-indoline]-6'-yl)benzamide
4-Methyl-3-(2'-oxospiro[cyclopentane-1,3'-indoline]-6'-yl)benzamide
3-(3,3-dimethyl-2-oxoindolin-6-yl)-4-methylbenzamide
N-Cyclobutyl-4-methyl-3-(2'-oxospiro[cyclopentane-1,3'-indoline]-6'-yl)benzamide
N-(Cyclopropylmethyl)-4-methyl-3-(2'-oxospiro[cyclopentane-1,3'-indoline]-6'-yl)benzamide
N-tert-Butyl-4-methyl-3-(2'-oxospiro[cyclopentane-1,3'-indoline]-6'-yl)benzamide
4-Methyl-3-(2'-oxospiro[cyclopentane-1,3'-indoline]-6'-yl)-N-(pyridin-2-yl)benzamide
N-(Isoxazol-3-yl)-4-methyl-3-(2'-oxospiro[cyclopentane-1,3'-indoline]-6'-yl)benzamide
4-Methyl-3-(2'-oxospiro[cyclopentane-1,3'-indoline]-6'-yl)-N-(1H-1,2,4-triazol-3-yl)benzamide
4-Chloro-N-cyclopropyl-3-(2'-oxospiro[cyclopentane-1,3'-indoline]-6'-yl)benzamide
N-Cyclopropyl-3-fluoro-4-methyl-5-(2'-oxospiro[cyclopentane-1,3'-indoline]-6'-yl)benzamide
N-Cyclopropyl-6-methyl-5-(2'-oxospiro[cyclopentane-1,3'-indoline]-6'-yl)nicotinamide
N-Cyclopropyl-3-(3,3-dimethyl-2-oxoindolin-6-yl)-4-methylbenzamide
N-(Cyclopropylmethyl)-3-(3,3-dimethyl-2-oxoindolin-6-yl)-4-methylbenzamide
3-(3,3-Dimethyl-2-oxo-2,3-dihydro-1H-indol-6-yl)-N-isoxazol-3-yl-4-methylbenzamide
N-Cyclopropyl-4-methyl-3-(1,3,3-trimethyl-2-oxoindolin-6-yl)benzamide
N-Cyclopropyl-4-methyl-3-(2'-oxospiro[cyclohexane-1,3'-indoline]-6'-yl)benzamide
N-Cyclopropyl-4-methyl-3-(2-oxo-2',3',5',6'-tetrahydrospiro[indoline-3,4'-pyran]-6-yl)benzamide
N-Isoxazol-3-yl-4-methyl-3-(2-oxo-1,2,2',3',5',6'-hexahydrospiro[indole-3,4'-pyran]-6-yl)benzamide
3-(3,3-bis(2-Hydroxyethyl)-2-oxoindolin-6-yl)-N-cyclopropyl-4-methylbenzamide
N-Cyclopropyl-4-methyl-3-(2-oxo-2',3',5',6'-tetrahydrospiro[indoline-3,4'-thiopyran]-6-yl)benzamide
N-Cyclopropyl-3-(2-oxo-1,2,2',3',5',6'-hexahydrospiro[indole-3,4'-thiopyran-1-oxide]-6-yl)-4-methylbenzamide
N-Cyclopropyl-3-(1',1'-dioxido-2-oxo-1,2,2',3',5',6'-hexahydrospiro[indole-3,4'-thiopyran]-6-yl)-4-methylbenzamide
N-(Cyclopropylmethyl)-3-(1',1'-dioxido-2-oxo-1,2,2',3',5',6'-hexahydrospiro[indole-3,4'-thiopyran]-6-yl)-5-fluoro-4-methylbenzamide
N-Cyclopropyl-4-methyl-3-(1'-methyl-2-oxospiro[indoline-3,4'-piperidine]-6-yl)benzamide
tert-Butyl 6-(5-(cyclopropylcarbamoyl)-2-methylphenyl)-2-oxospiro[indoline-3,4'-piperidine]-1'-carboxylate
N-cyclopropyl-3-fluoro-4-methyl-5-(1'-(methylsulfonyl)-2-oxospiro[indoline-3,4'-piperidine]-6-yl)benzamide
N-Cyclopropyl-3-(4,4-difluoro-2'-oxospiro[cyclohexane-1,3'-indoline]-6'-yl)-4-methylbenzamide
3-(4,4-Difluoro-2'-oxo-1',2'-dihydrospiro[cyclohexane-1,3'-indol]-6'-yl)-N-isoxazol-3-yl-4-methylbenzamide
N-cyclopropyl-3-(4-hydroxy-2'-oxospiro[cyclohexane-1,3'-indoline]-6'-yl)-4-methylbenzamide (Major Isomer)
N-cyclopropyl-3-(4-hydroxy-2'-oxospiro[cyclohexane-1,3'-indoline]-6'-yl)-4-methylbenzamide (Minor isomer)
N-cyclopropyl-3-(4-hydroxy-4-methyl-2'-oxospiro[cyclohexane-1,3'-indoline]-6'-yl)-4-methylbenzamide (major isomer)
N-cyclopropyl-3-(4-hydroxy-4-methyl-2'-oxospiro[cyclohexane-1,3'-indoline]-6'-yl)-4-methylbenzamide (minor isomer)
N-(cyclopropylmethyl)-3-(4-hydroxy-2'-oxospiro[cyclohexane-1,3'-indoline]-6'-yl)-4-methylbenzamide
N-cyclopropyl-4-methyl-3-(4-(2-morpholinoethoxy)-2'-oxospiro[cyclohexane-1,3'-indoline]-6'-yl)benzamide
N-cyclopropyl-4-methyl-3-(4-morpholino-2'-oxospiro[cyclohexane-1,3'-indoline]-6'-yl)benzamide (major isomer)
N-cyclopropyl-4-methyl-3-(4-morpholino-2'-oxospiro[cyclohexane-1,3'-indoline]-6'-yl)benzamide (minor isomer)
N-cyclopropyl-3-fluoro-4-methyl-5-(4-morpholino-2'-oxospiro[cyclohexane-1,3'-indoline]-6'-yl)benzamide (Major isomer)
N-Cyclopropyl-4-methyl-3-(2'-oxo-1',2'-dihydrospiro[cyclopentane-1,3'-pyrrolo[2,3-b]pyridine]-6'-yl)benzamide
3-(5'-Chloro-2'-oxospiro[cyclopentane-1,3'-indoline]-6'-yl)-N-cyclopropyl-benzamide
N-Cyclopropyl-3-(3,3-dimethyl-2-oxo-2,3-dihydro-1H-pyrrolo[3,2-b]pyridin-6-yl)-4-methylbenzamide
N-Cyclopropyl-4-methyl-3-(2'-oxo-1',2'-dihydrospiro[cyclopentane-1,3'-pyrrolo-[3,2-b]pyridine]-6'-yl)benzamide
N-Cyclopropyl-4-methyl-3-(2'-oxo-1',2,2',3,5,6-hexahydrospiro[pyran-4,3'-pyrrolo-[3,2-b]pyridine]-6'-yl)benzamide N-cyclopropyl-3-(4,4-difluoro-2'-oxo-1',2'-dihydrospiro[cyclohexane-1,3'-pyrrolo[3,2-b]pyridine]-6'-yl)-4-methylbenzamide hydrochloride N-cyclopropyl-4-methyl-3-(4-morpholino-2'-oxo-1,2'-dihydrospiro[cyclohexane-1,3'-pyrrolo[3,2-b]pyridine]-6'-yl)benzamide (major isomer)

N-cyclopropyl-4-methyl-3-(4-morpholino-2'-oxo-1,2'-dihydrospiro[cyclohexane-1,3'-pyrrolo[3,2-b]pyridine]-6'-yl)benzamide (minor isomer)

N-Cyclopropyl-4-methyl-3-(2'-oxo-1',2'-dihydrospiro[cyclopentane-1,3'-pyrrolo[3,2-c]pyridin]-6'-yl)benzamide N-Cyclopropyl-4-methyl-3-(6'-oxo-6',7'-dihydrospiro[cyclopentane-1,5'-pyrrolo[2,3-d]pyrimidin]-2'-yl)benzamide 6'-(2-Methyl-5-(5-methyl-4H-1,2,4-triazol-3-yl)phenyl)spiro[cyclopentane-1,3'-indolin]-2'-one 6'-[2-Methyl-5-(5-methyl-4H-1,2,4-triazol-3-yl)phenyl]spiro[cyclobutane-1,3'-indol]-2'(1'H)-one 6'-(2-Methyl-5-(4H-1,2,4-triazol-3-yl)phenyl)spiro[cyclopentane-1,3'-indolin]-2'-one 6'-(5-(5-Cyclopropyl-4H-1,2,4-triazol-3-yl)-2-methylphenyl)spiro[cyclopentane-1,3'-indolin]-2'-one 6'-(2-Methyl-5-(5-(trifluoromethyl)-4H-1,2,4-triazol-3-yl)phenyl)spiro[cyclopentane-1,3'-indolin]-2'-one 3,3-Dimethyl-6-(2-methyl-5-(5-methyl-4H-1,2,4-triazol-3-yl)phenyl)indolin-2-one 6-(2-Methyl-5-(5-methyl-4H-1,2,4-triazol-3-yl)phenyl)-2',3',5',6'-tetrahydrospiro[indoline-3,4'-pyran]-2-one 1-(4-chlorophenyl)-6-(2-methyl-5-(5-methyl-4H-1,2,4-triazol-3-yl)phenyl)spiro[indoline-3,4'-piperidin]-2-one 6-[3-Fluoro-2-methyl-5-(5-methyl-4H-1,2,4-triazol-3-yl)phenyl]-2',3',5',6'-tetrahydro-spiro[indole-3,4'-pyran]-2(1H)-one 6'-[2-methyl-5-(5-methyl-4H-1,2,4-triazol-3-yl)phenyl]-2,3,5,6-tetrahydrospiro[pyran-4,3'-pyrrolo[3,2-b]pyridin]-2'(1'H)-one hydrogen chloride 4,4-Difluoro-6'-(2-methyl-5-(5-methyl-4H-1,2,4-triazol-3-yl)phenyl)spiro[cyclohexane-1,3'-indolin]-2'-one 4-hydroxy-6'-(2-methyl-5-(5-methyl-4H-1,2,4-triazol-3-yl)phenyl)spiro[cyclohexane-1,3'-indolin]-2'-one 6'-(3-fluoro-2-methyl-5-(5-methyl-4H-1,2,4-triazol-3-yl)phenyl)-4-hydroxy-4-methylspiro[cyclohexane-1,3'-indolin]-2'-one 6'-(2-methyl-5-(5-methyl-4H-1,2,4-triazol-3-yl)phenyl)-4-(2-morpholinoethoxy)spiro[cyclohexane-1,3'-indolin]-2'-one 6-(2-methyl-5-(5-methyl-4H-1,2,4-triazol-3-yl)phenyl)-1'-(methylsulfonyl)spiro[indoline-3,4'-piperidin]-2-one 6-(2-methyl-5-(5-methyl-4H-1,2,4-triazol-3-yl)phenyl)-1'-tosylspiro[indoline-3,4'-piperidin]-2-one 6'-(2-methyl-5-(5-methyl-4H-1,2,4-triazol-3-yl)phenyl)-4-morpholinospiro[cyclohexane-1,3'-indolin]-2'-one 6'-(2-Methyl-5-(5-methyl-1,3,4-oxadiazol-2-yl)phenyl)spiro[cyclopentane-1,3'-indolin]-2'-one 6'-(2-Methyl-5-(1,3,4-oxadiazol-2-yl)phenyl)spiro[cyclopentane-1,3'-indolin]-2'-one 4,4-Difluoro-6'-(2-methyl-5-(5-methyl-1,3,4-oxadiazol-2-yl)phenyl)spiro-[cyclohexane-1,3'-indolin]-2'-one 4-hydroxy-6'-(2-methyl-5-(5-methyl-1,3,4-oxadiazol-2-yl)phenyl)spiro[cyclohexane-1,3'-indolin]-2'-one 6'-(5-(5-cyclopropyl-1,3,4-oxadiazol-2-yl)-2-methylphenyl)-4-hydroxyspiro[cyclohexane-1,3'-indolin]-2'-one 6'-(2-Methyl-5-(5-methyl-1,2,4-oxadiazol-3-yl)phenyl)spiro[cyclopentane-1,3'-indolin]-2'-one 6'-(2-Methyl-5-(3-methyl-1,2,4-oxadiazol-5-yl)phenyl)spiro[cyclopentane-1,3'-indolin]-2'-one 6-[2-Methyl-5-(2-methyl-1H-imidazol-5-yl)phenyl]-2',3',5',6'-tetrahydrospiro[indole-3,4'-pyran]-2(1H)-one 6-(2-methyl-5-(5-methyl-1H-imidazol-2-yl)phenyl)-2',3',5',6'-tetrahydrospiro-[indoline-3,4'-pyran]-2-one Of outstanding interest are:

N-Cyclopropyl-4-methyl-3-(2'-oxospiro[cyclopentane-1,3'-indoline]-6'-yl)benzamide N-Cyclopropyl-4-methyl-3-(2'-oxo-1',2'-dihydrospiro[cyclobutane-1,3'-indol]-6'-yl)benzamide N-(Isoxazol-3-yl)-4-methyl-3-(2'-oxospiro[cyclopentane-1,3'-indoline]-6'-yl)benzamide N-Cyclopropyl-3-fluoro-4-methyl-5-(2'-oxospiro[cyclopentane-1,3'-indoline]-6'-yl)benzamide 3-(3,3-Dimethyl-2-oxo-2,3-dihydro-1H-indol-6-yl)-N-isoxazol-3-yl-4-methylbenzamide N-Cyclopropyl-4-methyl-3-(2'-oxospiro[cyclohexane-1,3'-indoline]-6'-yl)benzamide N-Cyclopropyl-4-methyl-3-(2-oxo-2',3',5',6'-tetrahydrospiro[indoline-3,4'-pyran]-6-yl)benzamide N-Isoxazol-3-yl-4-methyl-3-(2-oxo-1,2,2',3',5',6'-hexahydrospiro[indole-3,4'-pyran]-6-yl)benzamide N-Cyclopropyl-4-methyl-3-(2-oxo-2',3',5',6'-tetrahydrospiro[indoline-3,4'-thiopyran]-6-yl)benzamide N-Cyclopropyl-3-(4,4-difluoro-2'-oxospiro[cyclohexane-1,3'-indoline]-6'-yl)-4-methylbenzamide 3-(4,4-Difluoro-2'-oxo-1',2'-dihydrospiro[cyclohexane-1,3'-indol]-6'-yl)-N-isoxazol-3-yl-4-methylbenzamide N-cyclopropyl-3-(4-hydroxy-2'-oxospiro[cyclohexane-1,3'-indoline]-6'-yl)-4-methylbenzamide N-cyclopropyl-3-(4-hydroxy-4-methyl-2'-oxospiro[cyclohexane-1,3'-indoline]-6'-yl)-4-methylbenzamide N-cyclopropyl-4-methyl-3-(4-morpholino-2'-oxospiro[cyclohexane-1,3'-indoline]-6'-yl)benzamide N-cyclopropyl-3-fluoro-4-methyl-5-(4-morpholino-2'-oxospiro[cyclohexane-1,3'-indoline]-6'-yl)benzamide (Major isomer)

N-Cyclopropyl-4-methyl-3-(2'-oxo-1',2'-dihydrospiro[cyclopentane-1,3'-pyrrolo[2,3-b]pyridine]-6'-yl)benzamide N-Cyclopropyl-4-methyl-3-(2'-oxo-1',2'-dihydrospiro[cyclopentane-1,3'-pyrrolo-[3,2-b]pyridine]-6'-yl)benzamide N-Cyclopropyl-4-methyl-3-(2'-oxo-1',2,2',3,5,6-hexahydrospiro[pyran-4,3'-pyrrolo-[3,2-b]pyridin]-6'-yl)benzamide N-cyclopropyl-3-(4,4-difluoro-2'-oxo-1',2'-dihydrospiro[cyclohexane-1,3'-pyrrolo[3,2-b]pyridine]-6'-yl)-4-methylbenzamide hydrochloride N-cyclopropyl-4-methyl-3-(4-morpholino-2'-oxo-1,2'-dihydrospiro[cyclohexane-1,3'-pyrrolo[3,2-b]pyridine]-6'-yl)benzamide N-Cyclopropyl-4-methyl-3-(2'-oxo-1',2'-dihydrospiro[cyclopentane-1,3'-pyrrolo[3,2-c]pyridin]-6'-yl)benzamide 6-(2-Methyl-5-(5-methyl-4H-1,2,4-triazol-3-yl)phenyl)-2',3',5',6'-tetrahydrospiro[indoline-3,4'-pyran]-2-one 4,4-Difluoro-6'-(2-methyl-5-(5-methyl-4H-1,2,4-triazol-3-yl)phenyl)spiro[cyclohexane-1,3'-indolin]-2'-one 4-hydroxy-6'-(2-methyl-5-(5-methyl-4H-1,2,4-triazol-3-yl)phenyl)spiro[cyclohexane-1,3'-indolin]-2'-one 4-hydroxy-6'-(2-methyl-5-(5-methyl-1,3,4-oxadiazol-2-yl)phenyl)spiro[cyclohexane-1,3'-indolin]-2'-one According to one feature of the present invention, compounds of general formula (I) may be prepared by the following synthetic route as illustrated in FIG. 1.

FIG. 1

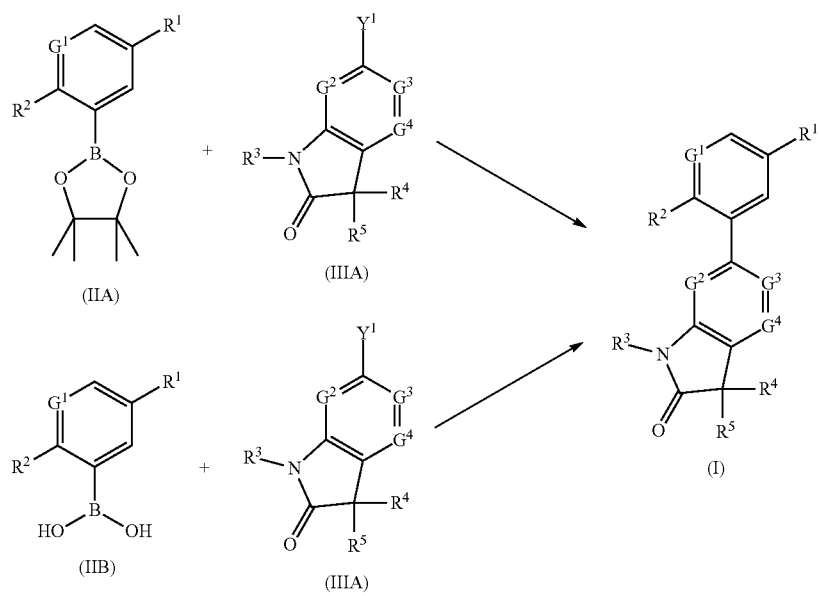

Compounds of formula (I) may be obtained by coupling of a suitable halo derivative (IIIA), with the corresponding boronate of formula (IIA) or boronic acid of formula (IIB), using a Suzuki-type reaction (Miyaura, N.; Suzuki, A. *Chem. Rev.* 1995, 95, 2457). Such reactions may be catalyzed by a suitable palladium catalyst such as [1,1'-bis(diphenylphosphino)-ferrocene]dichloropalladium (II) complex with dichloromethane (1:1), in a solvent such as 1,4-dioxane, in the presence of a base such as aqueous cesium carbonate, at a temperature ranging from 80-120° C.

Alternatively, compounds of formula (I) may be prepared following the scheme depicted in FIG. 2, by reacting halo derivatives of formula (IIC) with boronates of formula (IIIB), following the same synthetic procedure as described above.

-continued

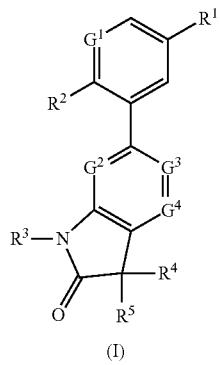

(I)

Intermediate compounds of formula (IIA) and (IIB) may be obtained from halo derivatives of formula (IIC) by following the synthetic scheme as depicted in FIG. 3.

FIG. 2

FIG. 3

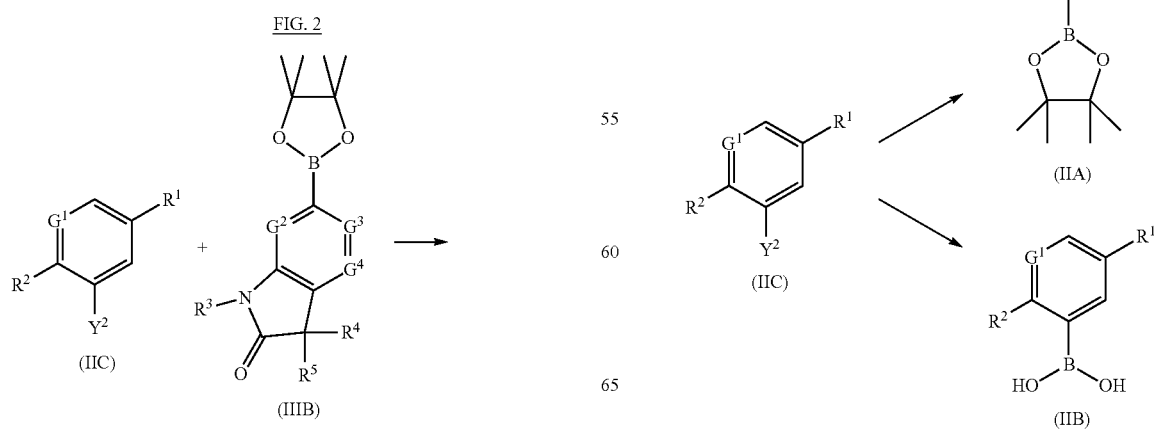

Boronates of general formula (IIA) can be obtained from halo derivatives of general formula (IIC), wherein $R^1$, $R^2$ and $G^1$ are as described above and $Y^2$ represents a halogen atom such as an iodine atom, with a suitable reagent such as bis(pinacolato)diboron in the presence of a suitable base such as potassium acetate and a palladium catalyst such as [1,1'-bis(diphenylphosphino)ferrocene]dichloro-palladium(II) complex with dichloromethane (1:1) in an aprotic organic solvent such as N,N'-dimethylformamide or dimethylsulfoxide at a temperature ranging from 80 to 120° C.

Boronic acids of general formula (IIB) may be synthesized by addition of a suitable organometallic reagent such as isopropylmagnesium chloride to a solution of (IIC) in a suitable solvent such as tetrahydrofuran at temperatures ranging from −78° C. to room temperature followed by addition of a suitable alkyl borate such as triisopropyl borate and allowing the reaction to proceed at temperatures ranging from −78° C. to room temperature.

In the particular case wherein $R^1$ represents a group of formula —CO—NHR$^6$, wherein $R^6$ is as above defined, intermediates of formula (IIA$^I$) may be prepared following the synthetic scheme as depicted in FIG. 4.

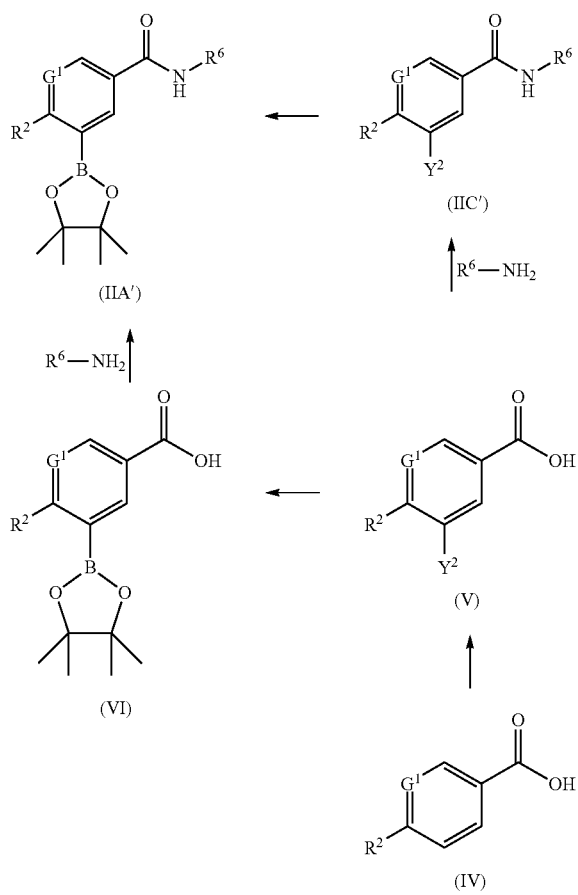

FIG. 4

Compounds of formula (V) may be transformed into the corresponding amides (IIC$^I$) by formation of the corresponding acid chloride with a chlorinating agent such as thionyl chloride in a solvent such as toluene at 100° C. followed by addition of the corresponding amines $R^6$—$NH_2$ in the presence of a suitable base such as sodium carbonate at room temperature.

Alternatively, amides of formula (IIC$^I$) can be obtained by treatment of the corresponding carboxylic acid (V) with a suitable activating agent such as O-(7-azabenzotriazol-1-yl)-N,N,N',N'-tetramethyluronium hexafluorophosphate, in the presence of a suitable organic base such as diisopropylethylamine in a polar aprotic solvent such as N,N'-dimethylformamide at room temperature followed by the addition of a suitable amine $R^6$—$NH_2$.

Boronates of formula (VI) and (IIA$^I$) may be prepared by treatment of the corresponding halo derivatives (V) and (IIC$^I$), respectively with a suitable reagent such as bis(pinacolato)diboron in the presence of a suitable base such as potassium acetate and a palladium catalyst such as [1,1'-bis(diphenylphosphino)ferrocene]dichloro-palladium(II) complex with dichloromethane (1:1) in an aprotic organic solvent such as N,N'-dimethylformamide or dimethylsulphoxide at a temperature ranging from 80 to 120° C.

Alternatively, amides of formula (IIA$^I$) may be prepared from the corresponding carboxylic acids (VI) by treatment with a suitable activating agent such as O-(7-azabenzotriazol-1-yl)-N,N,N',N'-tetramethyluronium hexafluorophosphate, in the presence of a suitable organic base such as diisopropylethylamine in a polar aprotic solvent such as N,N'-dimethylformamide at room temperature followed by the addition of a suitable amine $R^6$—$NH_2$.

In the particular case where $G_1$ is a nitrogen atom, intermediates of formula (VA) may be prepared following the synthetic route as depicted in FIG. 5.

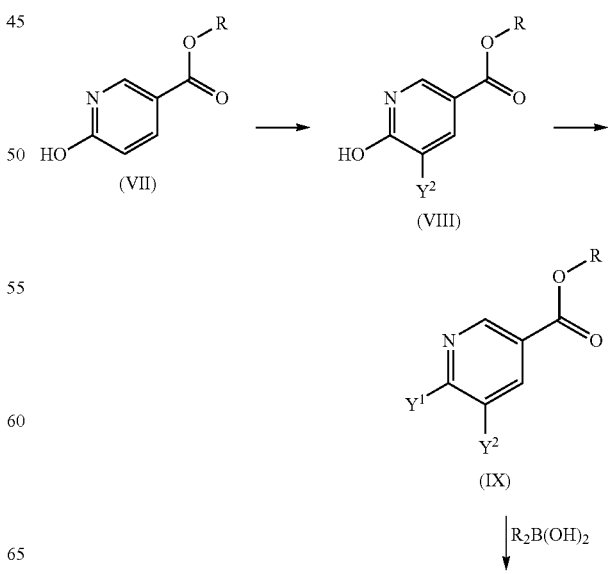

FIG. 5

Compounds of type (V), where $Y^2$ is a halogen atom, are commercially available or may be prepared from the corresponding carboxylic acid derivative (IV) using a suitable halogen source such as a N-halo succinimide or elemental divalent halogen in the presence of a strong acid such as trifluoromethanesulphonic acid or sulphuric acid at a temperature ranging from 0° C. to room temperature.

-continued

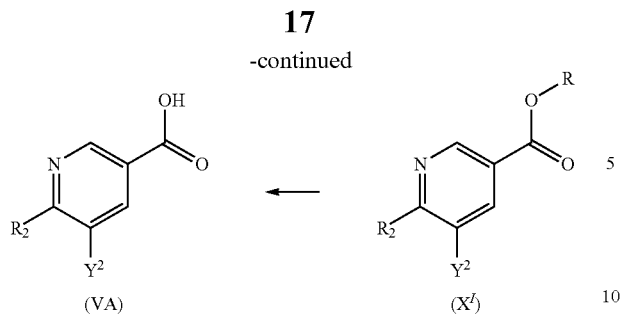

Intermediates of formula (VIII) are prepared from compounds of formula (VII) by treatment with a suitable electrophilic halogenating reagent such as N-bromosuccinimide in a solvent such as N,N'-dimethylformamide at ambient temperature. Treatment of pyridones of formula (VIII) with a halogenating source such as phosphorous oxybromide or phosphorous tribromide or a mixture of the latter two reagents at temperatures ranging from 80 to 120° C. furnishes bis-halogenated derivatives of formula (IX). Compounds of formula (IX) may be transformed into compounds of formula ($X^I$) using a Suzuki-type reaction (Miyaura, N.; Suzuki, A. Chem. Rev. 1995, 95, 2457). Such reactions may be catalyzed by a suitable palladium catalyst such as tetrakis(triphenylphosphino)palladium (0), in a solvent such as 1,4-dioxane, in the presence of a base such as potassium carbonate, at a temperature ranging from 80-110° C. Finally, compounds of formula ($X^I$) may be treated with a strong aqueous base such as sodium hydroxide in a solvent such as ethanol at temperatures ranging from ambient temperature to reflux to furnish acids of formula (VA).

In the particular case wherein $R^1$ represents a group of formula —CO—$NHR^6$, wherein $R^6$ is as above defined, intermediates of formula ($IA^I$) may be prepared following the synthetic scheme as depicted in FIG. 6.

FIG. 6

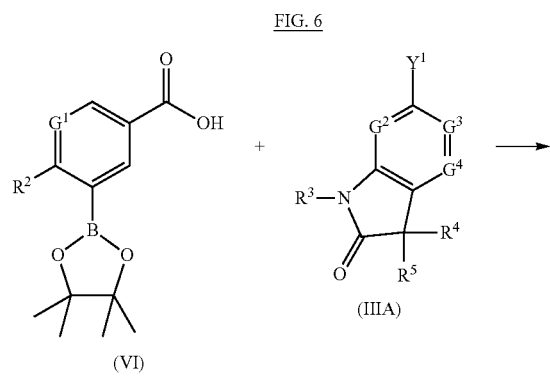

-continued

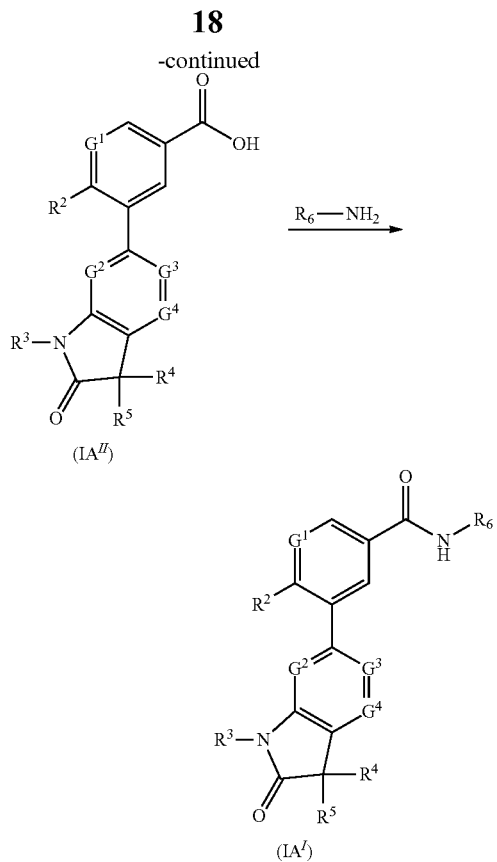

Compounds of formula ($IA^I$) may be obtained by treatment of the corresponding carboxylic acid derivative of formula ($IA^{II}$) with a suitable activating agent such as O-(7-azabenzotriazol-1-yl)-N,N,N',N'-tetramethyluronium hexafluorophosphate, in the presence of a suitable organic base such as diisopropylethylamine in a polar aprotic solvent such as N,N'-dimethylformamide at room temperature followed by the addition of a suitable amine $R^6$—$NH_2$.

Intermediates of formula ($IA^{II}$) may be prepared by reacting intermediates of formula (VI) with intermediates of formula (IIIA) following the same procedure described in FIG. 1 for obtaining compounds of formula (I).

In the particular case wherein $R^1$ represents a 5-membered heteroaromatic ring as defined above, intermediates of formula ($IIC^{II}$) may be prepared by following the synthetic routes as depicted in FIG. 7.

FIG. 7

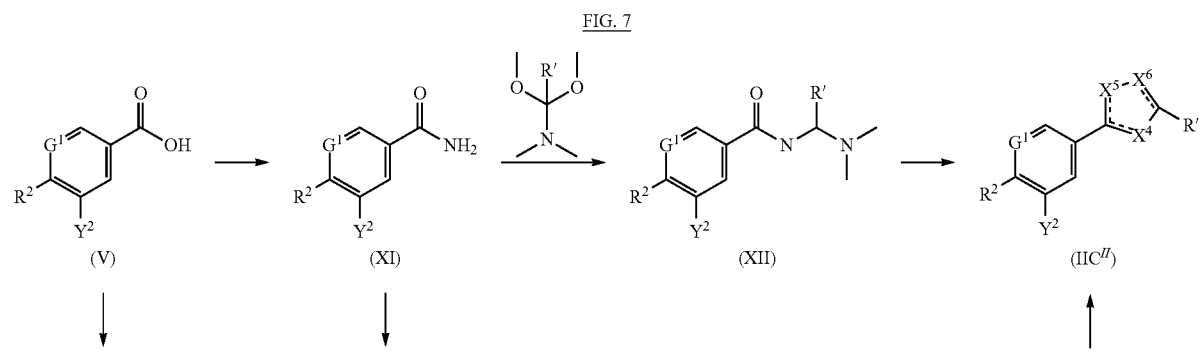

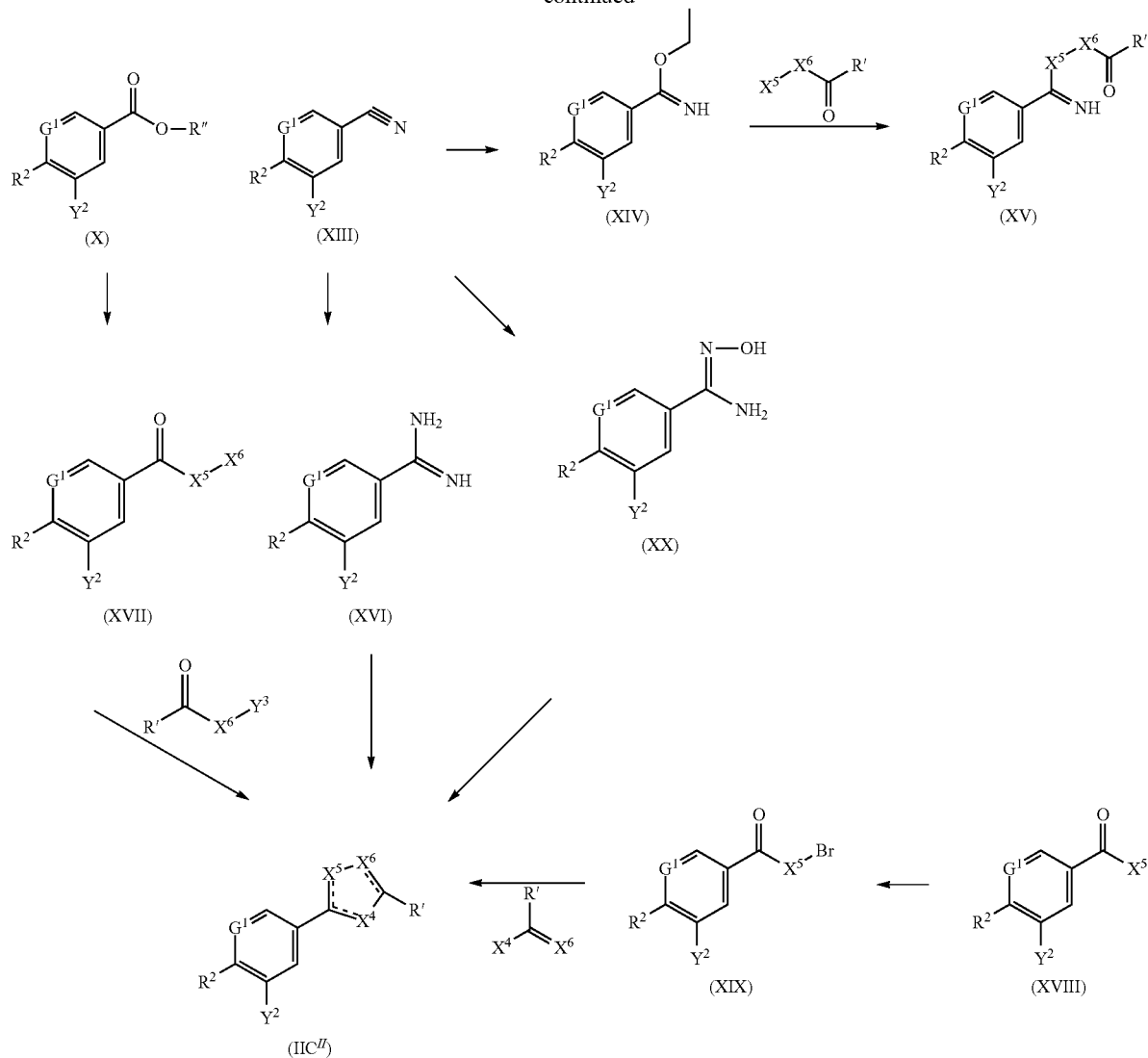

Compounds of formula (XI) are prepared from compounds of formula (V) by the addition of a suitable activating agent such as 1-(3-dimethylaminopropyl)-3-ethylcarbodiimide hydrochloride, in the presence of 1-hydroxybenzotriazole in a solvent such as N,N'-dimethylformamide at room temperature followed by the addition of a suitable ammonium source such as concentrated aqueous ammonia. Reaction of amides of formula (XI) with a suitable acetal derivative such as N,N'-dimethylformamide dimethylacetal or N,N'-dimethylacetamide dimethylacetal at temperatures ranging from 50° C. to reflux gives the corresponding derivatives of formula (XII). Reaction of compounds of formula (XII) with hydrazine hydrate in a suitable solvent such as ethanol at temperatures ranging from room temperature to reflux gives rise to derivatives of type (IIC$^{II}$) wherein $X^4$, $X^5$ and $X^6$ are all nitrogen atoms.

Intermediates of formula (XII) may also be treated with hydroxylamine hydrochloride in the presence of a suitable base such as sodium hydroxide in a solvent such as acetic acid at temperatures ranging from room temperature to 100° C. to give rise to derivatives of type (IIC$^{II}$) wherein $X^4$ and $X^6$ are nitrogen atoms and $X^5$ represents an oxygen atom.

Compounds of formula (XI) may also be reacted with a suitable dehydrating agent such as 2,2,2-trifluoroacetic anhydride in a solvent such as dichloromethane at a temperature ranging from 0° C. to room temperature to give intermediates of formula (XIII). Compounds of formula (XIII) react with alcohols in the presence of an acid such as hydrochloric acid in a suitable solvent such as benzene or an alcoholic solvent at temperatures ranging from −20° C. room temperature to give compounds of formula (XIV). Reaction of compounds of formula (XIV) with a corresponding carbohydrazide derivative in a solvent such as in methanol at temperatures ranging from room temperature to 75° C. furnishes compounds of formula (XV). Intermediates of type (XV) may spontaneously cyclise or may be treated with a suitable dehydrating agent such as phosphorous oxychloride at temperatures ranging from 70 to 110° C. providing another route of access to derivatives of formula (IIC$^{II}$) wherein $X^4$, $X^5$ and $X^6$ are all nitrogen atoms.

An alternative synthetic route for obtaining compounds of type (IIC$^{II}$) consists in the formation of intermediate amidine derivatives of formula (XVI) by, for example, addition of lithium bis(trimethylsilyl)amide to intermediates of formula (XIII) in a solvent such as tetrahydrofuran at temperature ranging from −40° C. to 10° C. followed by addition of hydrochloric acid at 0° C. Such intermediates of formula (XVI) can be transformed to (IIC$^{II}$), wherein X$^4$ and X$^5$ are nitrogen atoms and X$^6$ is a carbon atom, by addition of a 2-haloketone such as 1-chloropropan-2-one in a solvent such as tetrahydrofuran in the presence of a suitable base such as potassium bicarbonate at temperatures ranging from room temperature to reflux.

Following another synthetic pathway, compounds of formula (VI) can be transformed into ester derivatives of formula (X) by, for example, treatment with the corresponding alcohol in the presence of a suitable acid catalyst such as hydrochloric acid or sulphuric acid at temperatures ranging from room temperature to reflux. Esters of formula (X) may be treated with hydrazine hydrate in a solvent such as ethanol at temperatures ranging from room temperature to reflux to give hydrazides of formula (XVII) which may be transformed into compounds of formula (IIC$^{II}$), wherein X$^5$ and X$^6$ are nitrogen atoms and X$^4$ is an oxygen atom, by treatment with a trialkyl ortho ester such as triethylorthoacetate in a solvent such as acetic acid at temperatures ranging from 70° C. to 150° C. or by addition of the corresponding acid chloride and a base such as triethylamine in an inert solvent such as dichloromethane at a temperature ranging from 0° C. to room temperature followed by cyclisation of the intermediate hydrazide with a suitable dehydrating agent such as phosphorous oxychloride at temperatures ranging from 70 to 110° C.

In yet another synthetic pathway, the treatment of compounds of formula (XVIII) with a brominating agent such as molecular bromine in a halogenated solvent such as chloroform at room temperature provides compounds of formula (XIX), which may be transformed to compounds of formula (IIC$^{II}$), wherein X$^4$ and X$^6$ are nitrogen atoms and X$^5$ is a carbon atom. Such a transformation may be carried out by treatment of intermediates of formula (XIX) with a corresponding amidine derivative in the presence of a base such as potassium bicarbonate in a suitable solvent mixture such as tetrahydrofuran and water at temperatures ranging from room temperature to reflux.

Finally, nitriles derivatives of formula (XIII) may be treated with hydroxylamine hydrochloride in the presence of a base such as sodium acetate or sodium hydroxide in a solvent such as aqueous ethanol at temperature ranging from room temperature to reflux to give compounds of formula (XX) which may be transformed into compounds of formula (IIC$^{II}$), wherein X$^4$ and X$^5$ are nitrogen atoms and X$^6$ is an oxygen atom, by treatment with a trialkyl ortho ester such as triethylorthoacetate in a solvent such as acetic acid at temperatures ranging from 70° C. to 150° C. or by addition of the corresponding acid chloride and a base such as triethylamine in an inert solvent such as dichloromethane at a temperature ranging from 0° C. to room temperature.

Intermediates of formula (IIIA), (IIIA′) and (IIIB) may be obtained as described in the following synthetic scheme illustrated in FIG. 8.

FIG. 8

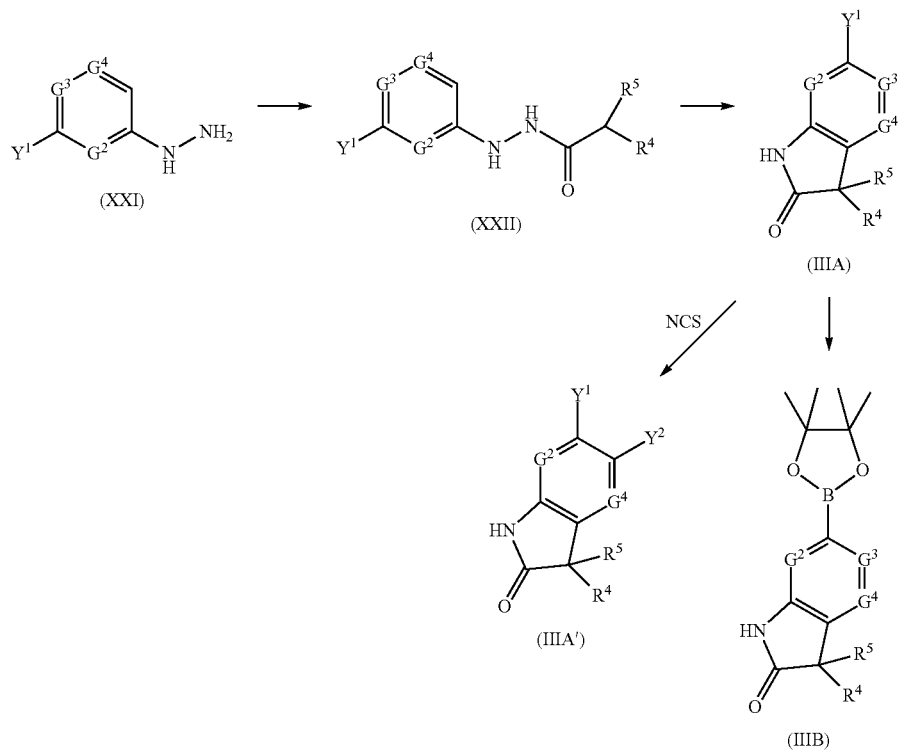

Treatment of hydrazines of formula (XXI), wherein Y$^1$ represents a halogen atom, preferably a bromine atom, with a suitable acid chloride or acid anhydride in the presence of a base such as triethylamine in a solvent such as dichloromethane at a temperature ranging from −40° C. to room temperature gives intermediates of formula (XXII), wherein R$^4$ and R$^5$ are as described above. Derivatives of formula (XXII) cyclise, upon treatment with a suitable base such as calcium hydride or calcium (II) oxide either without solvent or with a suitable high-boiling inert solvent such as quinoline or tetralin at temperatures ranging from 200-280° C., to give intermediates of formula (IIIA).

Intermediates of formula (IIIA) may be transformed into the corresponding boronates of formula (IIIB) with a suitable reagent such as bis(pinacolato)diboron in the presence of a suitable base such as potassium acetate and a palladium catalyst such as [1,1'-bis(diphenylphosphino)ferrocene]dichloropalladium(II) complex with dichloromethane (1:1) in an aprotic organic solvent such as N,N'-dimethylformamide or dimethylsulphoxide at a temperature ranging from 80 to 120° C.

In the particular case where $G^3$ is a —CCl═ group, intermediates of formula (IIIA) may be transformed into the corresponding derivatives of formula (IIIA$^I$), wherein $Y^2$ is a halogen atom such as fluorine or chlorine atom, by treatment of (IIIA) with a suitable electrophilic halogenating agent such as N-chlorosuccinimide in a solvent such as chloroform at reflux temperature.

In an alternative way, intermediates of formula (IIIA) may also be prepared from intermediates of formula (XXIII) following the synthetic schemes depicted in FIGS. 9 and 10.

In the particular case wherein $R^4$ and $R^5$ form together the heterocyclic ring as defined above, intermediates of formula (IIIA$^{II}$) may be prepared by following the synthetic route as depicted in FIG. 9.

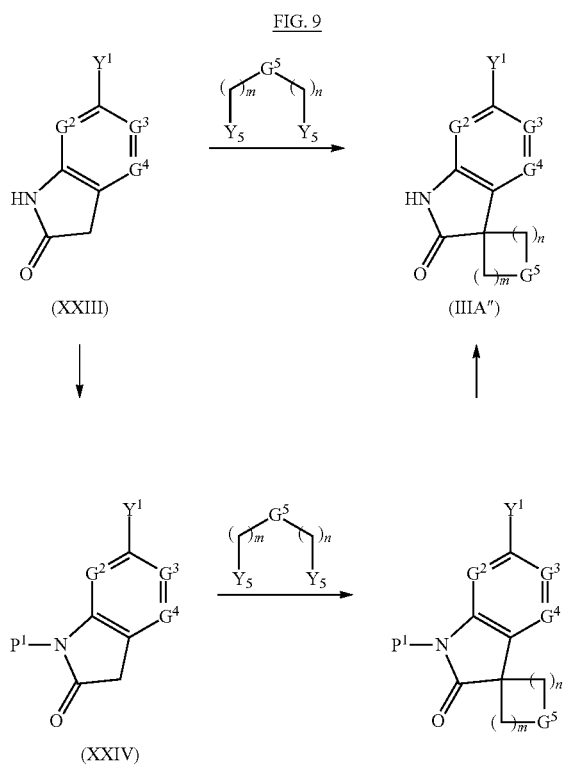

Intermediates (IIIA$^{II}$) may be obtained by reaction of the compounds of formula (XXIII) with a suitable base such as butyl lithium, lithium bis(trimethylsilyl)amide, cesium carbonate or sodium bis(trimethylsilyl)amide possibly in the presence of an additive agent such as N,N,N',N'-tetramethylethylenediamine in a solvent such as tetrahydrofuran or N,N'-dimethylformamide at a temperature ranging from −78° C. to room temperature followed by addition of a corresponding dihalo derivative and then allowing the reaction to proceed at temperatures ranging from −78° C. to room temperature. Alternatively, compounds of formula (XXIII) may be converted first to an intermediate of formula (XXIV) wherein P1 represents a suitable protecting group such as tert-butoxycarbonyl (BOC). Treatment of compounds of formula (XXIV) with a dihaloderivative following the conditions as described above followed by subsequent deprotection with a suitable reagent furnishes compounds of formula (IIIA$^{II}$).

In the particular case wherein both $R^4$ and $R^5$ represent a methyl group, intermediates of formula (IIIA$^{XIV}$) and (IIIA$^{XV}$) may be prepared by following the synthetic route depicted in FIG. 10.

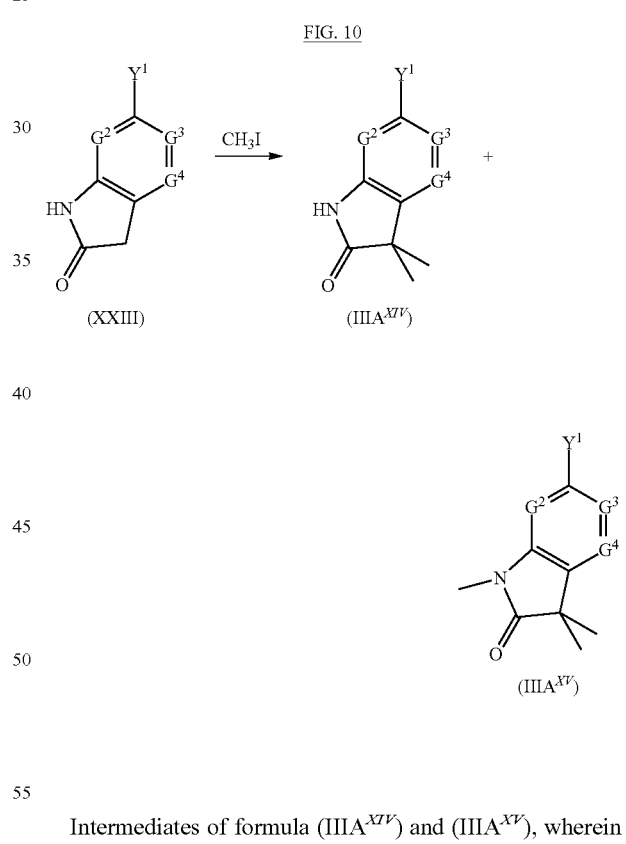

Intermediates of formula (IIIA$^{XIV}$) and (IIIA$^{XV}$), wherein $Y^1$, $G^2$, $G^3$ and $G^4$ are as described above, may be prepared following the same synthetic procedure as described in FIG. 9 for obtaining intermediates of formula (IIIA) from intermediates of formula (XXIII). In this particular case, the haloderivative added is iodomethane.

In the particular case wherein the spiroalkyl group represents a 4-substituted cyclohexyl moiety, the synthetic routes to prepare intermediate compounds of formula (IIIA$^{III}$ to IIIA$^{IX}$) are depicted in FIG. 11.

FIG. 11

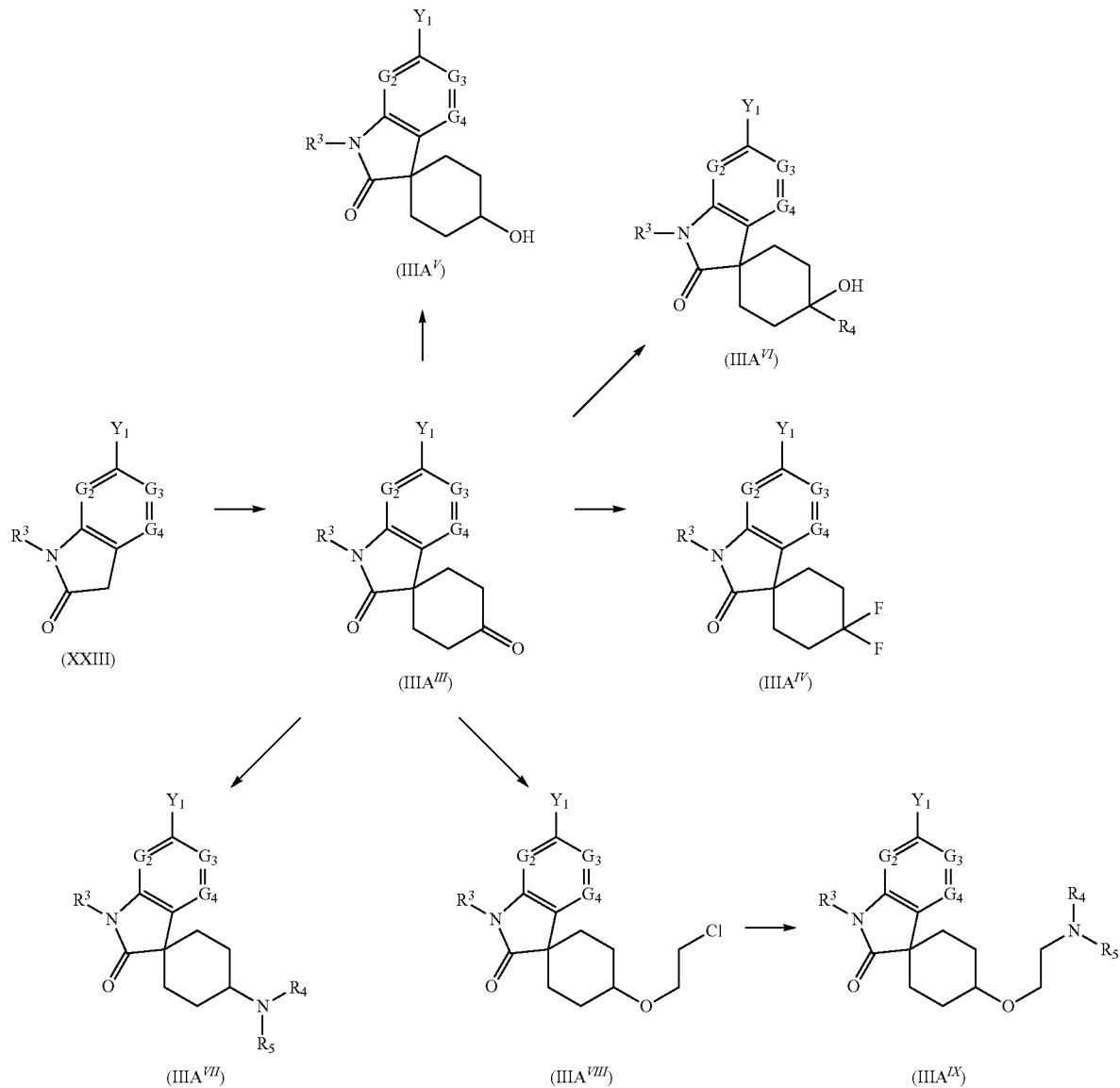

Compounds of formula (XXIII) may be treated with methyl acrylate in the presence of a suitable base such as potassium tert-butoxide in a solvent such as dimethylsulfoxide to give, after hydrolysis with water, cyclohexanone derivatives of formula (IIIA$^{III}$). These derivatives may be transformed into the difluoro compounds of formula (IIIA$^{IV}$) by treatment with a suitable reagent such as (diethylamino) sulfur trifluoride in a solvent such as dichloromethane at room temperature.

In another synthetic pathway compounds of formula (IIIA$^{III}$) may be treated with a reducing agent such as sodium borohydride in a suitable organic solvent such as methyl alcohol or tetrahydrofuran at temperatures ranging from −78° C. to ambient temperature to give alcohols of formula (IIIA$^{V}$) as mixtures of isomers.

Alternatively, compounds of formula (IIIA$^{III}$) may be treated with an organometallic reagent such as methyl lithium in a solvent such as tetrahydrofuran at temperatures ranging from −78° C. to reflux to furnish alcohols of formula (IIIA$^{VI}$).

In yet another synthetic pathway, compounds of formula (IIIA$^{III}$) can be transformed to compounds of formula (IIIA-$^{VII}$) using the standard conditions for reductive amination using an amine (R$_4$R$_5$NH) such as morpholine in the presence of a reducing agent such as sodium triacetoxyborohydride in a solvent such as 1,2-dichloroethane in the presence of an acid such as acetic acid at temperatures ranging from 0° C. to ambient temperature.

Finally, compounds of formula (IIIA$^{III}$) may be transformed to intermediates of type (IIIA$^{VIII}$) by treatment of compounds of formula (IIIA$^{III}$) with 2-chloroethanol in the presence of an acid such as methanesulphonic acid in a solvent such as dichloromethane/toluene at ambient temperature followed by treatment of the intermediate compound with a reducing agent such as zinc borohydride in the presence of trimethylsilyl chloride in a solvent such as dichloromethane or diethyl ether to give compounds of formula (IIIA$^{VIII}$). Compounds of formula (IIIA$^{VIII}$) may be converted to compounds of formula (IIIA$^{IX}$) by treatment of (IIIA$^{VIII}$) with an amine (R$_4$R$_5$NH) such as morpholine in the presence of an activating agent such as sodium iodide in a solvent such as N,N'-dimethylformamide at temperatures ranging from ambient temperature to reflux.

In the particular case of compounds of formula (IIIA$^{XI}$) and (IIIA$^{XIII}$) the synthesis is shown in FIG. 12.

tures ranging from room temperature to 60° C. gives rise to compounds of formula (IIIA$^{XI}$).

Alternatively, the compounds of formula (IIIA$^X$) can be transformed to compounds of formula (IIIA$^{XII}$) by addition of bromine to a solution of (IIIA$^X$) and triphenylphosphine in a suitable solvent such as dichloromethane at a temperature ranging from 0° C. to room temperature. Treatment of com-

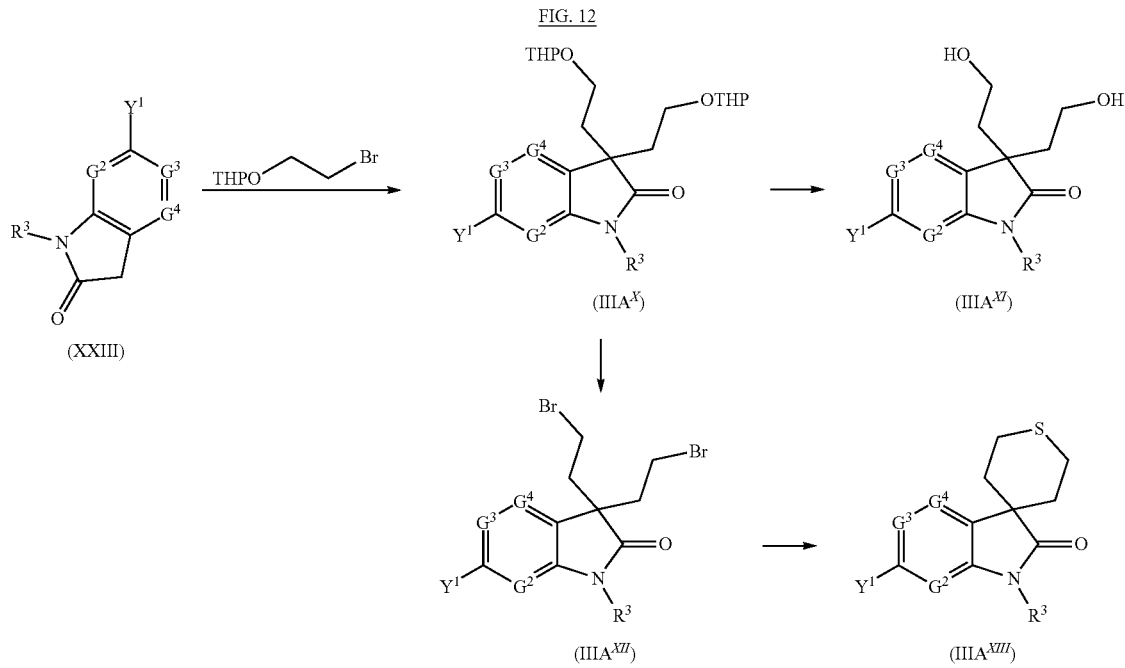

FIG. 12

Intermediates of formula (XXIII) are transformed to intermediates (IIIA$^X$) by treatment with a suitable base such as potassium tert-butoxide in a solvent such as tetrahydrofuran followed by addition of 2-(2-bromoethoxy)tetrahydro-2H-pyran at a temperature from −75° C. to room temperature. Treatment of intermediates (IIIA$^X$) with a suitable acidic medium such as hydrochloric acid in 1,4-dioxane at temperapounds of formula (IIIA$^{XII}$) with sodium sulphide in a solvent such as N,N'-dimethylformamide at temperatures ranging from room temperature to 50° C. gives rise to intermediates of formula (IIIA$^{XIII}$).

Intermediate compounds of formula (XXIII) may be prepared by following the synthetic route depicted in FIG. 13.

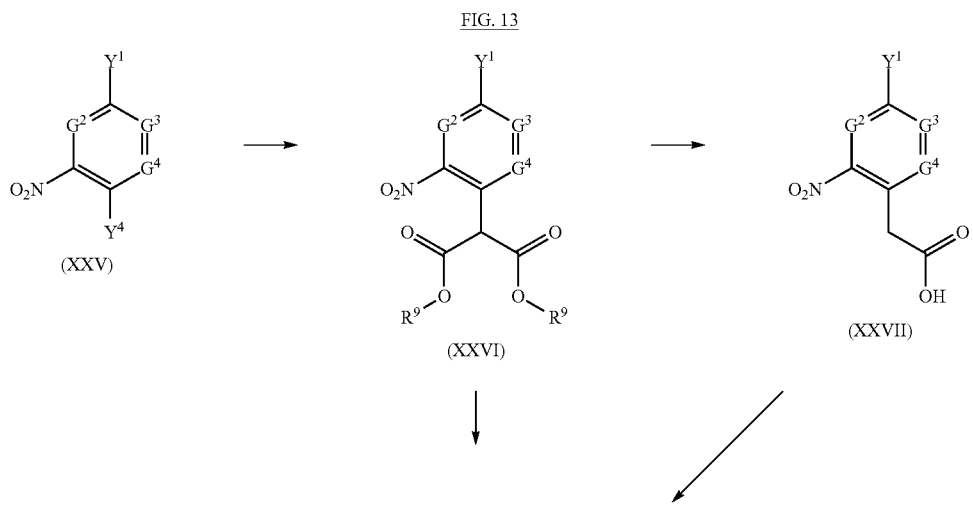

FIG. 13

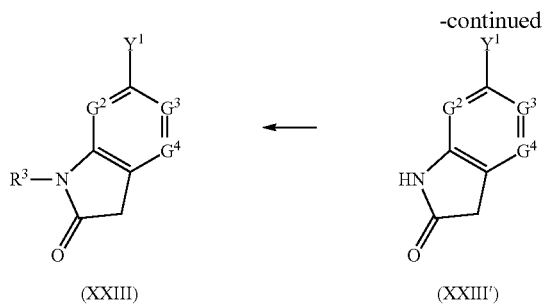

Nitroderivatives of formula (XXV), wherein $Y^4$ represents a halogen atom preferably chlorine or fluorine, react with alkyl malonate salts, prepared by the treatment of the corresponding alkyl malonate with a suitable base such as sodium hydride in an appropriate solvent such as 1,2-dimethoxyethane or N,N'-dimethylformamide at a temperature ranging from 10 to 80° C., to give the corresponding intermediates of formula (XXVI). Treatment of derivatives of formula (XXVI) with an inorganic mineral acid such as aqueous hydrochloric acid in a suitable solvent such as dimethylsulphoxide at temperatures ranging from 20-130° C., gives carboxylic acid derivatives of formula (XXVII). Derivatives of both formula (XXVI) and (XXVII) may be converted into oxindole derivatives of formula (XXIII') by treatment with a suitable reducing agent such as iron powder in a solvent such as ethanol/aqueous hydrochloric acid or acetic acid at temperatures ranging from 80-150° C.

In the particular case wherein $G^4$ represents a —CH group, intermediates of formula (IIIA$^X$) may be prepared following the scheme depicted in FIG. 14.

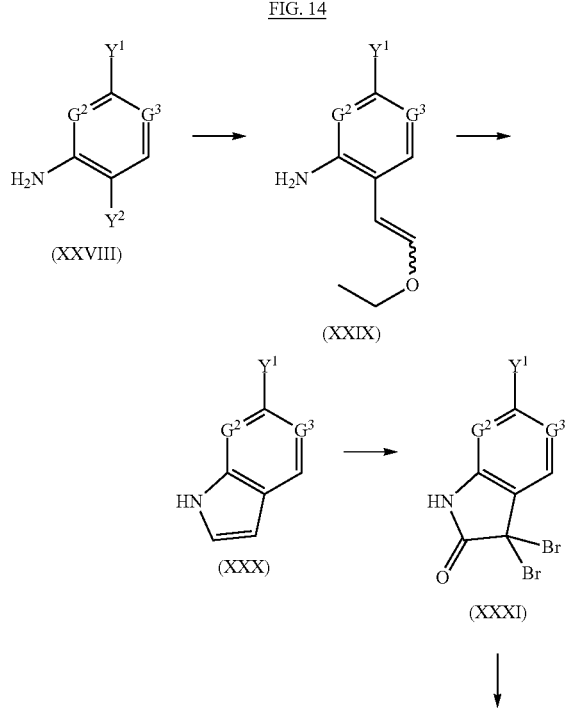

Compounds of formula (XXVIII), wherein $Y^1$ represents a halogen atom such as a chlorine atom and $Y^2$ represents a halogen atom such as an iodine or bromine atom, may be reacted with tris[(E)-2-ethoxyvinyl]borane or (Z)-tributyl(2-ethoxyvinyl)stannane, in the presence of a suitable palladium catalyst such as tetrakis(triphenylphosphine)palladium(0) in a suitable solvent such as tetrahydrofuran or toluene at temperature ranging from 70° C. to reflux temperature to give the corresponding intermediates of formula (XXIX). Treatment of intermediates (XXIX) with an appropriate acidic medium such as aqueous hydrochloric acid in a solvent such as methanol at temperatures ranging from room temperature to reflux gives cyclized derivatives of formula (XXX). These intermediates can be converted into brominated oxindole intermediates of formula (XXXI) with a brominating reagent such as pyridinium hydrobromide perbromide in a solvent such as tert-butyl alcohol at room temperature to 40° C. Treatment of intermediates of intermediates (XXXI) with an appropriate reducing agent such as zinc powder in a solvent such as acetic acid gives rise to intermediates of formula (XXIII), which may be subsequently converted into compounds of formula (IIIA$^X$) by treatment with a suitable base such as butyl lithium, lithium bis(trimethylsilyl)amide, or sodium bis(trimethylsilyl)amide possibly in the presence of a additive such as N,N,N',N'-tetramethylethylenediamine in a inert solvent such as tetrahydrofuran at a temperature ranging from −78° C. to room temperature followed by addition of a corresponding dihalo derivative and then allowing the reaction to proceed at temperatures ranging from −78° C. to room temperature.

In a particular case, the synthetic pathway as shown in FIG. 15 may be used to prepare compounds of general formula (IA$^{IV}$).

FIG. 15

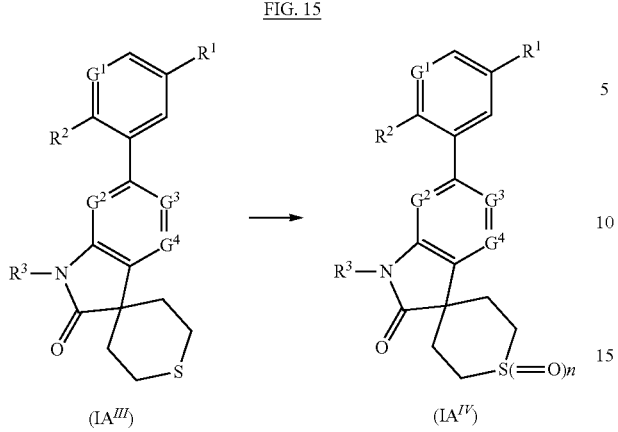

(IA^III) → (IA^IV)

Compounds of formula (IA^III) can be converted to the corresponding compounds of formula (IA^IV), where n=1 or 2, by addition of a suitable oxidizing agent such as 3-chloroperbenzoic acid or sodium periodate in a solvent such as dichloromethane or methyl alcohol at room temperature.

Biological Testing

Inhibition Assay

Enzymatic activity assay was performed in 96-well microtiter plates (Corning, catalog number #3686) using a total volume of 50 μl of an assay buffer composed of 50 mM HEPES pH 7.5, 10 mM $MgCl_2$, 1.75 mM $Na_3VO_4$.

Various concentrations of the test compound or vehicle controls were pre-incubated for one hour with 0.055 μg/ml of the human p38alfa (SAPKa) enzyme (obtained from University of Dundee). The reaction was started by addition of biotinylated ATF2 substrate and ATP in concentrations around their Km values (final concentration 0.62 μM and 60 μM respectively) and took place for one hour at 25° C. Addition of the detection reagents, streptavidin—XL665 and anti-phosphoresidue antibody coupled to Europium cryptate, caused the juxtaposition of the cryptate and the XL665 fluorophore, resulting in fluorescence energy transfer (FRET). The FRET intensity depends on the amount of bounded cryptate antibody, which is proportional to the extent of substrate phosphorylation. FRET intensity was measured using Victor 2V spectrofluorometer.

Data were analyzed by non-linear regression (Hill equation) to generate a dose-response curve. The calculated $IC_{50}$ value is the concentration of the test compound that caused a 50% decrease in the maximal FRET intensity.

Table 1 shows the activities inhibiting p38 assay of some compounds of the present invention.

TABLE 1

| Example | p38α $IC_{50}$ (nM) |
|---|---|
| 1 | 1.3 |
| 3 | 1.4 |
| 4 | 20 |
| 6 | 8.5 |
| 7 | 80 |
| 8 | 10 |
| 11 | 6.3 |
| 12 | 0.2 |
| 15 | 1.2 |
| 18 | 27 |
| 19 | 0.04 |
| 22 | 1.4 |
| 23 | 0.06 |

TABLE 1-continued

| Example | p38α $IC_{50}$ (nM) |
|---|---|
| 27 | 6.7 |
| 29 | 5.2 |
| 31 | 1 |
| 32 | 1.8 |
| 34 | 1.4 |
| 37 | 0.8 |
| 40 | 1.0 |
| 43 | 5.6 |
| 45 | 62 |
| 47 | 13 |
| 51 | 0.8 |
| 52 | 72 |
| 53 | 7.5 |
| 54 | 18 |
| 55 | 9 |
| 59 | 10 |
| 61 | 8 |
| 63 | 2 |
| 65 | 8 |
| 67 | 4.7 |
| 70 | 32 |
| 72 | 5.6 |
| 73 | 5.7 |

It can be seen from Table 1 that the compounds of formula (I) are potent inhibitors of the p38 mitogen-activated protein kinase. Preferred substituted spiro[cycloalkyl-1,3'-indol]-2'(1'H)-ones derivatives of the invention possess a $IC_{50}$ value of inhibition of p38α of less than 100 nM, more preferably less than 80 nM and most preferably less than 50 nM.

Functional Assay

The activity of compounds in inhibiting TNFα production was measured in a cellular assay using the human monocytic cell line THP-1. For this purpose, 2×10^5 cells/well were plated in tissue-culture treated round-bottom 96-well plates in RPMI (containing 10% FCS, L-Gln 2 mM, Hepes buffer 10 mM, sodium pyruvate 1 mM, glucose 4.5 gr/L, $HNaCO_3$ 1.5 g/L and beta-mercaptoethanol 50 μM), together with compounds at the desired test concentration and LPS (Sigma, L2630) at a final 10 μg/ml concentration. Compounds were resuspended in 100% DMSO at a concentration of 1 mM and titrated thereof in 10× dilutions in medium. Controls included stimulated cells alone and stimulated cells treated with the highest concentration of compound vehicle (1% DMSO). Cells were incubated for 5 h at 37° C. in a 5% $CO_2$ atmosphere. Cell supernatant was recovered by centrifugation and diluted 5-fold prior to testing in a standard human TNFα ELISA (RnD systems).

Data were analyzed by non-linear regression (Hill equation) to generate a dose-response curve. The calculated $IC_{50}$ value is the concentration of the test compound that caused a 50% decrease in the maximal TNFα production.

Compounds of the present invention are good inhibitors of TNFα production. Preferred derivatives of the invention possess an $IC_{50}$ value for inhibiting TNFα production of less than 100 μM, preferably less than 10 μM, more preferably less than 1 μM and most preferably less than 100 nM.

The substituted spiro[cycloalkyl-1,3'-indol]-2'(1'H)-one derivatives of the invention are useful in the treatment or prevention of diseases known to be susceptible to improvement by inhibition of the p38 mitogen-activated protein kinase. Such diseases are, for example rheumatoid arthritis, ischemia-reperfusion injury, cerebral focal ischemia, acute coronary syndrome, asthma, COPD, Crohn's disease, irritable bowel syndrome, adult respiratory distress syndrome, osteoporosis, Alzheimer's disease, rheumatoid spondylitis, psoriasis, atherosclerosis, osteoarthritis or multiple myeloma.

Accordingly, the substituted spiro[cycloalkyl-1,3'-indol]-2'(1'H)-one derivatives of the invention and pharmaceutically acceptable salts thereof, and pharmaceutical compositions comprising of such compound and/or salts thereof, may be used in a method of treatment of disorders of the human body which comprises administering to a subject requiring such treatment an effective amount of substituted spiro[cycloalkyl-1,3'-indol]-2'(1'H)-one derivatives of the invention or a pharmaceutically acceptable salt thereof.

When the substituted spiro[cycloalkyl-1,3'-indol]-2'(1'H)-one derivatives of the invention are used for the treatment of respiratory diseases such as asthma, chronic obstructive pulmonary disorder, pulmonary fibrosis or emphysema it may be advantageous to use them in combination with other active compounds known to be useful in the treatment of respiratory diseases such as (1) antagonists of M3 muscarinic receptors, (2) β2-agonists, (3) PDE4 inhibitors, (4) corticosteroids, (5) leukotriene D4 antagonists, (6) inhibitors of egfr-kinase, (7) antagonists of the $A_{2B}$ adenosine receptor, (8) NK1 receptor agonists, (9) CRTh2 antagonists, (10) syk kinase inhibitors, (11) CCR3 antagonists and (12) VLA-4 antagonists.

The present invention also provides pharmaceutical compositions comprising a substituted spiro[cycloalkyl-1,3'-indol]-2'(1'H)-one derivative of the invention and another active compound selected from the groups consisting of (1) antagonists of M3 muscarinic receptors, (2) β2-agonists, (3) PDE 4 inhibitors, (4) corticosteroids, (5) leukotriene D4 antagonists, (6) inhibitors of egfr-kinase, (7) antagonists of the $A_{2B}$ adenosine receptor, (8) NK1 receptor agonists, (9) CRTh2 antagonists, (10) syk kinase inhibitors, (11) CCR3 antagonists, (12) VLA-4 antagonists and (13) disease modifying antirheumatic drugs (DMARDs) such as methotrexate.

When substituted spiro[cycloalkyl-1,3'-indol]-2'(1'H)-one derivatives of the invention are used for the treatment of respiratory diseases such as asthma, chronic obstructive pulmonary disorder, pulmonary fibrosis and emphysema it may be advantageous to use them in combination with other active compounds known to be useful in the treatment of respiratory diseases such as (1) antagonists of M3 muscarinic receptors, (2) β2-agonists, (3) PDE4 inhibitors, (4) corticosteroids, (5) CysLT1 and/or CysLT2 antagonists, (6) inhibitors of egfr-kinase, (7) A2b antagonists, (8) NK1 receptor agonists, (9) CRTh2 antagonists, (10) syk kinase inhibitors, (11) CCR3 antagonists and (12) VLA-4 antagonists.

When substituted spiro[cycloalkyl-1,3'-indol]-2'(1'H)-one derivatives of the invention are used for the treatment of autoimmune diseases such as psoriasis, rheumatoid arthritis, psoriatic arthritis, ankylosing spondylitys, Reiter's syndrome, fibromyalgia, inflammatory bowel disease such as ulcerative colitis and Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, autoimmune chronic active hepatitis, myasthenia gravis, or Addison's disease it may be advantageous to use them in combination with other active compounds known to be useful in the treatment of autoimmune diseases such as PDE4 inhibitors, CysLT1 and/or CysLT2 antagonists, inhibitors of egfr-kinase, A2b antagonists, NK1 receptor agonists, CCR3 antagonists, VLA-4 antagonists and disease modifying antirheumatic drugs (DMARDs).

Examples of suitable M3 antagonists (anticholinergics) that can be combined with the inhibitors of the p38 mitogen-activated protein kinase of the present invention are tiotropium salts, oxitropium salts, flutropium salts, ipratropium salts, glycopyrronium salts, trospium salts, revatropate, espatropate, 3-[2-Hydroxy-2,2-bis(2-thienyl)acetoxy]-1-(3-phenoxypropyl)-1-azoniabicyclo[2.2.2]octane salts, 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl)piperidin-1-yl]-2(R)-[3,3-difluorocyclopent-1(R)-yl]-2-hydroxy-2-phenylethan-1-one (Banyu-280634), N—[N-[2-[N-[1-(Cyclohexylmethyl)piperidin-3(R)-ylmethyl]carbamoyl]ethyl]carbamoylmethyl]-3,3,3-triphenyl-propionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), UCB-101333, Merck's OrM3, 7-endo-(2-hydroxy-2,2-diphenylacetoxy)-9,9-dimethyl-3-oxa-9-azoniatricyclo[3.3.1.0(2,4)]nonane salts, 7-(2,2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts, chlorides, bromides, iodides and methane-sulphonates are preferred.

Examples of suitable β2-agonists that can be combined with the inhibitors of the p38 mitogen-activated protein kinase of the present invention are: arformoterol, bambuterol, bitolterol, broxaterol, carbuterol, clenbuterol, dopexamine, fenoterol, formoterol, hexoprenaline, ibuterol, isoetharine, isoprenaline, levosalbutamol, mabuterol, meluadrine, metaprotenerol, nolomirole, orciprenaline, pirbuterol, procaterol, reproterol, ritodrine, rimoterol, salbutamol, salmefamol, salmeterol, sibenadet, sotenerot, sulfonterol, terbutaline, tiaramide, tulobuterol, GSK-597901, milveterol, GSK-678007, GSK-642444, GSK-159802, LAS100977, HOKU-81, KUL-1248, carmoterol, indacaterol and 5-[2-(5,6-diethylindan-2-ylamino)-1-hydroxyethyl]-8-hydroxy-1H-quinolin-2-one, 4-hydroxy-7-[2-{[2-{[3-(2-phenylethoxy)propyl]sulfonyl}ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol and 1-(4-ethoxycarbonylamino-3-cyano-5-fluorophenyl)-2-(tert-butylamino)ethanol
optionally in the form of their racemates, their enantiomers, their diastereomers, and mixtures thereof, and optionally their pharmacologically-compatible acid addition salts and the compounds claimed in International Patent application numbers WO2006/122788A1 and WO2007/124898. When the β2-agonists are in the form of a salt or derivative it is particularly preferred that it is in a form selected from the sodium salts, sulfobenzoates, phosphates, isonicotinates, acetates, propionates, dihydrogen phosphates, palmitates, pivalates, fumarates, furoates, xinafoates or mixtures thereof.

The following β2-agonists are of special interest for the combination with the compounds of formula (I): arformoterol, bambuterol, bitolterol, broxaterol, carbuterol, clenbuterol, dopexamine, fenoterol, formoterol, hexoprenaline, ibuterol, isoprenaline, levosalbutamol, mabuterol, meluadrine, nolomirole, orciprenaline, pirbuterol, procaterol, (R,R)-formoterol, reproterol, ritodrine, rimoterol, salbutamol, salmeterol, sibenadet, sulfonterol, terbutaline, tulobuterol, GSK-597901, milveterol, LAS100977, KUL-1248, carmoterol and indacaterol optionally in the form of their racemates, their enantiomers, their diastereomers, and mixtures thereof, and optionally their pharmacologically-compatible acid addition salts Still most preferred are the following β2-agonists: formoterol, salmeterol and GSK-597901, GSK-159797, indacaterol optionally in the form of their racemates, their enantiomers, their diastereomers and mixtures thereof, and optionally their pharmacologically-compatible acid addition salts. Still more preferred are salmeterol and formoterol.

Examples of suitable PDE4 inhibitors that can be combined with the inhibitors of the p38 mitogen-activated protein kinase of the present invention are denbufylline, rolipram, cipamfylline, arofylline, filaminast, piclamilast, mesopram, drotaverine hydrochloride, lirimilast, cilomilast, oglemilast, apremilast, 6-[2-(3,4-Diethoxyphenyl)thiazol-4-yl]pyridine-2-carboxylic acid (tetomilast), (R)-(+)-4-[2-(3-Cyclopentyloxy-4-methoxyphenyl)-2-phenylethyl]pyridine, N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N-6-methyl-2-(trifluoromethyl)adenine, N-(3,5-Dichloro-4-pyridinyl)-8-methoxyquinoline-5-carboxamide, N-[9-Methyl-4-oxo-1-phenyl-3,4,6,7-tetrahydropyrrolo[3,2,1-jk][1,4]benzodiazepin-3(R)-yl]pyridine-4-carboxamide, 3-[3-(Cyclopentyloxy)-4-methoxybenzyl]-6-(ethylamino)-8-isopropyl-3H-purine hydrochloride, 4-[6,7-Diethoxy-2,3-bis(hydroxymethyl)naphthalen-1-yl]-1-(2-methoxyethyl)pyridin-2(1H)-one, 2-carbomethoxy-4-cyano-4-(3-cyclopropylmethoxy-4-difluoromethoxyphenyl)cyclohexan1-one, cis[4-cyano-4-(3-cyclopropylmethoxy-4-difluoromethoxyphenyl)cyclohexan-1-ol, ONO-6126 (Eur Respir J 2003, 22 (Suppl. 45): Abst 2557) and the compounds claimed in the PCT patent applications number WO03/097613, WO2004/058729, WO 2005/049581, WO 2005/123693 and WO 2005/123692

Examples of suitable corticosteroids and glucocorticoids that can be combined with β2-agonists are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, butixocort propionate, RPR-106541, halometasone, methylprednisolone suleptanate, mometasone furoate, rimexolone, prednisolone farnesylate, ciclesonide, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Examples of suitable CysLT1 and/or CysLT2 antagonists that can be combined with the inhibitors of the p38 mitogen-activated protein kinase of the present invention are tomelukast, Ibudilast, pobilukast, pranlukast hydrate, zafirlukast, ritolukast, verlukast, sulukast, tipelukast, cinalukast, iralukast sodium, masilukast, montelukast sodium, 5-[3-[3-(2-Quinolinylmethoxy)phenoxy]propyl]-1H-tetrazole, (E)-8-[2-[4-[4-(4-Fluorophenyl)butoxy]phenyl]vinyl]-2-(1H-tetrazol-5-yl)-4H-benzopyran-4-one sodium salt, 2-[N-[4-(4-Chlorophenylsulfonamido)butyl]-N-[3-(4-isopropylthiazol-2-ylmethoxy)benzyl]sulfamoyl]benzoic acid, (3R,4R)-3-[6-(5-Fluorobenzothiazol-2-ylmethoxy)-4-hydroxy-3,4-dihydro-2H-1-benzopyran-3-ylmethyl]benzoic acid, 2-[2-[2-(4-tert-Butylthiazol-2-yl)benzofuran-5-yloxymethyl]phenyl]acetic acid hydrochloride, 5-[2-[4-(Quinolin-2-ylmethoxy)phenoxymethyl]benzyl]-1H-tetrazole, (E)-2,2-Diethyl-3'-[2-[2-(4-isopropyl)thiazolyl]ethenyl]succinanilic acid; 4-[4-[3-(4-Acetyl-3-hydroxy-2-propylphenoxy)propylsulfonyl]phenyl]-4-oxobutyric acid, [[5-[[3-(4-Acetyl-3-hydroxy-2-propylphenoxy)propyl]thio]-1,3,4-thiadiazol-2-yl]thio]acetic acid, 9-[(4-Acetyl-3-hydroxy-2-n-propylphenoxy)methyl]-3-(1H-tetrazol-5-yl)-4H-pyrido[1,2-a]pyrimidin-4-one, 5-[3-[2-(7-Chloroquinolin-2-yl)vinyl]phenyl]-8-(N,N-dimethylcarbamoyl)-4,6-dithiaoctanoic acid sodium salt; 3-[1-[3-[2-(7-Chloroquinolin-2-yl)vinyl]phenyl]-1-[3-(dimethylamino)-3-oxopropylsulfanyl]methylsulfanyl]propionic acid sodium salt, 6-(2-Cyclohexylethyl)-[1,3,4]thiadiazolo[3,2-a]-1,2,3-triazolo[4,5-d]pyrimidin-9(1H)-one, (R)-3-[2-Methoxy-4-[N-(2-methylphenylsulfonyl)carbamoyl]benzyl]-1-methyl-N-(4,4,4-trifluoro-2-methylbutyl)indole-5-carboxamide, MCC-847 (from AstraZeneca), (+)-4(S)-(4-Carboxyphenylthio)-7-[4-(4-phenoxybutoxy)phenyl]-5(Z)-heptenoic acid and the compounds claimed in PCT patent application WO2004/043966A1.

Examples of suitable inhibitors of egfr-kinase that can be combined with the inhibitors of the p38 mitogen-activated protein kinase of the present invention are palifermin, cetuximab, gefitinib, repifermin, erlotinib hydrochloride, canertinib dihydrochloride, lapatinib, and N-[4-(3-Chloro-4-fluorophenylamino)-3-cyano-7-ethoxyquinolin-6-yl]-4-(dimethylamino)-2(E)-butenamide.

Examples of suitable antagonists of the A2b adenosine receptor that can be combined with the inhibitors of the p38 mitogen-activated protein kinase of the present invention are CVT-6883 from CV Therapeutics, 4-(1-butylxanthin-8-yl) benzoic acid, 8-[1-[3-(4-chlorophenyl)-1,2,4-oxadiazol-5-ylmethyl]-1H-pyrazol-4-yl]-1,3-dipropylxanthine, N-(1,3-benzodioxol-5-yl)-2-[5-(1,3-dipropylxanthin-8-yl)-1-methyl-1H-pyrazol-3-yloxy]acetamide, 8-[4-[5-(2-methoxyphenyl)-1,2,4-oxadiazol-3-ylmethoxy]phenyl]-1,3-dipropylxanthine, 3-[5-(2-methyl-1H-imidazol-1-yl)-2-(pyrazin-2-ylamino)thiazol-4-yl]benzonitrile, 4-(2,6-dioxo-1-propyl-2,3,6,7-tetrahydro-1H-purin-8-yl)benzenesulfonic acid, 1-[2-[8-(3-fluorophenyl)-9-methyl-9H-adenin-2-yl] ethynyl]cyclopentanol hydrochloride, N-(2-acetylphenyl)-2-[4-(1,3-dipropylxanthin-8-yl)phenoxy]acetamide, N-(4-acetylphenyl)-2-[4-(1,3-dipropylxanthin-8-yl)phenoxy] acetamide, N-(4-cyanophenyl)-2-[4-(1,3-dipropylxanthin-8-yl)phenoxy]acetamide, 4-(3,4-dichlorophenyl)-5-(4-pyridinyl)thiazol-2-amine or the compounds of international patent applications WO 2005/040155 A1, WO2005/100353 A1 WO 2007/039297A1 and WO2007/017096 A1.

Examples of suitable NK1-receptor antagonists that can be combined with the inhibitors of the p38 mitogen-activated protein kinase of the present invention are nolpitantium besilate, dapitant, lanepitant, vofopitant hydrochloride, aprepitant, ezlopitant, N-[3-(2-Pentylphenyl)propionyl]-threonyl-N-methyl-2,3-dehydrotyrosyl-leucyl-D-phenylalanyl-allo-threonyl-asparaginyl-serine C-1.7-O-3.1 lactone, 1-Methylindol-3-ylcarbonyl-[4(R)-hydroxy]-L-prolyl-[3-(2-naphthyl)]-L-alanine N-benzyl-N-methylamide, (+)-(2S, 3S)-3-[2-Methoxy-5-(trifluoromethoxy)benzylamino]-2-phenylpiperidine, (2R,4S)—N-[1-[3,5-Bis(trifluoromethyl)benzoyl]-2-(4-chlorobenzyl)piperidin-4-yl]quinoline-4-carboxamide, 3-[2(R)-[1(R)-[3,5-Bis(trifluoromethyl)phenyl]ethoxy]-3(S)-(4-fluorophenyl)morpholin-4-ylmethyl]-5-oxo-4,5-dihydro-1H-1,2,4-triazole-1-phosphinic acid bis(N-methyl-D-glucamine) salt; [3-[2(R)-[1(R)-[3,5-bis(trifluoromethyl)phenyl]ethoxy]-3(S)-(4-fluorophenyl)-4-morpholinylmethyl]-2,5-dihydro-5-oxo-1H-1,2,4-triazol-1-yl]phosphonic acid 1-deoxy-1-(methylamino)-D-glucitol (1:2) salt, 1'-[2-[2(R)-(3,4-Dichlorophenyl)-4-(3,4,5-trimethoxybenzoyl)morpholin-2-yl]ethyl]spiro[benzo[c]thiophen-1(3H)-4'-piperidine]2(S)-oxide hydrochloride and the compound CS-003 described in Eur Respir J 2003, 22 (Suppl. 45): Abst P2664.

Examples of suitable CRTh2 antagonists that can be combined with the inhibitors of the p38 mitogen-activated protein kinase of the present invention are 2-[5-Fluoro-2-methyl-1-[4-(methylsulfonyl)phenylsulfonyl]-1H-indol-3-yl]acetic acid, Ramatroban, [(3R)-4-(4-chlorobenzyl)-7-fluoro-5-(methylsulfonyl)-1,2,3,4tetrahydrocyclopenta[b]indol-3-yl] acetic acid and (1R,2R,3S,5S)-7-[2-(5-Hydroxybenzothiophen-3-ylcarboxamido)-6,6-dimethylbicyclo[3.1.1]hept-3-yl]-5(Z)-heptenoic acid.

Examples of suitable Syk kinase inhibitors that can be combined with the inhibitors of the p38 mitogen-activated protein kinase of the present invention are piceatannol, 2-(2-Aminoethylamino)-4-[3-(trifluoromethyl)phenylamino]pyrimidine-5-carboxamide, R-091 (from Rigel), R-112 (from Rigel), R-343 (from Rigel), R-788 (from Rigel), 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate, 1-(2,4,6-Trihydroxyphenyl)-2-(4-methoxyphenyl)ethan-1-one, N-[4-[6-(Cyclobutylamino)-9H-purin-2-ylamino]phenyl]-N-methylacetamide, 2-[7-(3,4-Dimethoxyphenyl)imidazo[1,2-c]pyrimidin-5-ylamino]pyridine-3-carboxamide dihydrochloride and AVE-0950 (from Sanofi-Aventis).

Examples of CCR3 antagonists that can be combined with the inhibitors of the p38 mitogen-activated protein kinase of the present invention are 4-[3-[4-(3,4-Dichlorobenzyl)morpholin-2(S)-ylmethyl]ureidomethyl]benzamide, N-[1(R)-[4-(3,4-Dichlorobenzyl)piperidin-1-ylmethyl]-2-methylpropyl]-N'-(3,4,5-trimethoxyphenyl)urea, N-[1(S)-[4-(4-Chlorobenzyl)piperidin-1-ylmethyl]-2-hydroxypropyl]-N'-(3,4,5-trimethoxyphenyl)urea, 3-[3-(3-Acetylphenyl)ureido]-2-[4-(4-fluorobenzyl)piperidin-1-ylmethyl]-N-methylbenzamide, 4-(3,4-Dichlorobenzyl)-1-methyl-1-[3-methyl-2(R)-[3-(3,4,5-trimethoxyphenyl)ureido]butyl]piperidinium chloride, N-[2-[4(R)-(3,4-Dichlorobenzyl)pyrrolidin-2(S)-yl]ethyl]-2-[5-(3,4-dimethoxyphenyl)pyrimidin-2-ylsulfanyl]acetamide, CRIC-3 (from IPF Pharmaceuticals), 2(R)-[1-[1-(2,4-Dichlorobenzyl)-4(S)-(3-thienyl)pyrrolidin-3(S)-ylmethyl]piperidin-4-ylmethyl]pentanoic acid, 8-[1-(2,4-Dichlorobenzyl)-4(S)-(3-thienyl)pyrrolidin-3(S)-ylmethyl]-3,3-dipropyl-1-oxa-8-azaspiro[4.5]decane-2(S)-carboxylic acid, 11-[1-(2,4-Dichlorobenzyl)-4(S)-(3-thienyl)pyrrolidin-3(S)-ylmethyl]-3,14-dioxa-11-azadispiro[5.1.5.2]pentadecane-15(S)-carboxylic acid, W-56750 (from Mitsubishi Pharma), N-[1(S)-[3endo-(4-Chlorobenzyl)-8-azabicyclo[3.2.1]oct-8-ylmethyl]-2(S)-hydroxypropyl]-N'-(3,4,5-trimethoxyphenyl)urea, N-(3-Acetylphenyl)-N'-[(1R,2S)-2-[3(S)-(4-fluorobenzyl)piperidin-1-ylmethyl]cyclohexyl]urea benzenesulfonate, trans-1-(Cycloheptylmethyl)-4-(2,7-dichloro-9H-xanthen-9-ylcarboxamido)-1-methylpiperidinium iodide, GW-782415 (from GlaxoSmithKline), GW-824575 (from GlaxoSmithKline), N-[1'-(3,4-Dichlorobenzyl)-1,4'-bipiperidin-3-ylmethyl]quinoline-6-carboxamide, N-[1-(6-Fluoronaphthalen-2-ylmethyl)pyrrolidin-3(R)-yl]-2-[1-(3-hydroxy-5-methylpyridin-2-ylcarbonyl)piperidin-4-ylidene]acetamide fumarate and DIN-106935 (from Bristol-Myers Squibb).

Examples of VLA-4 antagonists that can be combined with the inhibitors of the p38 mitogen-activated protein kinase of the present invention are N-[4-[3-(2-Methylphenyl)ureido]phenylacetyl]-L-leucyl-L-aspartyl-L-valyl-L-proline, 3(S)-[2(S)-[4,4-Dimethyl-3-[4-[3-(2-methylphenyl)ureido]benzyl]-2,5-dioxoimidazolidin-1-yl]-4-methylpentanoylamino]-3-phenylpropionic acid, 2(S)-(2,6-Dichlorobenzamido)-3-(2',6'-dimethoxybiphenyl-4-yl)propionic acid, RBx-4638 (from Ranbaxy), R-411 (from Roche), RBx-7796 (from Ranbaxy), SB-683699 (from GlaxoSmithKline), DW-908e (from Daiichi Pharmaceutical), RO-0270608 (from Roche), AJM-300 (from Ajinomoto), PS-460644 (from Pharmacopeia) and the compounds claimed in PCT patent application numbers WO 02/057242 A2 and WO 2004/099126 A1.

Examples of disease modifying antirheumatic drugs (DMARs) that can be combined with the inhibitors of the p38 mitogen-activated protein kinase of the present invention are auranofin, azathioprine, bucillamine, cyclosporine, iguratimod, leflunomide, methotrexate, pentostatin, rimacalib hydrochloride, romazarit, salazodine, sulphasalazine, teriflunomide, (E)-5-(3,5-Di-tert-butyl-4-hydroxybenzylidene)-2-ethylisothiazolidine 1,1-dioxide, cis-2-(4-Chlorophenyl)-4,5-diphenyl-4,5-dihydro-1H-imidazole hydrochloride, 2-[8-[2-[6-(Methylamino)pyridyl-2-ylethoxy]-3-oxo-2-(2,2,2-trifluoroethyl)-2,3,4,5-tetrahydro-1H-2-benzazepin-4-(S)-yl]acetic acid, 4-acetoxy-2-(4-methylphenyl)benzothiazole, 3-[4-Methyl-3-[N-methyl-N-(7H-pyrrolo[2,3-d]pyrimidin-4-yl)amino]piperidin-1-yl]-3-oxopropionitrile (CP-690550), 3-Deazadenosine, 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate (R-406), AD-452 from Sosei, AD-827 from Arakis, BB-2983 from British Biotech, SC-12267 from 4SC, CPH-82 from Conpharm, R-1295 from Roche, R-1503 from Roche and N2-[3-[1(S)-(2-Fluorobiphenyl-4-yl)ethyl]isoxazol-5-yl]morpholine-4-carboxamidine hydrochloride (SMP-114).

The combinations of the invention may be used in the treatment of disorders which are susceptible to amelioration by inhibition of the p38 mitogen-activated protein kinase. Thus, the present application encompasses methods of treatment of these disorders, as well as the use of the combinations of the invention in the manufacture of a medicament for the treatment of these disorders, especially for the treatment of rheumatoid arthritis.

The present invention also provides pharmaceutical compositions which comprise, as an active ingredient a substituted spiro[cycloalkyl-1,3'-indol]-2'(1'H)-one derivative of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably the compositions are made up in a form suitable for oral, topical, inhaled, nasal, rectal, percutaneous or injectable administration. Compositions for oral administration may be in the form of syrups, tablets, capsules, lozenges, controlled-release preparations, fast-dissolving preparations, etc. Compositions for topical administration may be in the form of creams, ointments, lotions, nasal sprays or aerosols, etc). Compositions for administration by injection may be in the form of subcutaneous, intradermic, intramuscular or intravenous compositions. Compositions for administration by inhalation may be in the form of a dry powder, a solution, a dispersion, etc.

The active compounds in the combination, i.e. the inhibitors of the p38 mitogen-activated protein kinase of the invention, and the other optional active compounds may be administered together in the same pharmaceutical composition or in different compositions intended for separate, simultaneous, concomitant or sequential administration by the same or a different route.

One execution of the present invention consists of a kit of parts comprising of inhibitors of the p38 mitogen-activated protein kinase of the present invention together with instructions for simultaneous, concurrent, separate or sequential use in combination with another active compound useful in the treatment of a respiratory disease which responds to inhibition of the p38 mitogen-activated protein kinase.

Another execution of the present invention consists of a package comprising of inhibitors of the p38 mitogen-activated protein kinase of formula (I) and another active compound useful in the treatment of a respiratory disease for the simultaneous, concurrent, separate or sequential use in the treatment of a respiratory disease which responds to the inhibition of the p38 mitogen-activated protein kinase.

The pharmaceutically acceptable excipients which are admixed with the active compound or salts of such compound, to form the compositions of this invention are well-known per se and the actual excipients used depend inter alia on the intended method of administering the compositions.

The diluents which may be used in the preparation of the compositions include those liquid and solid diluents which are compatible with the active ingredient, together with colouring or flavouring agents, if desired. Tablets or capsules may conveniently contain between 1 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred.

Packaging of the formulation may be suitable for unit dose or multi-dose delivery. in the case of multi-dose delivery, the formulation can be pre-metered or metered in use. Dry powder inhalers are thus classified into three groups: (a) single dose, (b) multiple unit dose and (c) multi dose devices.

For single dose inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients. Other drawbacks related to the use of hard gelatine capsules for inhalation powders are (a) poor protection against moisture uptake from the ambient air; (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported.

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (Ex. EP0069715) or disks (Ex. GB 2041763; EP 0424790; DE 4239402 and EP 0674533), rotatable cylinders (Ex. EP 0166294; GB 2165159 and WO 92/09322) and rotatable frustums (Ex. WO 92/00771), all having cavities which have to be filled with powder from the container. Other multi dose devices have measuring slides (Ex. U.S. Pat. No. 5,201,308 and WO 97/00703) or measuring plungers with a local or circumferential recess to displace a certain volume of powder from the container to a delivery chamber or an air conduit (Ex. EP 0505321, WO 92/04068 and WO 92/04928), or measuring slides such as the Genuair® (formerly known as Novolizer SD2FL), which is described in the following patent applications Nos.: WO97/000703, WO03/000325 and WO03/061742.

Apart from applications through dry powder inhalers the compositions of the invention can also be administered in aerosols which operate via propellant gases or by means of so-called atomisers, via which solutions of pharmacologically-active substances can be sprayed under high pressure so that a mist of inhalable particles results. Such atomisers are described, for example, in WO 91/14468 and WO 97/12687.

Effective doses are normally in the range of 1-2000 mg of active ingredient per day. Daily dosage may be administered in one or more treatments, preferably from 1 to 4 treatments, per day.

The syntheses of the compounds of the invention and of the intermediates for use therein are illustrated by the following Examples (1-78) including Preparation Examples (Intermediates 1-59) which do not limit the scope of the invention in any way.

$^1$H Nuclear Magnetic Resonance Spectra were recorded on a Varian Gemini 300 spectrometer. Melting points were recorded using a Büchi B-540 apparatus. The LCMS chromatographic separations were obtained using a Waters 2795 system equipped with a Symmetry C18 (2.1×100 mm, 3.5 mm) column. As detectors a Micromass ZMD mass spectrometer using ES ionization and a Waters 996 Diode Array detector were used. The mobile phase was formic acid (0.46 ml), ammonia (0.115 ml) and water (1000 ml) (A) and formic acid (0.4 ml), ammonia (0.1 ml), methanol (500 ml) and acetonitrile (500 ml) (B): initially from 0% to 95% of B in 20 min, and then 4 min. with 95% of B. The reequilibration time between two injections was 5 min. The flow rate was 0.4 ml/min. The injection volume was 5 μl. Diode array chromatograms were processed at 210 nm.

Preparation 1

6-Bromoindolin-2-one 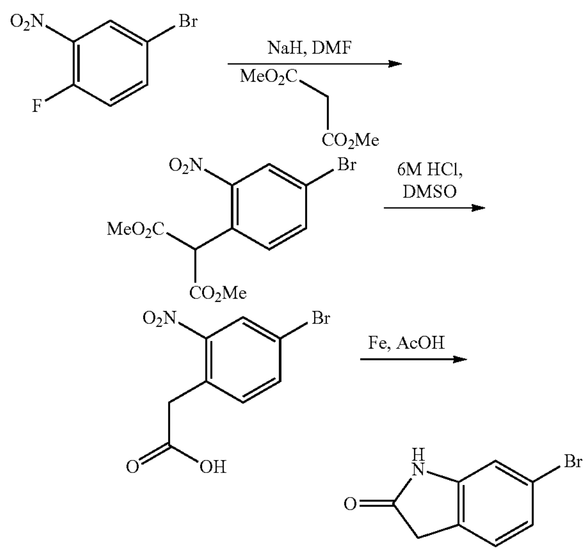 a) Dimethyl 2-(4-bromo-2-nitrophenyl)malonate

Dimethyl malonate (40.34 g, 0.305 mol) in N,N'-dimethylformamide (45 mL) was added dropwise to a stirred suspension of sodium hydride (60% dispersion in mineral oil, 16.2 g, 405 mmol) in N,N'-dimethylformamide (500 mL) at 10° C. The mixture was stirred for 1 hour at room temperature then 4-bromo-1-fluoro-2-nitrobenzene (44.38 g, 202 mmol) in N,N'-dimethylformamide (45 mL) was added dropwise to the reaction mixture. The mixture was stirred 75 minutes at room temperature and then was warmed to 65° C. After 1 hour, the solvent was removed under reduced pressure, the residue was taken up in a mixture of ethyl acetate and water and 2M aqueous hydrochloric acid was added until the mixture became pale yellow in colour. The organic layer was separated, washed with water, brine, dried ($MgSO_4$) and evaporated. The crude product was recrystallized from diisopropyl ether to give the title compound (55.0 g, 83%) as a pale yellow solid.

LRMS (m/z): 330/332 $(M-1)^-$.

$^1$H-NMR δ ($CDCl_3$): 3.81 (s, 6H), 5.28 (s, 1H), 7.43 (d, J=9.0 Hz, 1H), 7.78 (dd, J=9.0 and 3.0 Hz, 1H), 8.21 (d, J=4.0 Hz, 1H).

b) 2-(4-Bromo-2-nitrophenyl)acetic acid

6M Aqueous hydrochloric acid (200 mL) was added to a stirred solution of dimethyl 2-(4-bromo-2-nitrophenyl)malonate (preparation 1a, 55.45 g, 170 mmol) in dimethylsulphoxide (250 mL) at room temperature and then mixture was warmed to 130° C. with stirring. After 5 hours, the mixture was cooled and water (400 mL) was added with stirring and the mixture was left to cool overnight. The precipitate was filtered, washed with water and dried in vacuo to give the title compound (41.0 g, 94%) as a white solid.

LRMS (m/z): 258/260 $(M-1)^-$.

$^1$H-NMR δ (DMSO-$d_6$): 3.98 (s, 2H), 7.53 (d, J=9.0 Hz, 1H), 7.95 (d, J=9.0 Hz, 1H), 8.27 (s, 1H), 12.66 (s, 1H).

c) 6-Bromoindolin-2-one

Iron (40.0 g, 700 mmol) was added slowly to a stirred solution of 2-(4-bromo-2-nitrophenyl)acetic acid (preparation 1b, 46.6 g, 200 mmol) in acetic acid (390 mL) at 75° C., and then mixture was stirred for 1 hour at 100° C. The mixture was cooled and ethyl acetate was added. The mixture was filtered through Celite® and the solvent evaporated. The crude product was washed with 0.1M aqueous hydrochloric acid, water, diethyl ether and dried to give the title compound (22.0 g, 58%) as a solid.

LRMS (m/z): 212/214 $(M+1)^+$.

$^1$H-NMR δ (DMSO-$d_6$): 3.45 (s, 2H), 6.94 (s, 1H), 7.09-7.17 (m, 2H), 10.50 (s, 1H).

Preparation 2

6'-Bromospiro[cyclopentane-1,3'-indolin]-2'-one 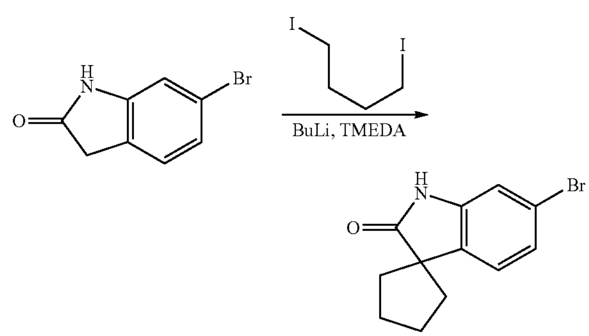 n-Butyl lithium (2.5 M in hexanes, 3.8 mL, 9.5 mmol) was added dropwise over 30 minutes to a stirred suspension of 6-bromoindolin-2-one (preparation 1, 1.00 g, 4.7 mmol) and N,N,N',N'-tetramethylethylenediamine (1.42 mL, 9.4 mmol) in tetrahydrofuran (20 mL) at −78° C. The mixture was stirred for 1 hour, then 1,4-diiodobutane (3.11 mL, 23.6 mmol) was added dropwise over 5 minutes. The mixture was warmed to −20° C. over a 1 hour period, was stirred for a further hour at this temperature and was then warmed to room temperature. After 3 hours stirring at room temperature, saturated aqueous ammonium chloride solution was added to the reaction and the mixture was extracted with ethyl acetate. The organic layer was washed with water, brine, dried (MgSO$_4$) and evaporated. Purification of the residue by flash chromatography (10:1 hexanes/ethyl acetate) gave the title compound (0.57 g, 45%) as a pale pink solid.

LRMS (m/z): 266/268 (M+1)$^+$.

$^1$H-NMR δ (CDCl$_3$): 1.81-2.20 (m, 8H), 7.02-7.06 (m, 2H), 7.14-7.18 (m, 1H), 7.83 (brs, 1H).

Preparation 3

6'Bromo-5'-chlorospiro[cyclopentane-1,3'-indolin]-2'-one

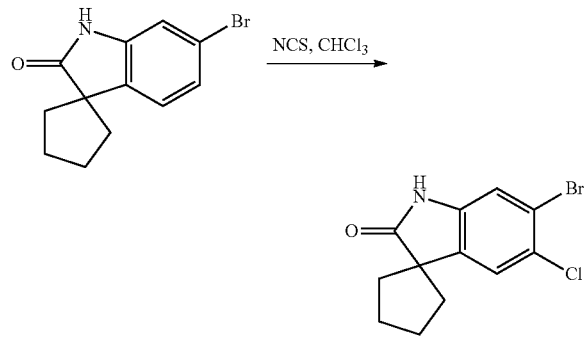

N-Chlorosuccinimide (0.50 g, 3.75 mmol) was added to a solution of 6'-bromospiro[cyclopentane-1,3'-indolin]-2'-one (preparation 2, 0.20 g, 0.75 mmol) in chloroform (5 mL). The mixture was stirred and heated to reflux. After 6 hours, the mixture was cooled to room temperature. Saturated aqueous sodium hydrogen carbonate solution was added to the reaction and the mixture was extracted with chloroform. The organic layer was washed with brine, dried (MgSO$_4$) and evaporated. Purification of the residue by flash chromatography (4:1 hexanes/ethyl acetate) gave the title compound (0.17 g, 75%) as a white solid.

LRMS (m/z): 298/300 (M−1)$^-$.

$^1$H-NMR δ (CDCl$_3$): 1.84-1.99 (m, 4H), 2.07-2.14 (m, 2H), 2.18-2.24 (m, 2H), 7.26 (brs, 2H).

Preparation 4

6'-(4,4,5,5-Tetramethyl-1,3,2-dioxaborolan-2-yl)spiro[cyclopentane-1,3'-indolin]-2'-one

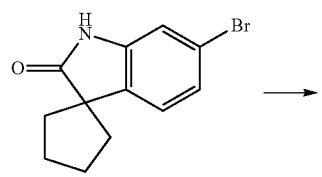

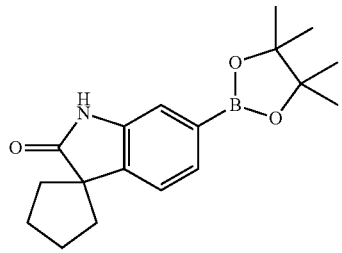

A mixture of 6'-bromospiro[cyclopentane-1,3'-indolin]-2'-one (preparation 2, 0.20 g, 0.77 mmol), bis(pinacolato)diboron (0.29 g, 1.15 mmol), potassium acetate (0.38 g, 3.85 mmol) and 1,1'-bis(diphenylphosphino)ferrocene-palladium (II) dichloride dichloromethane complex (0.06 g, 0.08 mmol) in N,N'-dimethylformamide (2 mL) was heated at 120° C. for 30 minutes in Biotage Initiator Microwave Synthesizer. The mixture was then cooled and the solvent was evaporated. Ethyl acetate was added to the residue and the organic layer was washed with saturated aqueous sodium hydrogen carbonate solution, dried (MgSO$_4$) and evaporated. Purification of the residue by flash chromatography (3:1 hexanes/ethyl acetate) gave the title compound (0.07 g, 30%) as a solid.

LRMS (m/z): 314 (M+1)$^+$.

$^1$H-NMR δ (CDCl$_3$): 1.34 (s, 12H), 1.83-1.91 (m, 2H), 1.94-2.10 (m, 4H), 2.15-2.23 (m, 2H), 7.21 (d, J=9.0 Hz, 1H), 7.29 (s, 1H), 7.45 (brs, 1H), 7.45 (d, J=9.0 Hz, 1H).

Preparation 5

6'Bromospiro[cyclohexane-1,3'-indolin]-2'-one

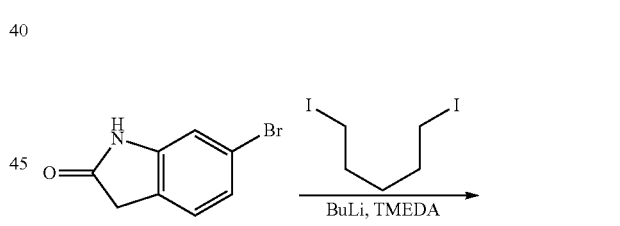

Obtained as a pink solid (24%) from 6-bromoindolin-2-one (preparation 1) and 1,5-diiodopentane following the experimental procedure as described in preparation 2 followed by purification by flash chromatography (3:1 hexanes/ethyl acetate).

LRMS (m/z): 280/282 (M+1)$^+$.

$^1$H-NMR δ (CDCl$_3$): 1.63-1.97 (m, 10H), 7.08 (d, J=3.0 Hz, 1H), 7.16 (dd, J=9.0 and 3.0 Hz, 1H), 7.30 (d, J=9.0 Hz, 1H), 8.13 (brs, 1H).

Preparation 6

6'-Bromospiro[cyclobutane-1,3'-indol]-2'(1'H)-one

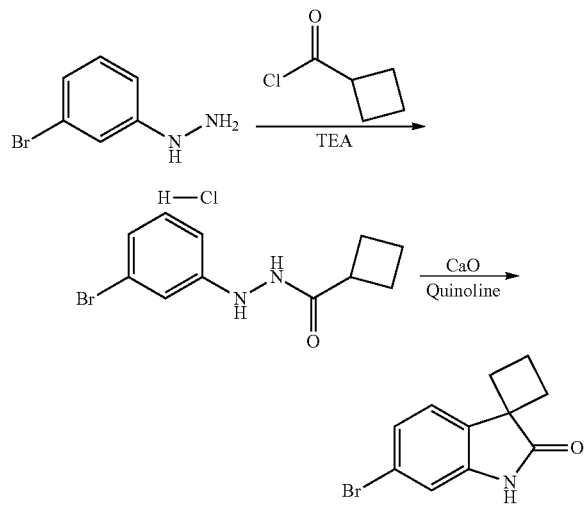

a) N'-(3-Bromophenyl)cyclobutanecarbohydrazide

Triethylamine (6.90 mL, 49.22 mmol) was added dropwise to a suspension of 3-bromophenylhydrazine hydrochloride (5.00 g, 22.37 mmol) in dichloromethane (60 mL) to give a solution. The mixture was cooled in an ice-salt bath and then cyclobutanecarbonyl chloride (2.68 mL, 23.49 mmol) in dichloromethane (10 mL) was added dropwise at such a rate that the internal temperature did not exceed −10° C. After the addition, the mixture was stirred at −5° C. to −10° C. for 1.5 hours. The cooling bath was removed and the mixture was stirred for a further 2 hours at room temperature. The mixture was evaporated in vacuo and 4% aqueous sodium hydrogen carbonate solution was added. The mixture was filtered and the semi-solid was washed with 4% aqueous sodium hydrogen carbonate solution, water and diethyl ether and dried in vacuo to give the title compound (3.60 g, 60%) as a white solid.

LRMS (m/z): 268/270 (M+1)$^+$.

$^1$H-NMR δ (DMSO-d$_6$): 1.80-2.20 (m, 6H), 3.11 (m, 1H), 6.63 (d, J=2 Hz, 1H), 6.80 (m, 2H), 7.08 (m, 1H), 7.96 (brs, 1H), 9.56 (brs, 1H).

b) N'-(3-Bromophenyl)cyclobutanecarbohydrazide

To a stirred suspension of calcium oxide (6.56 g, 117.0 mmol) in quinoline (14 mL) was added N'-(3-bromophenyl)cyclobutanecarbohydrazide (preparation 6a, 3.58 g, 13.3 mmol) portionwise over 2 minutes. The mixture was slowly heated to 265-270° C. to initiate the reaction. The mixture was then kept at 265° C. for 75 min and then cooled to room temperature. The mixture was digested with 2M aqueous hydrochloric acid and extracted with ethyl acetate. The organic layer was washed with 2M aqueous hydrochloric acid, brine, dried (MgSO$_4$) and the solvent evaporated under reduced pressure to give an oil (mixture of isomers) that was purified by flash chromatography (10:1 hexanes/ethyl acetate) to give the title compound (0.57 g, 17%) as the least polar isomer.

LRMS (m/z): 251/253 (M+1)$^+$.

$^1$H-NMR δ (CDCl$_3$): 2.10-2.30 (m, 4H), 2.50-2.70 (m, 2H), 7.08 (d, J=1.7 Hz, 1H), 7.22 (dd, J=8.0 and 1.7 Hz, 1H), 7.35 (d, J=8.0 Hz, 1H), 8.25 (brs, 1H).

Preparation 7

6-Bromo-2',3',5',6'-tetrahydrospiro[indoline-3,4'-pyran]-2-one

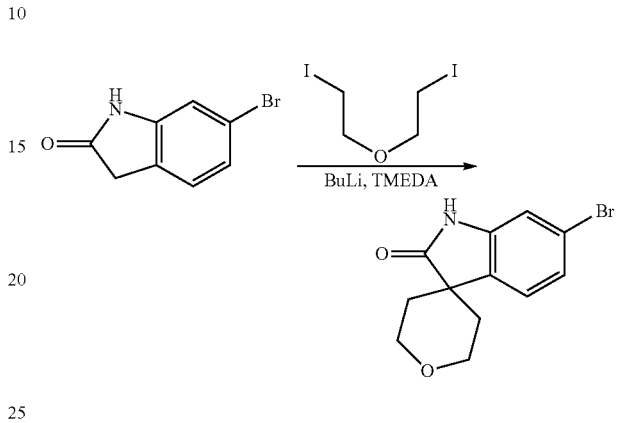

Obtained as a white solid (33%) from 6-bromoindolin-2-one (preparation 1) and 1-iodo-2-(2-iodoethoxy)ethane following the experimental procedure as described in preparation 2 followed by trituration of the crude product with diethyl ether/hexanes (1:1) followed by ethyl acetate and finally diethyl ether.

LRMS (m/z): 282/284 (M+1)$^+$.

$^1$H-NMR δ (DMSO-d$_6$): 1.71 (m, 4H), 3.81 (m, 2H), 4.01 (m, 2H), 6.98 (d, J=1.65 Hz, 1H), 7.14 (dd, J=7.97 Hz, J=1.65 Hz, 1H), 7.47 (d, J=7.97 Hz, 1H), 10.55 (s, NH).

Preparation 8

6-Bromo-2',3',5',6'-tetrahydrospiro[indoline-3,4'-pyran]-2-one

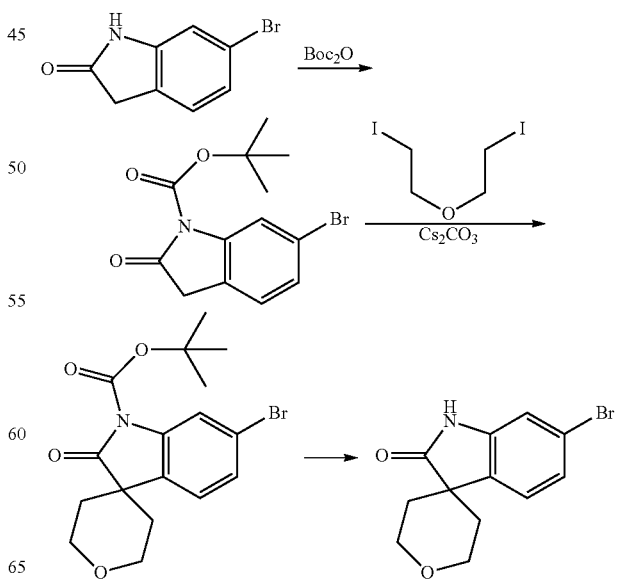

a) tert-butyl 6-bromo-2-oxoindoline-1-carboxylate

Di-tert-butyl dicarbonate (4.63 g, 21.2 mmol) and sodium hydrogen carbonate (10.7 g, 127 mmol) were added to a stirred solution of 6-bromoindolin-2-one (preparation 1, 3.0 g, 14.2 mmol) in tetrahydrofuran (150 mL) and the mixture was heated to reflux. After 3 hours the mixture was cooled and filtered and the filtrate was concentrated in vacuo. Purification of the residue by flash chromatography (10:1 hexanes/ethyl acetate) gave the title compound (3.58 g, 81%) as a white solid.

LRMS (m/z): 312/314 (M+1)$^+$.
$^1$H-NMR δ (CDCl$_3$): 1.65 (s, 9H), 3.66 (s, 2H), 7.10 (d, 1H), 7.27 (d, 1H), 8.03 (s, 1H).

b) tert-butyl 6-bromo-2-oxo-2',3',5',6'-tetrahydrospiro[indoline-3,4'-pyran]-1-carboxylate Cesium carbonate (20.7 g, 63.5 mmol) was added portion-wise over a 20 minute period to a stirred solution of tert-butyl 6-bromo-2-oxoindoline-1-carboxylate (preparation 8a, 6.0 g, 16.0 mmol) and 1-iodo-2-(2-iodoethoxy)ethane (6.58 g, 17.6 mmol) in N,N'-dimethylformamide (250 mL) at −20° C. under an argon atmosphere. After the addition the mixture was warmed to room temperature and stirred for 3 hours. Acetic acid (1.1 mL) followed by ethyl acetate and water were added to the reaction mixture and the organic layer was separated, washed with water, dried (MgSO$_4$) and evaporated. Purification of the residue by flash chromatography (10:1 to 5:1 hexanes/ethyl acetate) gave the title compound (4.50 g, 61%) as a pale yellow solid.

LRMS (m/z): 382/384 (M+1)$^+$.
$^1$H-NMR δ (CDCl$_3$): 1.65 (s, 9H), 1.86 (m, 4H), 3.90 (m, 2H), 4.23 (m, 2H), 7.17 (d, J=7.97 Hz, 1H), 7.33 (d, J=7.97 Hz, 1H), 8.07 (s, 1H)

c) 6-bromo-2',3',5',6'-tetrahydrospiro[indoline-3,4'-pyran]-2-one

A mixture of tert-butyl 6-bromo-2-oxo-2',3',5',6'-tetrahydrospiro[indoline-3,4'-pyran]-1-carboxylate (preparation 8b, 4.20 g, 11.0 mmol) and a 5M solution of hydrogen chloride in 1,4-dioxane (25 mL) was stirred at room temperature. After 5 hours, the mixture was concentrated in vacuo to give the title compound (3.20 g, 98%) as a pale pink solid.

LRMS (m/z): 278/280 (M−1)$^+$.
$^1$H-NMR δ (DMSO-d$_6$): 1.71 (m, 4H), 3.81 (m, 2H), 4.01 (m, 2H), 6.98 (d, J=1.65 Hz, 1H), 7.14 (dd, J=7.97 Hz, J=1.65 Hz, 1H), 7.47 (d, J=7.97 Hz, 1H), 10.55 (s, NH).

Preparation 9

6-(4,4,5,5-Tetramethyl-1,3,2-dioxaborolan-2-yl)-2',3',5',6'-tetrahydrospiro[indoline-3,4'-pyran]-2-one

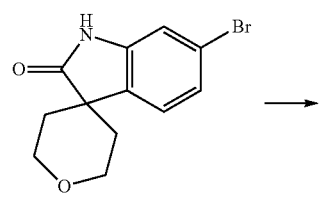

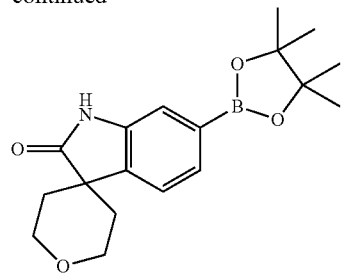

An oven dried resealable Schlenk tube was charged with 6-bromo-2',3',5',6'-tetrahydrospiro[indoline-3,4'-pyran]-2-one (preparation 8, 0.10 g, 0.35 mmol), bis(pinacolato)diboron (0.18 g, 0.71 mmol), potassium acetate (0.07 g, 0.70 mmol) and dimethylsulphoxide (1 mL). The Schlenk tube was subjected to three cycles of evacuation-backfilling with argon, and 1,1'-bis(diphenylphosphino)ferrocene-palladium(II) dichloride dichloromethane complex (0.02 g, 0.02 mmol) was added. After three further cycles of evacuation-backfilling with argon, the Schlenk tube was capped and placed in an oil bath at 90° C. After 16 h, the mixture was cooled and ethyl acetate was added. The organic layer was washed with water, dried (MgSO$_4$) and evaporated. The mixture was filtered through a silica cartridge eluting with hexanes/ethyl acetate to give the title compound in quantitative yield as a pale-yellow oily residue, which was used without further purification.

LRMS (m/z): 330 (M+1)$^+$.
$^1$H-NMR δ (CDCl$_3$): 1.35 (m, 12H), 1.89-1.91 (m, 4H), 3.91-3.95 (m, 2H), 4.23-4.27 (m, 2H), 7.33 (s, 1H), 7.40 (d, J=7.5 Hz, 1H), 7.56 (d, J=7.5 Hz, 1H), 7.77 (brs, 1H).

Preparation 10

6-Bromo-1'-methylspiro[indoline-3,4'-piperidin]-2-one

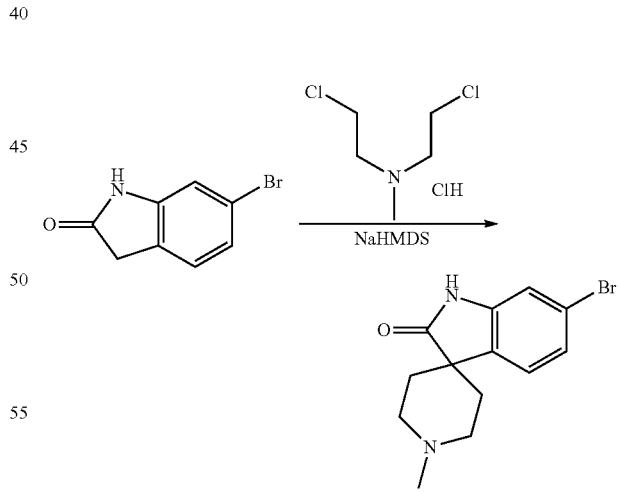

Sodium bis(trimethylsilyl)amide (1.0M in tetrahydrofuran, 9.40 mL, 9.40 mmol) was added dropwise to a stirred suspension of 6-bromoindolin-2-one (preparation 1, 0.40 g, 1.89 mmol) in tetrahydrofuran (4 mL) at −78° C. The mixture was stirred for 30 minutes, then 2-chloro-N-(2-chloroethyl)-N-methylethanamine hydrochloride (0.36 g, 1.89 mmol) was added and the mixture was warmed to room temperature. After stirring overnight, water was added to the reaction and the mixture was extracted with ethyl acetate. The organic layer was dried (MgSO$_4$) and evaporated. Purification of the residue by reverse phase chromatography (0% CH$_3$CN in H$_2$O to 100% CH$_3$CN in H$_2$O) gave the title compound as a yellow oil (0.17 g, 31%).

LRMS (m/z): 295/297 (M+1)$^+$.

$^1$H-NMR δ (DMSO-d$_6$): 1.68-1.86 (m, 4H), 2.51-2.62 (m, 4H), 2.80-2.87 (s, 3H), 7.00 (s, 1H), 7.14 (d, J=6.0 Hz, 1H), 7.41 (d, J=6.0 Hz, 1H), 8.28 (brs, 1H).

Preparation 11 tert-Butyl 6-bromo-2-oxospiro[indoline-3,4'-piperidine]-1'-carboxylate

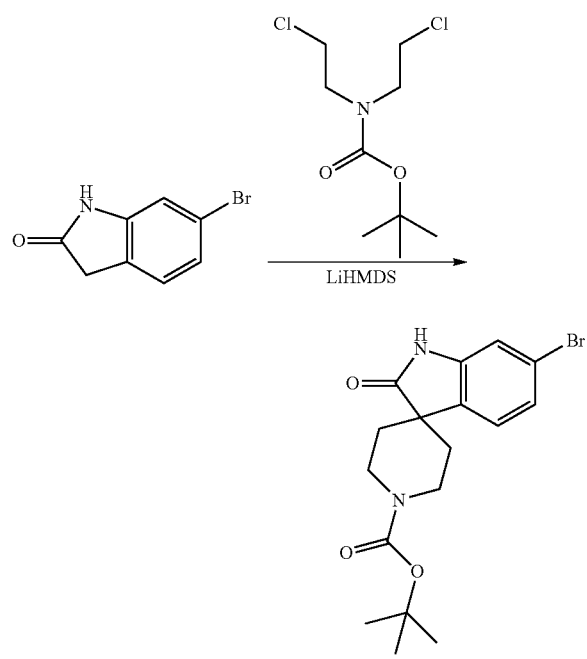

Lithium bis(trimethylsilyl)amide (1.0M in tetrahydrofuran, 2.80 mL, 2.80 mmol) was added dropwise to a stirred suspension of 6-bromoindolin-2-one (preparation 1, 0.20 g, 0.94 mmol) in tetrahydrofuran (1.5 mL) at 0° C. The mixture was stirred for 15 minutes, then tert-butyl bis(2-chloroethyl) carbamate (0.25 g, 1.04 mmol) in THF (1 mL) was added dropwise and the mixture was warmed to room temperature. After stirring overnight, 2M aqueous hydrochloric acid was added to the reaction and the mixture was extracted with ethyl acetate. The organic layer was dried (MgSO$_4$) and evaporated. Purification of the residue by flash chromatography (5:1 hexanes/ethyl acetate) gave the title compound (0.08 g, 22%) as a yellow solid.

LRMS (m/z): 381/383 (M+1)$^+$.

$^1$H-NMR δ (CDCl$_3$): 1.50 (s, 9H), 1.71-1.89 (m, 4H), 3.77-3.83 (m, 4H), 7.07 (d, 1H), 7.14 (s, 1H), 7.18 (d, 1H), 7.72 (brs, 1H).

Preparation 12

6-bromo-1'-(methylsulfonyl)spiro[indoline-3,4'-piperidin]-2-one

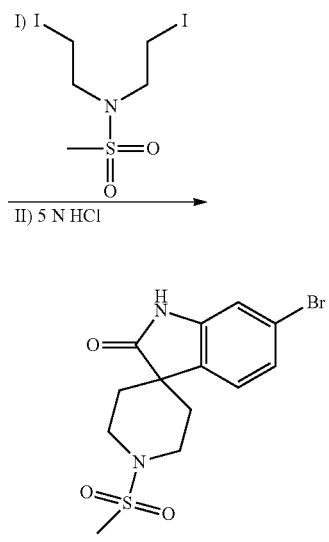

a) N,N-bis(2-chloroethyl)methanesulfonamide

Triethylamine (3.1 mL, 22.2 mmol) was added dropwise to a suspension of N,N-bis(2-chloroethyl)amine hydrochloride (2.0 g, 11.2 mmol) in dichloromethane and the mixture was stirred at room temperature for 20 minutes. The mixture was then cooled in an ice bath and methanesulfonyl chloride (1.41 g, 1.1 mmol) was added dropwise. The cooling bath was removed and the mixture was stirred for 4 hours at room temperature. Water was added to the reaction mixture and the organic layer was washed with 2M aqueous hydrochloric acid, water, dried (MgSO$_4$) and evaporated to give the title compound (1.80 g, 73%) as a white solid.

$^1$H-NMR δ (CDCl$_3$): 2.98 (s, 3H), 3.62 (m, 4H), 3.72 (m, 4H).

b) N,N-bis(2-iodoethyl)methanesulfonamide

N,N-bis(2-chloroethyl)methanesulfonamide (preparation 12a, 3.0 g, 13.6 mmol) was added to a stirred solution of sodium iodide (10.2 g, 68.1 mmol) in acetone (60 mL) and the mixture was heated to reflux in a sealed tube and left overnight. The mixture was then cooled and filtered. The filtrate was concentrated in vacuo and the residue was taken up in ethyl acetate and the organic layer was washed with water, brine, dried (MgSO$_4$) and evaporated to give the title compound (5.4 g, 98%) as a brown solid.

$^1$H-NMR δ (CDCl$_3$): 2.91 (s, 3H), 3.24 (m, 4H), 3.53 (m, 4H).

c) 6-bromo-1'-(methylsulfonyl)spiro[indoline-3,4'-piperidin]-2-one

Cesium carbonate (3.4 g, 10.6 mmol) was added portionwise over a 20 minute period to a stirred solution of tert-butyl 6-bromo-2-oxoindoline-1-carboxylate (preparation 8a, 1.0 g, 3.2 mmol) and N,N-bis(2-iodoethyl)methanesulfonamide (preparation 12b, 1.42 g, 3.5 mmol) in N,N'-dimethylformamide (50 mL) under an argon atmosphere. After the addition the mixture was warmed to room temperature and stirred overnight. Acetic acid (0.2 mL) followed by ethyl acetate and water were added to the reaction mixture and the organic layer was separated, washed with water, dried (MgSO$_4$) and evaporated. The residue was treated with a 5M solution of hydrogen chloride in 1,4-dioxane (25 mL) and the mixture was stirred and heated to 70° C. After 30 minutes, the mixture was concentrated in vacuo and the residue was purified by flash chromatography (98:2 dichloromethane/methanol) to give the title compound (0.33 g, 29%) as a pale yellow solid.

LRMS (m/z): 359/361 (M+1)$^+$.

$^1$H-NMR δ (DMSO-d$_6$): 1.82 (m, 4H), 2.96 (s, 3H), 3.38 (m, 2H), 3.52 (m, 2H), 6.99 (d, J=1.99 Hz, 1H), 7.15 (dd, J=7.97 Hz, J=1.92 Hz, 1H), 7.43 (d, J=7.97 Hz, 1H), 10.62 (s, 1H).

Preparation 13

6-bromo-1'-[(4-methylphenyl)sulfonyl]spiro[indole-3,4'-piperidin]-2(1H)-one $^1$H-NMR δ (CDCl$_3$): 2.45 (s, 3H), 3.29 (m, 4H), 3.49 (m, 4H), 7.34 (d, J=8.51 Hz, 2H), 7.70 (d, J=8.51 Hz, 2H).

c) 6-bromo-1'-(methylsulfonyl)spiro[indoline-3,4'-piperidin]-2-one

Obtained as a red solid (42%) from tert-butyl 6-bromo-2-oxoindoline-1-carboxylate (preparation 8a) and N,N-bis(2-iodoethyl)-4-methylbenzenesulfonamide (preparation 13b) following the experimental procedure as described in preparation 12c followed by purification by flash chromatography (98:2 dichloromethane/methanol).

LRMS (m/z): 435/437 (M+1)$^+$.

$^1$H-NMR δ (DMSO-d$_6$): 1.77 (m, 2H), 1.98 (m, 2H), 2.45 (s, 3H), 3.12 (m, 2H), 3.46 (m, 2H), 6.94 (s, 1H), 7.13 (d, 1H), 7.18 (d, 1H), 7.48 (d, J=7.97 Hz, 2H), 7.67 (d, J=7.97 Hz, 2H).

Preparation 14

6-bromo-1'-(4-chlorophenyl)spiro[indoline-3,4'-piperidin]-2-one

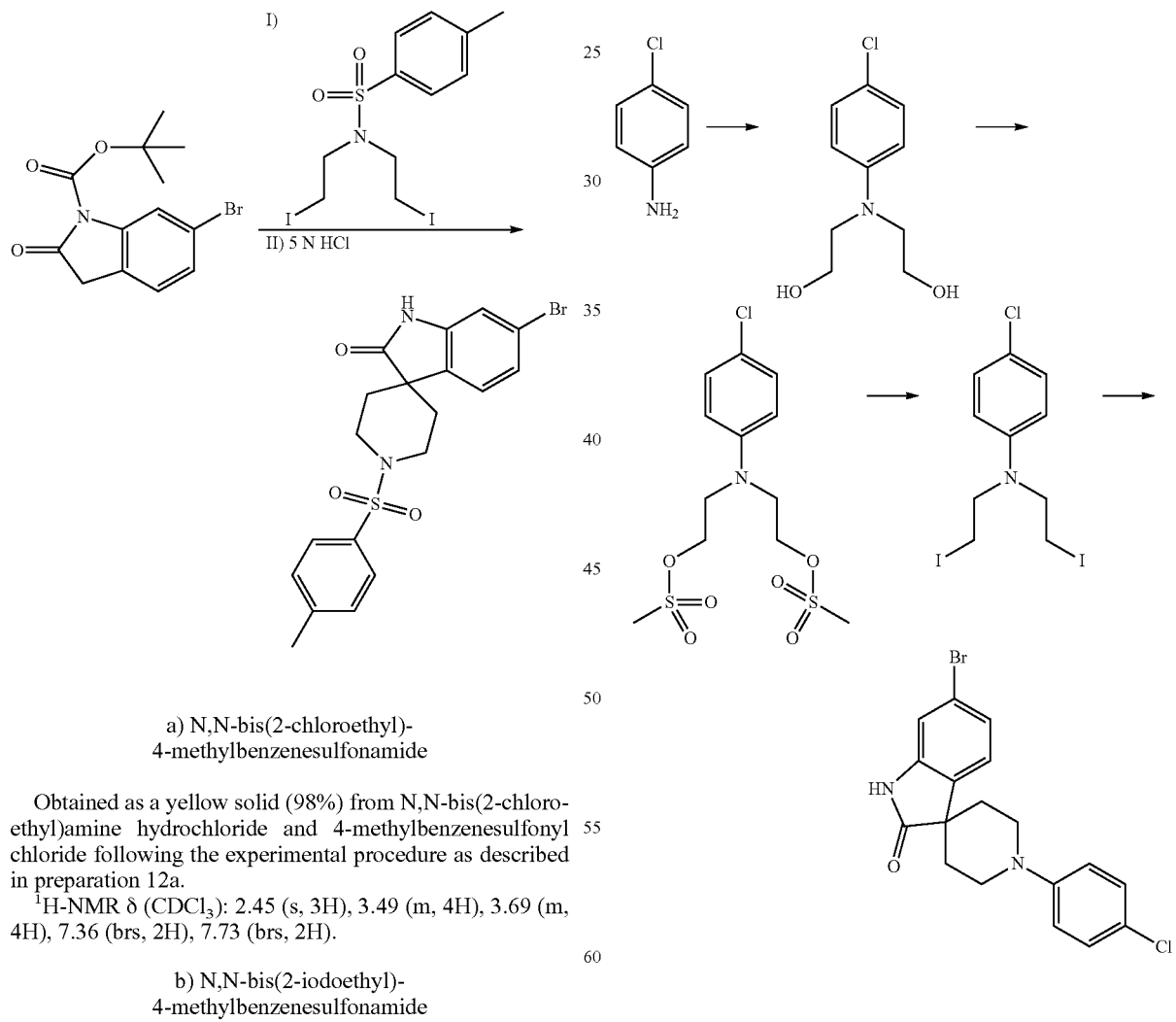

a) N,N-bis(2-chloroethyl)-4-methylbenzenesulfonamide

Obtained as a yellow solid (98%) from N,N-bis(2-chloroethyl)amine hydrochloride and 4-methylbenzenesulfonyl chloride following the experimental procedure as described in preparation 12a.

$^1$H-NMR δ (CDCl$_3$): 2.45 (s, 3H), 3.49 (m, 4H), 3.69 (m, 4H), 7.36 (brs, 2H), 7.73 (brs, 2H).

b) N,N-bis(2-iodoethyl)-4-methylbenzenesulfonamide

Obtained as a brown solid (88%) from N,N-bis(2-chloroethyl)-4-methylbenzenesulfonamide (preparation 13a) and sodium iodide following the experimental procedure as described in preparation 12b.

a) 2,2'-(4-chlorophenylazanediyl)diethanol

To a stirred suspension of 4-chloroaniline (4.51 g, 35 mmol) in water (36 mL) were added 2-chloroethanol (11.9 mL, 177 mmol) and calcium carbonate (5.0 g, 50 mmol) and the mixture was stirred and heated to reflux. After 18 hours, the mixture was cooled and extracted with diethyl ether. The organic layer was separated, dried (MgSO$_4$) and evaporated to give a semi-solid. Recrystallization from toluene (70 mL) gave the title compound (5.63 g, 74%) as a pink solid.

LRMS (m/z): 216 (M+1)$^+$.

$^1$H-NMR δ (DMSO-d$_6$): 3.37 (m, 4H), 3.49 (m, 4H), 4.73 (t, J=4.9 Hz, 2H), 6.64 (d, J=8.8 Hz, 2H), 7.11 (d, J=8.8 Hz, 2H).

b) 2,2'-(4-chlorophenylazanediyl)bis(ethane-2,1-diyl)dimethanesulfonate

A solution of 2,2'-(4-chlorophenylazanediyl)diethanol (preparation 14a, 2.0 g, 9.3 mmol) and triethylamine (2.58 mL, 18.5 mmol) in dichloromethane (10 mL) was added dropwise to a cooled (ice-bath), stirred solution of methanesulphonyl chloride (1.44 mL, 18.6 mmol) in dichloromethane (5 mL). The mixture was warmed to room temperature and stirred for 4 hours. The mixture was washed with water and the organic layer was dried (MgSO$_4$) and evaporated to give the title compound (3.5 g, 100%) as a colourless oil.

$^1$H-NMR δ (CDCl$_3$): 3.00 (s, 6H), 3.76 (m, 4H), 4.35 (m, 4H), 6.66 (d, J=7.2 Hz, 2H), 7.20 (d, J=7.2 Hz, 2H).

c) 4-chloro-N,N-bis(2-iodoethyl)aniline

A solution of 2,2'-(4-chlorophenylazanediyl)bis(ethane-2,1-diyl)dimethanesulfonate (preparation 14b, 3.45 g, 9.3 mmol) and sodium iodide (4.17 g, 27.8 mmol) in acetone (60 mL) was stirred and heated to reflux in a sealed tube. After 5 hours the suspension was cooled and filtered, washing the filter cake with several portions of acetone. The combined filtrate and washings were evaporated and the residue was partitioned between ethyl acetate and water. The organic layer was washed with saturated aqueous sodium thiosulphate solution, water, brine, dried (MgSO$_4$) and evaporated to give the title compound (3.51 g, 87%) as a white solid.

$^1$H-NMR δ (CDCl$_3$): 3.19 (t, J=7.7 Hz, 4H), 3.70 (t, J=7.7 Hz, 4H), 6.55 (d, J=9.1 Hz, 2H), 7.18 (d, J=9.1 Hz, 2H).

d) 6-bromo-1'-(4-chlorophenyl)spiro[indoline-3,4'-piperidin]-2-one

Cesium carbonate (2.09 g, 6.4 mmol) was added in portions over 5 mins to a solution of 4-chloro-N,N-bis(2-iodoethyl)aniline (preparation 14c, 0.73 g, 1.68 mmol) and tert-butyl 6-bromo-2-oxoindoline-1-carboxylate (preparation 8a, 0.50 g, 1.60 mmol) in N,N'-dimethylformamide (20 mL) was added and the mixture was stirred for 48 hours. The mixture was diluted with water and extracted with ethyl acetate and the organic layer was washed with water, brine, dried (MgSO$_4$) and evaporated. The residue was taken up in 1,4-dioxane (15 mL) and 5M aqueous hydrochloric acid (5 mL) and the mixture was stirred and heated to 70° C. After 30 minutes, the mixture was evaporated and partitioned between ethyl acetate and 2M aqueous hydrochloric acid. The organic layer was combined with an insoluble solid which separated and the mixture was evaporated. The residue was purified by flash chromatography (3:1 hexanes/ethyl acetate) to give the title compound (0.11 g, 17%) as a pink solid.

LRMS (m/z): 393 (M+1)$^+$.

$^1$H-NMR δ (DMSO-d$_6$): 1.83 (m, 4H), 3.41 (m, 2H), 3.60 (m, 2H), 7.02 (m, 3H), 7.13 (dd, J=8.2; 1.9 Hz, 1H), 7.24 (d, J=9.1 Hz, 2H), 7.42 (d, J=8.2 Hz, 1H), 10.58 (s, 1H).

Preparation 15

6-Bromo-3,3-dimethylindolin-2-one and 6-bromo-1,3,3-trimethylindolin-2-one

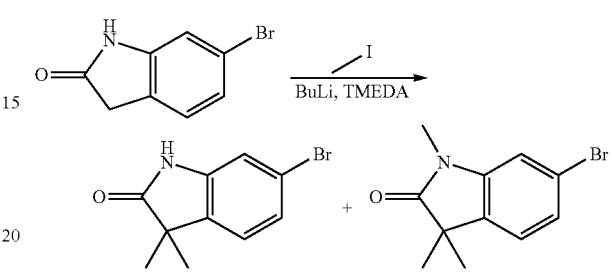

n-Butyl lithium (2.5 M in hexanes, 11.3 mL, 28.25 mmol) was added dropwise over 30 minutes to a stirred suspension of 6-bromoindolin-2-one (preparation 1, 3.00 g, 14.15 mmol) and N,N,N',N'-tetramethylethylenediamine (4.30 mL, 28.30 mmol) in tetrahydrofuran (40 mL) at −78° C. The mixture was stirred for 1 hour and then iodomethane (4.40 mL, 70.73 mmol) was added dropwise over 5 minutes. The mixture was warmed to −20° C. over a 1 hour period, was stirred for a further hour at this temperature and then was warmed to ambient temperature. After 1 hour, saturated aqueous sodium hydrogen carbonate solution was added to the reaction and the mixture was extracted with ethyl acetate. The organic layer was washed with water, brine, dried (MgSO$_4$) and evaporated. Purification of the residue by flash chromatography (5:1 hexanes/ethyl acetate) gave 6-bromo-3,3-dimethylindolin-2-one (0.97 g, 29%) and 6-bromo-1,3,3-trimethylindolin-2-one (0.68 g, 19%).

6-Bromo-3,3-dimethylindolin-2-one

LRMS (m/z): 240/242 (M+1)$^+$.

$^1$H-NMR δ (CDCl$_3$): 1.39 (s, 6H), 7.06 (d, J=9.0 Hz, 1H), 7.09 (s, 1H), 7.19 (d, J=9.0 Hz, 1H), 8.26 (brs, 1H).

6-Bromo-1,3,3-trimethylindolin-2-one

LRMS (m/z): 254/256 (M+1)$^+$.

$^1$H-NMR δ (CDCl$_3$): 1.36 (s, 6H), 3.20 (s, 3H), 7.00 (s, 1H), 7.07 (d, J=9.0 Hz, 1H), 7.20 (d, J=9.0 Hz, 1H).

Preparation 16

6-Bromo-3,3-dimethylindolin-2-one

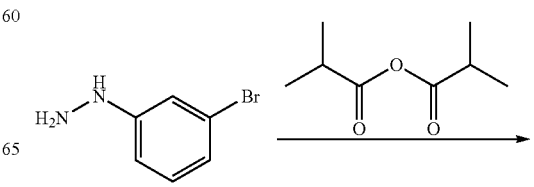

a) N'-(3-Bromophenyl)isobutyrohydrazide

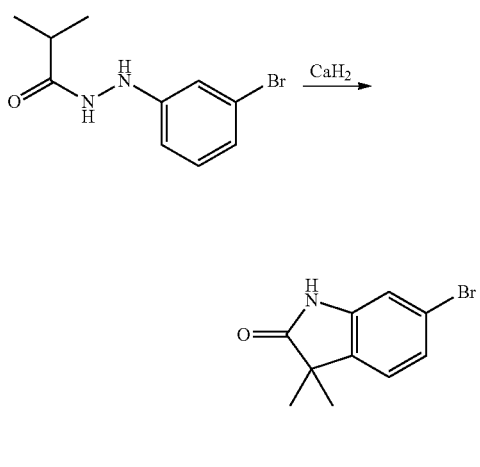

Isobutyric anhydride (4.80 mL, 28.70 mmol) was added dropwise to a stirred solution of 3-bromophenylhydrazine hydrochloride (6.10 g, 27.30 mmol) and triethylamine (7.60 mL, 54.50 mmol) in dichloromethane at 0° C. After the addition the mixture was warmed to ambient temperature and stirred for three hours. The mixture was then concentrated in vacuo and the residue was partitioned between ethyl acetate and water. The organic layer was washed with saturated aqueous sodium hydrogen carbonate solution, dried (MgSO$_4$) and evaporated. The residue was triturated with diethyl ether and the solid was filtered and dried to give the title compound (5.50 g, 78%) as a white solid.

LRMS (m/z): 257/259 (M+1)$^+$.

$^1$H-NMR δ (CDCl$_3$): 1.22-1.25 (d, 6H), 2.43-2.51 (m, 1H), 6.16 (brs, 1H), 6.72-6.75 (m, 1H), 6.95 (brs, 1H), 7.00-7.11 (m, 2H), 7.33 (brs, 1H).

b) 6-Bromo-3,3-dimethylindolin-2-one

A mixture of N'-(3-bromophenyl)isobutyrohydrazide (preparation 16a, 3.10 g, 11.90 mmol) and calcium hydride (0.75 g, 17.9 mmol) in a Schlenk tube equipped with an air condenser was heated to 180° C. over 25 minutes then to 210° C. over 15 minutes, and finally to 230° C. over 30 minutes. The mixture was then cooled to room temperature and a mixture of methanol and water was added with stirring and, after gas evolution had ceased, concentrated hydrochloric acid was added until the pH was 1-2. Water was then added and the mixture was heated to 100° C. After 1 hour the mixture was cooled to 0° C., taken to pH 3 with 6M aqueous sodium hydroxide solution and extracted with ethyl acetate. The organic layer was washed with water and brine, dried (MgSO$_4$) and evaporated. The residue was purified by flash chromatography (10:1 hexanes/EtOAc) to give the title compound (0.70 g, 24%) as a white solid.

LRMS (m/z): 240/242 (M+1)$^+$.

$^1$H-NMR δ (CDCl$_3$): 1.39 (s, 6H), 7.06 (d, J=9.0 Hz, 1H), 7.09 (s, 1H), 7.19 (d, J=9.0 Hz, 1H), 8.24 (brs, 1H).

Preparation 17

3,3-Dimethyl-6-(4,4,5,5-tetramethyl-1,3,2-dioxaborolan-2-yl)indolin-2-one

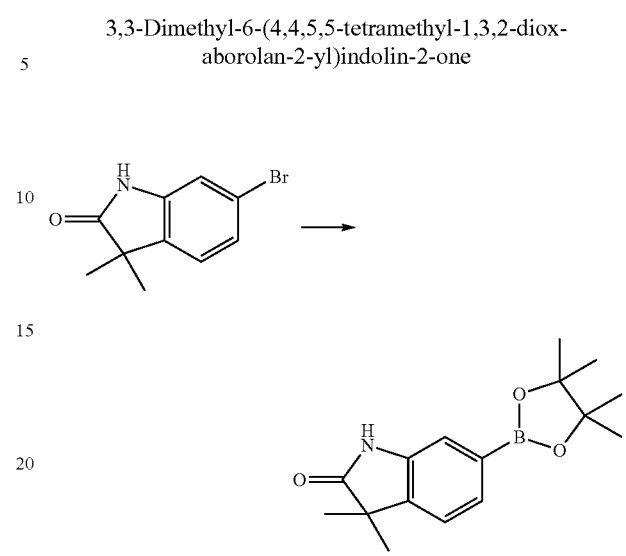

Obtained as a solid from 6-bromo-3,3-dimethylindolin-2-one (preparation 16) following the experimental procedure as described in preparation 9. The desired crude compound was obtained in quantitative yield and was used without further purification.

LRMS (m/z): 288 (M+1)$^+$.

$^1$H-NMR δ (CDCl$_3$): 1.26-1.40 (m, 18H), 7.23 (d, J=7.5 Hz, 1H), 7.34 (s, 1H), 7.54 (d, J=7.5 Hz, 1H), 8.00 (brs, 1H).

Preparation 18

6-Bromo-2',3',5',6'-tetrahydrospiro[indoline-3,4'-thiopyran]-2-one

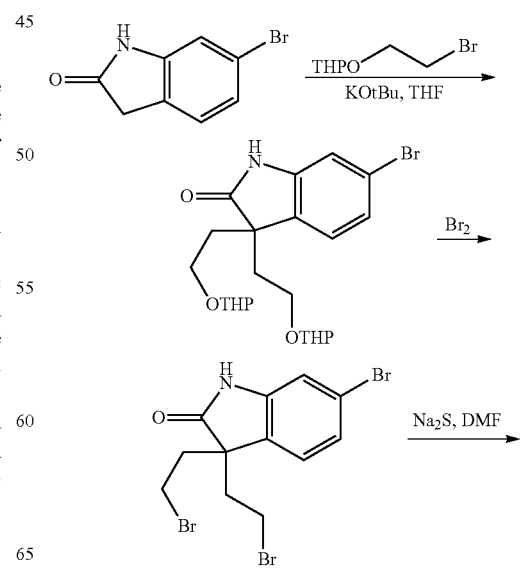

57

-continued

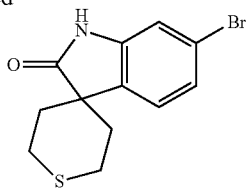

a) 6-Bromo-3,3-bis(2-(tetrahydro-2H-pyran-2-yloxy) ethyl)indolin-2-one

Potassium tert-butoxide (1.06 g, 9.43 mmol) was added portionwise to a stirred suspension of 6-bromoindolin-2-one (preparation 1, 0.50 g, 2.36 mmol) in tetrahydrofuran (5 mL) at −75° C. The mixture was warmed to room temperature and stirred for 1 hour and then recooled to −75° C. Then, 2-(2-bromoethoxy)tetrahydro-2H-pyran (0.75 mL, 4.95 mmol) was added dropwise and the reaction was warmed to room temperature. After 4 hours, water was added and the mixture was extracted with ethyl acetate. The organic layer was washed with brine, dried (MgSO$_4$) and evaporated. Purification of the residue by flash chromatography (3:1 hexanes/ethyl acetate) gave the title compound (0.65 g, 59%) as a pale yellow oil.

LRMS (m/z): 468/470 (M+1)$^+$.

$^1$H-NMR δ (CDCl$_3$): 1.40-1.62 (m, 12H), 2.20-2.13 (m, 2H), 2.28-2.38 (m, 2H), 3.08 (m, 2H), 3.33-3.66 (m, 8H), 7.05 (s, 1H), 7.07 (d, J=6.0 Hz, 1H), 7.18 (d, J=6.0 Hz, 1H).

b) 6-Bromo-3,3-bis(2-bromoethyl)indolin-2-one

Bromine (0.20 g, 1.28 mmol) was added dropwise to a stirred suspension of 6-bromo-3,3-bis(2-(tetrahydro-2H-pyran-2-yloxy)ethyl)indolin-2-one (preparation 18a, 0.30 g, 0.64 mmol) and triphenylphosphine (0.33 g, 1.28 mmol) in dichloromethane (7 mL) at 0° C. and then the mixture was warmed to room temperature. After 3 hours, water was added and the mixture was extracted with dichloromethane. The organic layer was washed with brine, dried (MgSO$_4$) and evaporated. Purification of the residue by flash chromatography (6:1 hexanes/ethyl acetate) gave the title compound (0.05 g, 18%) as a white solid.

$^1$H-NMR δ (CDCl$_3$): 2.27-2.37 (m, 2H), 2.47-2.57 (m, 2H), 2.90-2.99 (m, 2H), 3.05-3.13 (m, 2H), 7.06 (d, J=9.0 Hz, 1H), 7.10 (s, 1H), 7.26 (d, J=9.0 Hz, 1H).

c) N'-6-Bromo-2',3',5',6'-tetrahydrospiro[indoline-3,4'-thiopyran]-2-one

Sodium sulfide (0.33 g, 4.23 mmol) was added to a stirred solution of 6-bromo-3,3-bis(2-bromoethyl)indolin-2-one (preparation 18b, 0.60 g, 1.41 mmol) in N,N'-dimethylformamide (5 mL) at room temperature and then the mixture was warmed to 50° C. After 2 hours, water was added and the mixture was extracted with dichloromethane. The organic layer was washed with water, dried (MgSO$_4$) and evaporated give the title compound (0.40 g, 95%) as a white solid.

LRMS (m/z): 296/298 (M−1)$^−$.

58

$^1$H-NMR δ (DMSO-d$_6$): 1.85-1.93 (m, 4H), 2.64-2.70 (m, 2H), 3.04-3.13 (m, 2H), 6.99 (s, 1H), 7.15 (d, J=9.0 Hz, 1H), 7.39 (d, J=9.0 Hz, 1H), 10.56 (brs, 1H).

Preparation 19

6-Bromo-2',3',5',6'-tetrahydrospiro[indoline-3,4'-thiopyran]-2-one

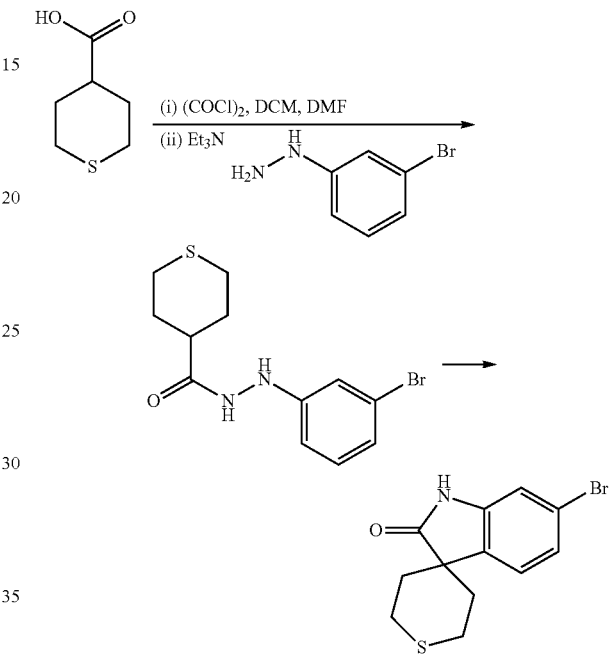

a) N'-(3-Bromophenyl)tetrahydro-2H-thiopyran-4-carbohydrazide

Oxalyl chloride (1.20 mL, 14.2 mmol) was added dropwise to a stirred solution of tetrahydro-2H-thiopyran-4-carboxylic acid (WO2007006732, 2.00 g, 13.7 mmol) in dichloromethane (25 mL). Then, two drops of N,N'-dimethylformamide were added and stirring was continued. After 1.5 hours, the resultant solution was added dropwise over 30 minutes to a stirred, cooled (ice-bath) solution of (3-bromophenyl)hydrazine hydrochloride (3.05 g, 13.7 mmol) and triethylamine (4.20 mL, 30.1 mmol) in dichloromethane (40 mL). After the addition, the mixture was warmed to room temperature and stirred for two hours. The mixture was then concentrated in vacuo and the residue was partitioned between ethyl acetate and water. The organic layer was washed with 4% aqueous sodium hydrogen carbonate solution, dried (MgSO$_4$) and evaporated. The residue was triturated with diethyl ether and the solid was filtered and dried to give the title compound (2.57 g, 60%) as an off-white solid.

LRMS (m/z): 315/317 (M+1)$^+$.

$^1$H-NMR δ (DMSO-d$_6$): 1.62-1.76 (m, 2H), 2.00-2.07 (m, 2H), 2.28-2.37 (m, 1H), 2.63-2.67 (m, 4H), 6.66 (d, J=9.0 Hz, 1H), 6.79 (t, J=3.0 Hz, 1H), 6.84 (d, J=9.0 Hz, 1H), 7.08 (t, J=9.0 Hz, 1H), 8.00 (brs, 1H), 9.71 (brs, 1H).

b) N'-6-Bromo-2',3',5',6'-tetrahydrospiro[indoline-3, 4'-thiopyran]-2-one

A suspension of N'-(3-bromophenyl)tetrahydro-2H-thiopyran-4-carbohydrazide (preparation 19a, 1.45 g, 4.60 mmol) in tetralin (20 mL) was subjected to three vacuum-argon cycles and then freshly ground calcium hydride (0.39 g, 9.30 mmol) was added. The stirred mixture was warmed slowly over a 3 hour period to 230-240° C. in a sand-bath and then stirred at this temperature for 3.5 hours. The mixture was cooled in an ice-bath and a mixture of methanol (2 mL) and water (2 mL) was added dropwise. After gas evolution had abated, the mixture was acidified with concentrated aqueous hydrochloric acid, diluted with water and extracted with ethyl acetate. The organic layer was washed with brine, dried (MgSO$_4$) and evaporated in vacuo. The resultant oil was purified by flash chromatography on silica gel (100% hexanes to 5:1 hexanes/ethyl acetate) to give the title compound (0.37 g, 27%) as a white solid.

LRMS (m/z): 296/298 (M−1)⁻.

$^1$H-NMR δ (DMSO-d$_6$): 1.85-1.93 (m, 4H), 2.64-2.70 (m, 2H), 3.04-3.13 (m, 2H), 6.99 (s, 1H), 7.15 (d, J=9.0 Hz, 1H), 7.39 (d, J=9.0 Hz, 1H), 10.56 (brs, 1H).

Preparation 20

6-Bromo-3,3-bis(2-hydroxyethyl)indolin-2-one

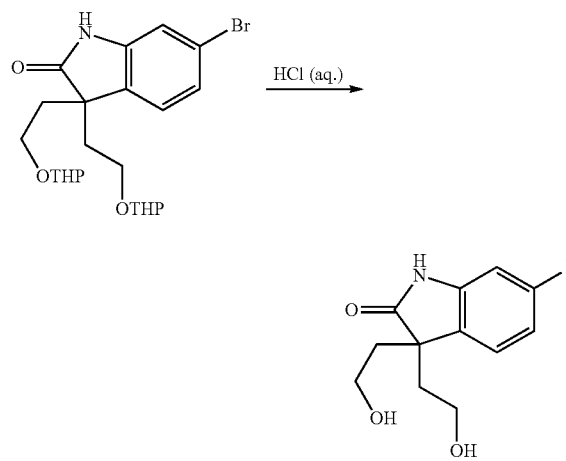

5M Aqueous hydrochloric acid (5M, 1.50 mL) was added to a stirred solution of 6-bromo-3,3-bis(2-(tetrahydro-2H-pyran-2-yloxy)ethyl)indolin-2-one (preparation 18a, 0.62 g, 1.32 mmol) in 1,4-dioxane (3 mL) at room temperature and then mixture was stirred and heated to 60° C. After 2 hours, the mixture was cooled and water was added to the mixture. The mixture was extracted with diethyl ether and the aqueous phase was evaporated in vacuo to give the title compound (0.20 g, 50%) as a solid.

LRMS (m/z): 300/302 (M+1)⁺.

$^1$H-NMR δ (DMSO-d$_6$): 1.92-1.98 (m, 4H), 2.99-3.14 (m, 4H), 6.98 (d, J=3.0 Hz, 1H), 7.19 (dd, J=9.0 and 3.0 Hz, 1H), 7.26 (d, J=9.0 Hz, 1H), 10.46 (brs, 1H).

Preparation 21

6'-Bromo-4,4-difluorospiro[cyclohexane-1,3'-indolin]-2'-one

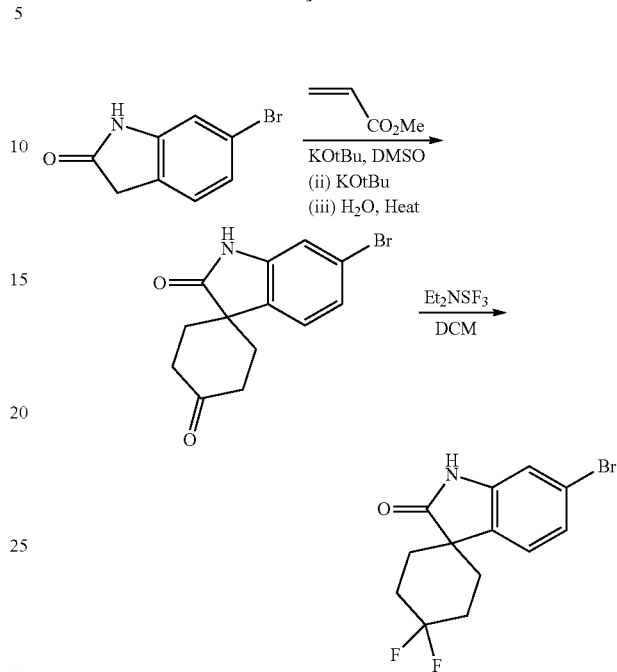

a) 6'-Bromospiro[cyclohexane-1,3'-indoline]-2',4-dione

Potassium tert-butoxide (0.085 g, 0.8 mmol) was added to a suspension of 6-bromoindolin-2-one (preparation 1, 3.00 g, 14.2 mmol) in dimethylsulphoxide (7 mL) and, after stirring for 10 minutes at room temperature, the mixture was heated to 40-45° C. and methyl acrylate (4.00 mL, 44.4 mmol) was added dropwise over 70 minutes. After the addition, the mixture was stirred for 1 hour and then further potassium tert-butoxide (3.82 g, 34.0 mmol) was added portionwise over 30 minutes keeping the temperature below 50° C. The mixture was then heated to 100° C. and stirred for 1.5 hours. Water (45 mL) was added and heating was continued at 85° C. for 4 hours and then the mixture was left to cool overnight. The resultant precipitate was filtered and the solid washed with water and hexanes to give the crude product. Recrystallization from ethyl alcohol gave the title compound (1.95 g, 42%) as a white solid.

LRMS (m/z): 292/294 (M−1)⁻.

$^1$H-NMR δ (DMSO-d$_6$): 1.99-2.08 (m, 2H), 2.13-2.22 (m, 2H), 2.41-2.50 (m, 2H), 2.82-2.92 (m, 2H), 7.07 (d, J=3.0 Hz, 1H), 7.21 (dd, J=9.0 and 3.0 Hz, 1H), 7.50 (d, J=9.0 Hz, 1H), 10.70 (brs, 1H).

b) 6'-Bromo-4,4-difluorospiro[cyclohexane-1,3'-indolin]-2'-one

Diethylaminosulfur trifluoride (0.40 mL, 3.1 mmol) was added dropwise to a suspension of 6'-bromospiro[cyclohexane-1,3'-indoline]-2',4-dione (preparation 21a, 0.30 g, 1.0 mmol) in dichloromethane (3 mL). The mixture was stirred at ambient temperature overnight and then added dropwise to an ice-water mixture. After stirring for 20 minutes, the mixture was neutralized with a 4% aqueous sodium hydrogen carbonate solution and extracted with ethyl acetate. The organic layer was dried (MgSO$_4$) and evaporated to give an oil. Purification by reverse phase chromatography (C-18 silica from Waters©, water/acetonitrile/methanol as eluents [0.1% v/v formic acid buffered] 0% to 60%) gave the title compound (0.13 g, 41%) as a white solid.

LRMS (m/z): 314/316 (M−1)$^-$.

$^1$H-NMR δ (CDCl$_3$): 1.80-2.20 (m, 6H), 2.60 (m, 2H), 7.02-7.21 (m, 3H), 7.80 (brs, 1H).

Preparation 22

4,4-Difluoro-6'-(4,4,5,5-tetramethyl-1,3,2-dioxaborolan-2-yl)spiro[cyclohexane-1,3'-indolin]-2'-one

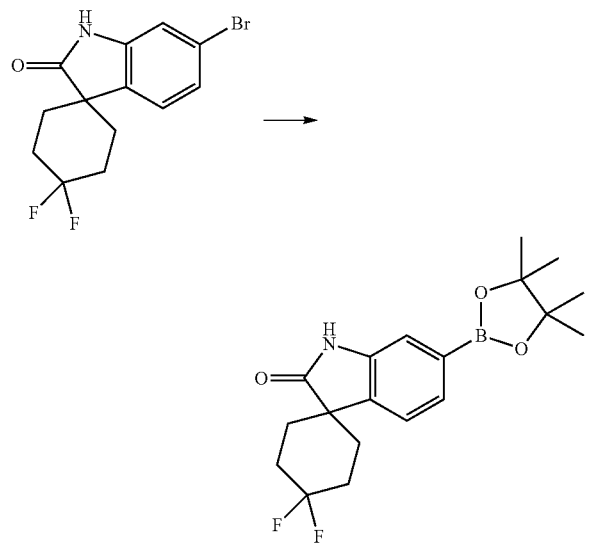

Obtained as a white solid (76%) from 6'-bromo-4,4-difluorospiro[cyclohexane-1,3'-indolin]-2'-on (preparation 21) following the experimental procedure as described in preparation 9, followed by purification of the crude product by flash chromatography (1:1 hexanes/ethyl acetate).

LRMS (m/z): 362 (M−1)$^-$.

$^1$H-NMR δ (CDCl$_3$): 1.36 (s, 12H), 1.94-2.18 (m, 6H), 2.54-2.75 (m, 2H), 7.27 (d, J=6.0 Hz, 1H), 7.36 (s, 1H), 7.55 (d, J=6.0 Hz, 1H), 8.26 (brs, 1H).

Preparation 23

6'-bromo-4-hydroxyspiro[cyclohexane-1,3'-indolin]-2'-one

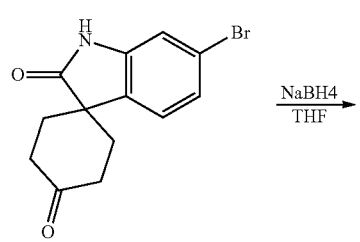

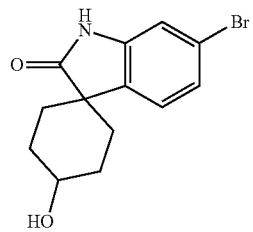

Sodium borohydride (77 mg, 2.0 mmol) was added portionwise to a stirred suspension of 6'-bromospiro[cyclohexane-1,3'-indoline]-2',4-dione (preparation 21a, 0.30 g, 1.0 mmol) in methanol (14 mL) at room temperature. After 2.5 hours the mixture was concentrated in vacuo and water was added. The mixture was extracted with ethyl acetate and the organic layer was dried (MgSO$_4$) and evaporated to give the title compound as a mixture of isomers. Separation of the isomers was achieved by reverse phase chromatography (C-18 silica from Waters©, water/acetonitrile/methanol as eluents [0.1% v/v formic acid buffered] 0% to 60%) to give, in order of elution, the pure minor isomer as a white solid (0.075 g, 25%):

LRMS (m/z): 296/298 (M+1)$^+$.

$^1$H-NMR δ (CDCl$_3$): 1.83 (m, 6H), 2.20 (m, 2H), 4.00 (m, 1H), 7.06 (d, J=1.65 Hz, 1H), 7.18 (dd, J=7.97 Hz, J=1.65 Hz 1H), 7.35 (d, J=7.97 Hz, 1H), 7.62 (s, 1H)

followed by the major isomer as a white solid (0.140 g, 46%):

LRMS (m/z): 296/298 (M+1)$^+$.

$^1$H-NMR δ (CDCl$_3$): 1.70 (m, 2H), 1.96 (m, 4H), 2.15 (m, 2H), 3.89 (m, 1H), 7.06 (m, 2H), 7.15 (m, 1H), 7.68 (brs, 1H).

Preparation 24

6'-bromo-4-hydroxy-4-methylspiro[cyclohexane-1,3'-indolin]-2'-one

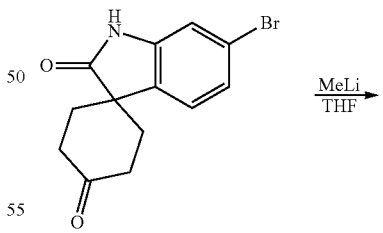

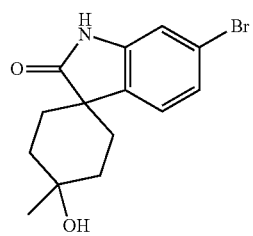

Methyl lithium (1.6M in diethyl ether, 4.89 mL, 7.82 mmol) was added dropwise to a stirred solution of 6'-bromospiro[cyclohexane-1,3'-indoline]-2',4-dione (preparation 21a, 1.00 g, 3.40 mmol) in tetrahydrofuran (30 mL) at −78° C. The mixture was warmed to 0° C. over 3 hours and stirred at room temperature for additional 4.5 hours. Saturated aqueous ammonium chloride solution (20 mL) was added to the reaction and the mixture was extracted with ethyl acetate. The organic layer was separated, washed with brine, dried (MgSO$_4$) and evaporated to give a mixture of isomers of the title compound. Purification of the residue by flash chromatography (97:3 dichloromethane/methanol) gave the two pure isomers of the title compound.

Major isomer (0.661 g, 63%) as a white solid

LRMS (m/z): 310/312 (M+1)$^+$.

$^1$H-NMR δ (CDCl$_3$): 1.39 (s, 3H), 1.47-1.60 (m, 3H), 1.78-1.97 (m, 4H), 2.16-2.26 (m, 2H), 7.08 (d, J=1.6 Hz, 1H), 7.15 (dd, J=8.0 Hz, J'=1.65 Hz, 1H), 7.21 (d, J=8.0 Hz, 1H), 7.66 (brs, 1H).

Minor isomer (0.244 g, 23%) as a white solid

LRMS (m/z): 310/312 (M+1)$^+$.

$^1$H-NMR δ (CDCl$_3$): 1.15 (brs, 1H), 1.39 (s, 3H), 1.61-1.73 (m, 2H), 2.02-2.12 (m, 3H), 2.19-2.28 (m, 3H), 7.01 (s, 1H), 7.16 (s, 2H), 7.51 (brs, 1H).

Preparation 25

4-hydroxy-4-methyl-6'-(4,4,5,5-tetramethyl-1,3,2-dioxaborolan-2-yl)spiro[cyclohexane-1,3'-indolin]-2'-one

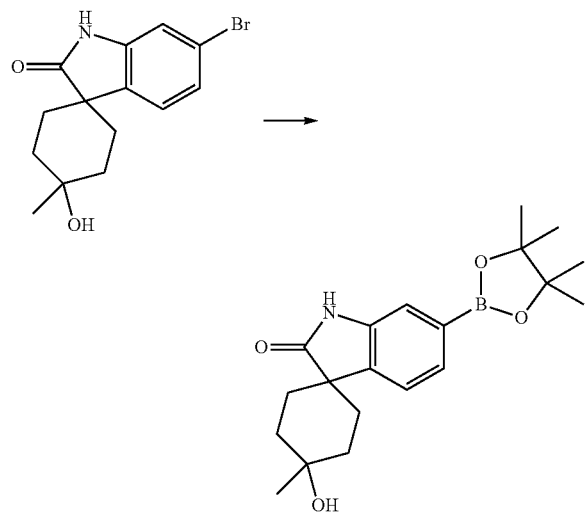

Obtained as a solid from 6'-bromo-4-hydroxy-4-methylspiro[cyclohexane-1,3'-indolin]-2'-one (preparation 24, major isomer) following the experimental procedure as described in preparation 9. The desired crude compound was obtained in quantitative yield and was used without further purification.

LRMS (m/z): 358 (M+1)$^+$.

$^1$H-NMR δ (CDCl$_3$): 1.35 (s, 12H), 1.41 (s, 3H), 1.54-1.62 (m, 2H), 1.83-1.96 (m, 4H), 2.16-2.26 (m, 2H), 2.63 (s, 1H), 7.35-7.37 (m, 2H), 7.50 (d, J=7.4 Hz, 1H), 7.73 (brs, 1H).

Preparation 26

6'-bromo-4-morpholin-4-ylspiro[cyclohexane-1,3'-indol]-2'(1'H)-one

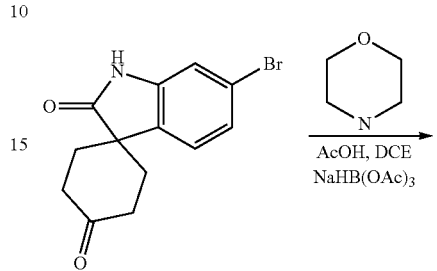

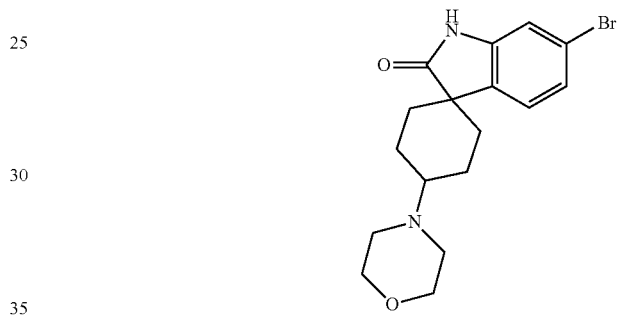

Acetic acid (74 µl, 1.29 mmol) was added to a stirred solution of 6'-bromospiro[cyclohexane-1,3'-indoline]-2',4-dione (preparation 21a, 0.38 g, 1.29 mmol) and morpholine (123 µl, 1.1 mmol) in 1,2-dichloroethane (5 mL). The mixture was cooled to 0° C. and sodium triacetoxy borohydride (0.356 g, 1.68 mmol) was added portionwise. After the addition, the cooling bath was removed and the mixture was stirred at room temperature for 18 hours. Water and dichloromethane were added to the reaction mixture and the organic layer was washed with water, dried (MgSO$_4$) and the solvent was evaporated to give the crude oily product as a mixture of isomers. Separation of the isomers was achieved by flash chromatography (98:2 dichloromethane/methanol):

Minor isomer (10%) as a white solid

LRMS (m/z): 363/365 (M−1)$^+$.

$^1$H-NMR δ (DMSO-d$_6$): 1.53-1.91 (m, 8H), 2.38 (m, 1H), 2.51 (m, 4H), 3.61 (m, 4H), 7.02 (d, J=1.74 Hz, 1H), 7.15 (d, J=7.97 Hz, 1H), 7.41 (dd, J=7.97 Hz, J=1.74 Hz, 1H), 10.56 (s, 1H)

Major isomer (23%) as a white solid:

LRMS (m/z): 363/365 (M−1)$^+$.

$^1$H-NMR δ (DMSO): 1.70-2.05 (m, 8H), 2.38 (m, 1H), 2.50 (m, 4H), 3.59 (m, 4H), 6.99 (d, 1H), 7.10 (m, 1H), 7.22 (m, 1H), 10.36 (s, 1H)

Preparation 27

6'-bromo-4-(2-morpholinoethoxy)spiro[cyclohexane-1,3'-indolin]-2'-one

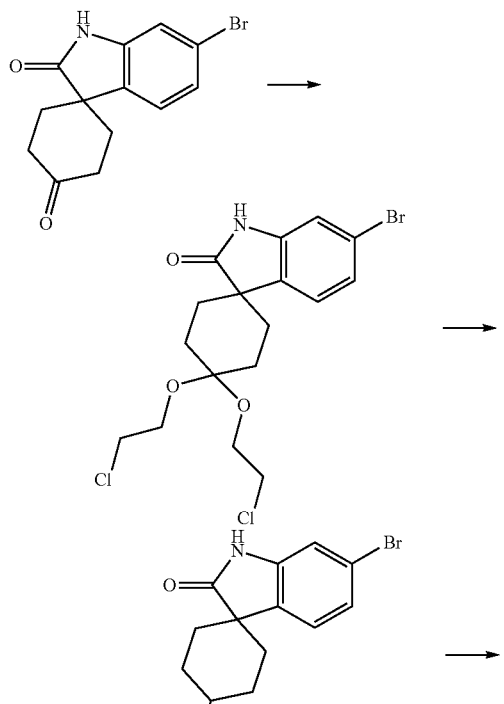

a) 6'-bromo-4,4-bis(2-chloroethoxy)spiro[cyclohexane-1,3'-indolin]-2'-one

A mixture of 6'-bromospiro[cyclohexane-1,3'-indoline]-2',4-dione (preparation 21a, 4.0 g, 13.6 mmol), 2-chloroethanol (20 mL), methanesulphonic acid (0.25 mL) and freshly activated molecular sieves (20 g) in dichloromethane (20 mL) and toluene (40 mL) was stirred at ambient temperature for 4 days. Solid sodium hydrogen carbonate was added to neutralize the mixture and the suspension was filtered and the filter cake was washed with several portions of dichloromethane. The filtrate and washings were combined and evaporated and the residue was purified by flash chromatography (200:1 dichloromethane/methanol) to give the title compound (3.9 g, 66%) as a white solid.

LRMS (m/z): 436 (M−1)$^+$.

$^1$H-NMR δ (DMSO-d$_6$): 1.69 (m, 4H), 1.86 (m, 2H), 2.15 (m, 2H), 3.74 (m, 6H), 3.81 (m, 2H), 6.96 (s, 1H), 7.16 (m, 2H), 10.48 (s, 1H).

b) 6'-bromo-4-(2-morpholinoethoxy)spiro[cyclohexane-1,3'-indolin]-2'-one

A solution of zinc borohydride (0.25 M in diethyl ether, 3.48 mL, 0.87 mmol) was added dropwise over a 5 minute period to a stirred, cooled (ice-bath) suspension of 6'-bromo-4,4-bis(2-chloroethoxy)spiro[cyclohexane-1,3'-indolin]-2'-one (preparation 27a, 0.81 g, 1.9 mmol) in dichloromethane (5 mL). Subsequently, trimethylsilyl chloride (0.46 mL, 3.64 mmol) was added dropwise and the mixture was warmed to room temperature and stirred overnight. Saturated aqueous sodium hydrogen carbonate solution and ethyl acetate were added to the mixture and stirring was continued for 1 hour. The organic layer was separated, washed with brine, dried (MgSO$_4$) and evaporated to give a white solid. The solid was taken up in N,N'-dimethylformamide (6 mL) and morpholine (0.45 mL, 5.14 mmol) and sodium iodide (0.2 g, 1.6 mmol) were added and the mixture was heated with stirring to 85° C. in a sealed tube. After stirring overnight, the mixture was diluted with water, saturated aqueous sodium hydrogen carbonate solution was added and the mixture was extracted with ethyl acetate. The organic layer was extracted with 2M aqueous hydrochloric acid solution (3×20 mL) and the combined aqueous layer was washed with ethyl acetate. The resulting aqueous solution was made strongly basic with solid sodium hydroxide and then extracted with ethyl acetate. The organic layer was dried (MgSO$_4$) and evaporated and the residue was purified by flash chromatography (100:1 to 25:1 dichloromethane/methanol) to give the title compound (0.21 g, 28%, 92:8 mixture of isomers) as a white solid.

LRMS (m/z): 409/411 (M+1)$^+$.

Preparation 28

4-(2-morpholinoethoxy)-6'-(4,4,5,5-tetramethyl-1,3,2-dioxaborolan-2-yl)spiro[cyclohexane-1,3'-indolin]-2'-one

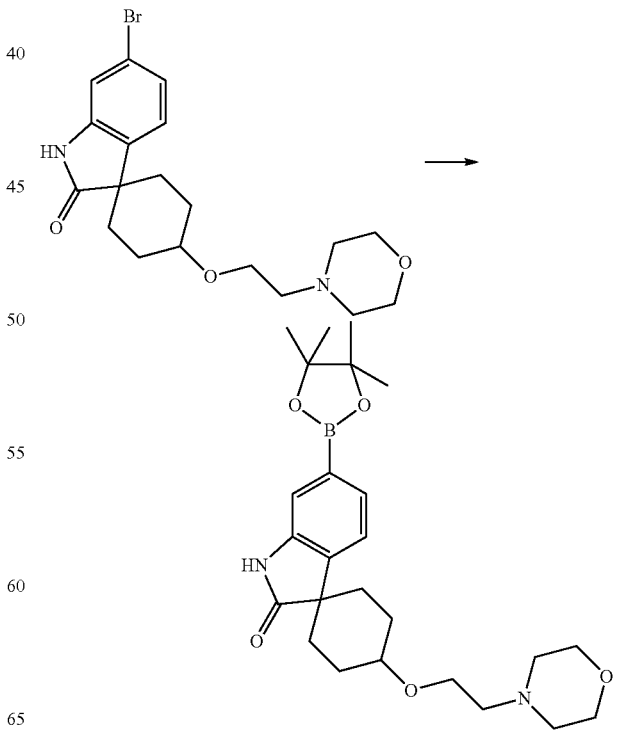

Obtained as a brown oil from 6'-bromo-4-(2-morpholinoethoxy)spiro[cyclohexane-1,3'-indolin]-2'-one (preparation 27) following the experimental procedure as described in preparation 9. The desired crude compound was obtained in quantitative yield and was used without further purification.

LRMS (m/z): 457 (M+1)$^+$.

Preparation 29

6'-Chlorospiro[cyclopentane-1,3'-pyrrolo[2,3-b]pyridin]-2'(1'H)-one

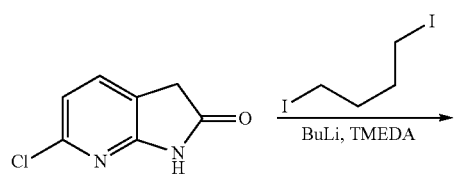

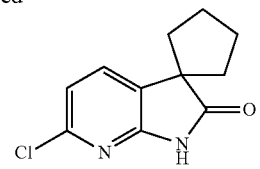

Obtained as a white solid (37%) from 6-chloro-1H-pyrrolo[2,3-b]pyridin-2(3H)-one 6-bromoindolin-2-one (US20040072836) and 1,4-diiodobutane following the experimental procedure as described in preparation 2 followed by purification of the crude product by flash chromatography (3:1 hexanes/ethyl acetate).

LRMS (m/z): 223 (M+1)$^+$.

$^1$H-NMR δ (CDCl$_3$): 1.81-1.97 (m, 4H), 2.05-2.12 (m, 2H), 2.17-2.25 (m, 2H), 6.98 (d, J=6.0 Hz, 1H), 7.37 (d, J=6.0 Hz, 1H), 7.81 (brs, 1H).

Preparation 30

6'-bromo-2,3,5,6-tetrahydrospiro[pyran-4,3'-pyrrolo[3,2-b]pyridin]-2'(1'H)-one

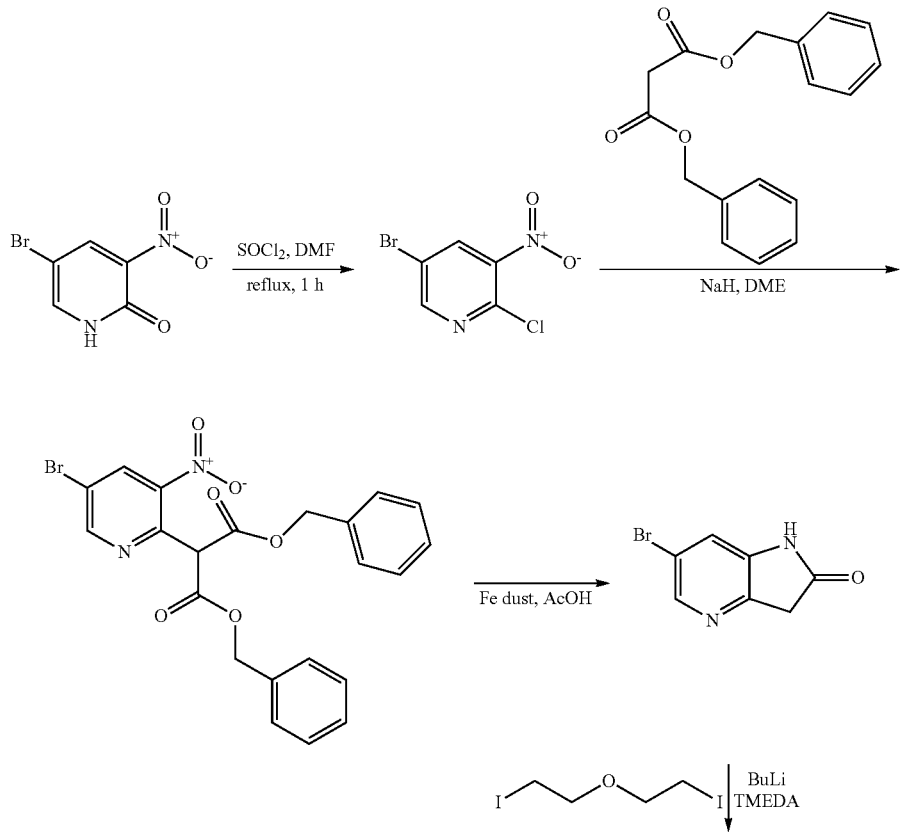

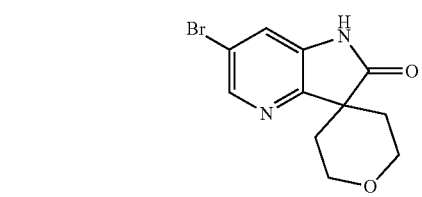

a) 5-Bromo-2-chloro-3-nitropyridine

N,N'-dimethylformamide (3 mL) was added to a mixture of 5-bromo-2-hydroxy-3-nitropyridine (16.54 g, 80 mmol) and thionyl chloride (43 mL) and the mixture was stirred and heated to reflux. After 1 hour, the solution was cooled and the solvent was evaporated. The mixture was co-evaporated with toluene to give a dark solid. Purification by flash chromatography (10:1 hexanes/ethyl acetate) gave the title compound (14.63 g, 82%) as a yellow solid.

$^1$H-NMR δ (CDCl$_3$): 8.38 (d, J=3.0 Hz, 1H), 8.70 (d, J=3.0 Hz, 1H).

b) Dibenzyl 2-(5-bromo-3-nitropyridin-2-yl)malonate

Dibenzyl malonate (14.35 g, 50.5 mmol) in dimethoxyethane (40 mL) was added dropwise to a suspension of sodium hydride (60% in mineral oil, 2.00 g, 50.5 mmol) in dimethoxyethane (55 mL). After the addition the mixture was stirred an additional 30 minutes, a solution of bromo-2-chloro-3-nitropyridine (preparation 30a, 6.00 g, 25.3 mmol) in dimethoxymethane (50 mL) was added dropwise, and the red mixture was stirred overnight. The mixture was poured into water, the pH of the solution was adjusted to 3 with 1M aqueous hydrochloric acid and the mixture was extracted with ethyl acetate. The organic layer was washed with brine, dried (MgSO$_4$) and evaporated. The residue was dissolved in the minimum amount of toluene and several volumes of hexanes were added whilst scratching the reaction vessel to give a solid which after filtration and drying furnished the title compound (10.60 g, 80%).

LRMS (m/z): 485/487 (M+1)$^+$.

$^1$H-NMR δ (CDCl$_3$): 5.24 (s, 1H), 5.25 (s, 1H), 7.30-7.35 (m, 10H), 8.61 (s, 1H), 8.80 (s, 1H).

c) 6-Bromo-1H-pyrrolo[3,2-b]pyridin-2(3H)-one

Iron dust (0.82 g, 14.60 mmol) was added to a solution of dibenzyl 2-(5-bromo-3-nitropyridin-2-yl)malonate (preparation 30b, 1.78 g, 3.70 mmol) in glacial acetic acid (50 mL) and the mixture was heated with stirring to 120° C. After 7 hours, the mixture was cooled and left to stand overnight. The reaction was poured onto ice-water and extracted first with ethyl acetate and then with chloroform. The combined organic extract was washed with brine, dried (MgSO$_4$) and evaporated in vacuo. Purification of the residue by flash chromatography (98:2 dichloromethane/methanol) gave the title compound (0.42 g, 54%) as a pink solid.

LRMS (m/z): 213/215 (M+1)$^+$.

$^1$H-NMR δ (DMSO-d$_6$): 3.58 (s, 2H), 7.31 (d, J=3.0 Hz, 1H), 8.18 (d, J=3.0 Hz, 1H), 10.69 (brs, 1H).

d) 6'-bromo-2,3,5,6-tetrahydrospiro[pyran-4,3'-pyrrolo[3,2-b]pyridin]-2'(1'H)-one Obtained as a off-white solid (13%) from 6-bromo-1H-pyrrolo[3,2-b]pyridin-2(3H)-one (preparation 30c) and 1-iodo-2-(2-iodoethoxy)ethane following the experimental procedure as described in preparation 2 followed by purification by flash chromatography (98:2 dichloromethane/methanol).

LRMS (m/z): 283/285 (M+1)$^+$.

$^1$H-NMR δ (DMSO-d$_6$): 1.63-1.84 (m, 4H), 3.87-4.07 (m, 4H), 7.41 (s, 1H), 8.26 (s, 1H), 10.78 (brs, 1H).

Preparation 31

2'-oxo-1',2,2',3,5,6-hexahydrospiro[pyran-4,3'-pyrrolo[3,2-b]pyridine]-6'-ylboronic acid

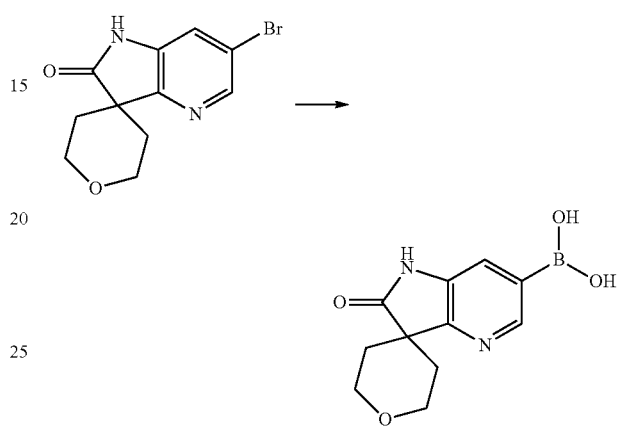

An oven dried resealable Schlenk tube was charged with 6'-bromo-2,3,5,6-tetrahydrospiro[pyran-4,3'-pyrrolo[3,2-b]pyridin]-2'(1'H)-one (preparation 30, 0.350 g, 1.24 mmol), bis(pinacolato)diboron (0.470 g, 1.85 mmol), potassium acetate (0.240 g, 2.48 mmol) and dimethylsulphoxide (4 mL). The Schlenk tube was subjected to three cycles of evacuation-backfilling with argon, and 1,1'-bis(diphenylphosphino)ferrocene-palladium(II) dichloride dichloromethane complex (0.06 g, 0.07 mmol) was added. After three further cycles of evacuation-backfilling with argon, the Schlenk tube was capped and placed in an oil bath at 110° C. After 16 hours, the mixture was cooled and ethyl acetate was added and the organic layer was extracted with 2M aqueous hydrochloric acid. The aqueous phase was washed with ethyl acetate and then the pH of the solution was adjusted to 6 with 6M aqueous sodium hydroxide solution and extracted with ethyl acetate. The organic layer was dried (MgSO$_4$) and evaporated to give the title compound in quantitative yield as a brown oily residue, which was used without further purification.

LRMS (m/z): 249 (M+1)$^+$.

Preparation 32

6'-bromo-4,4-difluorospiro[cyclohexane-1,3'-pyrrolo[3,2-b]pyridin]-2'(1'H)-one

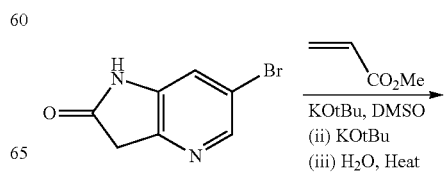

a) 6'-bromospiro[cyclohexane-1,3'-pyrrolo[3,2-b]pyridine]-2',4(1'H)-dione

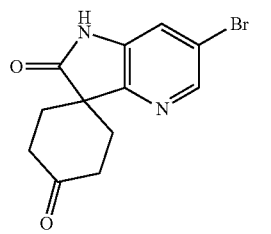

Potassium tert-butoxide (0.03 g, 0.27 mmol) was added to a suspension of 6-bromo-1H-pyrrolo[3,2-b]pyridin-2(3H)-one (preparation 30c, 0.87 g, 4.1 mmol) in dimethylsulphoxide (4 mL) and, after stirring for 10 minutes at room temperature, the mixture was heated to 40-45° C. and methyl acrylate (1.14 mL, 12.71 mmol) was added dropwise over 60 minutes. After the addition, the mixture was stirred for 2 hours and then further potassium tert-butoxide (1.4 g, 12.21 mmol) was added portionwise over 30 minutes keeping the temperature below 50° C. The mixture was then heated to 100° C. and stirred for 2 hours. Water (20 mL) was added and heating was continued at 85° C. for 2 hours and then the mixture was left to cool overnight. Ethyl acetate was added and the mixture was washed with water, brine, dried (MgSO$_4$) and evaporated to give the title compound (0.60 g, 50%) as a white solid.

LRMS (m/z): 293/295 (M−1)$^+$.

$^1$H-NMR δ (CDCl$_3$): 2.14 (m, 2H), 2.27 (m, 2H), 2.73 (m, 2H), 3.01 (m, 2H), 7.40 (d, J=1.5 Hz, 1H), 8.29 (d, J=1.5 Hz, 1H), 8.44 (brs, 1H).

b) 6'-bromo-4,4-difluorospiro[cyclohexane-1,3'-pyrrolo[3,2-b]pyridin]-2'(1'H)-one Obtained as a solid (16%) from 6'-bromospiro[cyclohexane-1,3'-pyrrolo[3,2-b]pyridine]-2',4(1'H)-dione (preparation 32a) following the experimental procedure as described in preparation 21b followed by purification by reverse phase chromatography (C-18 silica from Waters©, water/acetonitrile/methanol as eluents [0.1% v/v formic acid buffered] 0% to 60%).

LRMS (m/z): 315/317 (M−1)$^+$.

Preparation 33

6'-bromo-4-morpholinospiro[cyclohexane-1,3'-pyrrolo[3,2-b]pyridin]-2'(1'H)-one

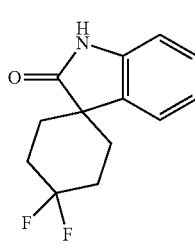

Obtained as a mixture of isomers from 6'-bromospiro[cyclohexane-1,3'-pyrrolo[3,2-b]pyridine]-2',4(1'H)-dione (preparation 32a) and morpholine following the experimental procedure as described in preparation 26. Purification by flash chromatography (0.1% Et$_3$N in 95:5 to 90:10 ethyl acetate/methanol) gave the two pure isomers of the title compound.
Major isomer (42%) as a white solid.
LRMS (m/z): 364/366 (M−1)$^−$.
Minor isomer (28%) as a white solid.
LRMS (m/z): 364/366 (M−1)$^−$.

Preparation 34

6'-Bromospiro[cyclopentane-1,3'-pyrrolo[3,2-b]pyridin]-2'(1'H)-one

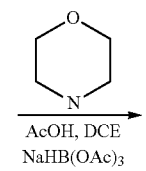

Obtained as a off-white solid (30%) from 6-bromo-1H-pyrrolo[3,2-b]pyridin-2(3H)-one (preparation 30c) and 1,4-diiodobutane following the experimental procedure as described in preparation 2 followed by purification by flash chromatography (98:2 dichloromethane/methanol).
LRMS (m/z): 265/267 (M−1)$^−$.

$^1$H-NMR δ (DMSO-d$_6$): 1.82-1.95 (m, 8H), 7.34 (s, 1H), 8.20 (s, 1H), 10.66 (b rs, 1H).

Preparation 35

6-Bromo-3,3-dimethyl-1H-pyrrolo[3,2-b]pyridin-2(3H)-one

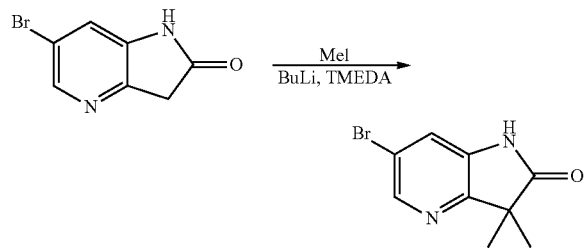

Obtained as a solid (11%) from 6-bromo-1H-pyrrolo[3,2-b]pyridin-2(3H)-one (preparation 30c) and iodomethane following the experimental procedure as described in preparation 2 followed by purification by flash chromatography (98:2 dichloromethane/methanol).

LRMS (m/z): 241/243 (M+1)$^+$.

$^1$H-NMR δ (CDCl$_3$): 1.45 (s, 6H), 7.39 (s, 1H), 8.29 (s, 1H), 9.39 (brs, 1H).

Preparation 36

6'-Chlorospiro[cyclopentane-1,3'-pyrrolo[3,2-c]pyridin]-2'(1'H)-one

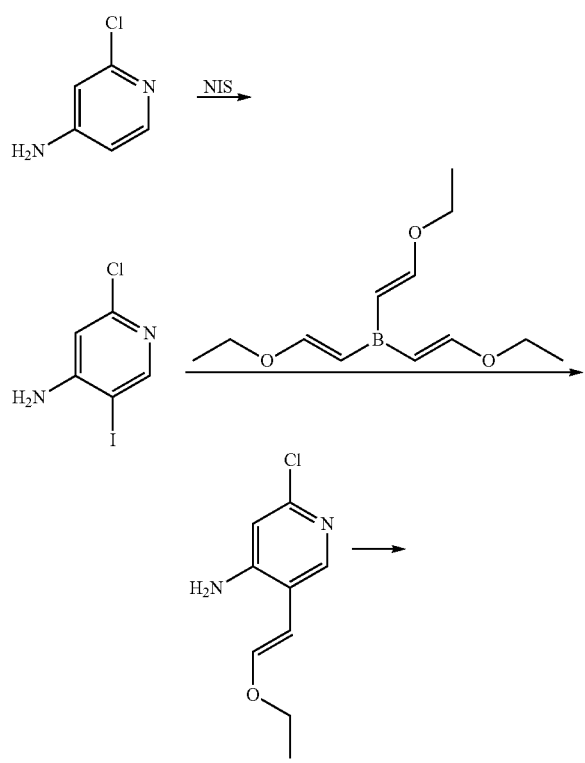

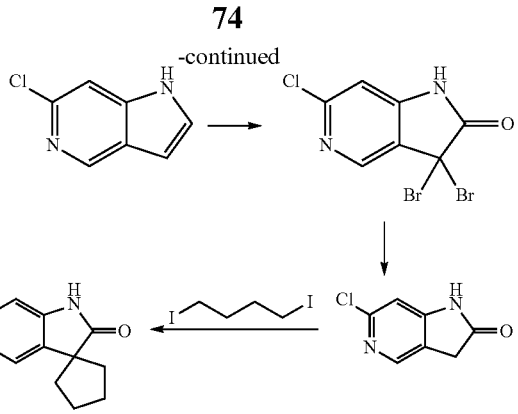

a) 2-Chloro-5-iodopyridin-4-amine

N-iodosuccinimide (15.75 g, 70 mmol) was added to a solution of 2-chloropyridin-4-amine (9.00 g, 70 mmol) in N,N'-dimethylformamide (140 mL) and the mixture was stirred at 80° C. for 6 hours. Further N-iodosuccinimide (7.80 g, 35 mmol) was added and the mixture was stirred at 60° C. overnight. After cooling to room temperature, the solvent was evaporated under reduced pressure and the residue was partitioned between water and ethyl acetate. The organic layer was washed with a saturated aqueous solution of sodium thiosulphate, water and brine, dried (MgSO$_4$) and concentrated. The residue was purified by flash chromatography (6:1 to 2:1 hexanes/ethyl acetate) to yield the title compound (6.80 g, 38%) as a beige solid.

LRMS (m/z): 255 (M+1)$^+$.

$^1$H-NMR δ (CDCl$_3$): 4.77 (brs, 2H), 6.63 (s, 1H), 8.34 (s, 1H).

b) 2-Chloro-5-[(E)-2-ethoxyvinyl]pyridin-4-amine

To a solution of 2-chloro-5-iodopyridin-4-amine (preparation 36a, 1.95 g, 7.66 mmol) in tetrahydrofuran (23 mL) under an argon atmosphere, was added powdered sodium hydroxide (0.92 g, 23 mmol), tetrakis(triphenylphosphine)palladium(0) (0.17 g, 0.15 mmol) and a 0.15M solution of tris[(E)-2-ethoxyvinyl]borane (20 mL, 3.0 mmol) in tetrahydrofuran and the resulting mixture was heated with stirring to 70° C. and left overnight. The mixture was poured into water and extracted with ethyl acetate. The organic layer was washed with brine, dried and the solvent was evaporated under reduced pressure. The residue was purified by flash chromatography (6:1 to 3:1 hexanes/ethyl acetate) to yield the title compound (1.00 g, 62%) as a beige solid.

LRMS (m/z): 199 (M+1)$^+$.

$^1$H-NMR δ (CDCl$_3$): 1.36 (t, J=7.1 Hz, 3H), 3.93 (q, J=7.1 Hz, 2H), 4.28 (brs, 2H), 5-50 (d, J=12.6 Hz, 1H), 6.54 (s, 1H), 6.72 (d, J=12.6 Hz, 1H), 7.89 (s, 1H).

c) 6-Chloro-1H-pyrrolo[3,2-c]pyridine

To a solution of 2-chloro-5-[(E)-2-ethoxyvinyl]pyridin-4-amine (preparation 36b, 1.00 g, 5.30 mmol) in methanol (20 mL) was added concentrated hydrochloric acid (1.00 mL, 32.64 mmol) and the mixture was stirred at 75° C. for 21 h. The mixture was concentrated under reduced pressure, treated with a saturated aqueous solution of potassium carbonate and extracted with ethyl acetate. The organic layer was dried and evaporated to yield the title compound (0.76 g, 99%) as a beige solid.

LRMS (m/z): 153 (M+1)$^+$.

¹H-NMR δ (CDCl₃): 6.65 (m, 1H), 7.20 (s, 2H), 8.60 (m, 2H).

d) 3,3-Dibromo-6-chloro-1,3-dihydro-2H-pyrrolo[3,2-c]pyridin-2-one

To a solution of 6-chloro-1H-pyrrolo[3,2-c]pyridine (preparation 36c, 0.05 g, 0.33 mmol) in tert-butyl alcohol (4 mL) at 28° C. was added pyridinium hydrobromide perbromide (0.31 g, 0.98 mmol) portionwise over 15 minutes. The mixture was stirred at 28° C. for 8 hours and then further pyridinium hydrobromide (0.10 g, 0.32 mmol) was added. The mixture was stirred at room temperature overnight, then diluted with water, extracted with ethyl acetate and the organic layer was washed with water, brine, dried (MgSO₄) and evaporated under reduced pressure to give the title compound (0.10 g, 94%) as an off-white solid.

¹H-NMR δ (CDCl₃): 7.00 (s, 1H), 8.50 (s, 1H), 8.70 (s, 1H).

e) 6-Chloro-1,3-dihydro-2H-pyrrolo[3,2-c]pyridin-2-one

To a solution of 3,3-dibromo-6-chloro-1,3-dihydro-2H-pyrrolo[3,2-c]pyridin-2-one (preparation 36d, 1.14 g, 3.49 mmol) in acetic acid (35 mL) was added zinc dust (2.23 g, 34.10 mmol) in one portion and the mixture was stirred at room temperature for 50 minutes. The mixture was diluted with methanol and filtered through a fine frit. The filtrate was evaporated under reduced pressure and the residue was purified by flash chromatography (95:5 dichloromethane/methanol) to give the title compound (0.56 g, 91%) as a white solid.

LRMS (m/z): 169 (M+1)⁺.

¹H-NMR δ (DMSO-d₆): 3.55 (s, 2H), 6.81 (s, 1H), 8.03 (s, 1H), 11.00 (brs, 1H).

f) 6'-Chlorospiro[cyclopentane-1,3'-pyrrolo[3,2-c]pyridin]-2'(1'H)-one

Obtained as an orange solid (20%) from 6-chloro-1,3-dihydro-2H-pyrrolo[3,2-c]pyridin-2-one (preparation 36e) and 1,4-diiodobutane following the experimental procedure as described in preparation 2 followed by purification by flash chromatography (97:3 dichloromethane/methanol).

LRMS (m/z): 223 (M+1)⁺.

¹H-NMR δ (DMSO-d₆): 1.81-1.95 (m, 8H), 6.88 (s, 1H), 8.14 (s, 1H).

Preparation 37

2'-Chlorospiro[cyclopentane-1,5'-pyrrolo[2,3-d]pyrimidin]-6'(7'H)-one

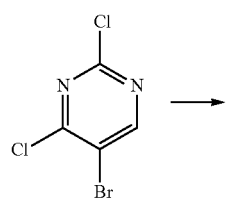

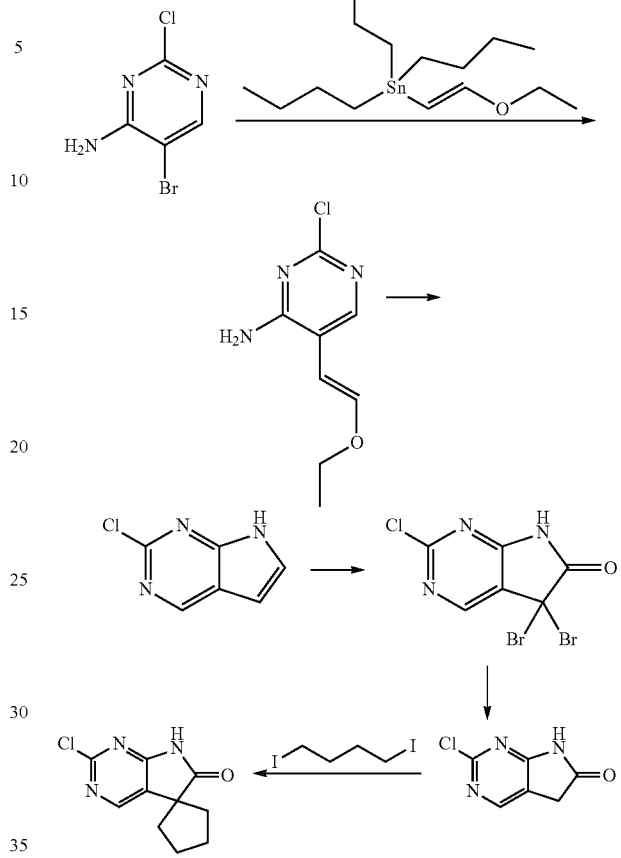

a) 5-Bromo-2-chloropyrimidin-4-amine

A solution of 5-bromo-2,4-dichloropyrimidine (8.54 g, 37.48 mmol) in methanol (12 mL) was added dropwise over 10 minutes to an ice-bath cooled solution of 7M ammonium hydroxide (60 mL, 420 mmol) in methanol (60 mL) and the resulting solution was stirred at room temperature for 24 hours. The mixture was concentrated and water was added. The solid was filtered and dried under reduced pressure to give the title compound (6.23 g, 73%) as a white solid.

LRMS (m/z): 207/209 (M+1)⁺.

¹H-NMR δ (CDCl₃): 5.80 (brs, 2H), 8.20 (s, 1H).

b) 2-Chloro-5-[(E)-2-ethoxyvinyl]pyrimidin-4-amine

To a degassed suspension of 5-bromo-2-chloropyrimidin-4-amine (preparation 37a, 2.50 g, 11.03 mmol) and (Z)-tributyl(2-ethoxyvinyl)stannane (4.76 g, 11.20 mmol) in toluene (40 mL) was added tetrakis(triphenylphosphine)palladium (0) (0.42 g, 0.36 mmol) and the mixture was subjected to several vacuum-argon cycles and then heated to reflux for 24 hours. Further catalyst (0.42 g, 0.36 mmol) was added and the mixture was refluxed an additional 24 hours. Further (Z)-tributyl(2-ethoxyvinyl)stannane (1.20 g, 2.82 mmol) was added and the reaction was refluxed overnight. The mixture was cooled and concentrated in vacuo and the oily residue was treated with hexanes to give a solid which was purified by flash chromatography (4:1 hexanes/ethyl acetate) to give the title compound (0.70 g, 32%) as a white solid.

LRMS (m/z): 200 (M+1)⁺.

$^1$H-NMR δ (CDCl$_3$): 1.30 (t, J=6.9 Hz, 3H), 4.00 (d, J=6.9 Hz, 2H), 4.95 (d, J=7.1 Hz, 1H), 5.97 (brs, 1H), 6.30 (d, J=7.1 Hz, 1H), 8.22 (s, 1H).

c) 2-Chloro-7H-pyrrolo[2,3-d]pyrimidine

Obtained as a white solid (47%) from 2-chloro-5-[(E)-2-ethoxyvinyl]pyrimidin-4-amine (preparation 37b) following the experimental procedure described in preparation 36c followed by purification by flash chromatography (200:1 to 50:1 dichloromethane/methanol).
LRMS (m/z): 154 (M+1)$^+$.
$^1$H-NMR δ (CDCl$_3$): 6.64 (m, 1H), 7.40 (m, 1H), 8.90 (s, 1H), 10.20 (brs, 1H).

d) 5,5-Dibromo-2-chloro-5,7-dihydro-6H-pyrrolo[2,3-d]pyrimidin-6-one

Obtained as an orange solid (93%) from 2-chloro-7H-pyrrolo[2,3-d]pyrimidine (preparation 37c) following the experimental procedure as described in preparation 36d.
LRMS (m/z): 326/328 (M+1)$^+$.
$^1$H-NMR δ (CDCl$_3$): 8.42 (s, 1H), 12.30 (brs, 1H).

e) 2-Chloro-5,7-dihydro-6H-pyrrolo[2,3-d]pyrimidin-6-one

Obtained as a beige solid (83%) from 5,5-dibromo-2-chloro-5,7-dihydro-6H-pyrrolo[2,3-d]pyrimidin-6-one (preparation 37d) following the experimental procedure described in preparation 36e.
LRMS (m/z): 170 (M+1)$^+$.
$^1$H-NMR δ (DMSO-d$_6$): 3.62 (s, 2H), 8.30 (s, 1H), 11.80 (brs, 1H).

f) 2-Chlorospiro[cyclopentane-1,5'-pyrrolo[2,3-d]pyrimidin]-6'(7'H)-one

Obtained as a white solid (38%) from 2-chloro-5,7-dihydro-6H-pyrrolo[2,3-d]pyrimidin-6-one (preparation 37e) following the experimental procedure described in preparation 36f.
LRMS (m/z): 224 (M+1)$^+$.
$^1$H-NMR δ (CDCl$_3$): 1.93-2.24 (m, 8H), 8.14 (s, 1H), 8.30 (brs, 1H).

Preparation 38

4-Methyl-3-(2'-oxospiro[cyclopentane-1,3'-indoline]-6'-yl)benzoic acid

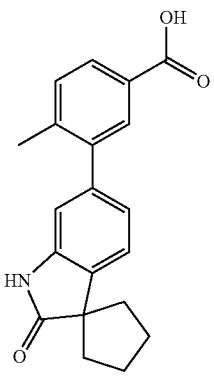

An oven-dried resealable Schlenk tube was charged with 6'-bromospiro[cyclopentane-1,3'-indolin]-2'-one (preparation 2, 0.650 g, 2.44 mmol), 4-methyl-3-(4,4,5,5-tetramethyl-1,3,2-dioxaborolan-2-yl)benzoic acid (WO200700565, 0.96 g, 3.66 mmol), 1,4-dioxane (25 mL) and a 2M aqueous cesium carbonate solution (3.7 mL, 7.4 mmol). The Schlenk tube was subjected to three cycles of evacuation-backfilling with argon, and 1,1'-bis(diphenylphosphino)ferrocene-palladium(II) dichloride dichloromethane complex (0.12 g, 0.15 mmol) was added. After three further cycles of evacuation-backfilling with argon, the Schlenk tube was sealed and the mixture was stirred and heated in an oil bath to 100-110° C. After 20 hours, the mixture was cooled and partitioned between water and ethyl acetate. The combined organic extract was dried (MgSO$_4$) and evaporated in vacuo. Purification of the residue by flash chromatography (95:5 dichloromethane/methanol) gave the title compound (0.64 g, 81%) as a yellow solid.

LRMS (m/z): 322 (M+1)$^+$.
$^1$H-NMR δ (DMSO-d$_6$): 1.79-1.83 (m, 2H), 1.94-2.06 (m, 6H), 2.31 (s, 3H), 6.76 (s, 1H), 6.94 (d, J=6.0 Hz, 1H), 7.32 (d, J=9.0 Hz, 1H), 7.43 (d, J=9.0 Hz, 1H), 7.73 (s, 1H), 7.83 (d, J=6.0 Hz, 1H), 10.34 (brs, 1H).

Preparation 39

3-(3,3-dimethyl-2-oxoindolin-6-yl)-4-methylbenzoic acid

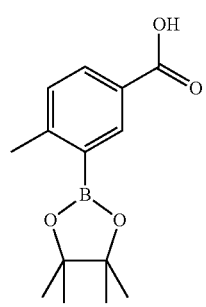 + 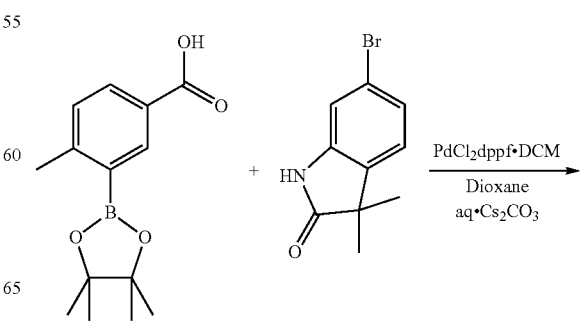

-continued

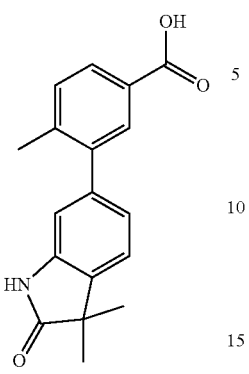

Obtained as an orange solid (82%) from 6-bromo-3,3-dimethylindolin-2-one (preparation 16) and 4-methyl-3-(4,4,5,5-tetramethyl-1,3,2-dioxaborolan-2-yl)benzoic acid following the experimental procedure described in preparation 38. The crude product was used without further purification.

LRMS (m/z): 296 (M+1)$^+$.

Preparation 40

N-Cyclopropyl-4-methyl-3-(4,4,5,5-tetramethyl-1,3,2-dioxaborolan-2-yl)benzamide

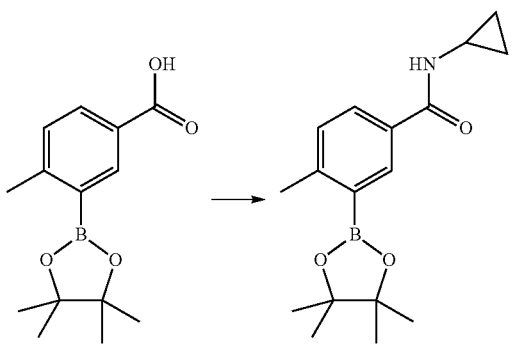 [SMILES: Cc1ccc(C(=O)O)cc1B1OC(C)(C)C(C)(C)O1 ; Cc1ccc(C(=O)NC2CC2)cc1B1OC(C)(C)C(C)(C)O1]

To a solution of 4-methyl-3-(4,4,5,5-tetramethyl-1,3,2-dioxaborolan-2-yl)benzoic acid (WO200700565, 5.47 g, 20.87 mmol) in N,N'-dimethylformamide (55 mL) were added cyclopropylamine (1.76 mL, 25.08 mmol), diisopropylethylamine (8.00 mL, 45.93 mmol) and O-(7-azabenzotriazol-1-yl)-N,N,N',N'-tetramethyluronium hexafluorophosphate (7.62 g, 20.04 mmol). The clear solution was stirred at room temperature overnight. The mixture was then concentrated in vacuo and the residue was taken up with ethyl acetate and the organic phase was washed with 4% aqueous sodium bicarbonate solution, water, brine, dried (MgSO$_4$) and concentrated to afford an oily residue. The oil was triturated with a mixture of hexanes and diethyl ether to give the title compound (5.78 g, 96%) as a white solid.

LRMS (m/z): 302 (M+1)$^+$.

$^1$H-NMR δ (DMSO-d$_6$): 0.56 (m, 2H), 0.65 (m, 2H), 1.30 (s, 12H), 2.45 (s, 3H), 2.82 (m, 1H), 7.23 (d, J=8.0 Hz, 1H), 7.76 (dd, J=8.0 and 2.2 Hz, 1H), 8.06 (d, J=2.2 Hz, 1H), 8.40 (brs, 1H).

Preparation 41

N-(Cyclopropylmethyl)-4-methyl-3-(4,4,5,5-tetramethyl-1,3,2-dioxaborolan-2-yl)benzamide

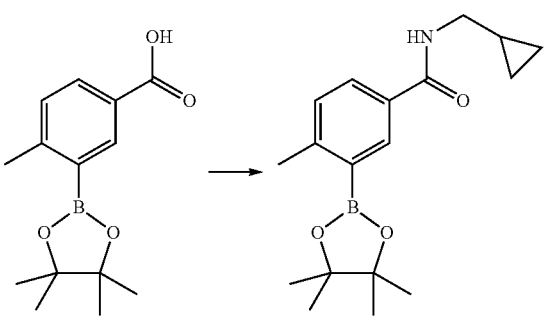 [SMILES: Cc1ccc(C(=O)O)cc1B1OC(C)(C)C(C)(C)O1 ; Cc1ccc(C(=O)NCC2CC2)cc1B1OC(C)(C)C(C)(C)O1]

Obtained as a white solid in quantitative yield from 4-methyl-3-(4,4,5,5-tetramethyl-1,3,2-dioxaborolan-2-yl)benzoic and cyclopropylmethanamine following the experimental procedure as described in preparation 40.

LRMS (m/z): 316 (M+1)+.

$^1$H-NMR δ (DMSO-d$_6$): 0.0-0.2 (m, 4H), 0.85 (m, 1H), 1.30 (s, 12H), 2.45 (s, 3H), 2.88 (t, J=6.3 Hz, 2H), 7.02 (d, J=8.0 Hz, 1H), 7.60 (dd, J=8.0 and 2.2 Hz, 1H), 7.86 (d, J=2.2 Hz, 1H), 8.30 (t, J=5.5 Hz, 1H).

Preparation 42

3-Iodo-N-isoxazol-3-yl-4-methylbenzamide

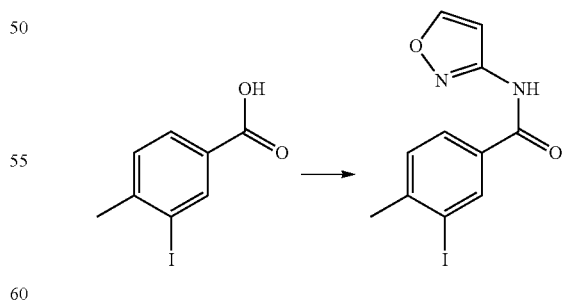

Obtained as a yellow solid (79%) from 3-iodo-4-methylbenzoic acid and isoxazol-3-ylamine following the experimental procedure as described in preparation 40 followed by purification by flash chromatography (3:1 hexanes/ethyl acetate to 1:3 hexanes/ethyl acetate).

LRMS (m/z): 329 (M+1)+.

¹H-NMR δ (CDCl₃): 2.52 (s, 3H), 7.22 (s, 1H), 7.37 (d, J=8.0 Hz, 1H), 7.81 (d, J=8.5 Hz, 1H), 8.37 (m, 2H), 9.14 (brs, 1H).

Preparation 43

N-Cyclopropyl-3-(4,4,5,5-tetramethyl-1,3,2-dioxaborolan-2-yl)benzamide

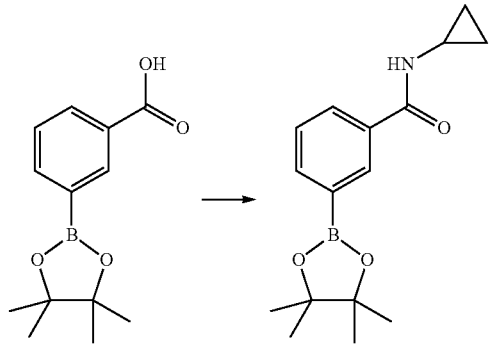 [SMILES: CC1(C)OB(c2cccc(C(=O)O)c2)OC1(C)C ; CC1(C)OB(c2cccc(C(=O)NC3CC3)c2)OC1(C)C]

Obtained as a white solid (52%) from 3-(4,4,5,5-tetramethyl-1,3,2-dioxaborolan-2-yl)benzoic acid and cyclopropylamine following the experimental procedure as described in preparation 40 followed by trituration with diethyl ether.

LRMS (m/z): 316 (M+1)+.

¹H-NMR δ (DMSO-d₆): 0.58 (m, 2H), 0.68 (m, 2H), 1.29 (s, 12H), 2.83 (m, 1H), 7.44 (m, 1H), 7.77 (d, J=7.4 Hz, 1H), 7.91 (d, J=8.0 Hz, 1H), 8.09 (s, 1H), 8.52 (d, J=3.9 Hz, 1H).

Preparation 44

4-Chloro-N-cyclopropyl-3-(4,4,5,5-tetramethyl-1,3,2-dioxaborolan-2-yl)benzamide

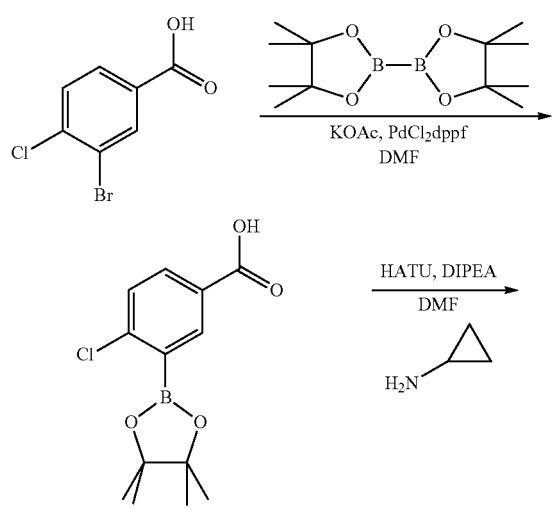

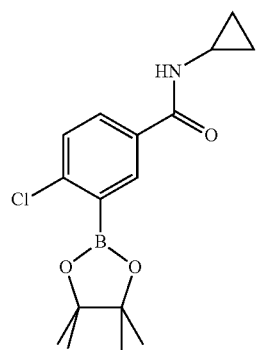

a) 4-Chloro-3-(4,4,5,5-tetramethyl-1,3,2-dioxaborolan-2-yl)benzoic acid

In a Schlenk tube were charged 3-bromo-4-chlorobenzoic acid (2.00 g, 8.49 mmol), bis(pinacolato)diboron (3.23 g, 12.72 mmol), potassium acetate (4.17 g, 42.49 mmol) and N,N'-dimethylformamide (40 mL). The mixture was submitted to three vacuum-argon cycles, then [1,1'-bis(diphenylphosphino)ferrocene]dichloro-palladium(II) complex with dichloromethane (1:1) (700 mg, 0.87 mmol) was added and the reaction vessel was purged in the same way and then stirred at 80° C. under argon for 5 hours. Subsequently, the solvent was removed in vacuo, 2M aqueous sodium hydroxide solution (50 mL) was added and the mixture was extracted with ethyl acetate. The mixture was cooled in an ice-water bath and the aqueous phase was acidified with 5M aqueous hydrochloric acid to pH 3. The solid that formed was filtered, washed with water and dried to give the title compound (1.30 g, 54%) as a white solid.

LRMS (m/z): 199 (M−1)⁻ (corresponding to the boronic acid generated under the HPLC conditions).

¹H-NMR δ (DMSO-d₆): 1.34 (s, 12H), 7.58 (d, J=8.3 Hz, 1H), 8.00 (d, J=8.3 Hz, 1H), 8.24 (s, 1H), 12.28 (brs, 1H).

b) 4-Chloro-N-cyclopropyl-3-(4,4,5,5-tetramethyl-1,3,2-dioxaborolan-2-yl)benzamide Obtained as a solid (72%) from 4-chloro-3-(4,4,5,5-tetramethyl-1,3,2-dioxaborolan-2-yl)benzoic acid (preparation 44a) and cyclopropylamine following the experimental procedure as described in preparation 40 followed by trituration of the crude product with a hexanes-diethyl ether mixture.

LRMS (m/z): 240 (M+1)⁺ (corresponding to the boronic acid generated under the HPLC conditions).

¹H-NMR δ (DMSO-d₆): 0.58 (m, 2H), 0.70 (m, 2H), 1.33 (s, 12H), 2.84 (m, 1H), 7.51 (d, J=8.3 Hz, 1H), 7.88 (d, J=8.3 Hz, 1H), 8.06 (s, 1H), 8.59 (brs 1H).

Preparation 45

N-Cyclopropyl-3-fluoro-4-methyl-5-(4,4,5,5-tetramethyl-1,3,2-dioxaborolan-2-yl)benzamide

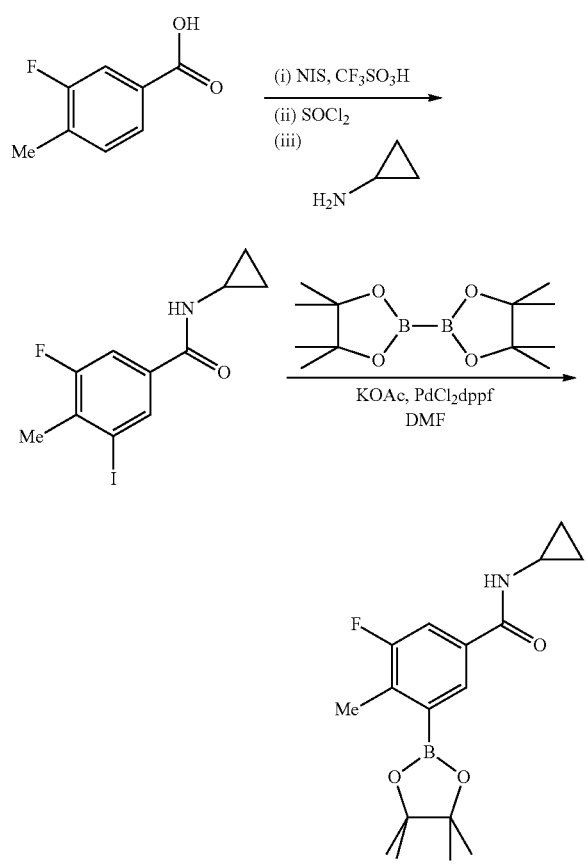

a) N-Cyclopropyl-3-fluoro-5-iodo-4-methylbenzamide

N-Iodosuccinimide (3.31 g, 20 mmol) was added in portions over 3 hours to a solution of 3-fluoro-4-methylbenzoic acid (2.27 g, 20 mmol) in trifluoromethanesulphonic acid (15 mL) kept at 0° C. Subsequently, the mixture was allowed to warm to room temperature and was stirred overnight. The reaction mixture was poured into ice/water and the precipitate that formed was collected by filtration and washed with water. The solid was dissolved in ethyl acetate, the organic layer was washed with saturated aqueous sodium thiosulphate solution and brine, dried (MgSO$_4$) and the solvent was removed under vacuum. The residue obtained was treated with thionyl chloride (20 mL) and heated at 100° C. for 2.5 hours. Excess thionyl chloride was removed in vacuo and the residue was dissolved in dichloromethane (20 mL). Sodium carbonate (3.70 g, 35 mmol) and cyclopropylamine (1.90 mL, 27 mmol) were added to the solution and the mixture was stirred at room temperature for 72 hours. The mixture was then filtered and the residue was washed with dichloromethane and ethyl acetate. The combined filtrate and washings were concentrated under vacuum and the residue was purified by flash chromatography (10:1 to 5:1 hexanes/ethyl acetate) to give the title compound (2.13 g, 45%) as a white solid.

LRMS (m/z): 320 (M+1)$^+$.
$^1$H-NMR δ (CDCl$_3$): 0.60 (m, 2H), 0.85 (m, 2H), 2.86 (m, 1H), 6.22 (brs, 1H), 7.39 (m, 1H), 7.90 (m, 1H).

b) N-Cyclopropyl-3-fluoro-4-methyl-5-(4,4,5,5-tetramethyl-1,3,2-dioxaborolan-2-yl)benzamide Obtained as a solid (57%) from N-cyclopropyl-3-fluoro-5-iodo-4-methylbenzamide (preparation 45a) following the experimental procedure as described in preparation 9 followed by purification of the crude product by flash chromatography (6:1 hexanes/ethyl acetate).

LRMS (m/z): 320 (M+1)$^+$.
$^1$H-NMR δ (CDCl$_3$): 0.62 (m, 2H), 0.85 (m, 2H), 1.34 (s, 12H), 2.86 (m, 1H), 6.30 (brs, 1H), 7.57 (dd, J=10.4 and 1.7 Hz, 1H), 7.71 (d, J=1.7 Hz, 1H).

Preparation 46

N-(Cyclopropylmethyl)-3-fluoro-4-methyl-5-(4,4,5,5-tetramethyl-1,3,2-dioxaborolan-2-yl)benzamide Obtained as a white solid (54%) from 3-fluoro-4-methylbenzoic acid and cyclopropylmethylamine following the experimental procedures as described in preparation 45.

LRMS (m/z): 334 (M+1)$^+$.
$^1$H-NMR δ (CDCl$_3$): 0.28-0.31 (m, 2H), 0.55-0.60 (m, 2H), 1.36 (s, 12H), 2.51 (s, 3H), 3.31-3.35 (m, 2H), 6.28 (brs, 1H), 7.63 (dd, J=1.5 and 10.5 Hz, 1H), 7.83 (d, J=1.5 Hz, 1H).

Preparation 47

5-Bromo-N-cyclopropyl-6-methylnicotinamide

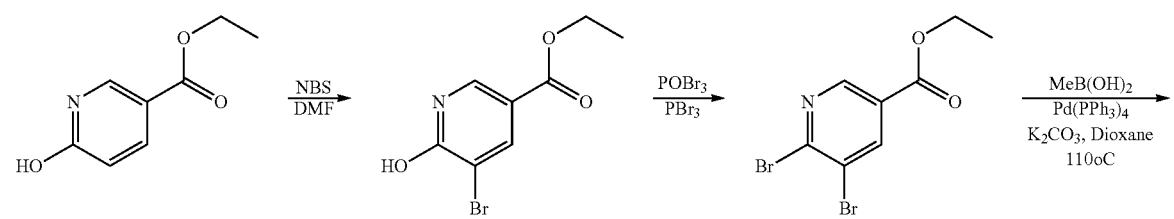

-continued

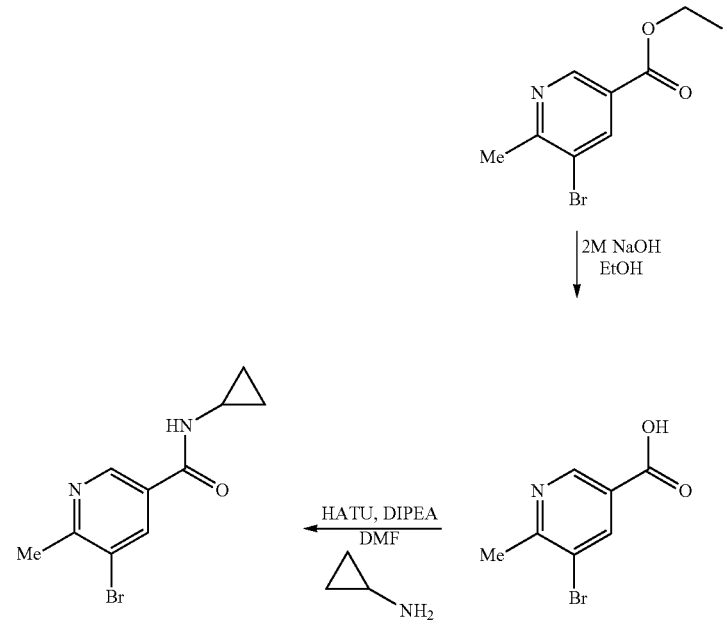

a) Ethyl 5-bromo-6-hydroxynicotinate

N-Bromosuccinimide (7.70 g, 43.3 mmol) was added to a stirred solution of methyl 6-hydroxynicotinate (6.01 g, 36.0 mmol) in N,N'-dimethylformamide (142 mL). After 20 hours, the reaction mixture was diluted with water and extracted with ethyl acetate. The organic layer was washed with brine, dried (MgSO$_4$) and evaporated. Trituration of the crude product with diethyl ether and hexanes gave the title compound (6.35 g, 72%) as a yellow solid.

LRMS (m/z): 246/248 (M+1)$^+$.

$^1$H-NMR δ (CDCl$_3$): 1.37 (t, J=9.0 Hz, 3H), 4.35 (q, J=9.0 Hz, 2H), 8.31 (d, J=3.0 Hz, 1H), 8.42 (d, J=3.0 Hz, 1H).

b) Ethyl 5,6-dibromonicotinate

A mixture of ethyl 5-bromo-6-hydroxynicotinate (preparation 47a, 6.35 g, 25.8 mmol), tribromophosphine (2.50 mL, 26 mmol) and phosphorus oxytribromide (7.50 g, 26.2 mmol) was stirred at 120° C. After 3 hours, the mixture was cooled, water was added and the mixture was extracted with ethyl acetate. The organic layer was washed with brine, dried (MgSO$_4$) and evaporated to yield the title compound (6.88 g, 86%) as a white solid.

LRMS (m/z): 310 (M+1)$^+$.

$^1$H-NMR δ (CDCl$_3$): 1.42 (t, J=9.0 Hz, 3H), 4.43 (q, J=9.0 Hz, 2H), 8.47 (d, J=3.0 Hz, 1H), 8.89 (d, J=3.0 Hz, 1H).

c) Ethyl 5-bromo-6-methylnicotinate

An oven-dried resealable Schlenk tube was charged with ethyl 5,6-dibromonicotinate (preparation 47b, 1.09 g, 3.5 mmol), methylboronic acid (0.24 g, 4.0 mmol), potassium carbonate (1.46 g, 10.6 mmol) and 1,4-dioxane (27 mL). The Schlenk tube was subjected to three cycles of evacuation-backfilling with argon, and then tetrakis(triphenylphosphine) palladium(0) (0.41 g, 0.35 mmol) was added. After three new cycles of evacuation-backfilling with argon, the Schlenk tube was sealed and the mixture was stirred and heated in an oil bath to 110° C. After 3 days, the mixture was cooled, filtered through Celite® and the filtrate was evaporated. Purification of the residue by flash chromatography (97:3 to 9:1 hexanes/ethyl acetate) gave the title compound (0.41 g, 45%) as a solid.

LRMS (m/z): 244/246 (M+1)$^+$.

$^1$H-NMR δ (CDCl$_3$): 1.41 (t, J=9.0 Hz, 3H), 2.74 (s, 3H), 4.41 (q, J=9.0 Hz, 2H), 8.40 (d, J=3.0 Hz, 1H), 9.01 (d, J=3.0 Hz, 1H).

d) 5-Bromo-6-methylnicotinic acid

2M Aqueous sodium hydroxide solution (1.91 mL, 3.8 mmol) was added to a stirred solution of ethyl 5-bromo-6-methylnicotinate (preparation 47c, 0.41 g, 1.7 mmol) in ethanol (14 mL) at room temperature. After 3 hours, the solvent was evaporated and water was added to the residue. The pH was adjusted to 4-5 with concentrated hydrochloric acid and the mixture was extracted with ethyl acetate. The organic layer was washed with water, dried (MgSO$_4$) and evaporated to give the title compound (0.16 g, 43%) as a white solid.

LRMS (m/z): 216/218 (M+1)$^+$.

e) 5-Bromo-N-cyclopropyl-6-methylnicotinamide

Obtained as a colourless oil (83%) from 5-bromo-6-methylnicotinic acid (preparation 47d) and cyclopropylamine following the experimental procedure as described in preparation 40 followed by purification by flash chromatography (7:3 to 3:7 hexanes/ethyl acetate).

LRMS (m/z): 255/257 (M+1)$^+$.

$^1$H-NMR δ (DMSO-d$_6$): 0.59-0.65 (m, 2H), 0.73-0.79 (m, 2H), 2.66 (s, 3H), 2.85-2.94 (m, 1H), 8.40 (d, J=3.0 Hz, 1H), 8.70 (brs, 1H), 8.87 (d, J=3.0 Hz, 1H).

Preparation 48

3-(3-iodo-4-methylphenyl)-4H-1,2,4-triazole

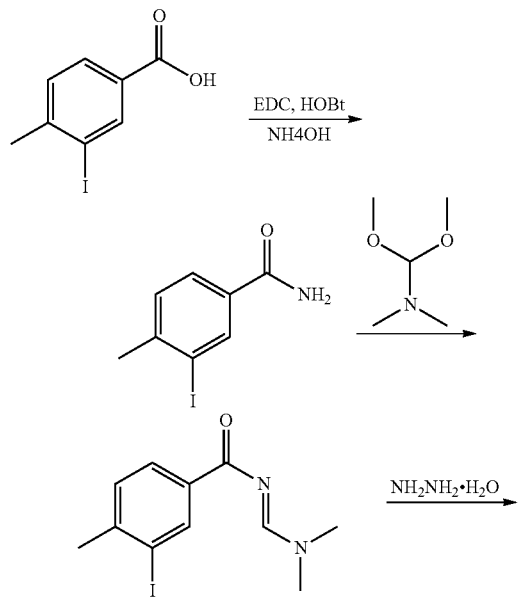

a) 3-Iodo-4-methylbenzamide 1-(3-Dimethylaminopropyl)-3-ethylcarbodiimide hydrochloride (5.49 g, 28.6 mmol), 1H-benzo[d][1,2,3]triazol-1-ol hydrate (3.90 g, 28.9 mmol) and 32% aqueous ammonium hydroxide solution (1.10 mL, 28.7 mmol) were sequentially added to a stirred solution of 3-iodo-4-methylbenzoic acid (5.00 g, 19.1 mmol) in N,N'-dimethylformamide (15 mL) at room temperature. After stirring overnight, the mixture was concentrated in vacuo and water and dichloromethane were added to the mixture. The organic layer was washed with 2N aqueous sodium hydroxide solution, brine, dried (MgSO$_4$) and evaporated to give the title compound (4.34 g, 70%) as a yellow solid.

LRMS (m/z): 262 (M+1)$^+$.

$^1$H-NMR δ (DMSO-d$_6$): 2.41 (s, 3H), 7.39-7.42 (m, 2H), 7.82 (d, J=8.0 Hz, 1H), 8.02 (brs, 1H), 8.32 (brs, 1H).

b) (E)-N-((dimethylamino)methylene)-3-iodo-4-methylbenzamide

A suspension of 3-iodo-4-methylbenzamide (preparation 48a, 2.00 g, 7.7 mmol) in 1,1-dimethoxy-N,N-dimethylmethanamine (4.0 mL, 30.1 mmol) was heated in a sealed tube at 90° C. with stirring. After 2 hours, the mixture was cooled and concentrated in vacuo. The residue was triturated with diethyl ether and hexanes, and the solid that formed was filtered and dried to give the title compound (1.90 g, 78%) as a yellow solid.

LRMS (m/z): 317 (M+1)$^+$.

$^1$H-NMR δ (CDCl$_3$): 2.48 (s, 3H), 3.20 (s, 3H), 3.23 (s, 3H), 7.28 (d, J=9.0 Hz, 1H), 8.14 (dd, J=9.0 and 3.0 Hz, 1H), 8.63 (s, 1H), 8.72 (d, J=9.0 Hz, 1H).

c) 3-(3-Iodo-4-methylphenyl)-4H-1,2,4-triazole

Hydrazine monohydrate (0.30 g, 6.0 mmol) was added to a stirred solution of (E)-N-((dimethylamino)methylene)-3-iodo-4-methylbenzamide (preparation 48b, 1.20 g, 3.8 mmol) in acetic acid (6 mL) and the mixture was stirred and heated to 90° C. After 2 hours, the mixture was concentrated in vacuo and water and 2N aqueous sodium hydroxide solution were added to the residue. The solid that formed was filtered, washed with water and dried in vacuo to give the title compound (0.98 g, 91%) as a solid.

LRMS (m/z): 286 (M+1)$^+$.

$^1$H-NMR δ (DMSO-d$_6$): 2.46 (s, 3H), 7.49 (d, J=9.0 Hz, 1H), 7.99 (d, J=9.0 Hz, 1H), 8.49 (d, J=9.0 Hz, 1H).

Preparation 49

3-Methyl-5-(4-methyl-3-(4,4,5,5-tetramethyl-1,3,2-dioxaborolan-2-yl)phenyl)-4H-1,2,4-triazole

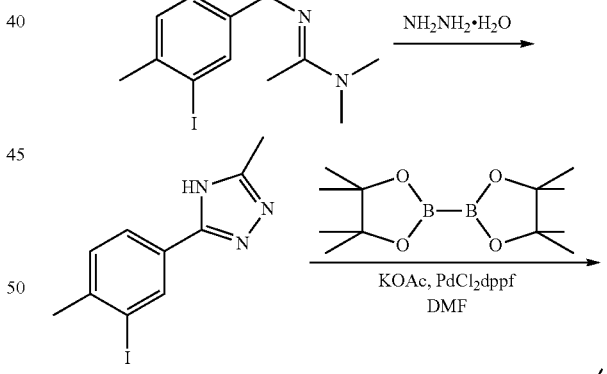

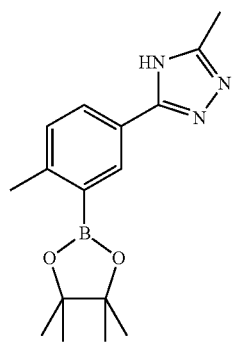

a) (E)-N-(1-(Dimethylamino)ethylidene)-3-iodo-4-methylbenzamide

Obtained as a solid (76%) from 3-iodo-4-methylbenzamide (preparation 48a) and 1,1-dimethoxy-N,N-dimethylethanamine following the experimental procedure as described in preparation 48b followed by purification of the crude product by flash chromatography (1:1 hexanes/ethyl acetate).

LRMS (m/z): 331 (M+1)$^+$.

$^1$H-NMR δ (DMSO-d$_6$): 2.25 (s, 3H), 2.45 (s, 3H), 3.13 (s, 6H), 7.39 (d, J=8.0 Hz, 1H), 7.93 (d, J=8.0 Hz, 1H), 8.41 (s, 1H).

b) 3-(3-Iodo-4-methylphenyl)-5-methyl-4H-1,2,4-triazole

Obtained (62%) from (E)-N-(1-(dimethylamino)ethylidene)-3-iodo-4-methylbenzamide (preparation 49a) following the experimental procedure as described in preparation 48c.

LRMS (m/z): 300 (M+1)$^+$.

$^1$H-NMR δ (CDCl$_3$): 2.46 (s, 3H), 2.51 (s, 3H), 7.30 (d, J=8.0 Hz, 1H). 7.89 (dd, J=1.5 Hz, J=8.0 Hz, 1H), 8.49 (d, J=1.5 Hz, 1H).

c) 3-Methyl-5-(4-methyl-3-(4,4,5,5-tetramethyl-1,3,2-dioxaborolan-2-yl)phenyl)-4H-1,2,4-triazole Obtained as a white solid (85%) from 3-(3-iodo-4-methylphenyl)-5-methyl-4H-1,2,4-triazole (preparation 49b) following the experimental procedure as described in preparation 9 followed by purification by reverse phase chromatography (0% CH$_3$CN in H$_2$O to 100% CH$_3$CN in H$_2$O).

LRMS (m/z): 300 (M+1)$^+$.

Preparation 50

3-[3-Fluoro-4-methyl-5-(4,4,5,5-tetramethyl-1,3,2-dioxaborolan-2-yl)phenyl]-5-methyl-4H-1,2,4-triazole

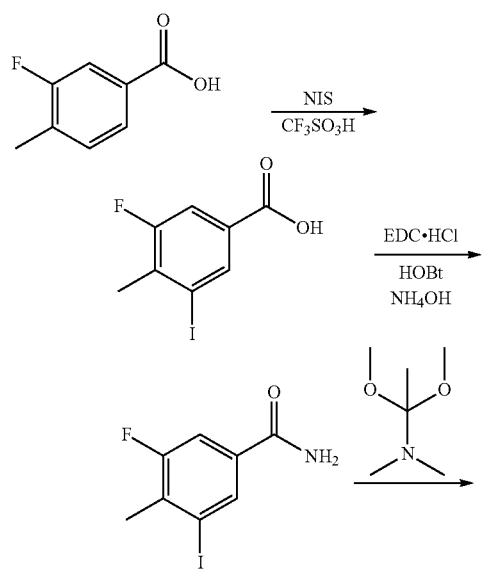

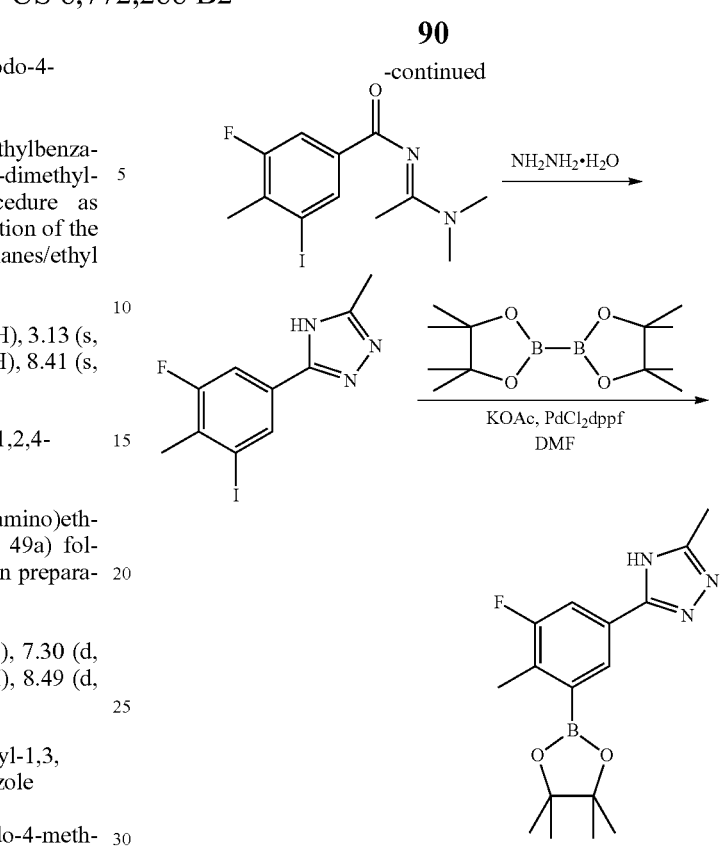

a) 3-fluoro-5-iodo-4-methylbenzoic acid

N-Iodosuccinimide (3.31 g, 14.7 mmol) was added in portions over a 3-hour period to a stirred solution of 3-fluoro-4-methylbenzoic acid (2.27 g, 14.7 mmol) in trifluoromethanesulphonic acid (15 mL) at 0° C. The mixture was warmed to room temperature, stirred overnight and then poured into an ice-water mixture and the precipitate that formed was collected by filtration and washed with water. The solid was dissolved in ethyl acetate, washed with aqueous sodium thiosulphate and brine, dried (MgSO$_4$) and dried to give the title compound (3.45 g, 59%) as a solid.

LRMS (m/z): 279 (M−1)$^−$.

$^1$H-NMR δ (CDCl$_3$): 2.41 (s, 3H), 2.86 (m, 1H), 6.30 (brs, 1H), 7.72 (m, 1H), 8.34 (m, 1H).

b) 3-Fluoro-5-iodo-4-methylbenzamide

Obtained as a white solid (89%) from 3-fluoro-5-iodo-4-methylbenzoic acid (preparation 50a) following the experimental procedure as described in preparation 48a.

LRMS (m/z): 280 (M+1)$^+$.

$^1$H-NMR δ (DMSO-d$_6$): 2.32 (s, 3H), 7.55 (brs, 1H), 7.65 (d, J=10.4 Hz, 1H), 8.07 (brs, 1H), 8.16 (s, 1H).

c) N-[(1E)-1-(Dimethylamino)ethylidene]-3-fluoro-5-iodo-4-methylbenzamide

A mixture of 3-fluoro-5-iodo-4-methylbenzamide (preparation 50b) and (1,1-dimethoxyethyl)dimethylamine was heated at 120° C. in a sealed tube. After 2 hours, the reaction mixture was cooled and the solvent was evaporated under reduced pressure to give the title compound (1.84 g, 100%) as an oil.

LRMS (m/z): 349 (M+1)$^+$.

$^1$H-NMR δ (CDCl$_3$): 2.33 (s, 3H), 2.40 (s, 3H), 3.15 (s, 3H), 3.21 (s, 3H), 7.75 (dd, J=10.2 and 1.1 Hz, 1H), 8.36 (d, J=1.1 Hz, 1H).

d) 3-(3-Fluoro-5-iodo-4-methylphenyl)-5-methyl-4H-1,2,4-triazole

Obtained as a solid (76%) from N-[(1E)-1-(dimethylamino)ethylidene]-3-fluoro-5-iodo-4-methylbenzamide (preparation 50c) following the experimental procedure as described in preparation 48c.
LRMS (m/z): 318 (M+1)$^+$.
$^1$H-NMR δ (DMSO-d$_6$): 2.32 (s, 3H), 2.37 (s, 3H), 7.65 (dd, J=10.4 Hz, 1H), 8.23 (s, 1H).

e) 3-[3-Fluoro-4-methyl-5-(4,4,5,5-tetramethyl-1,3,2-dioxaborolan-2-yl)phenyl]-5-methyl-4H-1,2,4-triazole Obtained as a solid (30%) from 3-(3-fluoro-5-iodo-4-methylphenyl)-5-methyl-4H-1,2,4-triazole (preparation 50d) following the experimental procedure as described in preparation 9.
LRMS (m/z): 318 (M+1)$^+$.
$^1$H-NMR δ (CDCl$_3$): 1.33 (s, 12H), 2.48 (s, 3H), 2.52 (s, 3H), 7.74 (d, J=10.4 Hz, 1H), 8.16 (s, 1H), 10.93 (brs, 1H).

Preparation 51

3-Cyclopropyl-5-(3-iodo-4-methylphenyl)-4H-1,2,4-triazole

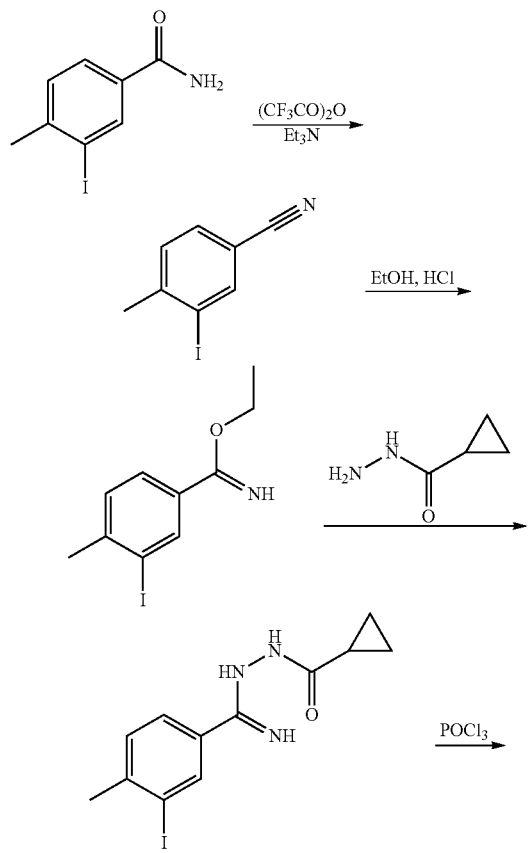

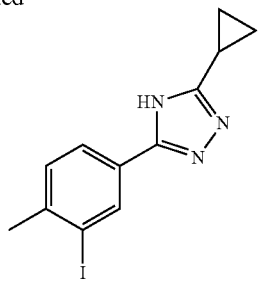

a) 3-Iodo-4-methylbenzonitrile 2,2,2-trifluoroacetic anhydride (8.00 mL, 57.5 mmol) was added dropwise to a stirred solution of 3-iodo-4-methylbenzamide (preparation 48a, 6.00 g, 23.0 mmol) and triethylamine (8.10 mL, 57.5 mmol) in dichloromethane (50 mL) at 0° C. The mixture was warmed to room temperature and stirred for 2 hours. Further dichloromethane and saturated aqueous potassium carbonate solution were added and the organic layer was washed with 2M aqueous hydrochloric acid, 2M aqueous sodium hydroxide solution, brine, dried (MgSO$_4$) and evaporated to give the title compound (4.50 g, 80%) as a pale orange solid.
$^1$H-NMR δ (CDCl$_3$): 2.50 (s, 3H), 7.33 (d, J=6.0 Hz, 1H), 7.54 (d, J=6.0 Hz, 1H), 8.08 (s, 1H).

b) Ethyl 3-iodo-4-methylbenzimidate

Hydrogen chloride gas was bubbled over a period of 35 minutes into a stirred solution of 3-iodo-4-methylbenzonitrile (preparation 51a, 2.00 g, 8.2 mmol) and ethanol (0.70 mL, 12.3 mmol) in benzene at 0° C. The mixture was stirred for 30 minutes at room temperature and then the mixture was placed in the refrigerator and left overnight. Diethyl ether (200 mL) was then added and a white solid precipitated. After leaving the mixture a further night in the refrigerator the precipitate was filtered. Dichloromethane and saturated aqueous potassium carbonate solution were added to the solid with stirring. The organic layer was dried (MgSO$_4$) and evaporated to give the title compound (4.50 g, 80%) as an oil.
$^1$H-NMR δ (CDCl$_3$): 1.42 (t, J=6.0 Hz, 3H), 2.46 (s, 3H), 4.29 (q, J=6.0 Hz, 2H), 7.26 (d, J=6.0 Hz, 1H), 7.61 (m, 2H), 8.18 (brs, 1H).

c) N'-(Imino(3-iodo-4-methylphenyl)methyl)cyclopropanecarbohydrazide

Cyclopropanecarbohydrazide (0.36 g, 2.7 mmol) was added to a stirred solution of ethyl 3-iodo-4-methylbenzimidate (preparation 51b, 0.70 g, 2.4 mmol) in methanol (6 mL) and the mixture was stirred at 75° C. After 1.5 hours, the mixture was cooled to give a suspension. Methanol was added to the suspension and the precipitate was filtered and dried to give the desired compound in quantitative yield. The crude material was used without further purification.
$^1$H-NMR δ (CDCl$_3$): 1.19-1.25 (m, 2H), 1.54-1.61 (m, 2H), 2.44 (s, 3H), 3.45-3.52 (m, 1H), 7.26 (d, J=6.0 Hz, 1H), 7.52 (d, J=6.0 Hz, 1H), 8.07 (s, 1H).

d) 3-Cyclopropyl-5-(3-iodo-4-methylphenyl)-4H-1,2,4-triazole

A solution of N'-(imino(3-iodo-4-methylphenyl)methyl)cyclopropanecarbohydrazide (preparation 51c, 0.76 g, 2.2 mmol) in phosphorus oxychloride (10 mL) was heated in a sealed tube at 110° C. with stirring. After 14 hours, the mixture was cooled and concentrated in vacuo. Ethyl acetate and saturated aqueous sodium hydrogen carbonate solution were added to the residue. The organic layer was dried (MgSO$_4$) and evaporated in vacuo. The residue was purified by flash chromatography (2:1 hexanes/ethyl acetate) to give the title compound (0.14 g, 20%) as a white solid.

LRMS (m/z): 326 (M+1)$^+$.

$^1$H-NMR δ (DMSO-d$_6$): 1.93-1.04 (m, 4H), 2.04 (m, 1H), 2.38 (s, 3H), 7.38 (d, J=8.0 Hz, 1H), 7.84 (dd, J=8.0 and 1.7 Hz, 1H), 8.34 (d, J=1.7 Hz, 1H).

Preparation 52

3-(3-Iodo-4-methylphenyl)-5-(trifluoromethyl)-4H-1,2,4-triazole 2,2,2-Trifluoroacetohydrazide (0.14 g, 1.0 mmol) was added to a stirred solution of ethyl 3-iodo-4-methylbenzimidate (preparation 51b, 0.30 g, 1.0 mmol) in methanol (3 mL) and the mixture was stirred and heated to 70° C. After 2 hours, the mixture was cooled and concentrated in vacuo. The residue was purified by flash chromatography (5:1 hexanes/ethyl acetate) to give the title compound (0.10 g, 27%) as a white solid.

LRMS (m/z): 352 (M−1)$^−$.

$^1$H-NMR δ (CDCl$_3$): 2.48 (s, 3H), 7.33 (d, J=6.0 Hz, 1H), 7.76 (dd, J=6.0 Hz and 3.0 Hz, 1H), 8.36 (d, J=3.0 Hz, 1H).

Preparation 53

4-Methyl-3-(2'-oxospiro[cyclopentane-1,3'-indoline]-6'-yl)benzohydrazide

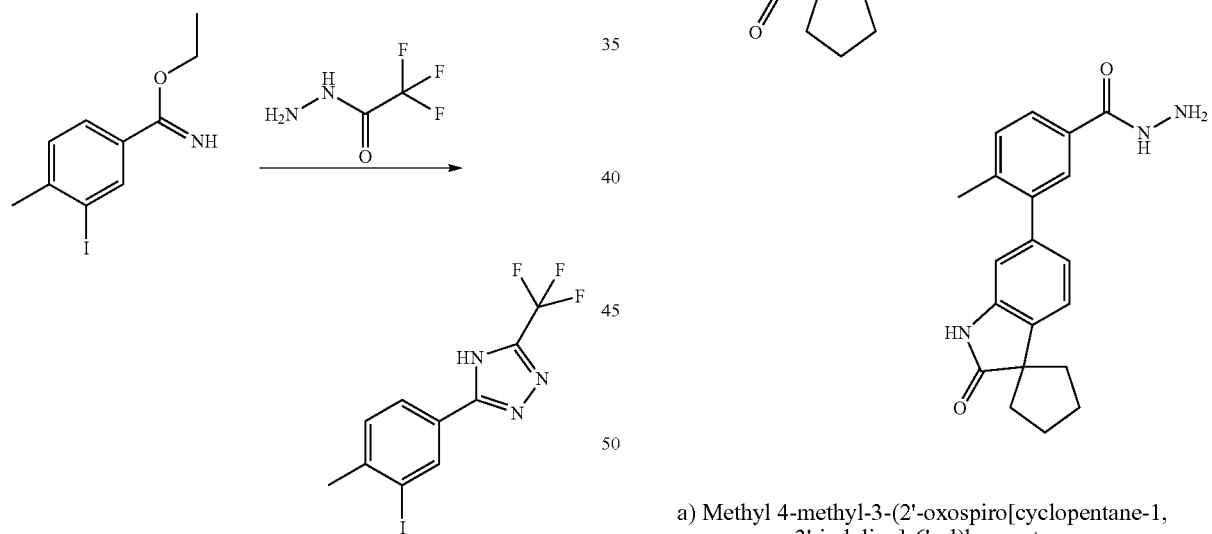

a) Methyl 4-methyl-3-(2'-oxospiro[cyclopentane-1,3'-indoline]-6'-yl)benzoate A suspension of 4-methyl-3-(2'-oxospiro[cyclopentane-1,3'-indoline]-6'-yl)benzoic acid (preparation 38, 0.47 g, 1.5 mmol) and a 4M solution of hydrochloric acid in dioxane (2.00 mL, 8.0 mmol) in methanol (2 mL) was heated in a sealed tube at 80° C. with stirring. After stirring overnight the mixture was cooled and ethyl acetate and saturated aqueous potassium carbonate solution were added. The organic layer was washed with brine, dried (MgSO$_4$) and evaporated in vacuo. The resultant oil was taken up in a small amount of ethyl acetate and the suspension was filtered. The filtrate was evaporated to give the title compound (0.46 g, 86%) as a foam.

LRMS (m/z): 336 (M+1)$^+$.

¹H-NMR δ (CDCl₃): 1.91-2.13 (m, 6H), 2.19-2.26 (m, 2H), 2.34 (s, 3H), 3.90 (s, 3H), 6.84 (s, 1H), 6.96 (d, J=6.0 Hz, 1H), 7.23 (d, J=9.0 Hz, 1H), 7.34 (d, J=9.0 Hz, 1H), 7.91 (s, 1H), 7.92 (d, J=6.0 Hz, 1H), 8.13 (brs, 1H).

b) 4-Methyl-3-(2'-oxospiro[cyclopentane-1,3'-indoline]-6'-yl)benzohydrazide

Hydrazine monohydrate (0.67 mL, 13.8 mmol) was added to a stirred solution of methyl 4-methyl-3-(2'-oxospiro[cyclopentane-1,3'-indoline]-6'-yl)benzoate (preparation 53a, 0.46 g, 1.3 mmol) in ethanol (6 mL) and the mixture was stirred at 80° C. After 3 days, the mixture was cooled and concentrated in vacuo. The crude material was purified by flash chromatography (50:1 dichloromethane/methanol) to give the title compound (0.16 g, 19%) as a solid.

LRMS (m/z): 336 (M+1)⁺.

Preparation 54

(E)-N'-Hydroxy-4-methyl-3-(2'-oxospiro[cyclopentane-1,3'-indoline]-6'-yl)benzimidamide

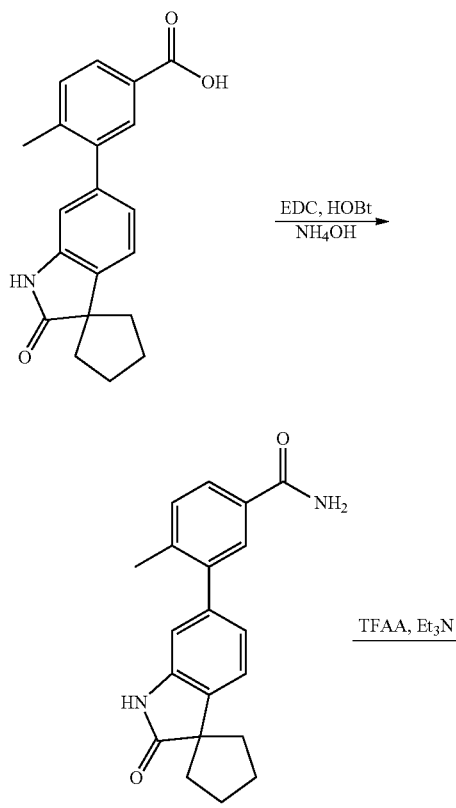

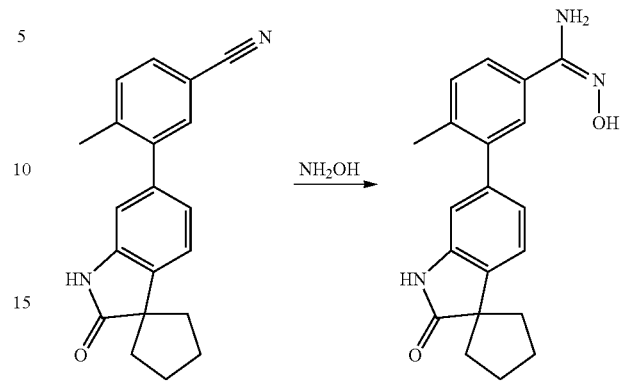

a) 4-Methyl-3-(2'-oxospiro[cyclopentane-1,3'-indoline]-6'-yl)benzamide

Obtained as a solid (22%) from 4-methyl-3-(2'-oxospiro[cyclopentane-1,3'-indoline]-6'-yl)benzoic acid (preparation 38) following the experimental procedure as described in preparation 48a followed by trituration of the crude product with a mixture of hexanes-ethyl acetate.

LRMS (m/z): 321 (M+1)⁺.

¹H-NMR δ (CDCl₃): 1.85-1.94 (m, 2H), 1.96-2.11 (m, 4H), 2.15-2.24 (m, 2H), 2.33 (s, 3H), 6.85 (d, J=3.0 Hz, 1H), 6.92 (dd, J=9.0 Hz and 3.0 Hz, 1H), 7.20 (d, J=6.0 Hz, 1H), 7.33 (d, J=9.0 Hz, 1H), 7.72 (d, J=3.0 Hz, 1H), 7.76 (dd, J=6.0 Hz and 3.0 Hz, 1H), 9.44 (brs, 1H).

b) 4-Methyl-3-(2'-oxospiro[cyclopentane-1,3'-indoline]-6'-yl)benzonitrile

Obtained as a pale yellow oil (48%) from 4-methyl-3-(2'-oxospiro[cyclopentane-1,3'-indoline]-6'-yl)benzamide (preparation 54a) following the experimental procedure as described in preparation 51a followed by purification by flash chromatography (99:1 dichloromethane/methanol).

LRMS (m/z): 303 (M+1)⁺.

c) (E)-N'-hydroxy-4-methyl-3-(2'-oxospiro[cyclopentane-1,3'-indoline]-6'-yl)benzimidamide A stirred mixture of 4-methyl-3-(2'-oxospiro[cyclopentane-1,3'-indoline]-6'-yl)benzonitrile (preparation 54b, 0.06 g, 0.20 mmol), hydroxylamine (0.02 g, 0.24 mmol) and sodium acetate (0.02 g, 0.27 mmol) in ethanol (0.60 mL) and water (0.10 mL) were heated to 85° C. in a sealed tube. After 6 hours, the mixture was cooled and concentrated in vacuo. Water was added to the residue and the resultant precipitate was filtered to give the title compound (0.06 g, 19%).

LRMS (m/z): 336 (M+1)⁺.

Preparation 55

2-Methyl-5-(5-methyl-1,3,4-oxadiazol-2-yl)phenylboronic acid

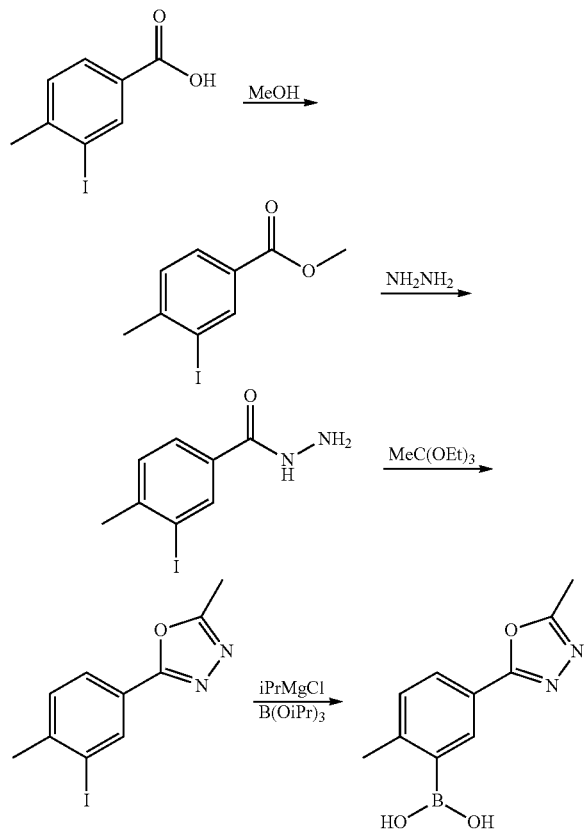

a) Methyl 3-iodo-4-methylbenzoate

Obtained (95%) from 3-iodo-4-methylbenzoic acid following the experimental procedure as described in preparation 53a.

LRMS (m/z): 277 (M+1)$^+$.

b) 3-Iodo-4-methylbenzohydrazide

Obtained (86%) from methyl 3-iodo-4-methylbenzoate (preparation 55a) following the experimental procedure as described in preparation 53b.

LRMS (m/z): 277 (M+1)$^+$.

$^1$H-NMR δ (DMSO-d6): 2.38 (s, 3H), 4.47 (brs, 2H), 7.38 (d, J=8.0 Hz, 1H), 7.74 (dd, J=8.0 and 2.0 Hz, 1H), 8.23 (d, J=2.0 Hz, 1H), 9.79 (brs, 1H).

c) 2-(3-Iodo-4-methylphenyl)-5-methyl-1,3,4-oxadiazole

A stirred mixture of 3-iodo-4-methylbenzohydrazide (preparation 55b, 5.00 g, 18.1 mmol) and triethyl orthoacetate (11.00 mL, 58.2 mmol) in acetic acid (30 mL) were heated to 150° C. in a sealed tube. After 3 hours, the mixture was cooled and concentrated in vacuo. Aqueous sodium hydrogen carbonate solution was added and the mixture was extracted with dichloromethane. The organic solution was dried (MgSO$_4$) and the solvent was removed in vacuo. The crude material was purified by flash chromatography (2:1 hexanes/ethyl acetate) to give the title compound (4.26 g, 78%) as a white solid.

LRMS (m/z): 301 (M+1)$^+$.

$^1$H-NMR δ (CDCl$_3$): 2.50 (s, 3H), 2.62 (s, 3H), 7.36 (d, J=9.0 Hz, 1H), 7.92 (d, J=9.0 Hz, 1H), 8.46 (s, 1H).

d) 2-Methyl-5-(5-methyl-1,3,4-oxadiazol-2-yl)phenylboronic acid

Isopropylmagnesium chloride (2.0 M in tetrahydrofuran, 10 mL, 20.0 mmol) was added dropwise over 20 minutes to a stirred solution of 2-(3-Iodo-4-methylphenyl)-5-methyl-1,3,4-oxadiazole (preparation 55c, 4.0 g, 13.3 mmol) in tetrahydrofuran (40 mL) at −10° C. The mixture was stirred for 1 hour at −10° C. then triisopropyl borate (4.71 mL, 20.0 mmol) was added dropwise over 10 minutes and the mixture was stirred for 1 hour at −10° C. Then, the mixture was warmed to room temperature and stirred overnight. Water was then added, the mixture was cooled by means of an ice-water bath and the pH was adjusted to 3-4 with 2M aqueous hydrochloric acid. The mixture was extracted with ethyl acetate and the organic layer was washed with brine, dried (MgSO$_4$) and evaporated. The residue was triturated with diethyl ether and the solid was filtered and dried to give the title compound (1.92 g, 66%) as a white solid.

LRMS (m/z): 219 (M+1)$^+$.

$^1$H-NMR δ (DMSO-d6): 2.46 (s, 3H), 2.56 (s, 3H), 7.32 (d, J=8.0 Hz, 1H), 7.81 (dd, J=8.0 and 2.0 Hz, 1H), 8.02 (d, J=2.0 Hz, 1H), 8.25 (brs, 2H).

Preparation 56

5-(5-Cyclopropyl-1,3,4-oxadiazol-2-yl)-2-methylphenylboronic acid

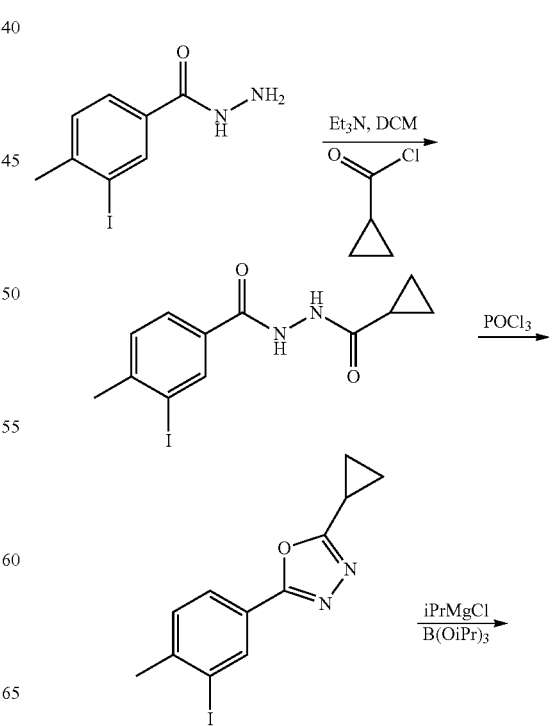

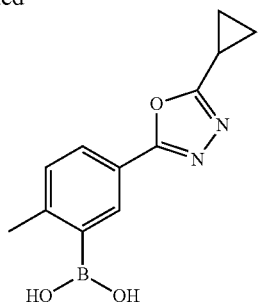

a) N'-(Cyclopropanecarbonyl)-3-iodo-4-methylbenzohydrazide

A solution of cyclopropanecarbonyl chloride (1.81 mL, 20.0 mmol) in dichloromethane (20 mL) was added dropwise to a stirred solution of 3-iodo-4-methylbenzohydrazide (preparation 55b, 5.00 g, 18.1 mmol) and triethylamine (2.78 mL, 20.0 mmol) in dichloromethane (80 mL) at 0° C. After 2 hours stirring at ambient temperature, the mixture was concentrated in vacuo and water was added to the residue. The resultant precipitate was filtered and was washed with water and diethyl ether to give the title compound (4.75 g, 76%) as a white solid.
LRMS (m/z): 345 (M+1)⁺.

b) 2-Cyclopropyl-5-(3-iodo-4-methylphenyl)-1,3,4-oxadiazole

Obtained (92%) from N'-(cyclopropanecarbonyl)-3-iodo-4-methylbenzohydrazide (preparation 56a) following the experimental procedure as described in preparation 51d.
LRMS (m/z): 327 (M+1)⁺.

c) 5-(5-Cyclopropyl-1,3,4-oxadiazol-2-yl)-2-methylphenylboronic acid

Obtained as a pale yellow solid (37%) from 2-cyclopropyl-5-(3-iodo-4-methylphenyl)-1,3,4-oxadiazole (preparation 56b) following the experimental procedure as described in preparation 55d followed by trituration of the crude product with diethyl ether.
LRMS (m/z): 245 (M+1)⁺.
¹H-NMR δ (DMSO-d6): 1.06-1.19 (m, 4H), 2.27 (m, 1H), 2.46 (s, 3H), 7.30 (d, J=8.0 Hz, 1H), 7.79 (dd, J=8.0 and 2.2 Hz, 1H), 7.99 (d, J=2.2 Hz, 1H), 8.25 (brs, 2H).

Preparation 57

3-Methyl-5-(4-methyl-3-(4,4,5,5-tetramethyl-1,3,2-dioxaborolan-2-yl)phenyl)-1,2,4-oxadiazole

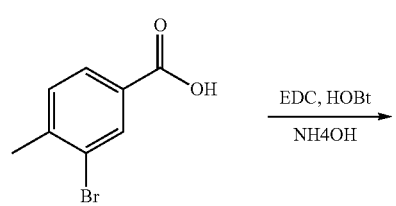

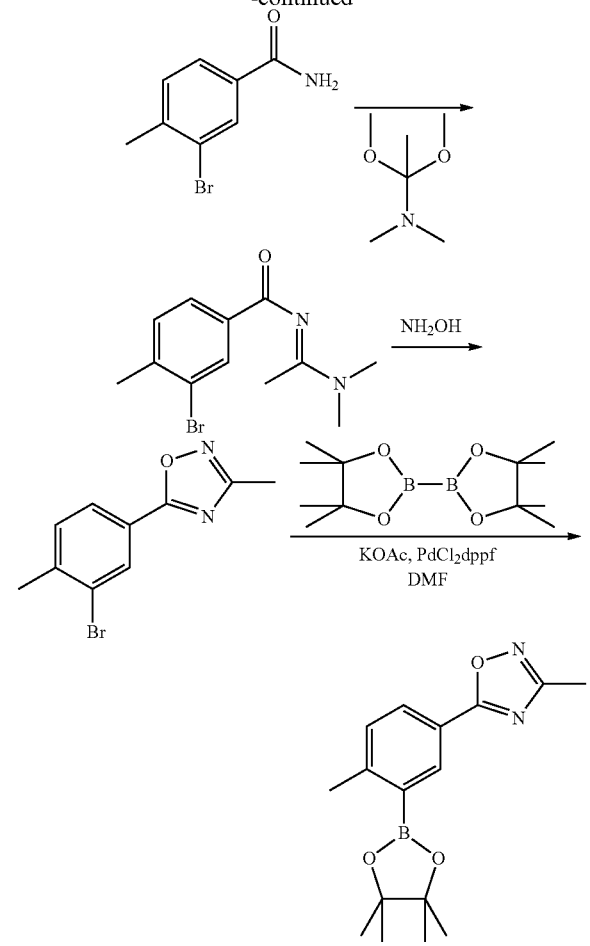

a) 3-Bromo-4-methylbenzamide

Obtained as a white solid (70%) from 3-bromo-4-methylbenzoic acid following the experimental procedure as described in preparation 48a followed by flash chromatography (1:1 hexanes/ethyl acetate).
LRMS (m/z): 214/216 (M+1)⁺.
¹H-NMR δ (DMSO-d₆): 2.37 (s, 3H), 7.42 (d, J=8.0 Hz, 1H), 7.44 (brs, 1H), 7.77 (dd, J=8.0 and 1.9 Hz, 1H), 8.02 (brs, 1H), 8.07 (d, J=1.9 Hz, 1H).

b) (E)-3-Bromo-N-(1-(dimethylamino)ethylidene)-4-methylbenzamide

Obtained from 3-bromo-4-methylbenzamide (preparation 57a) and 1,1-dimethoxy-N,N-dimethylethanamine following the experimental procedure as described in preparation 48b. The desired compound was obtained in quantitative yield and was used without further purification.
LRMS (m/z): 283/285 (M+1)⁺.

c) 5-(3-Bromo-4-methylphenyl)-3-methyl-1,2,4-oxadiazole

A solution of (E)-3-bromo-N-(1-(dimethylamino)ethylidene)-4-methylbenzamide (preparation 57b, 0.20 g, 0.71 mmol) in dioxane (1.20 mL) was added dropwise to a stirred solution of hydroxylamine (0.06 g, 0.85 mmol) and sodium hydroxide (0.03 g, 0.85 mmol) in acetic acid (2.50 mL) and the mixture was stirred at 100° C. After 0.5 hours, the mixture was concentrated in vacuo, 4% aqueous sodium hydrogen carbonate solution was added to the residue and the mixture was extracted with ethyl acetate. The organic solution was dried (MgSO$_4$) and the solvent removed in vacuo to give the title compound (0.10 g, 56%) as a white solid.

LRMS (m/z): 253/255 (M+1)$^+$.

d) 3-Methyl-5-(4-methyl-3-(4,4,5,5-tetramethyl-1,3,2-dioxaborolan-2-yl)phenyl)-1,2,4-oxadiazole Obtained as a solid (65%) from 5-(3-bromo-4-methylphenyl)-3-methyl-1,2,4-oxadiazole (preparation 57c) following the experimental procedure as described in preparation 9 followed by purification by flash chromatography (100% hexanes to 100% ethyl acetate).

LRMS (m/z): 301 (M+1)$^+$.

Preparation 58

5-(3-Bromo-4-methylphenyl)-2-methyl-1H-imidazole

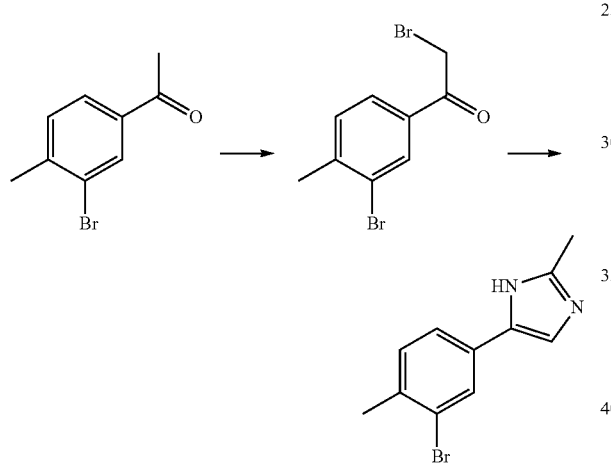

a) 2-Bromo-1-(3-bromo-4-methylphenyl)ethanone

A solution of bromine (0.68 mL, 13.3 mmol) in chloroform (13 mL) was added dropwise over a 35 minute period to a stirred solution of 1-(3-bromo-4-methylphenyl)ethanone (2.96 g, 13.9 mmol) in chloroform (40 mL) at 0° C. After the addition, the ice-bath was removed and the mixture was stirred at room temperature for 2 hours. The solvent was removed under reduced pressure to give an oil which crystallized to give the title compound (4.11 g, 95%) as an orange solid.

LRMS (m/z): 295/293/291 (M+1)$^+$.

$^1$H-NMR δ (CDCl$_3$): 2.42 (s, 3H), 4.40 (s, 2H), 7.36 (d, J=7.7 Hz, 1H), 7.82 (d, J=7.7 Hz, 1H), 8.15 (s, 1H).

b) 5-(3-Bromo-4-methylphenyl)-2-methyl-1H-imidazole

Potassium bicarbonate (2.10 g, 20.7 mmol) was added portionwise to a solution of acetimidamide hydrochloride (1.06 g, 11.2 mmol) in tetrahydrofuran (20 mL) and water (5 mL). The resulting mixture was heated to reflux and 2-bromo-1-(3-bromo-4-methylphenyl)ethanone (preparation 58a, 2.74 g, 9.4 mmol) was added dropwise over a period of 20 minutes. After 3 hours, further acetamidamide hydrochloride (1.06 g, 11.2 mmol) and potassium bicarbonate (1.03 g, 10.1 mmol) were added and the was mixture refluxed overnight. The mixture was evaporated to dryness and partitioned between 2M aqueous hydrochloric acid and ethyl acetate. The acidic aqueous layer was bascified with solid sodium hydroxide and extracted with ethyl acetate. The organic layer was dried (MgSO$_4$) and the solvent was evaporated under reduced pressure to give a semi solid. This semi solid was heated in vacuo at 70° C. for one hour in order to remove excess acetamidamide to give the pure title compound (0.10 g, 5%) as a white solid.

LRMS (m/z): 251/253 (M+1)$^+$.

$^1$H-NMR δ (CDCl$_3$): 2.37 (s, 3H), 2.47 (s, 3H), 7.16 (s, 1H), 7.21 (d, J=8.0 Hz, 1H), 7.53 (d, J=8.0 Hz, 1H), 7.88 (s, 1H).

Preparation 59

2-(3-Iodo-4-methylphenyl)-5-methyl-1H-imidazole

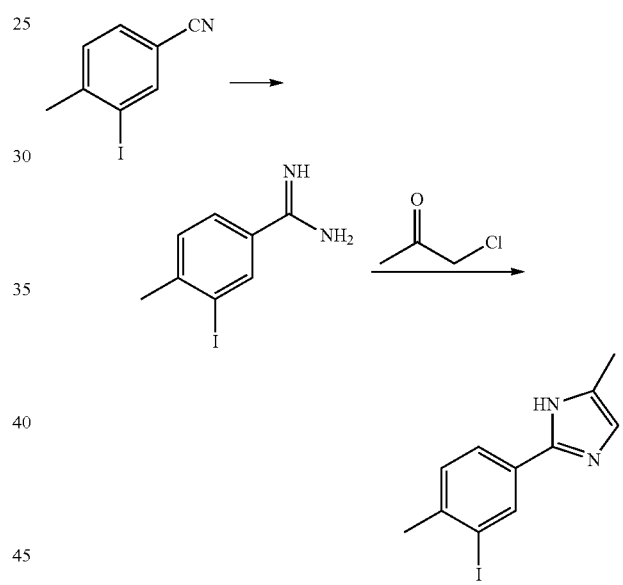

a) 3-Iodo-4-methylbenzenecarboximidamide

Lithium bis(trimethylsilyl)amide (1M in tetrahydrofuran, 9.9 mL, 9.9 mmol) was added dropwise over 2 minutes to a cooled (10° C.) solution of 3-iodo-4-methylbenzonitrile (preparation 51a, 2.00 g, 8.2 mmol) in tetrahydrofuran (10 mL). After 1.5 hours, the mixture was cooled to 0° C. and water (20 mL) was slowly added. The pH was adjusted to 1 with 3M aqueous hydrochloric acid and then the mixture was stirred for 30 minutes. The aqueous layer was extracted with diethyl ether and ethyl acetate and then made basic with sodium hydroxide pellets which resulted in the separation of an oil. The mixture was extracted with ethyl acetate and the organic layer was dried and evaporated under reduced pressure. The residue was triturated with diethyl ether to give the title compound (0.54 g, 25%) as a yellow solid.

LRMS (m/z): 244 (M+1)$^+$.

$^1$H-NMR δ (DMSO-d6): 2.35 (s, 3H), 6.90 (brs, 2H), 7.36 (d, J=7.7 Hz, 1H), 7.70 (d, J=7.7 Hz, 1H), 8.22 (s, 1H).

b) 2-(3-Iodo-4-methylphenyl)-5-methyl-1H-imidazole

Potassium hydrogen carbonate (0.204 g, 2.0 mmol) was added to a solution of 3-iodo-4-methylbenzenecarboximidamide (preparation 59a, 0.53 g, 0.54 mmol) in tetrahydrofuran (5 mL) and water (1 mL) and the mixture was heated to reflux. Then 1-chloropropan-2-one (0.16 mL, 2.1 mmol) in tetrahydrofuran (2.50 mL) was added dropwise over 20 min and the mixture was refluxed overnight. The mixture was evaporated and the residue purified by flash chromatography (2:1 hexanes/ethyl acetate) to give the title compound (0.13 g, 22%) as a white solid.

LRMS (m/z): 299 (M+1)+.

$^1$H-NMR δ (CDCl$_3$): 2.30 (s, 3H), 2.42 (s, 3H), 6.83 (s, 1H), 7.23 (d, J=7.7 Hz, 1H), 7.65 (d, J=7.7 Hz, 1H), 8.22 (s, 1H).

EXAMPLE 1

N-Cyclopropyl-4-methyl-3-(2'-oxospiro[cyclopentane-1,3'-indoline]-6'-yl)benzamide

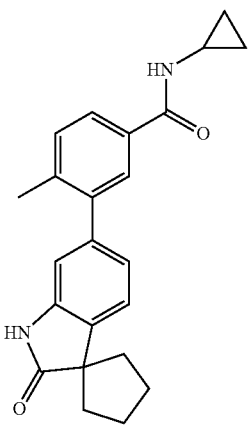 [SMILES: Cc1ccc(C(=O)NC2CC2)cc1-c1ccc2c(c1)NC(=O)C21CCCC1]

Obtained as a white solid (56%) from 6'-bromospiro[cyclopentane-1,3'-indolin]-2'-one (preparation 2) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (98:2 dichloromethane/methanol).

LRMS (m/z): 361 (M+1)+.

$^1$H-NMR δ (CDCl$_3$): 0.58-0.66 (m, 2H), 0.83-0.89 (m, 2H), 1.88-2.12 (m, 6H), 2.17-2.24 (m, 2H), 2.31 (s, 3H), 2.87-2.95 (m, 1H), 6.36 (brs, 1H), 6.81 (s, 1H), 6.94 (d, J=6.0 Hz, 1H), 7.21 (d, J=6.0 Hz, 1H), 7.31 (d, J=6.0 Hz, 1H), 7.57 (d, J=3.0 Hz, 1H), 7.66 (dd, J=6.0 Hz and 3.0 Hz, 1H), 7.86 (brs, 1H).

EXAMPLE 2

N-cyclopropyl-3-(2'-oxospiro[cyclopentane-1,3'-indoline]-6'-yl)benzamide

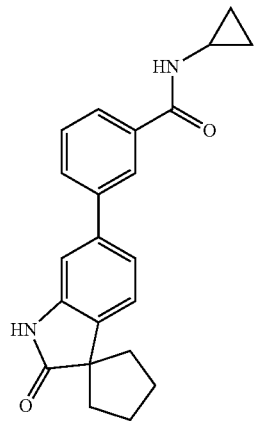 [SMILES: O=C(NC1CC1)c1cccc(-c2ccc3c(c2)NC(=O)C32CCCC2)c1]

Obtained as a white solid (70%) from 6'-bromospiro[cyclopentane-1,3'-indolin]-2'-one (preparation 2) and N-cyclopropyl-3-(4,4,5,5-tetramethyl-1,3,2-dioxaborolan-2-yl)benzamide (preparation 43) following the experimental procedure as described in preparation 38 followed by purification by flash chromatography (98:2 dichloromethane/methanol).

LRMS (m/z): 347 (M+1)+.

$^1$H-NMR δ (DMSO-d$_6$): 0.64-0.68 (m, 2H), 0.81-0.86 (m, 2H), 1.87-1.95 (m, 2H), 2.03-2.15 (m, 6H), 2.85-2.90 (m, 1H), 7.17 (d, J=2 Hz, 1H), 7.31-7.36 (m, 2H), 7.49-7.58 (m, 1H), 7.74-7.80 (m, 2H), 8.03-8.06 (m, 1H).

EXAMPLE 3

N-Cyclopropyl-4-methyl-3-(2'-oxo-1',2'-dihydrospiro[cyclobutane-1,3'-indol]-6'-yl)benzamide

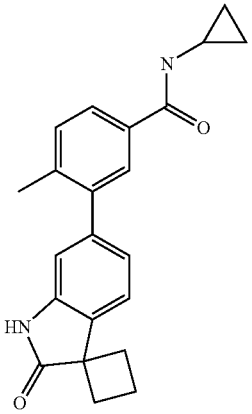 [SMILES: Cc1ccc(C(=O)NC2CC2)cc1-c1ccc2c(c1)NC(=O)C21CCC1]

Obtained as a white solid (89%) from 6'-bromospiro[cyclobutane-1,3'-indol]-2'(1'H)-one (preparation 6) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (98:2 dichloromethane/methanol).

LRMS (m/z): 347 (M+1)+.

¹H-NMR δ (DMSO-d₆): 0.55-0.56 (m, 2H), 0.68 (m, 2H), 2.23-2.45 (m, 6H), 2.27 (s, 3H), 2.81-2.87 (m, 1H), 6.73 (s, 1H), 7.00 (m, 1H), 7.38 (d, J=8.0 Hz, 1H), 7.64 (d, J=8.0 Hz, 1H), 7.67 (s, 1H), 7.75 (m, 1H), 8.40 (s, 1H), 10.30 (s, 1H).

EXAMPLE 4

N-Isopropyl-4-methyl-3-(2'-oxospiro[cyclopentane-1,3'-indoline]-6'-yl)benzamide

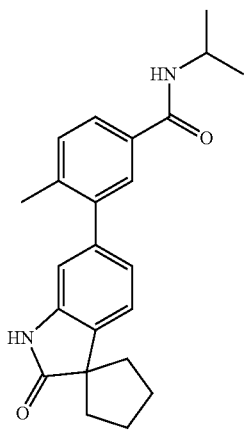 [SMILES: Cc1ccc(C(=O)NC(C)C)cc1-c1ccc2c(c1)NC(=O)C21CCCC1]

Obtained as a white solid (62%) from 4-methyl-3-(2'-oxospiro[cyclopentane-1,3'-indoline]-6'-yl)benzoic acid (preparation 38) and isopropylamine following the experimental procedure as described in preparation 40 followed by trituration of the crude product with diethyl ether.

LRMS (m/z): 363 (M+1)⁺.

¹H-NMR δ (CDCl₃): 1.24 (s, 3H), 1.26 (s, 3H), 1.90-2.12 (m, 6H), 2.19-2.25 (m, 2H), 2.31 (s, 3H), 4.24-4.35 (m, 1H), 5.93 (brs, 1H), 6.82 (s, 1H), 6.96 (d, J=6.0 Hz, 1H), 7.23 (d, J=9.0 Hz, 1H), 7.33 (d, J=9.0 Hz, 1H), 7.57 (d, J=3.0 Hz, 1H), 7.67 (dd, J=6.0 Hz and 3.0 Hz, 1H), 7.75 (brs, 1H).

EXAMPLE 5

N-4-Dimethyl-3-(2'-oxospiro[cyclopentane-1,3'-indoline]-6'-yl)benzamide

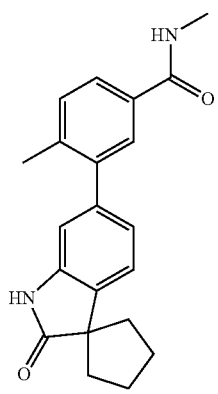

Obtained as a white solid (40%) from 4-methyl-3-(2'-oxospiro[cyclopentane-1,3'-indoline]-6'-yl)benzoic acid (preparation 38) and methylamine hydrochloride following the experimental procedure as described in preparation 40 followed by trituration of the crude product with hexanes.

LRMS (m/z): 335 (M+1)⁺.

¹H-NMR δ (CDCl₃): 1.89-2.12 (m, 6H), 2.19-2.25 (m, 2H), 2.32 (s, 3H), 3.01 (d, J=6.0 Hz, 3H), 6.80 (brs, 1H), 6.80 (s, 1H), 6.95 (d, J=6.0 Hz, 1H), 7.22 (d, J=9.0 Hz, 1H), 7.33 (d, J=9.0 Hz, 1H), 7.53 (brs, 1H), 7.61 (d, J=~3.0 Hz, 1H), 7.66 (dd, J=6.0 Hz and 3.0 Hz, 1H).

EXAMPLE 6

4-Methyl-3-(2'-oxospiro[cyclopentane-1,3'-indoline]-6'-yl)benzamide

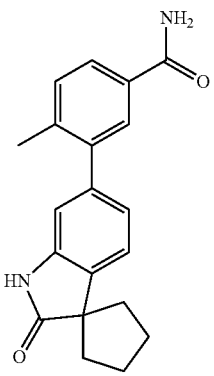 [SMILES: Cc1ccc(C(N)=O)cc1-c1ccc2c(c1)NC(=O)C21CCCC1]

Obtained as a white solid (22%) from 4-methyl-3-(2'-oxospiro[cyclopentane-1,3'-indoline]-6'-yl)benzoic acid (preparation 38) and aqueous ammonium hydroxide solution following the experimental procedure as described in preparation 40 followed by trituration with hexanes and ethyl acetate.

LRMS (m/z): 321 (M+1)⁺.

¹H-NMR δ (CDCl₃): 1.85-1.93 (m, 2H), 1.96-2.11 (m, 4H), 2.15-2.22 (m, 2H), 2.33 (s, 3H), 6.85 (d, J=3.0 Hz, 1H), 6.92 (dd, J=9.0 Hz and 3.0 Hz, 1H), 7.20 (d, J=9.0 Hz, 1H), 7.33 (d, J=9.0 Hz, 1H), 7.72 (d, J=3.0 Hz, 1H), 7.76 (dd, J=9.0 Hz and 3.0 Hz, 1H), 9.44 (brs, 1H).

EXAMPLE 7

3-(3,3-dimethyl-2-oxoindolin-6-yl)-4-methylbenzamide

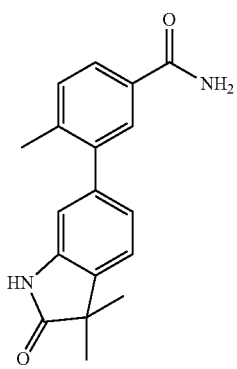 [SMILES: Cc1ccc(C(N)=O)cc1-c1ccc2c(c1)NC(=O)C2(C)C]

Obtained as a white solid (23%) from 3-(3,3-dimethyl-2-oxoindolin-6-yl)-4-methylbenzoic acid (preparation 39) and aqueous ammonium hydroxide solution following the experimental procedure as described in preparation 40 followed by purification by flash chromatography (98:2 dichloromethane/methanol).

LRMS (m/z): 295 (M+1)⁺.

¹H-NMR δ (CD₃OD): 1.39 (s, 6H), 2.31 (s, 3H), 6.89 (s, 1H), 6.99 (d, J=6.32 Hz, 1H), 7.34 (m, 1H), 7.75 (m, 1H).

EXAMPLE 8

N-Cyclobutyl-4-methyl-3-(2'-oxospiro[cyclopentane-1,3'-indoline]-6'-yl)benzamide

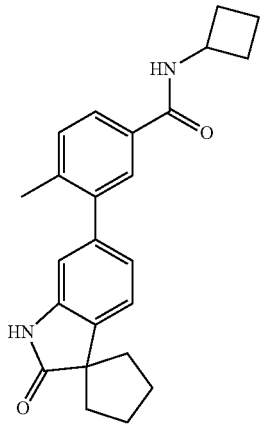 [SMILES: Cc1ccc(C(=O)NC2CCC2)cc1-c1ccc2c(c1)NC(=O)C21CCCC1]

Obtained as a white solid (67%) from 4-methyl-3-(2'-oxospiro[cyclopentane-1,3'-indoline]-6'-yl)benzoic acid (preparation 38) and cyclobutanamine following the experimental procedure as described in preparation 40 followed by trituration with hexanes.

LRMS (m/z): 375 (M+1)$^+$.

$^1$H-NMR δ (CDCl$_3$): 1.71-1.81 (m, 2H), 1.89-2.12 (m, 8H), 2.18-2.25 (m, 2H), 2.31 (s, 3H), 2.38-2.48 (m, 2H), 4.53-4.67 (m, 1H), 6.33 (brs, 1H), 6.82 (s, 1H), 6.96 (d, J=9.0 Hz, 1H), 7.22 (d, J=9.0 Hz, 1H), 7.32 (d, J=9.0 Hz, 1H), 7.59 (d, J=3.0 Hz, 1H), 7.68 (dd, J=9.0 Hz and 3.0 Hz, 1H), 7.83 (brs, 1H).

EXAMPLE 9

N-(Cyclopropylmethyl)-4-methyl-3-(2'-oxospiro[cyclopentane-1,3'-indoline]-6'-yl)benzamide

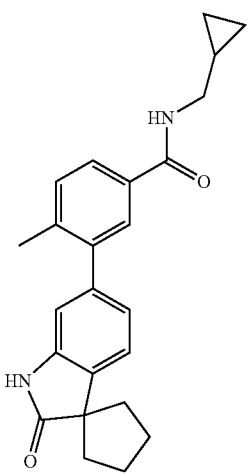 [SMILES: Cc1ccc(C(=O)NCC2CC2)cc1-c1ccc2c(c1)NC(=O)C21CCCC1]

Obtained as a white solid (46%) from 4-methyl-3-(2'-oxospiro[cyclopentane-1,3'-indoline]-6'-yl)benzoic acid (preparation 38) and cyclopropylmethanamine following the experimental procedure as described in preparation 40 followed by trituration with hexanes.

LRMS (m/z): 375 (M+1)$^+$.

$^1$H-NMR δ (CDCl$_3$): 0.24-0.29 (m, 2H), 0.52-0.58 (m, 2H), 1.00-1.09 (m, 1H), 1.90-2.12 (m, 6H), 2.19-2.25 (m, 2H), 2.32 (s, 3H), 3.29-3.34 (m, 2H), 6.23 (brs, 1H), 6.83 (s, 1H), 6.97 (d, J=6.0 Hz, 1H), 7.23 (d, J=9.0 Hz, 1H), 7.34 (d, J=9.0 Hz, 1H), 7.62 (d, J=3.0 Hz, 1H), 7.71 (dd, J=6.0 Hz and 3.0 Hz, 1H), 7.75 (brs, 1H).

EXAMPLE 10

N-tert-Butyl-4-methyl-3-(2'-oxospiro[cyclopentane-1,3'-indoline]-6'-yl)benzamide

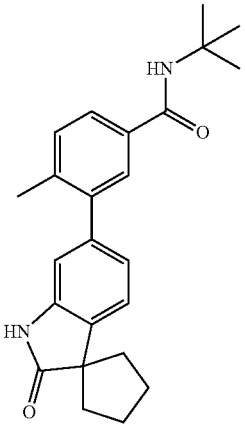 [SMILES: Cc1ccc(C(=O)NC(C)(C)C)cc1-c1ccc2c(c1)NC(=O)C21CCCC1]

Obtained as a white solid (64%) from 4-methyl-3-(2'-oxospiro[cyclopentane-1,3'-indoline]-6'-yl)benzoic acid (preparation 38) and 2-methylpropan-2-amine following the experimental procedure as described in preparation 40 followed by trituration with hexanes.

LRMS (m/z): 377 (M+1)$^+$.

$^1$H-NMR δ (CDCl$_3$): 1.46 (s, 9H), 1.91-2.13 (m, 6H), 2.19-2.26 (m, 2H), 2.31 (s, 3H), 5.92 (brs, 1H), 6.81 (s, 1H), 6.97 (d, J=9.0 Hz, 1H), 7.23 (d, J=9.0 Hz, 1H), 7.32 (d, J=9.0 Hz, 1H), 7.48 (brs, 1H), 7.53 (d, J=3.0 Hz, 1H), 7.64 (dd, J=6.0 Hz and 3.0 Hz, 1H).

EXAMPLE 11

4-Methyl-3-(2'-oxospiro[cyclopentane-1,3'-indoline]-6'-yl)-N-(pyridin-2 yl)benzamide

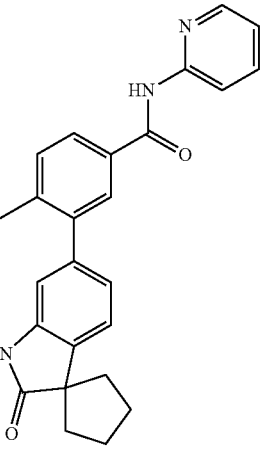

Obtained as a white solid (49%) from 4-methyl-3-(2'-oxospiro[cyclopentane-1,3'-indoline]-6'-yl)benzoic acid (preparation 38) and pyridin-2-amine following the experimental procedure as described in preparation 40 followed by purification by flash chromatography (99:1 dichloromethane/methanol).

LRMS (m/z): 398 (M+1)$^+$.

¹H-NMR δ (CDCl₃): 1.91-2.14 (m, 6H), 2.20-2.27 (m, 2H), 2.37 (s, 3H), 6.83 (s, 1H), 6.99 (d, J=9.0 Hz, 1H), 7.05-7.10 (m, 1H), 7.25 (d, J=9.0 Hz, 1H), 7.36 (brs, 1H), 7.41 (d, J=9.0 Hz, 1H), 7.78 (d, J=3.0 Hz, 1H), 7.83 (dd, J=6.0 Hz and 3.0 Hz, 1H) 8.29-8.31 (m, 1H), 8.37-8.40 (m, 1H), 8.57 (brs, 1H).

EXAMPLE 12

N-(Isoxazol-3-yl)-4-methyl-3-(2'-oxospiro[cyclopentane-1,3'-indoline]-6'-yl)benzamide

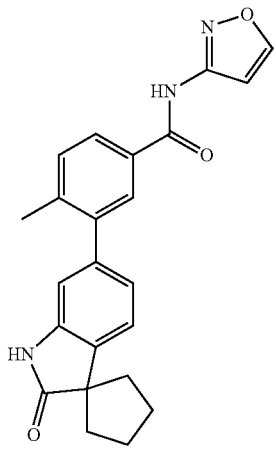 [SMILES: Cc1ccc(C(=O)Nc2ccon2)cc1-c1ccc2c(c1)NC(=O)C21CCCC1]

Obtained as a white solid (64%) from 4-methyl-3-(2'-oxospiro[cyclopentane-1,3'-indoline]-6'-yl)benzoic acid (preparation 38) and isoxazol-3-amine following the experimental procedure as described in preparation 40 followed by purification by flash chromatography (99:1 dichloromethane/methanol).

LRMS (m/z): 388 (M+1)⁺.

¹H-NMR δ (DMSO-d₆): 1.79-1.86 (m, 2H), 1.94-2.03 (m, 6H), 2.33 (s, 3H), 6.83 (s, 1H), 6.98-7.07 (m, 2H), 7.33 (d, J=9.0 Hz, 1H), 7.46 (d, J=9.0 Hz, 1H), 7.90-7.95 (m, 2H), 8.85 (d, J=3.0 Hz, 1H), 10.38 (brs, 1H), 11.44 (brs, 1H).

EXAMPLE 13

4-Methyl-3-(2'-oxospiro[cyclopentane-1,3'-indoline]-6'-yl)-N-(1H-1,2,4-triazol-3-yl)benzamide

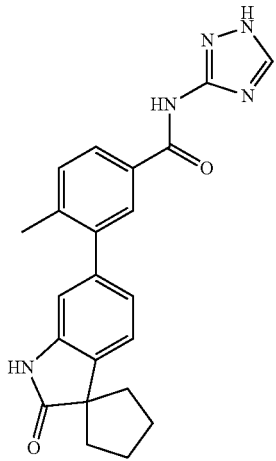 [SMILES: Cc1ccc(C(=O)Nc2nc[nH]n2)cc1-c1ccc2c(c1)NC(=O)C21CCCC1]

Obtained as a white solid (47%) from 4-methyl-3-(2'-oxospiro[cyclopentane-1,3'-indoline]-6'-yl)benzoic acid (preparation 38) and 1H-1,2,4-triazol-3-amine following the experimental procedure as described in preparation 40 followed by purification by flash chromatography (95:5 dichloromethane/methanol).

LRMS (m/z): 388 (M+1)⁺.

¹H-NMR δ (DMSO-d₆): 1.79-1.83 (m, 2H), 1.92-2.03 (m, 6H), 2.33 (s, 3H), 6.79 (s, 1H), 6.96 (d, J=9.0 Hz, 1H), 7.33 (d, J=6.0 Hz, 1H), 7.48 (d, J=6.0 Hz, 1H), 7.71 (s, 2H), 7.95-8.00 (m, 2H), 10.37 (brs, 1H).

EXAMPLE 14

4-Chloro-N-cyclopropyl-3-(2'-oxospiro[cyclopentane-1,3'-indoline]-6'-yl)benzamide

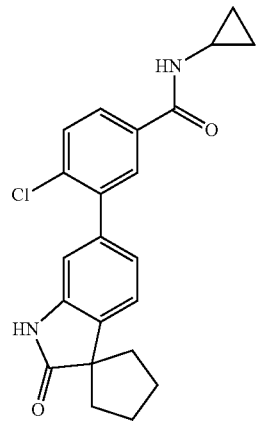 [SMILES: O=C(NC1CC1)c1ccc(Cl)c(-c2ccc3c(c2)NC(=O)C32CCCC2)c1]

Obtained as a solid (32%) from 6'-bromospiro[cyclopentane-1,3'-indolin]-2'-one (preparation 2) and 4-chloro-N-cyclopropyl-3-(4,4,5,5-tetramethyl-1,3,2-dioxaborolan-2-yl)benzamide (preparation 44) following the experimental procedure as described in preparation 38 followed by purification by flash chromatography (3:1 hexanes/ethyl acetate).

LRMS (m/z): 381 (M+1)⁺.

¹H-NMR δ (DMSO-d₆): 1.89-1.95 (m, 2H), 2.04-2.19 (m, 6H), 6.97 (s, 1H), 7.09 (d, J=6.0 Hz, 1H), 7.33 (d, J=6.0 Hz, 1H), 7.59 (d, J=6.0 Hz, 1H), 7.76 (d, J=6.0 Hz, 1H), 7.80 (s, 1H), 8.56 (brs, 1H).

EXAMPLE 15

N-Cyclopropyl-3-fluoro-4-methyl-5-(2'-oxospiro[cyclopentane-1,3'-indoline]-6'-yl)benzamide

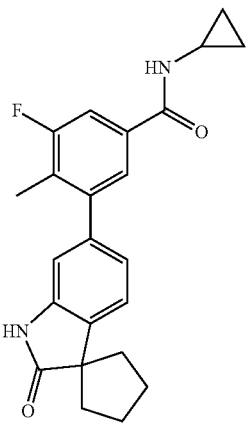 [SMILES: Cc1c(F)cc(C(=O)NC2CC2)cc1-c1ccc2c(c1)NC(=O)C21CCCC1]

Obtained as a solid (86%) from 6'-bromospiro[cyclopentane-1,3'-indolin]-2'-one (preparation 2) and N-cyclopropyl- 3-fluoro-4-methyl-5-(4,4,5,5-tetramethyl-1,3,2-dioxaborolan-2-yl)benzamide (preparation 45) following the experimental procedure as described in preparation 38 followed by purification by flash chromatography (99:1 dichloromethane/methanol).

LRMS (m/z): 379 (M+1)+.

1H-NMR δ (CDCl3): 0.58-0.64 (m, 2H), 0.84-0.90 (m, 2H), 1.86-2.14 (m, 6H), 2.17-2.21 (m, 2H), 2.22 (s, 3H), 2.86-2.94 (m, 1H), 6.30 (brs, 1H), 6.79 (s, 1H), 6.94 (d, J=9.0 Hz, 1H), 7.23 (d, J=9.0 Hz, 1H), 7.36 (d, J=3.0 Hz, 1H), 7.46 (dd, J=9.0 Hz and 3.0 Hz, 1H), 7.67 (brs, 1H).

EXAMPLE 16

N-Cyclopropyl-6-methyl-5-(2'-oxospiro[cyclopentane-1,3'-indoline]-6'-yl)nicotinamide

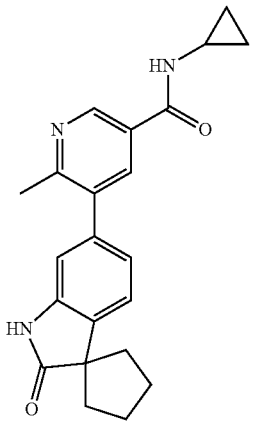 [SMILES: Cc1ncc(C(=O)NC2CC2)cc1-c1ccc2c(c1)NC(=O)C21CCCC1]

Obtained as a white solid (39%) from 6'-(4,4,5,5-tetramethyl-1,3,2-dioxaborolan-2-yl)spiro[cyclopentane-1,3'-indolin]-2'-one (preparation 4) and 5-bromo-N-cyclopropyl-6-methylnicotinamide (preparation 47) following the experimental procedure as described in preparation 38 followed by purification by reverse phase chromatography (30% CH3CN in H2O to 60% CH3CN in H2O).

LRMS (m/z): 362 (M+1)+.

1H-NMR δ (DMSO-d6): 0.62-0.67 (m, 2H), 0.79-0.85 (m, 2H), 1.89-1.94 (m, 2H), 2.04-2.16 (m, 6H), 2.53 (s, 3H), 2.83-2.91 (m, 1H), 6.90 (s, 1H), 7.01 (d, J=6.0 Hz, 1H), 7.36 (d, J=6.0 Hz, 1H), 8.03 (s, 1H), 8.83 (s, 1H).

EXAMPLE 17

N-Cyclopropyl-3-(3,3-dimethyl-2-oxoindolin-6-yl)-4-methylbenzamide

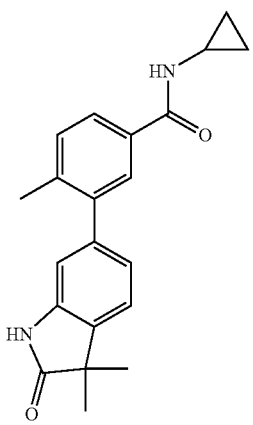 [SMILES: Cc1ccc(C(=O)NC2CC2)cc1-c1ccc2c(c1)NC(=O)C2(C)C]

Obtained as a white solid (30%) from 6-bromo-3,3-dimethylindolin-2-one (preparation 16) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (98:2 dichloromethane/methanol).

LRMS (m/z): 335 (M+1)+.

1H-NMR δ (CDCl3): 0.58-0.64 (m, 2H), 0.83-0.90 (m, 2H), 1.44 (s, 6H), 2.31 (s, 3H), 2.87-2.95 (m, 1H), 6.30 (brs, 1H), 6.84 (d, J=3.0 Hz, 1H), 6.97 (dd, J=6.0 Hz and 3.0 Hz, 1H), 7.23 (d, J=9.0 Hz, 1H), 7.32 (d, J=9.0 Hz, 1H), 7.57 (d, J=3.0 Hz, 1H), 7.67 (dd, J=6.0 Hz and 3.0 Hz, 1H), 7.75 (brs, 1H).

EXAMPLE 18

N-(Cyclopropylmethyl)-3-(3,3-dimethyl-2-oxoindolin-6-yl)-4-methylbenzamide

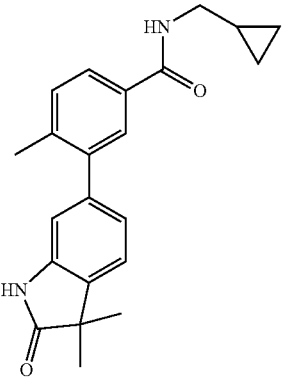 [SMILES: Cc1ccc(C(=O)NCC2CC2)cc1-c1ccc2c(c1)NC(=O)C2(C)C]

Obtained as a solid (30%) from 6-bromo-3,3-dimethylindolin-2-one (preparation 16) and N-(cyclopropylmethyl)-4-methyl-3-(4,4,5,5-tetramethyl-1,3,2-dioxaborolan-2-yl)benzamide (preparation 41) following the experimental procedure as described in preparation 38 followed by purification by flash chromatography (98:2 dichloromethane/methanol).

LRMS (m/z): 349 (M+1)+.

1H-NMR δ (CDCl3): 0.24-0.29 (m, 2H), 0.51-0.57 (m, 2H), 0.99-1.10 (m, 1H), 1.43 (s, 6H), 2.32 (s, 3H), 3.30-3.34 (m, 2H), 6.41 (brs, 1H), 6.87 (s, 1H), 6.98 (d, J=9.0 Hz, 1H), 7.22 (d, J=9.0 Hz, 1H), 7.33 (d, J=9.0 Hz, 1H), 7.63 (d, J=3.0 Hz, 1H), 7.72 (dd, J=9.0 Hz and 3.0 Hz, 1H), 8.47 (brs, 1H).

EXAMPLE 19

3-(3,3-Dimethyl-2-oxo-2,3-dihydro-1H-indol-6-yl)-N-isoxazol-3-yl-4-methylbenzamide

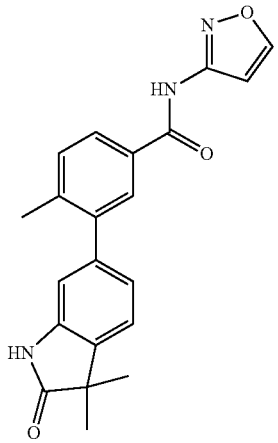 [SMILES: Cc1ccc(C(=O)Nc2ccon2)cc1-c1ccc2c(c1)NC(=O)C2(C)C]

Obtained as a brown solid (62%) from 3,3-dimethyl-6-(4,4,5,5-tetramethyl-1,3,2-dioxaborolan-2-yl)-1,3-dihydro-2H-indol-2-one (preparation 17) and 3-iodo-N-isoxazol-3-yl-4-methylbenzamide (preparation 42) following the experimental procedure as described in preparation 38 followed by purification by flash chromatography (dichloromethane to 95:5 dichloromethane/methanol).

LRMS (m/z): 362 (M+1)$^+$.

$^1$H-NMR δ (DMSO-d$_6$): 1.30 (s, 6H), 2.33 (s, 3H), 6.85 (s, 1H), 7.01 (d, J=8.0 Hz 1H), 7.04 (s, 1H), 7.37 (d, J=6.0 Hz, 1H), 7.45 (d, J=6.0 Hz, 1H), 7.91 (d, J=8.0 Hz, 1H), 7.93 (s, 1H), 8.84 (s, 1H), 10.43 (s, 1H), 11.43 (s, 1H).

EXAMPLE 20

N-Cyclopropyl-4-methyl-3-(1,3,3-trimethyl-2-oxoindolin-6-yl)benzamide

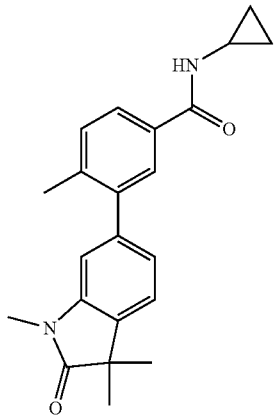 [SMILES: Cc1ccc(C(=O)NC2CC2)cc1-c1ccc2c(c1)N(C)C(=O)C2(C)C]

Obtained as a pale yellow solid (92%) from 6-bromo-1,3,3-trimethylindolin-2-one (preparation 15) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (98:2 dichloromethane/methanol).

LRMS (m/z): 349 (M+1)$^+$.

$^1$H-NMR δ (CDCl$_3$): 0.58-0.63 (m, 2H), 0.84-0.90 (m, 2H), 1.42 (s, 6H), 2.32 (s, 3H), 2.86-2.95 (m, 1H), 3.23 (s, 3H), 6.22 (brs, 1H), 6.78 (d, J=3.0 Hz, 1H), 6.98 (dd, J=9.0 Hz and 3.0 Hz, 1H), 7.25 (d, J=9.0 Hz, 1H), 7.33 (d, J=9.0 Hz, 1H), 7.60 (d, J=3.0 Hz, 1H), 7.65 (dd, J=6.0 Hz and 3.0 Hz, 1H).

EXAMPLE 21

N-Cyclopropyl-4-methyl-3-(2'-oxospiro[cyclohexane-1,3'-indoline]-6'-yl)benzamide

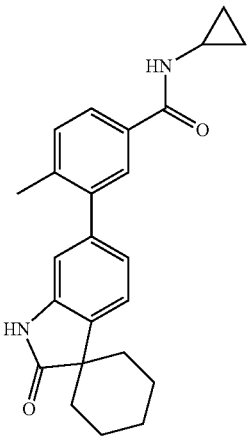 [SMILES: Cc1ccc(C(=O)NC2CC2)cc1-c1ccc2c(c1)NC(=O)C21CCCCC1]

Obtained as a white solid (50%) from 6'-bromospiro[cyclohexane-1,3'-indolin]-2'-one (preparation 5) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (98:2 dichloromethane/methanol).

LRMS (m/z): 375 (M+1)$^+$.

$^1$H-NMR δ (CDCl$_3$): 0.58-0.64 (m, 2H), 0.84-0.90 (m, 2H), 1.62-2.00 (m, 10H), 2.32 (s, 3H), 2.87-2.95 (m, 1H), 6.27 (brs, 1H), 6.83 (s, 1H), 6.96 (d, J=9.0 Hz, 1H), 7.33 (d, J=9.0 Hz, 1H), 7.49 (d, J=9.0 Hz, 1H), 7.57 (d, J=3.0 Hz, 1H), 7.60 (brs, 1H), 7.66 (dd, J=9.0 Hz and 3.0 Hz, 1H).

EXAMPLE 22

N-Cyclopropyl-4-methyl-3-(2-oxo-2',3',5',6'-tetrahydrospiro[indoline-3,4'-pyran]-6-yl)benzamide

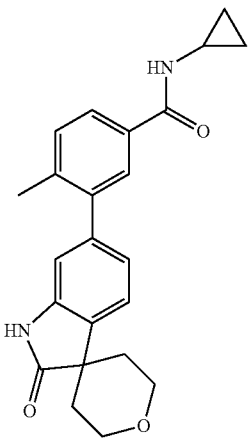 [SMILES: Cc1ccc(C(=O)NC2CC2)cc1-c1ccc2c(c1)NC(=O)C21CCOCC1]

Obtained as a white solid (47%) from 6-bromo-2',3',5',6'-tetrahydrospiro[indoline-3,4'-pyran]-2-one (preparation 7) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (98:2 to 95:5 dichloromethane/methanol).

LRMS (m/z): 377 (M+1)$^+$.

$^1$H-NMR δ (DMSO-d$_6$): 0.52-0.59 (m, 2H), 0.64-0.70 (m, 2H), 1.69-1.82 (m, 4H), 2.27 (s, 3H), 2.79-2.90 (m, 1H), 3.81-3.88 (m, 2H), 4.00-4.14 (m, 2H), 6.79 (s, 1H), 6.96 (d, J=6.0 Hz, 1H), 7.37 (d, J=7.0 Hz, 1H), 7.59 (d, J=7.0 Hz, 1H), 7.68 (s, 1H), 7.74 (d, J=6.0 Hz, 1H), 8.40 (s, 1H), 10.49 (s, 1H).

EXAMPLE 23

N-Isoxazol-3-yl-4-methyl-3-(2-oxo-1,2,2',3',5',6'-hexahydrospiro[indole-3,4'-pyran]-6-yl)benzamide

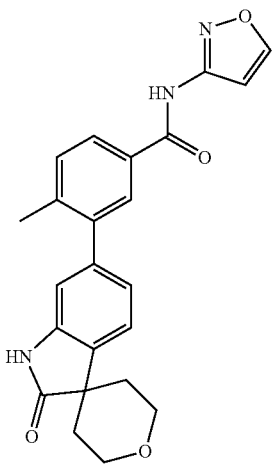 [SMILES: Cc1ccc(C(=O)Nc2ccon2)cc1-c1ccc2c(c1)NC(=O)C21CCOCC1]

Obtained as an orange solid (63%) from 6-(4,4,5,5-tetramethyl-1,3,2-dioxaborolan-2-yl)-2',3',5',6'-tetrahydrospiro[indoline-3,4'-pyran]-2-one (preparation 9) and 3-iodo-N-isoxazol-3-yl-4-methylbenzamide (preparation 42) following the experimental procedure as described in preparation 38 followed by purification by flash chromatography (dichloromethane to 95:5 dichloromethane/methanol).

LRMS (m/z): 404 (M+1)$^+$.

$^1$H-NMR δ (DMSO-d$_6$): 1.75-1.81 (m, 4H), 2.33 (s, 3H), 3.80-3.91 (m, 3H), 3.99-4.15 (m, 2H), 6.86 (s, 1H), 7.02 (s, J=9.0 Hz, 2H), 7.05 (s, 1H), 7.46 (d, J=6.0 Hz, 1H), 7.61 (d, J=9.0 Hz, 1H), 7.92 (d, J=6.0 Hz, 1H), 7.93 (s, 1H), 8.84 (s, 1H), 10.51 (s, 1H), 11.44 (s, 1H).

EXAMPLE 24

3-(3,3-bis(2-Hydroxyethyl)-2-oxoindolin-6-yl)-N-cyclopropyl-4-methylbenzamide

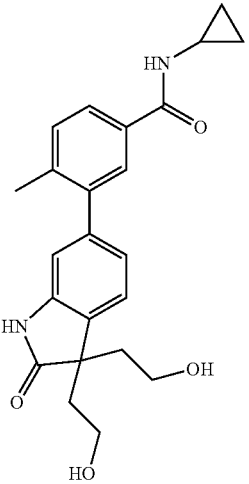 [SMILES: Cc1ccc(C(=O)NC2CC2)cc1-c1ccc2c(c1)NC(=O)C2(CCO)CCO]

Obtained as a white solid (33%) from 6-bromo-3,3-bis(2-hydroxyethyl)indolin-2-one (preparation 20) and N-cyclopropyl-4-methyl-3-(4,4,5,5-tetramethyl-1,3,2-dioxaborolan-2-yl)benzamide (preparation 40) following the experimental procedure as described in preparation 38 followed by purification by reverse phase chromatography on a C18 cartridge (water/acetonitrile:methanol 1:1).

LRMS (m/z): 395 (M+1)$^+$.

$^1$H-NMR δ (DMSO-d$_6$): 0.53-0.61 (m, 2H), 0.63-0.70 (m, 2H), 1.91-2.04 (m, 4H), 2.26 (s, 3H), 2.80-2.89 (m, 1H), 3.00-3.09 (m, 2H), 3.11-3.21 (m, 2H), 4.39 (bs, 2H), 6.74 (s, 1H), 6.95 (d, J=6.0 Hz, 1H), 7.32 (d, J=6.0 Hz, 1H), 7.36 (d, J=8.0 Hz, 1H), 7.70 (s, 1H), 7.74 (d, J=8.0 Hz, 1H), 8.44 (d, J=6.0 Hz, 1H), 10.37 (s, 1H).

EXAMPLE 25

N-Cyclopropyl-4-methyl-3-(2-oxo-2',3',5',6'-tetrahydrospiro[indoline-3,4'-thiopyran]-6-yl)benzamide

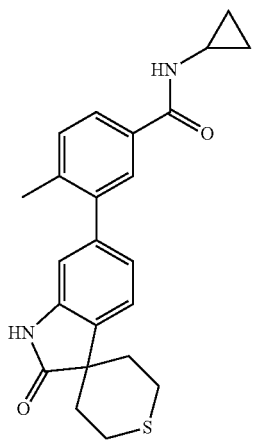 [SMILES: Cc1ccc(C(=O)NC2CC2)cc1-c1ccc2c(c1)NC(=O)C21CCSCC1]

Obtained as a white solid (67%) from 6-bromo-2',3',5',6'-tetrahydrospiro[indoline-3,4'-thiopyran]-2-one (preparation 18) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (98:2 dichloromethane/methanol).

LRMS (m/z): 393 (M+1)$^+$.

$^1$H-NMR δ (CDCl$_3$): 0.57-0.64 (m, 2H), 0.81-0.91 (m, 2H), 1.95-2.09 (m, 2H), 2.12-2.24 (m, 2H), 2.32 (s, 3H), 2.68-2.91 (m, 2H), 2.85-2.95 (m, 2H), 3.24-3.37 (m, 2H), 6.23 (bs, 1H), 6.83 (s, 1H), 6.99 (d, J=6.0 Hz, 1H), 7.32 (d, J=8.0 Hz, 1H), 7.36 (d, J=8.0 Hz, 1H), 7.57 (s, 2H), 7.65 (d, J=6.0 Hz, 1H).

EXAMPLE 26

N-Cyclopropyl-3-(2-oxo-1,2,2',3',5',6'-hexahydrospiro[indole-3,4-thiopyran-1-oxide]-6-yl)-4-methylbenzamide

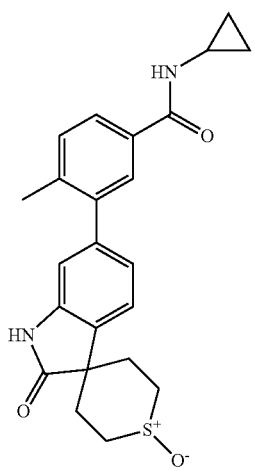 [SMILES: Cc1ccc(C(=O)NC2CC2)cc1-c1ccc2c(c1)NC(=O)C21CC[S+]([O-])CC1]

A solution of sodium periodate (54 mg, 0.25 mmol) in water was added to a suspension of N-cyclopropyl-4-methyl-3-(2-oxo-2',3',5',6'-tetrahydrospiro[indoline-3,4'-thiopyran]-6-yl)benzamide (example 25, 0.10 g, 0.25 mmol) in methanol (2 mL) at 0° C. The resulting mixture was stirred at room temperature overnight and then the solvent was evaporated. Ethyl acetate and water were added and the organic layer was separated. The aqueous phase was extracted with chloroform and the organic layers were combined and concentrated under reduced pressure and the residue was purified by flash chromatography (95:5 dichloromethane/methanol) to give the title compound (exact isomeric form not determined) as a pale brown solid. (51%).

LRMS (m/z): 409 (M+1)$^+$ $^1$H-NMR δ (DMSO-d$_6$): 0.57 (m, 2H), 0.69 (m, 2H), 1.72 (m, 2H), 2.28 (s, 3H), 2.60 (m, 2H), 2.90 (m, 3H), 3.38 (m, 2H), 6.82 (s, 1H), 7.02 (d, 1H), 7.40 (m, 2H), 7.69 (s, 1H), 7.76 (d, 1H), 8.42 (d, 1H), 10.59 (s, NH).

EXAMPLE 27

N-Cyclopropyl-3-(1',1'-dioxido-2-oxo-1,2,2',3',5',6'-hexahydrospiro[indole-3,4'-thiopyran]-6-yl)-4-methylbenzamide

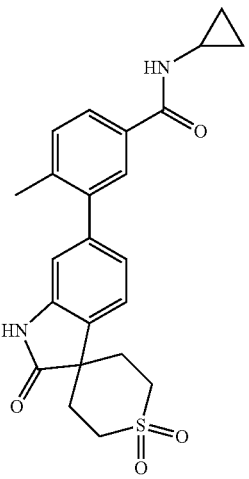 [SMILES: Cc1ccc(C(=O)NC2CC2)cc1-c1ccc2c(c1)NC(=O)C21CCS(=O)(=O)CC1]

3-Chloroperbenzoic acid (55%, 0.09 g, 0.51 mmol) was added portionwise to a solution of N-cyclopropyl-4-methyl-3-(2-oxo-2',3',5',6'-tetrahydrospiro[indoline-3,4'-thiopyran]-6-yl)benzamide (example 25, 0.10 g, 0.25 mmol) in dichloromethane (5 mL) at 0° C. The resulting mixture was stirred at room temperature overnight and then the solvent was evaporated. Ethyl acetate was added and the organic layer was washed with water, 4% aqueous sodium bicarbonate solution and 2M aqueous sodium hydroxide solution. The solvent was concentrated under reduced pressure and the residue was purified by flash chromatography (1:1 hexanes/ethyl acetate) to yield the title compound (0.05 g, 47%) as a white solid.

LRMS (m/z): 425 (M+1)$^+$.

$^1$H-NMR δ (DMSO-d$_6$): 0.52-0.58 (m, 2H), 0.64-0.70 (m, 2H), 2.14-2.19 (m, 2H), 2.27 (s, 3H), 2.38-2.42 (m, 2H), 2.79-2.88 (m, 1H), 3.14-3.18 (m, 2H), 3.69-3.77 (m, 2H), 6.83 (s, 1H), 6.99 (d, J=8.0 Hz, 1H), 7.37 (d, J=7.0 Hz, 1H), 7.48 (d, J=8.0 Hz, 1H), 7.67 (s, 1H), 7.74 (d, J=7.0, 1H), 8.41 (s, 1H), 10.74 (s, 1H).

EXAMPLE 28

N-(Cyclopropylmethyl)-3-(1',1'-dioxido-2-oxo-1,2,2',3',5',6'-hexahydrospiro[indole-3,4'-thiopyran]-6-yl)-5-fluoro-4-methylbenzamide

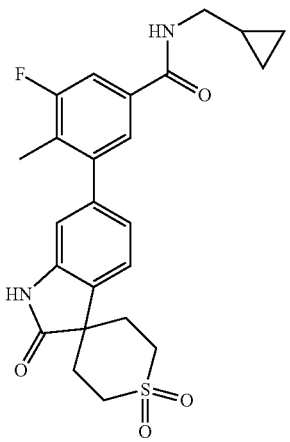 [SMILES: Cc1c(F)cc(C(=O)NCC2CC2)cc1-c1ccc2c(c1)NC(=O)C21CCS(=O)(=O)CC1]

a) N-(cyclopropylmethyl)-3-fluoro-4-methyl-5-(2-oxo-1,2,2',3',5',6'-hexahydrospiro-[indole-3,4'-thiopyran]-6-yl)benzamide Obtained as a white solid (47%) from 6-bromo-2',3',5',6'-tetrahydrospiro[indole-3,4'-thiopyran]-2(1H)-one (preparation 18) and N-(cyclopropylmethyl)-3-fluoro-4-methyl-5-(4,4,5,5-tetramethyl-1,3,2-dioxaborolan-2-yl)benzamide (preparation 45) following the experimental procedure as described in preparation 38 followed by purification by flash chromatography (98:2 dichloromethane/methanol).

LRMS (m/z): 425 (M+1)⁺.

¹H-NMR δ (DMSO-d₆): 0.16-0.28 (m, 2H), 0.36-0.48 (m, 2H), 0.94-1.10 (m, 1H), 1.91-2.03 (m, 4H), 2.18 (s, 3H), 2.66-2.80 (m, 2H), 3.04-3.20 (m, 4H), 6.83 (s, 1H), 6.99 (d, J=6.0 Hz, 1H), 7.52 (d, J=9.0 Hz, 1H), 7.62 (d, J=9.0 Hz, 1H), 7.64 (s, 1H), 8.67 (s, 1H), 10.54 (s, 1H).

b) N-(Cyclopropylmethyl)-3-(1',1'-dioxido-2-oxo-1,2,2',3',5',6'-hexahydrospiro-[indole-3,4'-thiopyran]-6-yl)-5-fluoro-4-methylbenzamide 3-chloroperbenzoic acid (0.04 g, 0.23 mmol) was added portionwise to a solution of N-(cyclopropylmethyl)-3-fluoro-4-methyl-5-(2-oxo-1,2,2',3',5',6'-hexahydrospiro-[indole-3,4'-thiopyran]-6-yl)benzamide (example 28a, 0.10 g, 0.24 mmol) in dichloromethane (4 mL) at 0° C. The mixture was warmed to ambient temperature. After 2 hours, the mixture was cooled to 0° C. and further 3-chloroperbenzoic acid (0.04 g, 0.23 mmol) was added portionwise and the resulting mixture was stirred at room temperature for 1 additional hour. Water and dichloromethane were added, the organic layer was separated and washed with a 4% aqueous sodium hydrogen carbonate solution, dried (MgSO₄) and the solvent evaporated under reduced pressure. The residue was triturated with diethyl ether to yield the title compound (0.09 g, 79%) as a white solid.

LRMS (m/z): 457 (M+1)⁺.

¹H-NMR δ (DMSO-d₆): 0.51-0.59 (m, 2H), 0.62-0.74 (m, 2H), 1.87-2.01 (m, 5H), 2.17 (s, 3H), 2.66-2.91 (m, 3H), 3.15 (s, 3H), 6.81 (s, 1H), 6.97 (d, J=7.0 Hz, 1H), 7.52 (d, J=6.0 Hz, 1H), 7.58 (s, 1H), 7.59 (d, J=7.0 Hz, 1H), 8.50 (s, 1H), 10.53 (s, 1H).

EXAMPLE 29

N-Cyclopropyl-4-methyl-3-(1'-methyl-2-oxospiro[indoline-3,4'-piperidine]-6-yl)benzamide

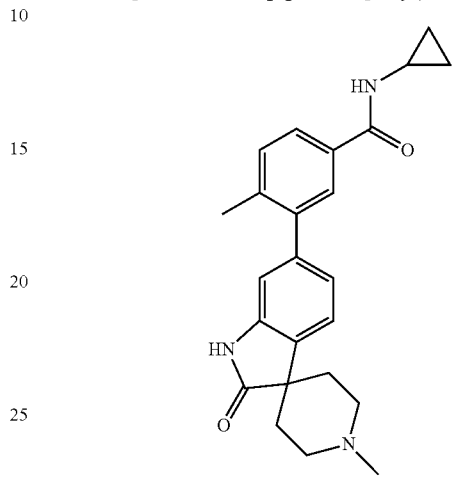

Obtained as a white solid (35%) from 6-bromo-1'-methyl-spiro[indoline-3,4'-piperidin]-2-one (preparation 10) and N-cyclopropyl-4-methyl-3-(4,4,5,5-tetramethyl-1,3,2-dioxaborolan-2-yl)benzamide (preparation 40) following the experimental procedure as described in preparation 38.

LRMS (m/z): 389 (M+1)⁺.

¹H-NMR δ (DMSO-d₅): 0.51-0.57 (m, 2H), 0.63-0.70 (m, 2H), 1.63-1.75 (m, 2H), 1.82-1.90 (m, 2H), 2.26 (s, 3H), 2.32 (s, 3H), 2.75-2.87 (m, 4H), 6.79 (s, 1H), 6.94 (d, J=6.0 Hz, 1H), 7.36 (d, J=6.0 Hz, 1H), 7.53 (d, J=8.0 Hz, 1H), 7.68 (s, 1H), 7.73 (d, J=8.0 Hz, 1H), 8.39 (d, J=6.0 Hz, 1H), 10.46 (s, 1H).

EXAMPLE 30 tert-Butyl 6-(5-(cyclopropylcarbamoyl)-2-methylphenyl)-2-oxospiro[indoline-3,4'-piperidine]-1'-carboxylate

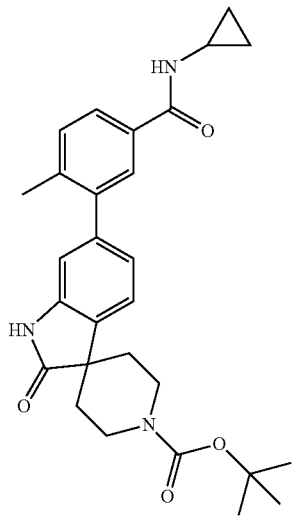 [SMILES: Cc1ccc(C(=O)NC2CC2)cc1-c1ccc2c(c1)NC(=O)C21CCN(C(=O)OC(C)(C)C)CC1]

Obtained as a white solid (30%) from tert-butyl 6-bromo-2-oxospiro[indoline-3,4'-piperidine]-1'-carboxylate (preparation 11) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (96:4 dichloromethane/methanol).

LRMS (m/z): 476 (M+1)$^+$.

$^1$H-NMR δ (CDCl$_3$): 0.59-0.69 (m, 2H), 0.80-0.88 (m, 2H), 1.50 (s, 9H), 1.66-1.89 (m, 4H), 2.29 (s, 3H), 2.85-2.99 (m, 1H), 3.65-3.94 (m, 4H), 6.88 (s, 1H), 6.90-6.95 (m, 2H), 7.27 (d, J=8.0 Hz, 1H), 7.29 (d, J=8.0 Hz, 1H), 7.64 (s, 1H), 7.71 (d, J=8.0 Hz, 1H), 9.04 (s, 1H).

EXAMPLE 31

N-cyclopropyl-3-fluoro-4-methyl-5-(1'-(methylsulfonyl)-2-oxospiro[indoline-3,4'-piperidine]-6-yl)benzamide

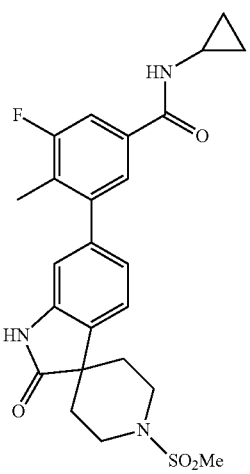 [SMILES: Cc1c(F)cc(C(=O)NC2CC2)cc1-c1ccc2c(c1)NC(=O)C21CCN(S(C)(=O)=O)CC1]

Obtained as a pale yellow solid (52%) from 6-bromo-1'-(methylsulfonyl)spiro[indoline-3,4'-piperidin]-2-one (preparation 12) and N-(cyclopropylmethyl)-3-fluoro-4-methyl-5-(4,4,5,5-tetramethyl-1,3,2-dioxaborolan-2-yl)benzamide (preparation 45) following the experimental procedure as described in preparation 38 followed by purification by flash chromatography (96:4 dichloromethane/methanol).

LRMS (m/z): 472 (M+1)$^+$ $^1$H-NMR δ (DMSO-d$_6$): 0.57 (m, 2H), 0.69 (m, 2H), 1.89 (m, 4H), 2.18 (s, 3H), 2.86 (m, 1H), 2.99 (s, 3H), 3.42 (m, 2H), 3.57 (m, 2H), 6.82 (s, 1H), 7.00 (d, 1H), 7.59 (m, 3H), 8.50 (s, 1H), 10.62 (s, NH)

EXAMPLE 32

N-Cyclopropyl-3-(4,4-difluoro-2'-oxospiro[cyclohexane-1,3'-indoline]-6'-yl)-4-methylbenzamide

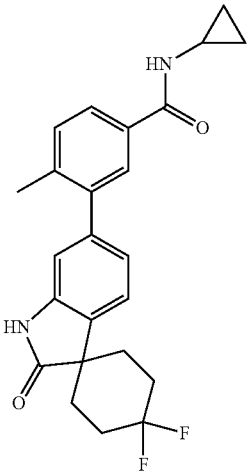 [SMILES: Cc1ccc(C(=O)NC2CC2)cc1-c1ccc2c(c1)NC(=O)C21CCC(F)(F)CC1]

Obtained as a white solid (49%) from 6'-bromo-4,4-difluorospiro[cyclohexane-1,3'-indolin]-2'-one (preparation 21) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (99:1 dichloromethane/methanol).

LRMS (m/z): 411 (M+1)$^+$.

$^1$H-NMR δ (CDCl$_3$): 0.58-0.65 (m, 2H), 0.81-0.92 (m, 2H), 1.19-1.30 (m, 2H), 1.99-2.10 (m, 4H), 2.11-2.23 (m, 2H), 2.31 (s, 3H), 2.52-2.75 (m, 2H), 2.85-2.97 (m, 1H), 6.23 (bs, 1H), 6.84 (s, 1H), 6.98 (d, J=8.0 Hz, 1H), 7.26-7.29 (m, 1H), 7.31-7.35 (m, 1H), 7.58 (s, 1H), 7.61-7.68 (m, 2H).

EXAMPLE 33

3-(4,4-Difluoro-2'-oxo-1',2'-dihydrospiro[cyclohexane-1,3'-indol]-6'-yl)-N-isoxazol-3-yl-4-methylbenzamide

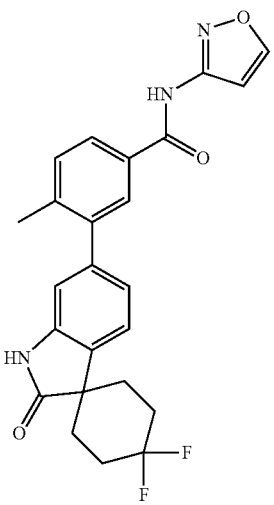 [SMILES: Cc1ccc(C(=O)Nc2ccon2)cc1-c1ccc2c(c1)NC(=O)C21CCC(F)(F)CC1]

123

Obtained as a white solid (60%) from 4,4-difluoro-6'-(4,4,5,5-tetramethyl-1,3,2-dioxaborolan-2-yl)spiro[cyclohexane-1,3'-indol]-2'(1'H)-one (preparation 22) and 3-iodo-N-isoxazol-3-yl-4-methylbenzamide (preparation 42) following the experimental procedure as described in preparation 38 followed by purification by flash chromatography (dichloromethane to 95:5 dichloromethane/methanol).

LRMS (m/z): 438 (M+1)$^+$.

$^1$H-NMR δ (MeOD): 2.08-2.24 (m, 4H), 2.35 (s, 3H), 2.46-2.69 (m, 4H), 6.93 (s, 1H), 7.04 (s, 1H), 7.05 (d, J=6.0 Hz, 1H), 7.41-7.47 (m, 3H), 7.82 (s, 1H), 7.87 (d, J=9.0 Hz, 1H), 8.57 (s, 1H).

EXAMPLE 34

N-cyclopropyl-3-(4-hydroxy-2'-oxospiro[cyclohexane-1,3'-indoline]-6'-yl)-4-methylbenzamide (isomeric form A)

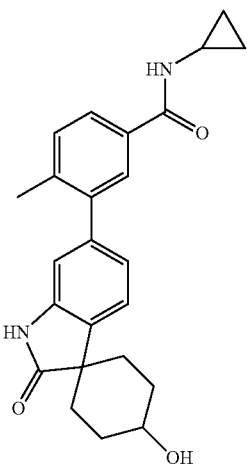 [SMILES: Cc1ccc(C(=O)NC2CC2)cc1-c1ccc2c(c1)NC(=O)C21CCC(O)CC1]

Obtained as a white solid (50%) from 6'-bromo-4-hydroxyspiro[cyclohexane-1,3'-indolin]-2'-one (preparation 23, major isomer) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (96:4 dichloromethane/methanol).

LRMS (m/z): 391 (M+1)$^+$ $^1$H-NMR δ (DMSO-d$_6$): 0.61 (m, 2H), 0.73 (m, 2H), 1.66-1.78 (m, 6H), 2.04 (m, 2H), 2.33 (s, 3H), 2.91 (m, 1H), 4.78 (m, 1H), 6.87 (s, 1H), 7.03 (d, 1H), 7.44 (d, 1H), 7.65 (d, 1H), 7.75 (s, 1H), 7.81 (d, 1H), 8.46 (brs, 1H), 10.50 (brs, NH)

124

EXAMPLE 35

N-cyclopropyl-3-(4-hydroxy-2'-oxospiro[cyclohexane-1,3'-indoline]-6'-yl)-4-methylbenzamide (isomeric form B)

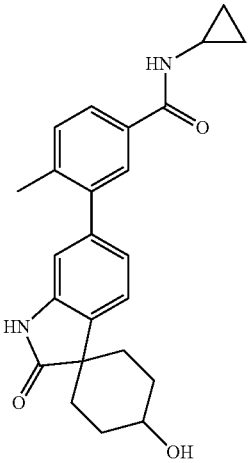 [SMILES: Cc1ccc(C(=O)NC2CC2)cc1-c1ccc2c(c1)NC(=O)C21CCC(O)CC1]

Obtained as a white solid (50%) from 6'-bromo-4-hydroxyspiro[cyclohexane-1,3'-indolin]-2'-one (preparation 23, minor isomer) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (96:4 dichloromethane/methanol).

LRMS (m/z): 391 (M+1)$^+$ $^1$H-NMR δ (DMSO-d$_6$): 0.60 (m, 2H), 0.73 (m, 2H), 1.65 (m, 2H), 1.85-2.03 (m, 6H), 2.32 (s, 3H), 2.90 (m, 1H), 4.66 (m, 1H), 6.81 (s, 1H), 6.98 (d, 1H), 7.40-7.47 (m, 2H), 7.74 (s, 1H), 7.78 (d, 1H), 8.45 (brs, 1H), 10.38 (brs, NH)

EXAMPLE 36

N-cyclopropyl-3-(4-hydroxy-4-methyl-2'-oxospiro[cyclohexane-1,3'-indoline]-6'-yl)-4-methylbenzamide (isomeric form A)

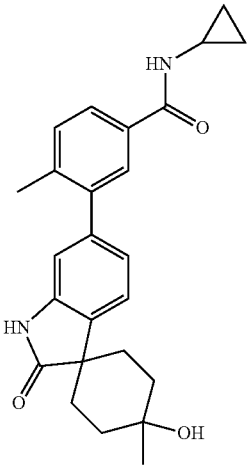 [SMILES: Cc1ccc(C(=O)NC2CC2)cc1-c1ccc2c(c1)NC(=O)C21CCC(C)(O)CC1]

Obtained as a pale yellow solid (76%) from 6'-bromo-4-hydroxy-4-methylspiro[cyclohexane-1,3'-indolin]-2'-one (preparation 24, major isomer) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (96:4 dichloromethane/methanol).

LRMS (m/z): 405 (M+1)$^+$.

$^1$H-NMR δ (CDCl$_3$): 0.58-0.64 (m, 2H), 0.83-0.90 (m, 2H), 1.25 (s, 1H), 1.40 (s, 3H), 1.54-1.61 (m, 2H), 1.91-1.94 (m, 4H), 2.18-2.29 (m, 2H), 2.32 (s, 3H), 2.85-2.92 (m, 1H), 3.42 (brs, 1H), 6.55 (brs, 1H), 6.87 (d, J=1.5 Hz, 1H), 6.94 (dd, J=7.6 Hz, J'=1.5 Hz, 1H), 7.32 (d, J=7.6 Hz, 1H), 7.39 (d, J=7.6 Hz, 1H), 7.58 (d, J=1.9 Hz, 1H), 7.63 (dd, J=7.6 Hz, J'=1.9 Hz, 1H).

EXAMPLE 37

N-cyclopropyl-3-(4-hydroxy-4-methyl-2'-oxospiro[cyclohexane-1,3'-indoline]-6'-yl)-4-methylbenzamide (isomeric form B)

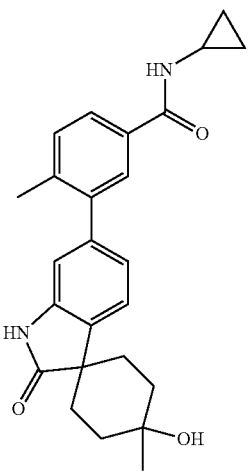 [SMILES: Cc1ccc(C(=O)NC2CC2)cc1-c1ccc2c(c1)NC(=O)C21CCC(C)(O)CC1]

Obtained as a pale yellow solid (57%) from 6'-bromo-4-hydroxy-4-methylspiro[cyclohexane-1,3'-indolin]-2'-one (preparation 24, minor isomer) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (96:4 dichloromethane/methanol).

LRMS (m/z): 405 (M+1)$^+$.

$^1$H-NMR δ (CDCl$_3$): 0.61 (m, 2H), 0.84 (m, 2H), 1.25 (brs, 1H), 1.38 (brs, 5H), 1.70 (brs, 2H), 2.06 (m, 2H), 2.24 (m, 2H), 2.30 (s, 3H), 2.90 (0, 1H), 3.66 (brs, 1H), 6.47 (s, 1H), 6.80 (s, 1H), 6.92 (d, J=7.4 Hz, 1H), 7.28 (d, J=7.1 Hz, 1H), 7.58 (s, 1H), 7.67 (d, J=7.4 Hz, 1H), 8.03 (s, 1H).

EXAMPLE 38

N-(cyclopropylmethyl)-3-(4-hydroxy-2'-oxospiro[cyclohexane-1,3'-indoline]-6'-yl)-4-methylbenzamide

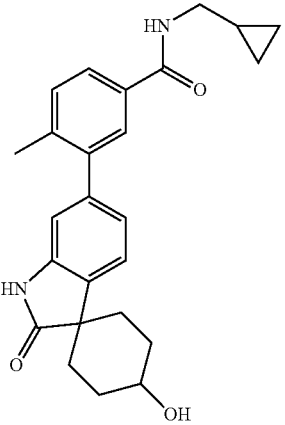 [SMILES: Cc1ccc(C(=O)NCC2CC2)cc1-c1ccc2c(c1)NC(=O)C21CCC(O)CC1]

Obtained as a pale yellow solid (71%) from 6'-bromo-4-hydroxyspiro[cyclohexane-1,3'-indolin]-2'-one (preparation 23, major isomer) and N-(cyclopropylmethyl)-4-methyl-3-(4,4,5,5-tetramethyl-1,3,2-dioxaborolan-2-yl)benzamide (preparation 41) following the experimental procedure as described in preparation 38 followed by purification by flash chromatography (3:1 hexanes/ethyl acetate to 9:1 ethyl acetate/methanol).

LRMS (m/z): 405 (M+1)$^+$.

$^1$H-NMR δ (CDCl$_3$): 0.27 (m, 2H), 0.56 (m, 2H), 0.89 (m, 1H), 1.05 (m, 1H), 1.77 (m, 2H), 2.01 (m, 4H), 2.17 (m, 2H), 2.32 (s, 3H), 3.30 (t, J=6.3 Hz, 2H), 3.92 (m, 1H), 6.34 (brs, 1H), 6.84 (s, 1H), 6.97 (d, J=7.4 Hz, 1H), 7.25 (d, J=7.4 Hz, 1H), 7.33 (d, J=8.0 Hz, 1H), 7.62 (s, 1H), 7.68 (d, J=8.0 Hz, 1H).

EXAMPLE 39

N-cyclopropyl-4-methyl-3-(4-(2-morpholinoethoxy)-2'-oxospiro[cyclohexane-1,3'-indoline]-6'-yl)benzamide

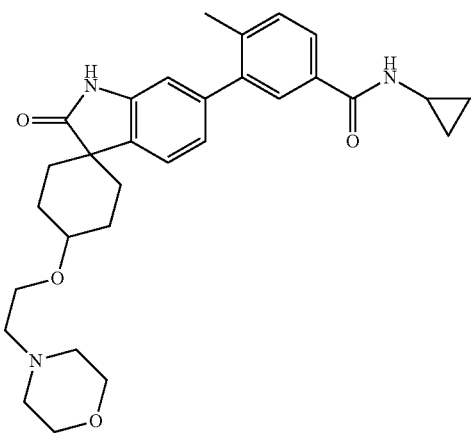 [SMILES: Cc1ccc(C(=O)NC2CC2)cc1-c1ccc2c(c1)NC(=O)C21CCC(OCCN2CCOCC2)CC1]

Obtained as a white solid (81%) as a single isomer (exact isomeric form not determined) from 6'-bromo-4-(2-morpholinoethoxy)spiro[cyclohexane-1,3'-indolin]-2'-one (preparation 27) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (98:2 to 20:1 dichloromethane/methanol).

LRMS (m/z): 504 (M+1)$^+$.

$^1$H-NMR δ (DMSO-d$_6$): 0.62 (m, 2H), 0.87 (m 2H), 1.26-1.64 (m, 5H), 2.03-2.10 (m, 4H), 2.32 (s, 3H), 2.88 (m, 1H), 3.10 (m, 2H), 3.33 (m, 2H), 3.28 (m, 3H), 4.04 (m, 4H), 4.24 (m 2H), 6.85 (s, 1H), 6.94 (d, J=7.4 Hz, 1H), 7.30 (m, 3H), 7.57 (d, J=1.7 Hz, 1H), 7.63 (dd, J=1.7; 7.9 Hz, 1H).

EXAMPLE 40

N-cyclopropyl-4-methyl-3-(4-morpholino-2'-oxospiro[cyclohexane-1,3'-indoline]-6'-yl)benzamide (isomeric form A)

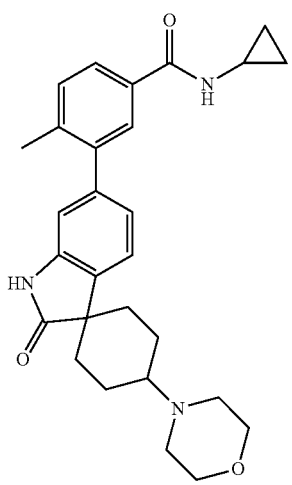

Obtained as a beige solid (65%) from 6'-bromo-4-morpholin-4-ylspiro[cyclohexane-1,3'-indol]-2'(1'H)-one (preparation 26, major isomer) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (98:2 dichloromethane/methanol).

LRMS (m/z): 460 (M+1)$^+$ $^1$H-NMR δ (DMSO-d$_6$): 0.62 (m, 2H), 0.74 (m, 2H), 1.85 (m, 6H), 2.17 (m, 2H), 2.32 (s, 3H), 2.59 (m, 4H), 2.91 (m, 1H), 3.66 (m, 4H), 6.80 (s, 1H), 7.00 (d, J=7.69 Hz, 1H), 7.40 (m, 2H), 7.74 (s, 1H), 7.80 (d, 1H), 8.45 (d, 1H), 10.36 (s, NH)

EXAMPLE 41

N-cyclopropyl-4-methyl-3-(4-morpholino-2'-oxospiro[cyclohexane-1,3'-indoline]-6'-yl)benzamide (isomeric form B)

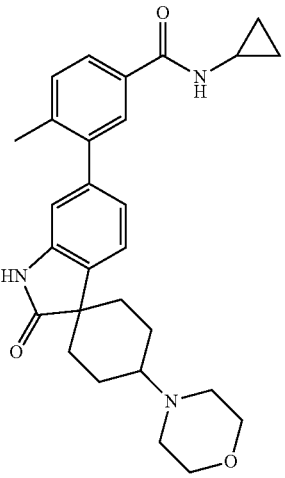 [SMILES: Cc1ccc(C(=O)NC2CC2)cc1-c1ccc2c(c1)NC(=O)C21CCC(N2CCOCC2)CC1]

Obtained as a white solid (46%) from 6'-bromo-4-morpholin-4-ylspiro[cyclohexane-1,3'-indol]-2'(1'H)-one (preparation 26, minor isomer) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (98:2 dichloromethane/methanol).

LRMS (m/z): 460 (M+1)$^+$ $^1$H-NMR δ (DMSO-d$_6$): 0.60 (m, 2H), 0.73 (m, 2H), 1.61 (m, 2H), 1.80 (m, 4H), 1.97 (m, 2H), 2.32 (s, 3H), 2.63 (m, 4H), 2.90 (m, 1H), 3.66 (m, 4H), 6.87 (s, 1H), 7.02 (d, 1H), 7.43 (d, J=7.69 Hz, 1H), 7.58 (d, J=7.69 Hz, 1H), 7.74 (s, 1H), 7.80 (d, 1H), 8.44 (d, 1H), 10.53 (s, NH)

EXAMPLE 42

N-cyclopropyl-3-fluoro-4-methyl-5-(4-morpholino-2'-oxospiro[cyclohexane-1,3'-indoline]-6'-yl)benzamide

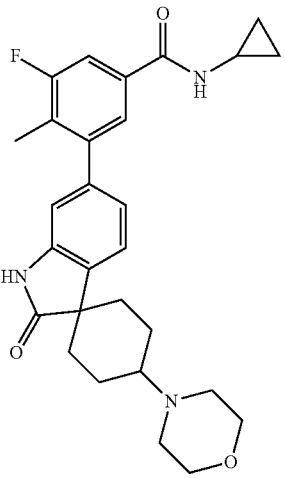 [SMILES: Cc1c(F)cc(C(=O)NC2CC2)cc1-c1ccc2c(c1)NC(=O)C21CCC(N2CCOCC2)CC1]

Obtained as a beige solid (43%) from 6'-bromo-4-morpholin-4-ylspiro[cyclohexane-1,3'-indol]-2'(1'H)-one (preparation 26, major isomer) and N-(cyclopropylmethyl)-3-fluoro-4-methyl-5-(4,4,5,5-tetramethyl-1,3,2-dioxaborolan-2-yl)benzamide (preparation 45) following the experimental procedure as described in preparation 38 followed by purification by flash chromatography (98:2 dichloromethane/methanol).

LRMS (m/z): 478 (M+1)$^+$ $^1$H-NMR δ (DMSO-d$_6$): 0.56 (m, 2H), 0.69 (m, 2H), 1.85-2.45 (m, 12H), 2.17 (s, 3H), 2.86 (m, 1H), 3.78 (m, 2H), 4.05 (m, 2H), 6.78 (s, 1H), 6.89 (d, 1H), 7.33 (d, 1H), 7.58 (m, 2H), 8.50 (d, 1H), 10.50 (s, NH)

EXAMPLE 43

N-Cyclopropyl-4-methyl-3-(2'-oxo-1',2'-dihydrospiro[cyclopentane-1,3'-pyrrolo[2,3-b]pyridine]-6'-yl)benzamide

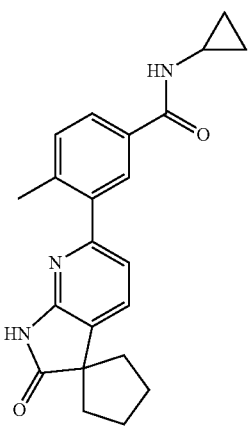 [SMILES: Cc1ccc(C(=O)NC2CC2)cc1-c1ccc2c(n1)NC(=O)C21CCCC1]

Obtained as a white solid (49%) from 6'-chlorospiro[cyclopentane-1,3'-pyrrolo[2,3-b]pyridin]-2'(1'H)-one (preparation 29) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (97:3 dichloromethane/methanol).

LRMS (m/z): 362 (M+1)$^+$.

$^1$H-NMR δ (DMSO-d$_6$): 0.52-0.58 (m, 2H), 0.64-0.71 (m, 2H), 1.78-1.88 (m, 2H), 1.94-2.04 (m, 6H), 2.37 (s, 3H), 2.81-2.89 (m, 1H), 7.11 (d, J=6.0 Hz, 1H), 7.36 (d, J=6.0 Hz, 1H), 7.71 (d, J=9.0 Hz, 1H), 7.75 (d, J=9.0 Hz, 1H), 7.84 (s, 1H), 8.41 (s, 1H), 11.02 (s, 1H).

EXAMPLE 44

3-(5'-Chloro-2'-oxospiro[cyclopentane-1,3'-indoline]-6'-yl)-N-cyclopropyl-benzamide

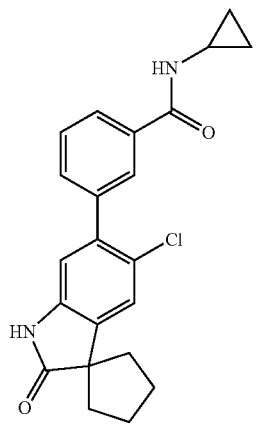 [SMILES: O=C(NC1CC1)c1cccc(-c2cc3c(cc2Cl)C2(CCCC2)C(=O)N3)c1]

Obtained as a white solid (33%) from 6'-bromo-5'-chlorospiro[cyclopentane-1,3'-indolin]-2'-one (preparation 3) and N-cyclopropyl-4-methyl-3-(4,4,5,5-tetramethyl-1,3,2-dioxaborolan-2-yl)benzamide (preparation 40) following the experimental procedure as described in preparation 38 followed by purification by reverse phase chromatography on a C18 cartridge (water/acetonitrile:methanol 1:1).

LRMS (m/z): 381 (M+1)$^+$.

$^1$H-NMR δ (CDCl$_3$): 0.57-0.65 (m, 2H), 0.86-0.92 (m, 2H), 1.50 (s, 6H), 2.33 (s, 3H), 2.87-2.98 (m, 1H), 6.33 (bs, 1H), 7.13 (s, 1H), 7.35 (d, J=8.0 Hz, 1H), 7.60 (s, 1H), 7.67 (d, J=8.0 Hz, 1H), 8.16 (s, 1H), 8.28 (bs, 1H).

EXAMPLE 45

N-Cyclopropyl-3-(3,3-dimethyl-2-oxo-2,3-dihydro-1H-pyrrolo[3,2-b]pyridin-6-yl)-4-methylbenzamide

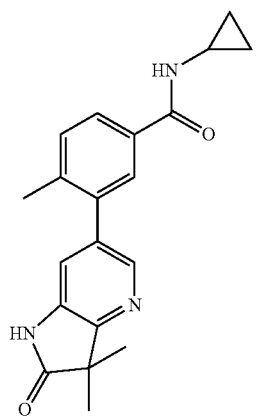 [SMILES: Cc1ccc(C(=O)NC2CC2)cc1-c1cnc2c(c1)NC(=O)C2(C)C]

Obtained as a white solid (47%) from 6-bromo-3,3-dimethyl-1H-pyrrolo[3,2-b]pyridin-2(3H)-one (preparation 35) and N-cyclopropyl-4-methyl-3-(4,4,5,5-tetramethyl-1,3,2- dioxaborolan-2-yl)benzamide (preparation 40) following the experimental procedure as described in preparation 38 followed by purification by flash chromatography (97:3 dichloromethane/methanol).

LRMS (m/z): 336 (M+1)⁺.

$^1$H-NMR δ (CDCl$_3$): 0.60-0.65 (m, 2H), 0.83-0.92 (m, 2H), 1.50 (s, 6H), 2.33 (s, 3H), 2.86-2.96 (m, 1H), 6.33 (bs, 1H), 7.13 (s, 1H), 7.35 (d, J=8.0 Hz, 1H), 7.61 (s, 1H), 7.67 (d, J=9.0 Hz, 1H), 8.16 (s, 1H), 8.28 (bs, 1H).

EXAMPLE 46

N-Cyclopropyl-4-methyl-3-(2'-oxo-1',2'-dihydrospiro[cyclopentane-1,3'-pyrrolo-[3,2-b]pyridin]-6'-yl)benzamide

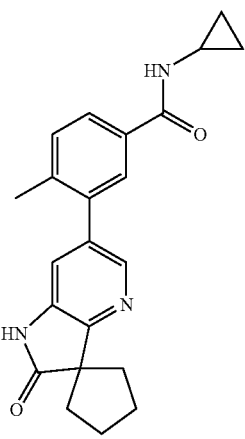 [SMILES: Cc1ccc(C(=O)NC2CC2)cc1-c1cnc2c(c1)NC(=O)C21CCCC1]

Obtained as an off-white solid (52%) from 6'-bromospiro[cyclopentane-1,3'-indolin]-2'-one (preparation 34) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (97:3 dichloromethane/methanol).

LRMS (m/z): 362 (M+1)⁺.

$^1$H-NMR δ (DMSO-d$_6$): 0.52-0.57 (m, 2H), 0.65-0.71 (m, 2H), 1.83-2.05 (m, 8H), 2.28 (s, 3H), 2.81-2.89 (m, 1H), 7.12 (s, 1H), 7.40 (d, J=8.0 Hz, 1H), 7.71 (s, 1H), 7.78 (d, J=8.0 Hz, 1H), 8.08 (s, 1H), 8.41 (s, 1H), 10.59 (s, 1H).

EXAMPLE 47

N-Cyclopropyl-4-methyl-3-(2'-oxo-1',2,2',3,5,6-hexahydrospiro[pyran-4,3'-pyrrolo-[3,2-b]pyridin]-6'-yl)benzamide

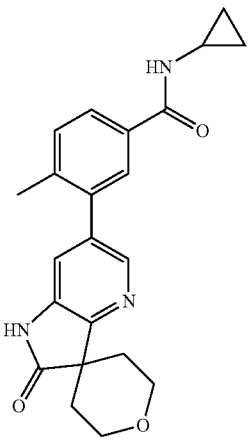 [SMILES: Cc1ccc(C(=O)NC2CC2)cc1-c1cnc2c(c1)NC(=O)C21CCOCC1]

Obtained as an off-white solid (41%) from 6'-bromo-2,3,5,6-tetrahydrospiro[pyran-4,3'-pyrrolo[3,2-b]pyridin]-2'(1'H)-one (preparation 30) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (97:3 dichloromethane:methanol).

LRMS (m/z): 378 (M+1)⁺.

$^1$H-NMR δ (DMSO-d$_6$): 0.52-0.57 (m, 2H), 0.64-0.71 (m, 2H), 1.65-1.76 (m, 2H), 1.81-1.90 (m, 2H), 2.29 (s, 3H), 2.80-2.89 (m, 1H), 3.90-4.01 (m, 1H), 4.06-4.15 (m, 1H), 7.18 (s, 1H), 7.40 (d, J=9 Hz, 1H), 7.72 (s, 1H), 7.78 (d, J=9 Hz, 1H), 8.14 (s, 1H), 8.40 (d, J=1.5 Hz, 1H), 10.72 (s, 1H).

EXAMPLE 48

N-cyclopropyl-3-(4,4-difluoro-2'-oxo-1',2'-dihydrospiro[cyclohexane-1,3'-pyrrolo[3,2-b]pyridine]-6'-yl)-4-methylbenzamide hydrochloride

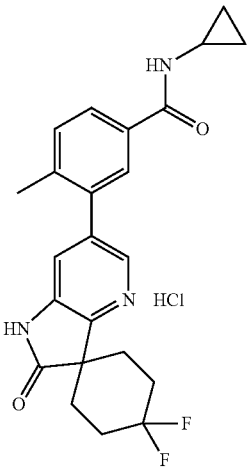 [SMILES: Cc1ccc(C(=O)NC2CC2)cc1-c1cnc2c(c1)NC(=O)C21CCC(F)(F)CC1 ; Cl]

Obtained from 6'-bromo-4,4-difluorospiro[cyclohexane-1,3'-pyrrolo[3,2-b]pyridin]-2'(1'H)-one (preparation 32) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (3:1 ethyl acetate/hexanes). The obtained compound was dissolved in methanol (1 mL) and treated with a 1.25 M solution of hydrogen chloride in methanol (520 μL, 0.65 mmol). The solvent was evaporated and the residue triturated with diethyl ether to give the title compound as an orange solid (54%).

LRMS (m/z): 412 (M+1)$^+$.

$^1$H-NMR δ (CD$_3$OD): 0.64 (m, 2H), 0.81 (d, J=6.9 Hz, 2H), 2.08 (m, 4H), 2.34 (s, 3H), 2.44 (m, 4H), 2.83 (m, 1H), 7.37 (s, 1H), 7.43 (d, J=7.7 Hz, 1H), 7.69 (s, 1H), 7.76 (d, J=7.7 Hz, 1H), 8.18 (s, 1H).

EXAMPLE 49

N-cyclopropyl-4-methyl-3-(4-morpholino-2'-oxo-1',2'-dihydrospiro[cyclohexane-1,3'-pyrrolo[3,2-b]pyridine]-6'-yl)benzamide (isomeric form A)

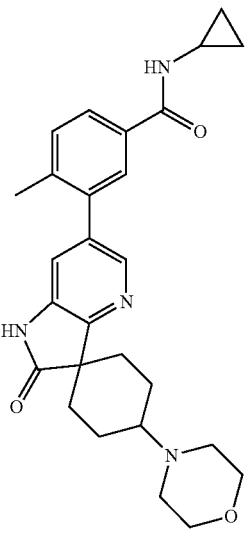 [SMILES: Cc1ccc(C(=O)NC2CC2)cc1-c1cnc2c(c1)NC(=O)C21CCC(N2CCOCC2)CC1]

Obtained as a pale yellow solid (70%) from 6'-bromo-4-morpholinospiro[cyclohexane-1,3'-pyrrolo[3,2-b]pyridin]-2'(1'H)-one (preparation 33, major isomer) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (0.1% Et$_3$N in 95:5 ethyl acetate/methanol).

LRMS (m/z): 461 (M+1)$^+$.

$^1$H-NMR δ (CDCl$_3$): 0.61 (m, 2H), 0.88 (m, 2H), 1.59 (brs, 4H), 1.95 (m, 6H), 2.33 (s, 3H), 2.50 (m, 1H), 2.69 (m, 2H), 2.90 (m, 1H), 3.78 (m, 4H), 6.23 (brs, 1H), 7.09 (d, J=1.5 Hz, 1H), 7.35 (d, J=7.8 Hz, 1H), 7.59 (d, J=1.5 Hz, 1H), 7.66 (dd, J=7.8 Hz, J'=1.5 Hz, 1H), 7.77 (s, 1H), 8.14 (d, J=1.5 Hz, 1H).

EXAMPLE 50

N-cyclopropyl-4-methyl-3-(4-morpholino-2'-oxo-1',2'-dihydrospiro[cyclohexane-1,3'-pyrrolo[3,2-b]pyridine]-6'-yl)benzamide (isomeric form B)

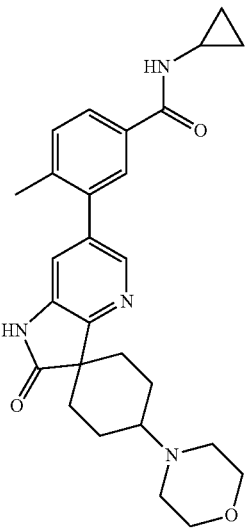

Obtained as a grey solid (47%) from 6'-bromo-4-morpholinospiro[cyclohexane-1,3'-pyrrolo[3,2-b]pyridin]-2'(1'H)-one (preparation 33, minor isomer) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (0.1% Et$_3$N in 95:5 dichloromethane/methanol).

LRMS (m/z): 459 (M−1)$^−$.

$^1$H-NMR δ (CD$_3$OD): 0.63 (brs, 2H), 0.79 (brs, 2H), 2.01 (m, 4H), 2.25 (m, 5H), 2.57 (m, 2H), 2.73 (brs, 4H), 2.84 (brs, 1H), 3.17 (m, 1H), 3.75 (brs, 4H), 7.23 (s, 1H), 7.41 (d, J=7.3 Hz, 1H), 7.67 (s, 1H), 7.75 (d, J=7.3 Hz, 1H), 8.09 (s, 1H).

EXAMPLE 51

N-Cyclopropyl-4-methyl-3-(2'-oxo-1',2'-dihydrospiro[cyclopentane-1,3'-pyrrolo[3,2-c]pyridin]-6'-yl)benzamide

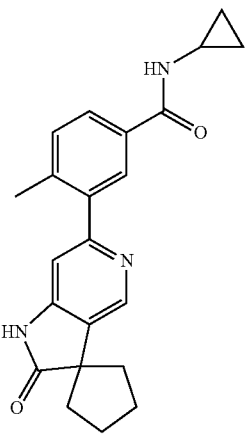 [SMILES: Cc1ccc(C(=O)NC2CC2)cc1-c1cc2c(cn1)C1(CCCC1)C(=O)N2]

Obtained as an off-white solid (39%) from 6'-chlorospiro[cyclopentane-1,3'-pyrrolo[3,2-c]pyridin]-2'(1'H)-one (preparation 36) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (96:4 dichloromethane/methanol).

LRMS (m/z): 362 (M+1)$^+$.

$^1$H-NMR δ (DMSO-d$_6$): 0.53-0.59 (m, 2H), 0.64-0.71 (m, 2H), 1.78-2.06 (m, 8H), 2.35 (s, 3H), 2.80-2.89 (m, 1H), 6.95 (s, 1H), 7.36 (d, J=8.0 Hz, 1H), 7.76 (d, J=8.0 Hz, 1H), 7.81 (s, 1H), 8.42 (s, 1H), 10.82 (s, 1H).

EXAMPLE 52

N-Cyclopropyl-4-methyl-3-(6'-oxo-6',7'-dihydrospiro[cyclopentane-1,5'-pyrrolo[2,3-c]pyrimidin]-2'-yl)benzamide

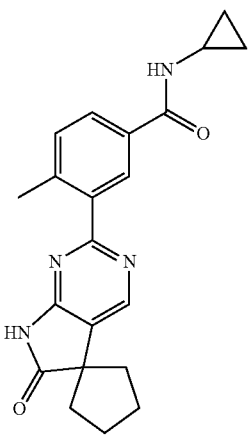 [SMILES: Cc1ccc(C(=O)NC2CC2)cc1-c1ncc2c(n1)NC(=O)C21CCCC1]

Obtained as a light yellow solid (19%) from 2'-chlorospiro[cyclopentane-1,5'-pyrrolo[2,3-d]pyrimidin]-6'(7'H)-one (preparation 37) and N-cyclopropyl-4-methyl-3-(4,4,5,5-tetramethyl-1,3,2-dioxaborolan-2-yl)benzamide (preparation 40) following the experimental procedure as described in preparation 38 followed by purification by flash chromatography (99:1 dichloromethane/methanol).

LRMS (m/z): 363 (M+1)$^+$.

$^1$H-NMR δ (DMSO-d$_6$): 0.51-0.56 (m, 2H), 0.62-0.69 (m, 2H), 1.86-2.02 (m, 8H), 2.47 (s, 3H), 2.78-2.87 (m, 1H), 7.34 (d, J=7.0 Hz, 1H), 7.76 (dd, J=7.0 and 1.5 Hz, 1H), 8.17 (d, J=1.5 Hz, 1H), 8.41 (d, J=3.0 Hz, 1H), 8.53 (s, 1H), 11.46 (brs, 1H).

EXAMPLE 53

6'-(2-Methyl-5-(5-methyl-4H-1,2,4-triazol-3-yl)phenyl)spiro[cyclopentane-1,3'-indolin]-2'-one

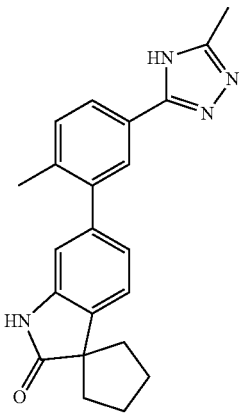 [SMILES: Cc1nnc(-c2ccc(C)c(-c3ccc4c(c3)NC(=O)C43CCCC3)c2)[nH]1]

Obtained as a white solid (25%) from 6'-(4,4,5,5-tetramethyl-1,3,2-dioxaborolan-2-yl)spiro[cyclopentane-1,3'-indolin]-2'-one (preparation 4) and (3-iodo-4-methylphenyl)-5-methyl-4H-1,2,4-triazole (preparation 49b) following the experimental procedure as described in preparation 38 followed by purification by flash chromatography (1:1 hexanes/ethyl acetate).

LRMS (m/z): 359 (M+1)$^+$.

EXAMPLE 54

6'-[2-Methyl-5-(5-methyl-4H-1,2,4-triazol-3-yl)phenyl]spiro[cyclobutane-1,3'-indol]-2'(1'H)-one

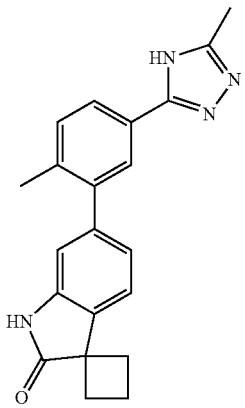 [SMILES: Cc1nnc(-c2ccc(C)c(-c3ccc4c(c3)NC(=O)C43CCC3)c2)[nH]1]

Obtained as a beige solid (24%) from 6'-bromospiro[cyclobutane-1,3'-indol]-2'(1'H)-one (preparation 6) and 3-methyl-5-(4-methyl-3-(4,4,5,5-tetramethyl-1,3,2-dioxaborolan-2-yl)phenyl)-4H-1,2,4-triazole (preparation 49) following the experimental procedure as described in preparation 38 followed by purification by flash chromatography (98:2 to 96:4 dichloromethane/methanol).

LRMS (m/z): 345 (M+1)$^+$.

$^1$H-NMR δ (DMSO-d$_6$): 2.18-2.44 (m, 6H), 2.27 (s, 3H), 2.36 (s, 3H), 6.75 (s, 1H), 7.00 (d, J=9.0 Hz, 1H), 7.36 (d, J=9.0 Hz, 1H), 7.62 (d, J=9.0 Hz, 1H), 7.79 (s, 1H), 7.84 (d, J=9.0 Hz, 1H), 10.29 (s, 1H).

EXAMPLE 55

6'-(2-Methyl-5-(4H-1,2,4-triazol-3-yl)phenyl)spiro[cyclopentane-1,3'-indolin]-2'-one

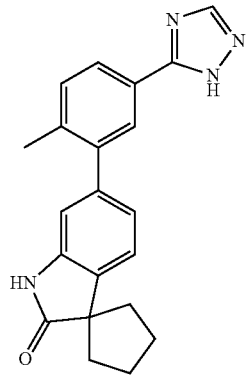 [SMILES: Cc1ccc(-c2ncn[nH]2)cc1-c1ccc2c(c1)NC(=O)C21CCCC1]

Obtained as a brown solid (23%) from 6'-(4,4,5,5-tetramethyl-1,3,2-dioxaborolan-2-yl)spiro[cyclopentane-1,3'-indolin]-2'-one (preparation 4) and 3-(3-iodo-4-methylphenyl)-4H-1,2,4-triazole (preparation 48) following the experimental procedure as described in preparation 38 followed by purification by flash chromatography (97:3 dichloromethane/methanol).

LRMS (m/z): 345 (M+1)$^+$.
$^1$H-NMR δ (DMSO-d$_6$): 1.84-2.03 (m, 8H), 2.33 (s, 3H), 6.84 (s, 1H), 7.03 (d, J=7.5 Hz, 1H), 7.38-7.44 (m, 2H) 7.89-7.97 (m, 2H), 8.66 (s, 1H), 10.40 (brs, 1H).

EXAMPLE 56

6'-(5-(5-Cyclopropyl-4H-1,2,4-triazol-3-yl)-2-methylphenyl)spiro[cyclopentane-1,3'-indolin]-2'-one

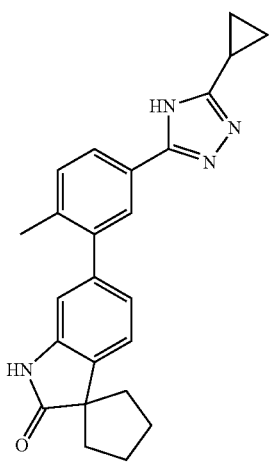 [SMILES: Cc1ccc(-c2nnc(C3CC3)[nH]2)cc1-c1ccc2c(c1)NC(=O)C21CCCC1]

Obtained as a white solid (29%) from 6'-(4,4,5,5-tetramethyl-1,3,2-dioxaborolan-2-yl)spiro[cyclopentane-1,3'-indolin]-2'-one (preparation 4) and 3-cyclopropyl-5-(3-iodo-4-methylphenyl)-4H-1,2,4-triazole (preparation 51) following the experimental procedure as described in preparation 38 followed by purification by reverse phase chromatography on a C18 cartridge (water/acetonitrile:methanol 1:1).

LRMS (m/z): 385 (M+1)$^+$.
$^1$H-NMR δ (CD$_3$OD): 0.94-1.20 (m, 4H), 1.90-1.99 (m, 2H), 2.01-2.17 (m, 7H), 2.31 (s, 3H), 6.89 (s, 1H), 7.01 (d, J=9.0 Hz, 1H), 7.31 d, J=9.0 Hz, 1H), 7.33 (d, J=9.0 Hz, 1H), 7.82 (s, 1H).

EXAMPLE 57

6'-(2-Methyl-5-(5-(trifluoromethyl)-4H-1,2,4-triazol-3-yl)phenyl)spiro[cyclopentane-1,3'indolin]-2'-one

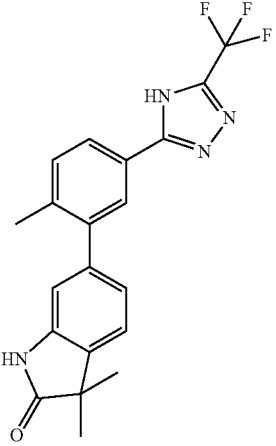 [SMILES: Cc1ccc(-c2nnc(C(F)(F)F)[nH]2)cc1-c1ccc2c(c1)NC(=O)C2(C)C]

Obtained as a white solid (48%) from 3,3-dimethyl-6-(4,4,5,5-tetramethyl-1,3,2-dioxaborolan-2-yl)indolin-2-one (preparation 17) and (3-iodo-4-methylphenyl)-5-(trifluoromethyl)-4H-1,2,4-triazole (preparation 52) following the experimental procedure as described in preparation 38 followed by purification by flash chromatography (5:1 hexanes/ethyl acetate).

LRMS (m/z): 387 (M+1)$^+$.
$^1$H-NMR δ (CDCl$_3$): 1.29 (s, 6H), 2.38 (s, 3H), 6.64 (s, 1H), 7.04 (d, J=8.0 Hz, 1H), 7.16 (d, J=8.0 Hz, 1H), 7.45 (d, J=6.0 Hz, 1H), 7.83 (s, 1H), 8.03 (dd, J=7.0 and 1.5 Hz, 1H), 6.86 (dd, J=8.0 and 1.5 Hz, 1H), 9.53 (brs, 1H).

EXAMPLE 58

3,3-Dimethyl-6-(2-methyl-5-(5-methyl-4H-1,2,4-triazol-3-yl)phenyl)indolin-2-one

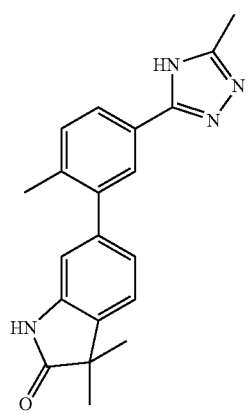 [SMILES: Cc1nnc(-c2ccc(C)c(-c3ccc4c(c3)NC(=O)C4(C)C)c2)[nH]1]

Obtained as a white solid (29%) from 6-bromo-3,3-dimethylindolin-2-one (preparation 16) and 3-methyl-5-(4-methyl-3-(4,4,5,5-tetramethyl-1,3,2-dioxaborolan-2-yl)phenyl)-4H-1,2,4-triazole (preparation 49) following the experimental procedure as described in preparation 38 followed by purification by flash chromatography (97:3 dichloromethane/methanol).

LRMS (m/z): 333 (M+1)$^+$.

$^1$H-NMR δ (DMSO-d$_6$): 1.30 (s, 6H), 2.28 (s, 3H), 2.37 (s, 3H), 6.81 (s, 1H), 6.97 (d, J=8.0 Hz, 1H), 7.36 (d, J=6.0 Hz, 2H), 7.50 (bs, 1H), 7.79 (s, 1H), 7.84 (d, J=8.0 Hz, 1H), 10.39 (s, 1H).

EXAMPLE 59

6-(2-Methyl-5-(5-methyl-4H-1,2,4-triazol-3-yl)phenyl)-2',3',5',6'-tetrahydrospiro[indoline-3,4'-pyran]-2-one

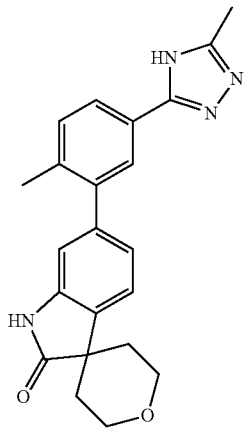 [SMILES: Cc1nnc(-c2ccc(C)c(-c3ccc4c(c3)NC(=O)C43CCOCC3)c2)[nH]1]

Obtained as a white solid (41%) from 6-(4,4,5,5-tetramethyl-1,3,2-dioxaborolan-2-yl)-2',3',5',6'-tetrahydrospiro[indoline-3,4'-pyran]-2-one (preparation 9) and (3-iodo-4-methylphenyl)-5-methyl-4H-1,2,4-triazole (preparation 49b) following the experimental procedure as described in preparation 38.

LRMS (m/z): 375 (M+1)$^+$.

$^1$H-NMR δ (DMSO-d$_6$): 1.70-1.89 (m, 4H), 2.28 (s, 3H), 2.37 (s, 3H), 3.81-3.94 (m, 2H), 4.03-4.11 (m, 2H), 6.83 (s, 1H), 6.98 (d, J=8.0 Hz, 1H), 7.39 (d, J=8.0 Hz, 1H), 7.60 (d, J=6.0 Hz, 1H), 7.80 (s, 1H), 7.85 (d, J=6.0 Hz, 1H), 10.49 (s, 1H).

EXAMPLE 60

1'-(4-chlorophenyl)-6-(2-methyl-5-(5-methyl-4H-1,2,4-triazol-3-yl)phenyl)spiro[indoline-3,4'-piperidin]-2-one

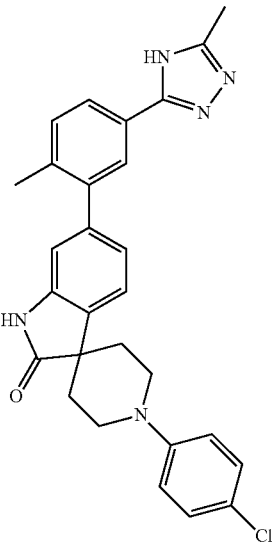 [SMILES: Cc1nnc(-c2ccc(C)c(-c3ccc4c(c3)NC(=O)C43CCN(c4ccc(Cl)cc4)CC3)c2)[nH]1]

Obtained as a white solid (44%) from 6-bromo-1'-(4-chlorophenyl)spiro[indoline-3,4'-piperidin]-2-one (preparation 14) and 3-methyl-5-(4-methyl-3-(4,4,5,5-tetramethyl-1,3,2-dioxaborolan-2-yl)phenyl)-4H-1,2,4-triazole (preparation 49) following the experimental procedure as described in preparation 38 followed by purification by flash chromatography (100:1 to 40:1 dichloromethane/methanol).

LRMS (m/z): 484 (M+1)$^+$.

$^1$H-NMR δ (DMSO-d$_6$): 2.01 (m, 4H), 2.25 (s, 3H), 2.50 (s, 3H), 3.45 (m, 2H), 3.69 (m, 2H), 6.71 (s, 1H), 6.94 (m, 3H), 7.28 (m, 5H), 7.89 (m, 2H), 8.39 (s, 1H).

EXAMPLE 61

6-[3-Fluoro-2-methyl-5-(5-methyl-4H-1,2,4-triazol-3-yl)phenyl]-2',3',5',6'-tetrahydro-spiro[indole-3,4'-pyran]-2(1H)-one

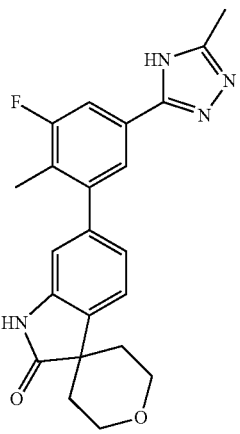 [SMILES: Cc1nnc(-c2cc(F)c(C)c(-c3ccc4c(c3)NC(=O)C43CCOCC3)c2)[nH]1]

Obtained as a light yellow solid (48%) from 6-bromo-2',3',5',6'-tetrahydrospiro[indoline-3,4'-pyran]-2-one (preparation 8) and 3-[3-fluoro-4-methyl-5-(4,4,5,5-tetramethyl-1,3,2-dioxaborolan-2-yl)phenyl]-5-methyl-4H-1,2,4-triazole (preparation 50) following the experimental procedure as described in preparation 38 followed by purification by flash chromatography (98:2 to 95:5 dichloromethane/methanol).

LRMS (m/z): 393 (M+1)$^+$.

$^1$H-NMR δ (DMSO-d$_6$): 1.72-1.83 (m, 4H), 2.18 (s, 3H), 2.40 (s, 3H), 3.79-3.92 (m, 2H), 4.00-4.13 (m, 2H), 6.83 (s, 1H), 6.99 (d, J=8.0 Hz, 1H), 7.62 (d, J=8.0 Hz, 1H), 7.66 (s, 1H), 10.51 (s, 1H).

EXAMPLE 62

6'-[2-methyl-5-(5-methyl-4H-1,2,4-triazol-3-yl)phenyl]-2,3,5,6-tetrahydrospiro[pyran-4,3'-pyrrolo[3,2-b]pyridin]-2'(1'H)-one hydrogen chloride

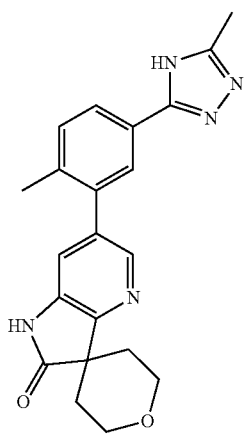 [SMILES: Cc1nnc(-c2ccc(C)c(-c3cnc4c(c3)NC(=O)C43CCOCC3)c2)[nH]1]

Obtained as a pale orange solid (33%) from 6'-bromo-2,3,5,6-tetrahydrospiro[pyran-4,3'-pyrrolo[3,2-b]pyridin]-2'(1'H)-one (preparation 30) and 3-methyl-5-(4-methyl-3-(4,4,5,5-tetramethyl-1,3,2-dioxaborolan-2-yl)phenyl)-4H-1,2,4-triazole (preparation 49) following the experimental procedure as described in preparation 38 followed by purification by flash chromatography (96:4 dichloromethane/methanol) to give a solid which was dissolved in 3 mL of a 1.25 M solution of hydrogen chloride in methanol. Subsequent evaporation afforded the title compound.

LRMS (m/z): 376 (M+1)$^+$ $^1$H-NMR δ (CD$_3$OD): 1.95 (m, 4H), 2.40 (s, 3H), 2.82 (s, 3H), 4.22 (m, 4H), 7.44 (s, 1H), 7.60 (d, 1H), 7.90 (s, 1H), 7.95 (d, 1H), 8.27 (s, 1H)

EXAMPLE 63

4,4-Difluoro-6'-(2-methyl-5-(5-methyl-4H-1,2,4-triazol-3-yl)phenyl)spiro[cyclohexane-1,3'-indolin]-2'-one

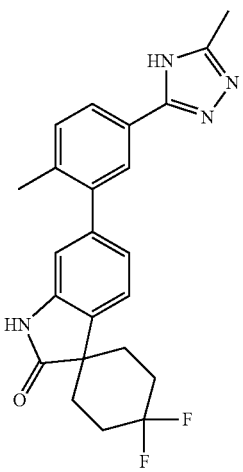 [SMILES: Cc1nnc(-c2ccc(C)c(-c3ccc4c(c3)NC(=O)C43CCC(F)(F)CC3)c2)[nH]1]

Obtained as a white solid (16%) from 6'-bromo-4,4-difluorospiro[cyclohexane-1,3'-indolin]-2'-one (preparation 21) and 3-methyl-5-(4-methyl-3-(4,4,5,5-tetramethyl-1,3,2-dioxaborolan-2-yl)phenyl)-4H-1,2,4-triazole (preparation 49) following the experimental procedure as described in preparation 38 followed by purification by reverse phase chromatography on a C18 cartridge (water/acetonitrile:methanol 1:1).

LRMS (m/z): 409 (M+1)$^+$.

$^1$H-NMR δ (CD$_3$OD): 1.96-2.02 (m, 2H), 2.09-2.23 (m, 4H), 2.30 (s, 3H), 2.47 (s, 3H), 2.51-2.69 (m, 2H), 6.92 (s, 1H), 7.03 (d, J=9.0 Hz, 1H), 7.38 (d, J=6.0 Hz, 1H), 7.40 (d, J=6.0 Hz, 1H), 7.81 (s, 1H), 7.84 (d, J=9.0 Hz, 1H).

EXAMPLE 64

4-hydroxy-6'-(2-methyl-5-(5-methyl-4H-1,2,4-triazol-3-yl)phenyl)spiro[cyclohexane-1,3'-indolin]-2'-one

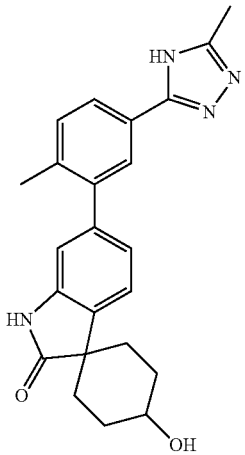 [SMILES: Cc1nnc(-c2ccc(C)c(-c3ccc4c(c3)NC(=O)C43CCC(O)CC3)c2)[nH]1]

Obtained as a white solid (30%) from 6'-bromo-4-hydroxyspiro[cyclohexane-1,3'-indolin]-2'-one (preparation 23, major isomer) and 3-methyl-5-(4-methyl-3-(4,4,5,5-tetramethyl-1,3,2-dioxaborolan-2-yl)phenyl)-4H-1,2,4-triazole (preparation 49) following the experimental procedure as described in preparation 38 followed by purification by reverse phase chromatography (C-18 silica from Waters©, water/acetonitrile/methanol as eluents [0.1% v/v formic acid buffered] 0% to 50%).

LRMS (m/z): 389 (M+1)$^+$.

$^1$H-NMR δ (CD$_3$OD): 1.78 (m, 2H), 1.97 (brs, 4H), 2.15 (m, 2H), 2.30 (s, 3H), 2.46 (s, 3H), 3.90 (m, 1H), 6.88 (s, 1H), 6.99 (d, J=7.4 Hz, 1H), 7.37 (d, J=7.7 Hz, 2H), 7.83 (m, 2H).

EXAMPLE 65

6'-(3-fluoro-2-methyl-5-(5-methyl-4H-1,2,4-triazol-3-yl)phenyl)-4-hydroxy-4-methylspiro[cyclohexane-1,3'-indolin]-2'-one

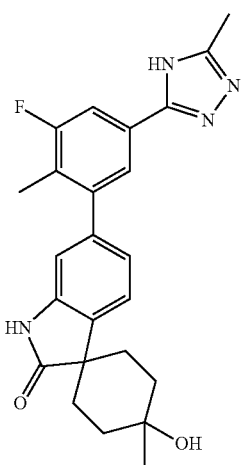 [SMILES: Cc1nnc(-c2cc(F)c(C)c(-c3ccc4c(c3)NC(=O)C43CCC(C)(O)CC3)c2)[nH]1]

Obtained as a white solid (41%) from 4-hydroxy-4-methyl-6'-(4,4,5,5-tetramethyl-1,3,2-dioxaborolan-2-yl)spiro[cyclohexane-1,3'-indolin]-2'-one (preparation 25) and 3-(3-fluoro-5-iodo-4-methylphenyl)-5-methyl-4H-1,2,4-triazole (preparation 50d) following the experimental procedure as described in preparation 38 followed by purification by flash chromatography (98:2 ethyl acetate/methanol).

LRMS (m/z): 421 (M+1)$^+$.

$^1$H-NMR δ (CD$_3$OD): 1.38 (s, 3H), 1.47 (m, 2H), 1.91 (brs, 5H), 2.21 (s, 3H), 2.29 (m, 2H), 2.48 (brs, 2H), 6.94 (s, 1H), 7.00 (d, J=7.7 Hz, 1H), 7.55 (d, J=7.7 Hz, 1H), 7.65 (d, J=10.5 Hz, 1H), 7.69 (s, 1H).

EXAMPLE 66

6'-(2-methyl-5-(5-methyl-4H-1,2,4-triazol-3-yl)phenyl)-4-(2-morpholinoethoxy)spiro[cyclohexane-1,3'-indolin]-2'-one

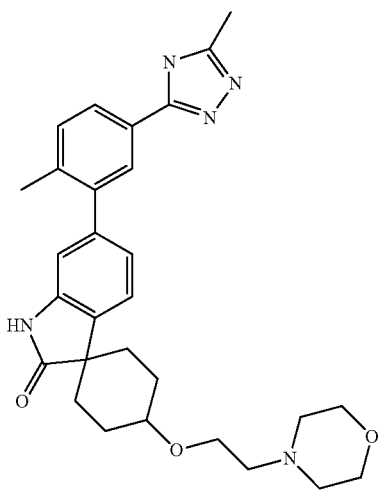 [SMILES: Cc1nnc(-c2ccc(C)c(-c3ccc4c(c3)NC(=O)C43CCC(OCCN4CCOCC4)CC3)c2)[nH]1]

Obtained as a white solid (29%) from 6'-bromo-4-(2-morpholinoethoxy)spiro[cyclohexane-1,3'-indolin]-2'-one (preparation 27) and 3-methyl-5-(4-methyl-3-(4,4,5,5-tetramethyl-1,3,2-dioxaborolan-2-yl)phenyl)-4H-1,2,4-triazole (preparation 49) following the experimental procedure as described in preparation 38 followed by purification by flash chromatography (97:3 dichloromethane/methanol).

LRMS (m/z): 502 (M+1)$^+$ $^1$H-NMR δ (DMSO-d$_6$): 1.23 (m, 2H), 1.59 (m, 2H), 1.86-1.94 (m, 4H), 2.28 (s, 3H), 2.36 (s, 3H), 3.35-3.59 (m, 13H), 6.80 (s, 1H), 6.98 (d, 1H), 7.37-7.47 (m, 2H), 7.80 (s, 1H), 7.85 (d, 1H), 8.14 (s, 1H), 10.34 (s, NH)

EXAMPLE 67

6-(2-methyl-5-(5-methyl-4H-1,2,4-triazol-3-yl)phenyl)-1'-(methylsulfonyl)spiro[indoline-3,4'-piperidin]-2-one

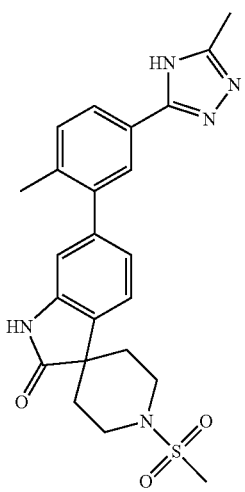 [SMILES: Cc1nnc(-c2ccc(C)c(-c3ccc4c(c3)NC(=O)C43CCN(S(C)(=O)=O)CC3)c2)[nH]1]

Obtained as a white solid (43%) from 6-bromo-1'-(methylsulfonyl)spiro[indoline-3,4'-piperidin]-2-one (preparation 12) and 3-methyl-5-(4-methyl-3-(4,4,5,5-tetramethyl-1,3,2-dioxaborolan-2-yl)phenyl)-4H-1,2,4-triazole (preparation 49) following the experimental procedure as described in preparation 38 followed by purification by flash chromatography (96:4 dichloromethane/methanol).

LRMS (m/z): 452 (M+1)$^+$ $^1$H-NMR δ (DMSO-d$_6$): 1.91 (m, 4H), 2.29 (s, 3H), 2.36 (s, 3H), 2.99 (s, 3H), 3.46 (m, 2H), 3.58 (m, 2H), 6.83 (s, 1H), 7.01 (d, J=7.69 Hz, 1H), 7.40 (d, J=7.97 Hz, 1H), 7.57 (d, J=7.69 Hz, 1H), 7.81 (s, 1H), 7.87 (d, J=7.97 Hz, 1H), 10.57 (s, NH)

EXAMPLE 68

6-(2-methyl-5-(5-methyl-4H-1,2,4-triazol-3-yl)phenyl)-1'-tosylspiro[indoline-3,4'-piperidin]-2-one

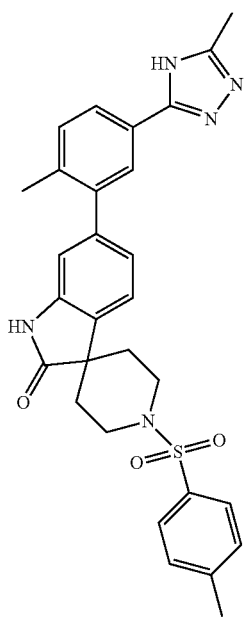 [SMILES: Cc1ccc(S(=O)(=O)N2CCC3(CC2)C(=O)Nc2cc(-c4cc(-c5nnc(C)[nH]5)ccc4C)ccc23)cc1]

Obtained as an orange solid (69%) from 6-bromo-1'-tosyl-spiro[indoline-3,4'-piperidin]-2-one (preparation 13) and 3-methyl-5-(4-methyl-3-(4,4,5,5-tetramethyl-1,3,2-dioxaborolan-2-yl)phenyl)-4H-1,2,4-triazole (preparation 49) following the experimental procedure as described in preparation 38 followed by purification by flash chromatography (96:4 dichloromethane/methanol).

LRMS (m/z): 426 (M−1)$^−$.

$^1$H-NMR δ (DMSO-d$_6$): 1.81 (d, J=14.6 Hz, 2H), 1.99 (m, 2H), 2.25 (s, 3H), 2.38 (s, 3H), 2.45 (s, 3H), 3.18 (m, 3H), 3.46 (m, 2H), 6.77 (s, 1H), 6.94 (d, J=7.5 Hz, 1H), 7.27 (d, J=7.9 Hz, 1H), 7.34 (d, J=7.5 Hz, 1H), 7.50 (d, J=8.3 Hz, 2H), 7.70 (d, J=8.3 Hz, 2H), 7.79 (s, 1H), 7.84 (d, J=7.9 Hz, J'=1.8 Hz, 1H), 10.43 (s, 1H).

EXAMPLE 69

6'-(2-methyl-5-(5-methyl-4H-1,2,4-triazol-3-yl)phenyl)-4-morpholinospiro[cyclohexane-1,3'-indolin]-2'-one

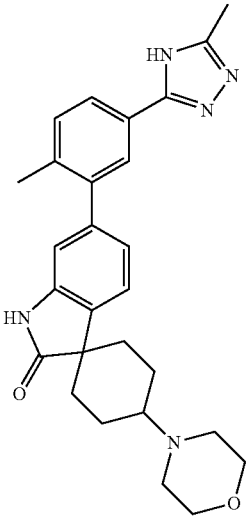 [SMILES: Cc1nnc(-c2ccc(C)c(-c3ccc4c(c3)NC(=O)C43CCC(N4CCOCC4)CC3)c2)[nH]1]

Obtained as a white solid (29%) from 6'-bromo-4-morpholin-4-ylspiro[cyclohexane-1,3'-indol]-2'(1'H)-one (preparation 26, major isomer) and 3-methyl-5-(4-methyl-3-(4,4,5,5-tetramethyl-1,3,2-dioxaborolan-2-yl)phenyl)-4H-1,2,4-triazole (preparation 49) following the experimental procedure as described in preparation 38 followed by purification by flash chromatography (97:3 dichloromethane/methanol).

LRMS (m/z): 458 (M+1)$^+$ $^1$H-NMR δ (DMSO-d$_6$): 1.85-2.65 (m, 12H), 2.87 (s, 3H), 2.92 (m, 1H), 3.68 (m, 4H), 6.82 (s, 1H), 7.00 (d, 1H), 7.39 (m, 2H), 7.88 (d, 2H), 10.38 (s, NH)

EXAMPLE 70

6'-(2-Methyl-5-(5-methyl-1,3,4-oxadiazol-2-yl)phenyl)spiro[cyclopentane-1,3'-indolin]-2'-one

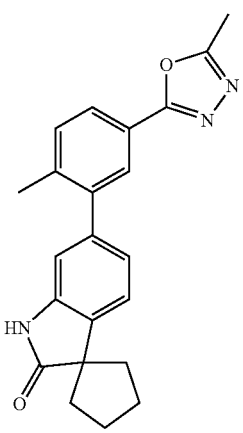 [SMILES: Cc1nnc(-c2ccc(C)c(-c3ccc4c(c3)NC(=O)C43CCCC3)c2)o1]

A stirred mixture of 4-methyl-3-(2'-oxospiro[cyclopentane-1,3'-indoline]-6'-yl)benzohydrazide (preparation 53, 0.05 g, 0.16 mmol) and trimethylorthoacetate (0.04 mL, 0.19 mmol) in acetic acid (1 mL) were heated to 150° C. in a sealed tube. After 3 hours, the mixture was cooled, poured into water and extracted with ethyl acetate. The organic layer was washed with water, brine, dried (MgSO$_4$) and evaporated in vacuo. Purification of the residue by flash chromatography (1:1 hexanes/ethyl acetate) gave the title compound (0.02 g, 35%) as a white solid.

LRMS (m/z): 360 (M+1)$^+$.

$^1$H-NMR δ (DMSO-d$_6$): 1.80 (m, 4H), 1.93 (m, 4H), 2.31 (s, 3H), 2.55 (s, 3H), 6.79 (s, 1H), 6.96 (d, 1H), 7.32 (d, 1H), 7.51 (d, 1H), 7.72 (s, 1H), 7.86 (d, 1H), 10.35 (brs, 1H).

EXAMPLE 71

6'-(2-Methyl-5-(1,3,4-oxadiazol-2-yl)phenyl)spiro[cyclopentane-1,3'-indolin]-2'-one

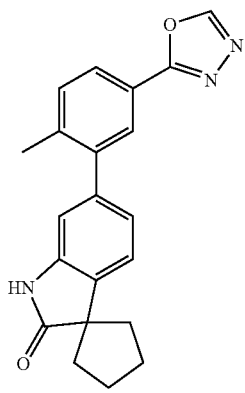 [SMILES: Cc1ccc(-c2nnco2)cc1-c1ccc2c(c1)NC(=O)C21CCCC1]

A stirred mixture of 4-methyl-3-(2'-oxospiro[cyclopentane-1,3'-indoline]-6'-yl)benzohydrazide (preparation 53, 0.16 g, 0.24 mmol) and trimethylorthoformate (0.24 mL, 1.44 mmol) in acetic acid (3 mL) were heated to 150° C. in a sealed tube. After 3 hours, the mixture was cooled, poured into water and extracted with ethyl acetate. The organic layer was washed with water, brine, dried (MgSO$_4$) and evaporated in vacuo. Purification of the residue by flash chromatography (1:1 hexanes/ethyl acetate) gave the title compound (0.05 g, 60%) as a white solid.

LRMS (m/z): 346 (M+1)$^+$.

$^1$H-NMR δ (CDCl$_3$): 1.92-2.16 (m, 6H), 2.18-2.30 (m, 2H), 2.38 (s, 3H), 6.87 (s, 1H), 6.99 (d, J=9.0 Hz, 1H), 7.23-7.26 (m, 2H), 7.43 (d, J=6.0 Hz, 1H), 7.95 (s, 1H), 7.97 (d, J=9.0 Hz, 1H), 8.46 (s, 1H).

EXAMPLE 72

4,4-Difluoro-6'-(2-methyl-5-(5-methyl-1,3,4-oxadiazol-2-yl)phenyl)spiro-[cyclohexane-1,3'-indolin]-2'-one

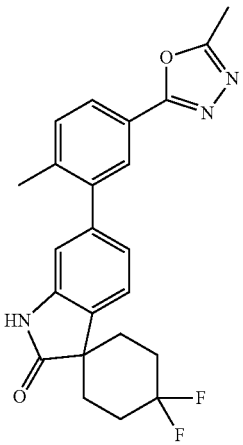 [SMILES: Cc1nnc(-c2ccc(C)c(-c3ccc4c(c3)NC(=O)C43CCC(F)(F)CC3)c2)o1]

Obtained as a white solid (88%) from 6'-bromo-4,4-difluorospiro[cyclohexane-1,3'-indolin]-2'-one (preparation 21) and 2-methyl-5-(5-methyl-1,3,4-oxadiazol-2-yl)phenylboronic acid (preparation 55) following the experimental procedure as described in preparation 38 followed by purification by flash chromatography (dichloromethane to 9:1 dichloromethane/methanol).

LRMS (m/z): 410 (M+1)$^+$.

$^1$H-NMR δ (CDCl$_3$): 1.58 (s, 2H), 1.99-2.23 (m, 6H), 2.36 (s, 3H), 2.60 (s, 3H), 6.88 (s, 1H), 7.02 (d, J=6.0 Hz, 1H), 7.29 (d, J=9.0 Hz, 1H), 7.41 (d, J=9.0 Hz, 1H), 7.70 (s, 1H) 7.87-7.89 (m, 1H), 7.92 (d, J=9.0 Hz, 1H).

EXAMPLE 73

4-hydroxy-6'-(2-methyl-5-(5-methyl-1,3,4-oxadiazol-2-yl)phenyl)spiro[cyclohexane-1,3'-indolin]-2'-one

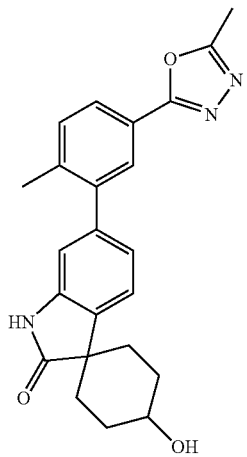 [SMILES: Cc1nnc(-c2ccc(C)c(-c3ccc4c(c3)NC(=O)C43CCC(O)CC3)c2)o1]

Obtained as a pale yellow solid (99%) from 6'-bromo-4-hydroxyspiro[cyclohexane-1,3'-indolin]-2'-one (preparation 23, major isomer) and 2-methyl-5-(5-methyl-1,3,4-oxadiazol-2-yl)phenylboronic acid (preparation 55) following the experimental procedure as described in preparation 38 followed by purification by flash chromatography (98:2 ethyl acetate/methanol).

LRMS (m/z): 390 (M+1)$^+$.

$^1$H-NMR δ (CDCl$_3$): 1.77 (m, 3H), 2.05 (m, 4H), 2.22 (m, 2H), 2.36 (s, 3H), 2.61 (s, H), 3.95 (m, 1H), 6.93 (s, 1H), 6.99 (dd, J=7.7 Hz, J'=1.4 Hz, 1H), 7.26 (d, J=8.5 Hz, 1H), 7.39 (d, J=8.5 Hz, 1H), 7.91 (m, 2H), 8.64 (s, 1H).

EXAMPLE 74

6'-(5-(5-cyclopropyl-1,3,4-oxadiazol-2-yl)-2-methylphenyl)-4-hydroxyspiro [cyclohexane-1,3'-indolin]-2'-one

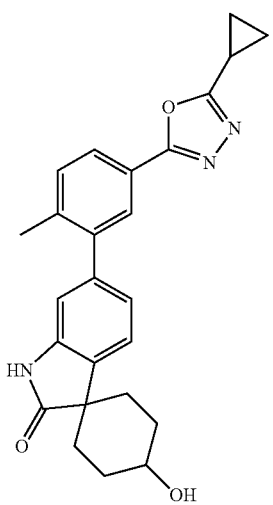 [SMILES: Cc1ccc(-c2nnc(C3CC3)o2)cc1-c1ccc2c(c1)NC(=O)C21CCC(O)CC1]

Obtained as a pale yellow solid (63%) from 6'-bromo-4-hydroxyspiro[cyclohexane-1,3'-indolin]-2'-one (preparation 23, major isomer) and 5-(5-cyclopropyl-1,3,4-oxadiazol-2-yl)-2-methylphenylboronic acid (preparation 56) following the experimental procedure as described in preparation 38 followed by purification by flash chromatography (100% ethyl acetate).

LRMS (m/z): 416 (M+1)$^+$.

$^1$H-NMR δ (CDCl$_3$): 1.19 (m, 4H), 1.78 (m, 2H), 2.05 (m, 5H), 2.20 (m, 3H), 2.35 (s, 3H), 3.93 (m, 1H), 6.86 (d, J=1.2 Hz, 1H), 6.99 (dd, J=7.5 Hz, J'=1.2 Hz, 1H), 7.27 (m, 1H), 7.39 (d, J=8.0 Hz, 1H), 7.52 (brs, 1H), 7.84 (s, 1H), 7.89 (dd, J=8.0 Hz, J'=1.5 Hz, 1H).

EXAMPLE 75

6'-(2-Methyl-5-(5-methyl-1,2,4-oxadiazol-3-yl)phenyl)spiro[cyclopentane-1,3'-indolin]-2'-one

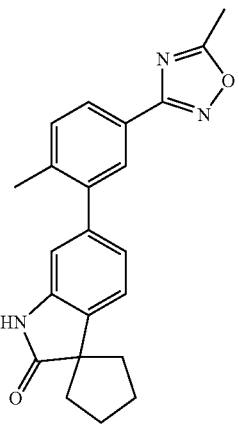

A mixture of (E)-N'-hydroxy-4-methyl-3-(2'-oxospiro[cyclopentane-1,3'-indoline]-6'-yl)benzimidamide (preparation 54, 31 mg, 0.09 mmol) and acetic anhydride (0.03 mL, 0.28 mmol) was heated in a sealed tube 130° C. for 1 h. The solvent was concentrated under reduced pressure and the residue was dissolved in ethyl acetate, washed with aqueous sodium bicarbonate solution, brine, dried (MgSO$_4$) and the solvent evaporated under reduced pressure. The residue was purified by flash chromatography (8:2 hexanes/ethyl acetate to ethyl acetate) to yield the title compound (0.01 g, 32%) as a white solid.

LRMS (m/z): 360 (M+1)$^+$.

$^1$H-NMR δ (DMSO-d$_6$): 1.25-1.32 (m, 4H), 1.95-2.05 (m, 4H), 2.34 (s, 3H), 2.67 (s, 3H), 6.81 (s, 1H), 6.99 (d, J=12.0 Hz, 1H), 7.34 (d, J=9.0 Hz, 1H), 7.51 (d, J=12.0 Hz, 1H), 7.79 (s, J=12.0 Hz, 1H), 7.90 (d, J=9.0 Hz, 1H), 10.38 (s, 1H).

EXAMPLE 76

6'-(2-Methyl-5-(3-methyl-1,2,4-oxadiazol-5-yl)phenyl)spiro[cyclopentane-1,3'-indolin]-2'-one

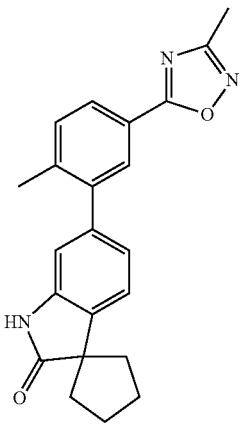 [SMILES: Cc1noc(-c2ccc(C)c(-c3ccc4c(c3)NC(=O)C43CCCC3)c2)n1]

Obtained as a white solid (33%) from 6'-bromospiro[cyclopentane-1,3'-indolin]-2'-one (preparation 2) and 3-methyl-5-(4-methyl-3-(4,4,5,5-tetramethyl-1,3,2-dioxaborolan-2-yl)phenyl)-1,2,4-oxadiazole (preparation 57) following the experimental procedure as described in preparation 38 followed by purification by flash chromatography (8:2 hexanes/ethyl acetate to ethyl acetate).

LRMS (m/z): 360 (M+1)$^+$.

$^1$H-NMR δ (DMSO-d$_6$): 2.15 (m, 4H), 2.01 (m, 4H), 2.37 (s, 3H), 2.49 (s, 3H), 6.80 (s, 1H), 6.98 (d, 1H), 7.32 (d, 1H), 7.55 (d, 1H), 7.84 (s, 1H), 7.96 (d, 1H), 10.34 (brs, 1H).

EXAMPLE 77

6-[2-Methyl-5-(2-methyl-1H-imidazol-5-yl)phenyl]-2',3',5',6'-tetrahydrospiro[indole-3,4'-pyran]-2(1H)-one

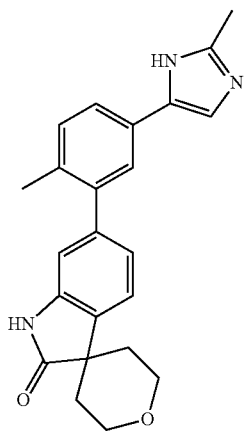 [SMILES: Cc1ncc(-c2ccc(C)c(-c3ccc4c(c3)NC(=O)C43CCOCC3)c2)[nH]1]

Obtained as a brownish solid (26%) from 6-(4,4,5,5-tetramethyl-1,3,2-dioxaborolan-2-yl)-2',3',5',6'-tetrahydrospiro[indole-3,4'-pyran]-2(1H)-one (preparation 9) and 5-(3-bromo-4-methylphenyl)-2-methyl-1H-imidazole (preparation 58) following the experimental procedure as described in preparation 38 followed by purification by flash chromatography (98:2 to 95:5 dichloromethane/methanol).

LRMS (m/z): 374 (M+1)$^+$.

$^1$H-NMR δ (DMSO-d$_6$): 1.68-1.85 (m, 4H), 2.21 (s, 3H), 2.29 (s, 3H), 3.79-3.91 (m, 2H), 4.00-4.12 (m, 2H), 6.80 (s, 1H), 6.95 (d, J=6.0 Hz, 1H), 7.23 (d, J=9.0 Hz, 1H), 7.40 (s, 1H), 7.53 (s, 1H), 7.57 (d, J=9.0 Hz, 2H).

EXAMPLE 78

6-(2-methyl-5-(5-methyl-1H-imidazol-2-yl)phenyl)-2',3',5',6'-tetrahydrospiro-[indoline-3,4'-pyran]-2-one

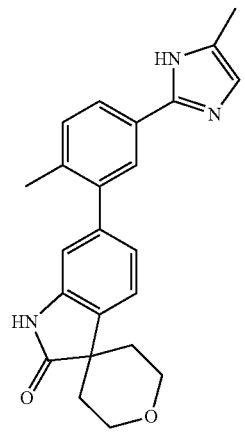 [SMILES: Cc1cnc(-c2ccc(C)c(-c3ccc4c(c3)NC(=O)C43CCOCC3)c2)[nH]1]

Obtained as a pale green solid (16%) from 6-(4,4,5,5-tetramethyl-1,3,2-dioxaborolan-2-yl)-2',3',5',6'-tetrahydrospiro[indole-3,4'-pyran]-2(1H)-one (preparation 9) and 2-(3-iodo-4-methylphenyl)-5-methyl-1H-imidazole (preparation 59) following the experimental procedure as described in preparation 38 followed by purification by flash chromatography (96:4 to 95:5 dichloromethane/methanol).

LRMS (m/z): 374 (M+1)$^+$.

$^1$H-NMR δ (DMSO-d$_6$): 1.71-1.85 (m, 4H), 2.17 (s, 3H), 2.26 (s, 3H), 3.82-3.91 (m, 2H), 4.04-4.12 (m, 2H), 6.79 (brs, 1H), 6.83 (s, 1H), 6.99 (d, J=6.0 Hz, 1H), 7.33 (d, J=6.0 Hz, 1H), 7.61 (d, J=6.0 Hz, 1H), 7.74 (s, 1H), 7.79 (d, J=6.0 Hz, 1H), 10.50 (s, 1H), 12.16 (brs, 1H).

The invention claimed is:
1. A compound of formula (I)

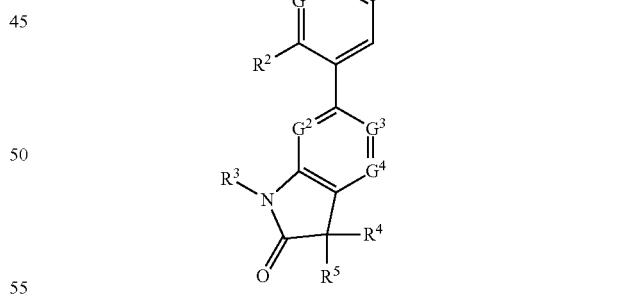

wherein:
R$^1$ represents
a 5-membered heteroaromatic ring having 1, 2, or 3 heteroatoms chosen from nitrogen, oxygen and sulphur atoms, wherein the heteroaromatic ring is optionally substituted by one or two groups chosen from linear and branched C$_{1-4}$ alkyl groups, and —(CH$_2$)$_p$—C$_{3-6}$ cycloalkyl groups; wherein each of the C$_{1-4}$ alkyl and —(CH$_2$)$_p$—C$_{3-6}$ cycloalkyl groups is optionally substituted by one, two, or three groups chosen from fluorine atoms, —OR groups, and —NRR' groups, wherein R and R' each independently is chosen from a hydrogen atom, linear and branched $C_{1-4}$ alkyl, and $C_{3-6}$ cycloalkyl groups, wherein p is an integer ranging from 0 to 3, or $R^1$ represents a group of formula —CO—NHR$^6$, wherein $R^6$ is chosen from a hydrogen atom, linear and branched $C_{1-4}$ alkyl groups, $C_{3-6}$ cycloalkyl groups, $C_{3-6}$ cycloalkyl-$C_{1-2}$ alkylene groups, and 5 to 6 membered heteroaromatic groups having 1, 2, or 3 heteroatoms chosen from nitrogen, oxygen and sulphur atoms, wherein the heteroaromatic group is optionally substituted by 1 or 2 groups chosen from linear and branched $C_{1-4}$ alkyl groups and $C_{3-6}$ cycloalkyl groups;

$R^2$ is chosen from a hydrogen atom, a chlorine atom, and a methyl group;

$R^3$ is chosen from a hydrogen atom and $C_{1-4}$ alkyl groups;

$R^4$ and $R^5$ each independently is chosen from $C_{1-3}$ alkyl groups optionally substituted by a hydroxy group, or, $R^4$ and $R^5$ form together with the carbon atom to which they are attached a cyclic group of formula

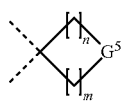

wherein n and m each independently is an integer chosen from 1 and 2, and $G^5$ is chosen from —O—, —S—, —SO—, —SO$_2$—, —C($R^7R^8$)— and —N(L$R^9$)—, wherein:

$R^7$ is chosen from a hydrogen atom, halogen atoms, a hydroxyl group, $C_{1-4}$ alkyl groups, morpholine groups, and morpholino-ethoxy groups;

$R^8$ is chosen from a hydrogen atom, halogen atoms, and $C_{1-4}$ alkyl groups;

L is chosen from a direct bond, —SO$_2$—, —CO—, —(CO)O—, —(CO)NH—, and —(SO$_2$)NH—; and $R^9$ is chosen from a hydrogen atom, linear and branched $C_{1-4}$ alkyl groups, —(CH$_2$)$_q$—$C_{3-6}$ cycloalkyl groups, $C_5$-$C_{10}$ aryl groups, and 5 to 10-membered heteroaryl groups containing at least one heteroatom chosen from N, S, and O, wherein each of the $C_{1-4}$ alkyl and —(CH$_2$)$_q$—$C_{3-6}$ cycloalkyl groups is optionally substituted by one or two groups chosen from halogen atoms, —OR" groups, and —NR"R'" groups, and wherein each of the $C_5$-$C_{10}$ aryl and 5 to 10-membered heteroaryl groups is optionally substituted by one or two groups chosen from linear and branched $C_1$-$C_4$ alkyl groups, halogen atoms, —OR" groups, and —NR"R'" groups, wherein R" and R'" each is independently chosen from a hydrogen atom, $C_{1-4}$ alkyl groups, and $C_{3-6}$ cycloalkyl groups, or R" and R'" together with the nitrogen atom to which they are attached form a 5 or 6-membered saturated heterocyclic ring optionally containing one further heteroatom chosen from N, O, and S, and q is an integer ranging from 0 to 3;

$G^1$ is chosen from a nitrogen atom, —CH=, and —CF=;
$G^2$ is chosen from a nitrogen atom, —CH=, and —CF=;
$G^3$ is chosen from a nitrogen atom, —CH=, —CCl=, and —CF=; and
$G^4$ is chosen from a nitrogen atom, —CH=, and —CF=;
or a pharmaceutically acceptable salt or an N-oxide thereof.

2. The compound according to claim 1, wherein $R^1$ is chosen from triazolyl, oxadiazolyl, and imidazolyl groups wherein each of the triazolyl, oxadiazolyl, and imidazolyl groups is optionally substituted by one group chosen from linear and branched $C_{1-4}$ alkyl groups, $C_{3-6}$ cycloalkyl groups, and —CF$_3$;

or $R^1$ represents a group of formula —CO—NHR$^6$, wherein $R^6$ is chosen from a hydrogen atom, linear and branched $C_{1-4}$ alkyl groups, $C_{3-6}$ cycloalkyl groups, $C_{3-6}$ cycloalkyl-$C_{1-2}$ alkylene groups, isoxazolyl groups, triazolyl groups, and pyridyl groups.

3. The compound according to claim 2, wherein $R^1$ is chosen from triazolyl groups optionally substituted by one methyl group, or $R^1$ represents a group of formula —CO—NHR$^6$, wherein $R^6$ is chosen from a hydrogen atom, a methyl group, a cyclopropyl group, cyclopropylmethyl groups, a cyclobutyl group, and isoxazolyl groups.

4. The compound according to claim 3, wherein $R^1$ is chosen from triazolyl groups optionally substituted by one methyl group, or $R^1$ represents a group of formula —CO—NHR$^6$, wherein $R^6$ is chosen from a cyclopropyl group and isoxazolyl groups.

5. The compound according to claim 1, wherein $R^2$ is chosen from a chlorine atom and a methyl group.

6. The compound according to claim 5, wherein $R^2$ is a methyl group.

7. The compound according to claim 1, wherein $R^3$ is chosen from a hydrogen atom and a methyl group.

8. The compound according to claim 7, wherein $R^3$ is a hydrogen atom.

9. The compound according to claim 1, wherein $R^4$ and $R^5$ each independently is chosen from a methyl group and a 2-hydroxyethyl group, or $R^4$ and $R^5$ form together with the carbon atom to which they are attached a cyclic group of formula

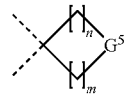

wherein n and m each independently is an integer chosen from 1 and 2, and $G^5$ is chosen from —O—, —S—, —SO—, SO$_2$—, —C($R^7R^8$)— and —N(L$R^9$)—, wherein:

$R^7$ is chosen from a hydrogen atom, a fluorine atom, a hydroxyl group, a methyl group, morpholine groups, and morpholino-ethoxy groups;

$R^8$ is chosen from a hydrogen atom, a fluorine atom, and a methyl group;

L is chosen from a direct bond, —SO$_2$—, —O—, —(CO)O— and —C(O)NH—; and $R^9$ is chosen from linear and branched $C_{1-4}$ alkyl groups, $C_{3-6}$ cycloalkyl groups, phenyl groups, and pyridyl groups, wherein each of the $C_{1-4}$ alkyl and $C_{3-6}$ cycloalkyl groups is optionally substituted with one group chosen from a chlorine atom, piperazine groups attached at nitrogen, and morpholine groups attached at nitrogen, and wherein each of the phenyl and pyridyl groups is optionally substituted with one group chosen from a chlorine atom, a methyl group, piperazine groups, and morpholine groups.

10. The compound according to claim 1, wherein $R^4$ and $R^5$ form together with the carbon atom to which they are attached a cyclic group of formula

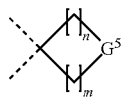

wherein n and m each independently is an integer chosen from 1 and 2, and $G^5$ is chosen from —O—, —S—, —SO—, $SO_2$—, —C($R^7R^8$)— and —N(L$R^9$)—, wherein:
- $R^7$ is chosen from a hydrogen atom, a fluorine atom, a hydroxyl group, a methyl group, morpholine groups, and morpholino-ethoxy groups;
- $R^8$ is chosen from a hydrogen atom, a fluorine atom, and a methyl group;
- L is chosen from a direct bond, —$SO_2$—, —CO—, —(CO)O— and —C(O)NH—; and
- $R^9$ is chosen from linear and branched $C_{1-4}$ alkyl groups, $C_{3-6}$ cycloalkyl groups, phenyl groups, and pyridyl groups, wherein each of the $C_{1-4}$ alkyl and $C_{3-6}$ cycloalkyl groups is optionally substituted with one group chosen from a chlorine atom, piperazine groups attached at nitrogen, and morpholine groups attached at nitrogen, and wherein each of the phenyl and pyridyl groups is optionally substituted with one group chosen from a chlorine atom, a methyl group, piperazine groups, and morpholine groups.

11. The compound according to claim 9, wherein $G^5$ is chosen from —O—, —S—, —C($R^7R^8$)— and —N(L$R^9$)—, wherein:
- $R^7$ is chosen from a hydrogen atom, a fluorine atom, a hydroxyl group, morpholine groups, and morpholino-ethoxy groups;
- $R^8$ is chosen from a hydrogen atom, a fluorine atom, and a methyl group;
- L is chosen from a direct bond, —$SO_2$—(CO)O— and —C(O)NH—; and
- $R^9$ is chosen from a methyl group, a tert-butyl group, a cyclopropyl group, and phenyl groups optionally substituted by a chlorine atom, piperazine groups, and morpholine groups.

12. The compound according to claim 11, wherein L is chosen from a direct bond and —$SO_2$—, and $R^9$ is a methyl group.

13. The compound according to claim 1, wherein $G^1$ is is chosen from —CH= and —CF=.

14. The compound according to claim 1, wherein $G^2$ is chosen from a nitrogen atom and —CH=.

15. The compound according to claim 1, wherein $G^3$ is chosen from a nitrogen atom, —CH=, and —CCl=.

16. The compound according to claim 15, wherein $G^3$ is chosen from a nitrogen atom and —CH=.

17. The compound according to claim 1, wherein $G^4$ is chosen from a nitrogen atom and —CH=.

18. The compound according to claim 1, wherein:
- $R^1$ is chosen from triazolyl groups optionally substituted by one methyl group, or $R^1$ represents a group of formula —CO—NH$R^6$, wherein $R^6$ is chosen from a cyclopropyl group and isoxazolyl groups;
- $R^2$ is a methyl group;
- $R^3$ is a hydrogen atom;
- $R^4$ and $R^5$ form together with the carbon atom to which they are attached a cyclic group of formula

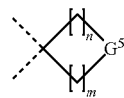

wherein n and m each independently is an integer chosen from 1 and 2, and $G^5$ is chosen from —O—, —S—, —C($R^7R^8$)—, and —N(L$R^9$)—, wherein:
- $R^7$ is chosen from a hydrogen atom, a fluorine atom, a hydroxyl group, morpholine groups, and morpholino-ethoxy groups;
- $R^8$ is chosen from a hydrogen atom, a fluorine atom, and a methyl group;
- L is chosen from a direct bond and —$SO_2$—;
- $R^9$ is a methyl group;
- $G^1$ is chosen from —CH= and —CF=; and
- $G^2$, $G^3$ and $G^4$ each independently is chosen from a nitrogen atom and —CH=.

19. The compound according to claim 1 chosen from:
- N-Cyclopropyl-4-methyl-3-(2'-oxospiro[cyclopentane-1,3'-indoline]-6'-yl)benzamide;
- N-cyclopropyl-3-(2'-oxospiro[cyclopentane-1,3'-indoline]-6'-yl)benzamide;
- N-Cyclopropyl-4-methyl-3-(2'-oxo-1',2'-dihydrospiro[cyclobutane-1,3'-indol]-6'-yl)benzamide;
- N-Isopropyl-4-methyl-3-(2'-oxospiro[cyclopentane-1,3'-indoline]-6'-yl)benzamide;
- N-4-Dimethyl-3-(2'-oxospiro[cyclopentane-1,3'-indoline]-6'-yl)benzamide;
- 4-Methyl-3-(2'-oxospiro[cyclopentane-1,3'-indoline]-6'-yl)benzamide;
- 3-(3,3-dimethyl-2-oxoindolin-6-yl)-4-methylbenzamide;
- N-Cyclobutyl-4-methyl-3-(2'-oxospiro[cyclopentane-1,3'-indoline]-6'-yl)benzamide;
- N-(Cyclopropylmethyl)-4-methyl-3-(2'-oxospiro[cyclopentane-1,3'-indoline]-6'-yl)benzamide;
- N-tert-Butyl-4-methyl-3-(2'-oxospiro[cyclopentane-1,3'-indoline]-6'-yl)benzamide;
- 4-Methyl-3-(2'-oxospiro[cyclopentane-1,3'-indoline]-6'-yl)-N-(pyridin-2yl)benzamide;
- N-(Isoxazol-3-yl)-4-methyl-3-(2'-oxospiro[cyclopentane-1,3'-indoline]-6'-yl)benzamide;
- 4-Methyl-3-(2'-oxospiro[cyclopentane-1,3'-indoline]-6'-yl)-N-(1H-1,2,4-triazol-3-yl)benzamide;
- 4-Chloro-N-cyclopropyl-3-(2'-oxospiro[cyclopentane-1,3'-indoline]-6'-yl)benzamide;
- N-Cyclopropyl-3-fluoro-4-methyl-5-(2'-oxospiro[cyclopentane-1,3'-indoline]-6'-yl)benzamide;
- N-Cyclopropyl-6-methyl-5-(2'-oxospiro[cyclopentane-1,3'-indoline]-6'-yl)nicotinamide;
- N-Cyclopropyl-3-(3,3-dimethyl-2-oxoindolin-6-yl)-4-methylbenzamide;
- N-(Cyclopropylmethyl)-3-(3,3-dimethyl-2-oxoindolin-6-yl)-4-methylbenzamide;
- 3-(3,3-Dimethyl-2-oxo-2,3-dihydro-1H-indol-6-yl)-N-isoxazol-3-yl-4-methylbenzamide;
- N-Cyclopropyl-4-methyl-3-(1,3,3-trimethyl-2-oxoindolin-6-yl)benzamide;
- N-Cyclopropyl-4-methyl-3-(2'-oxospiro[cyclohexane-1,3'-indoline]-6'-yl)benzamide;
- N-Cyclopropyl-4-methyl-3-(2-oxo-2',3',5',6'-tetrahydrospiro[indoline-3,4'-pyran]-6-yl)benzamide;
- N-Isoxazol-3-yl-4-methyl-3-(2-oxo-1,2,2',3',5',6'-hexahydrospiro[indole-3,4'-pyran]-6-yl)benzamide;

3-(3,3-bis(2-Hydroxyethyl)-2-oxoindolin-6-yl)-N-cyclopropyl-4-methylbenzamide;

N-Cyclopropyl-4-methyl-3-(2-oxo-2',3',5',6'-tetrahydrospiro[indoline-3,4'-thiopyran]-6-yl)benzamide;

N-Cyclopropyl-3-(2-oxo-1,2,2',3',5',6'-hexahydrospiro[indole-3,4'-thiopyran-1-oxide]-6-yl)-4-methylbenzamide;

N-Cyclopropyl-3-(1',1'-dioxido-2-oxo-1,2,2',3',5',6'-hexahydrospiro[indole-3,4'-thiopyran]-6-yl)-4-methylbenzamide;

N-(Cyclopropylmethyl)-3-(1',1'-dioxido-2-oxo-1,2,2',3',5',6'-hexahydrospiro[indole-3,4'-thiopyran]-6-yl)-5-fluoro-4-methylbenzamide;

N-Cyclopropyl-4-methyl-3-(1'-methyl-2-oxospiro[indoline-3,4'-piperidine]-6-yl)benzamide;

tert-Butyl 6-(5-(cyclopropylcarbamoyl)-2-methylphenyl)-2-oxospiro[indoline-3,4'-piperidine]-1'-carboxylate;

N-cyclopropyl-3-fluoro-4-methyl-5-(1'-(methylsulfonyl)-2-oxospiro[indoline-3,4'-piperidine]-6-yl)benzamide;

N-Cyclopropyl-3-(4,4-difluoro-2'-oxospiro[cyclohexane-1,3'-indoline]-6'-yl)-4-methylbenzamide;

3-(4,4-Difluoro-2'-oxo-1',2'-dihydrospiro[cyclohexane-1,3'-indol]-6'-yl)-N-isoxazol-3-yl-4-methylbenzamide;

N-cyclopropyl-3-(4-hydroxy-2'-oxospiro[cyclohexane-1,3'-indoline]-6'-yl)-4-methylbenzamide (Major Isomer);

N-cyclopropyl-3-(4-hydroxy-2'-oxospiro[cyclohexane-1,3'-indoline]-6'-yl)-4-methylbenzamide (Minor isomer);

N-cyclopropyl-3-(4-hydroxy-4-methyl-2'-oxospiro[cyclohexane-1,3'-indoline]-6'-yl)-4-methylbenzamide (major isomer);

N-cyclopropyl-3-(4-hydroxy-4-methyl-2'-oxospiro[cyclohexane-1,3'-indoline]-6'-yl)-4-methylbenzamide (minor isomer);

N-(cyclopropylmethyl)-3-(4-hydroxy-2'-oxospiro[cyclohexane-1,3'-indoline]-6'-yl)-4-methylbenzamide;

N-cyclopropyl-4-methyl-3-(4-(2-morpholinoethoxy)-2'-oxospiro[cyclohexane-1,3'-indoline]-6'-yl)benzamide;

N-cyclopropyl-4-methyl-3-(4-morpholino-2'-oxospiro[cyclohexane-1,3'-indoline]-6'-yl)benzamide (major isomer);

N-cyclopropyl-4-methyl-3-(4-morpholino-2'-oxospiro[cyclohexane-1,3'-indoline]-6'-yl)benzamide (minor isomer);

N-cyclopropyl-3-fluoro-4-methyl-5-(4-morpholino-2'-oxospiro[cyclohexane-1,3'-indoline]-6'-yl)benzamide (Major isomer);

N-Cyclopropyl-4-methyl-3-(2'-oxo-1',2'-dihydrospiro[cyclopentane-1,3'-pyrrolo[2,3-b]pyridine]-6'-yl)benzamide;

3-(5'-Chloro-2'-oxospiro[cyclopentane-1,3'-indoline]-6'-yl)-N-cyclopropyl-benzamide;

N-Cyclopropyl-3-(3,3-dimethyl-2-oxo-2,3-dihydro-1H-pyrrolo[3,2-b]pyridin-6-yl)-4-methylbenzamide;

N-Cyclopropyl-4-methyl-3-(2'-oxo-1',2'-dihydrospiro[cyclopentane-1,3'-pyrrolo-[3,2-b]pyridin]-6'-yl)benzamide;

N-Cyclopropyl-4-methyl-3-(2'-oxo-1',2',3,5,6-hexahydrospiro[pyran-4,3'-pyrrolo-[3,2-b]pyridin]-6'-yl)benzamide;

N-cyclopropyl-3-(4,4-difluoro-2'-oxo-1',2'-dihydrospiro[cyclohexane-1,3'-pyrrolo[3,2-b]pyridin]-6'-yl)-4-methylbenzamide hydrochloride;

N-cyclopropyl-4-methyl-3-(4-morpholino-2'-oxo-1',2'-dihydrospiro[cyclohexane-1,3'-pyrrolo[3,2-b]pyridine]-6'-yl)benzamide (major isomer);

N-cyclopropyl-4-methyl-3-(4-morpholino-2'-oxo-1',2'-dihydrospiro[cyclohexane-1,3'-pyrrolo[3,2-b]pyridine]-6'-yl)benzamide (minor isomer);

N-Cyclopropyl-4-methyl-3-(2'-oxo-1',2'-dihydrospiro[cyclopentane-1,3'-pyrrolo[3,2-c]pyridin]-6'-yl)benzamide;

N-Cyclopropyl-4-methyl-3-(6'-oxo-6',7'-dihydrospiro[cyclopentane-1,5'-pyrrolo[2,3-d]pyrimidin]-2'-yl)benzamide;

6'-(2-Methyl-5-(5-methyl-4H-1,2,4-triazol-3-yl)phenyl)spiro[cyclopentane-1,3'-indolin]-2'-one;

6'-[2-Methyl-5-(5-methyl-4H-1,2,4-triazol-3-yl)phenyl]spiro[cyclobutane-1,3'-indol]-2'(1'H)-one;

6'-(2-Methyl-5-(4H-1,2,4-triazol-3-yl)phenyl)spiro[cyclopentane-1,3'-indolin]-2'-one;

6'-(5-(5-Cyclopropyl-4H-1,2,4-triazol-3-yl)-2-methylphenyl)spiro[cyclopentane-1,3'-indolin]-2'-one;

6'-(2-Methyl-5-(5-(trifluoromethyl)-4H-1,2,4-triazol-3-yl)phenyl)spiro[cyclopentane-1,3'-indolin]-2'-one;

3,3-Dimethyl-6-(2-methyl-5-(5-methyl-4H-1,2,4-triazol-3-yl)phenyl)indolin-2-one;

6-(2-Methyl-5-(5-methyl-4H-1,2,4-triazol-3-yl)phenyl)-2',3',5',6'-tetrahydrospiro[indoline-3,4'-pyran]-2-one;

1'-(4-chlorophenyl)-6-(2-methyl-5-(5-methyl-4H-1,2,4-triazol-3-yl)phenyl)spiro[indoline-3,4'-piperidin]-2-one;

6-[3-Fluoro-2-methyl-5-(5-methyl-4H-1,2,4-triazol-3-yl)phenyl]-2',3',5',6'-tetrahydro-spiro[indole-3,4'-pyran]-2(1H)-one;

6'-[2-methyl-5-(5-methyl-4H-1,2,4-triazol-3-yl)phenyl]-2,3,5,6-tetrahydrospiro[pyran-4,3'-pyrrolo[3,2-b]pyridin]-2'(1'H)-one hydrogen chloride;

4,4-Difluoro-6'-(2-methyl-5-(5-methyl-4H-1,2,4-triazol-3-yl)phenyl)spiro[cyclohexane-1,3'-indolin]-2'-one;

4-hydroxy-6'-(2-methyl-5-(5-methyl-4H-1,2,4-triazol-3-yl)phenyl)spiro[cyclohexane-1,3'-indolin]-2'-one;

6'-(3-fluoro-2-methyl-5-(5-methyl-4H-1,2,4-triazol-3-yl)phenyl)-4-hydroxy-4-methylspiro[cyclohexane-1,3'-indolin]-2'-one;

6'-(2-methyl-5-(5-methyl-4H-1,2,4-triazol-3-yl)phenyl)-4-(2-morpholinoethoxy)spiro[cyclohexane-1,3'-indolin]-2'-one;

6-(2-methyl-5-(5-methyl-4H-1,2,4-triazol-3-yl)phenyl)-1'-(methylsulfonyl)spiro[indoline-3,4'-piperidin]-2-one;

6-(2-methyl-5-(5-methyl-4H-1,2,4-triazol-3-yl)phenyl)-1'-tosylspiro[indoline-3,4'-piperidin]-2-one;

6'-(2-methyl-5-(5-methyl-4H-1,2,4-triazol-3-yl)phenyl)-4-morpholinospiro[cyclohexane-1,3'-indolin]-2'-one;

6'-(2-Methyl-5-(5-methyl-1,4-oxadiazol-2-yl)phenyl)spiro[cyclopentane-1,3'-indolin]-2'-one;

6'-(2-Methyl-5-(1,3,4-oxadiazol-2-yl)phenyl)spiro[cyclopentane-1,3'-indolin]-2'-one;

4,4-Difluoro-6'-(2-methyl-5-(5-methyl-1,3,4-oxadiazol-2-yl)phenyl)spiro-[cyclohexane-1,3'-indolin]-2'-one;

4-hydroxy-6'-(2-methyl-5-(5-methyl-1,3,4-oxadiazol-2-yl)phenyl)spiro[cyclohexane-1,3'-indolin]-2'-one;

6'-(5-(5-cyclopropyl-1,3,4-oxadiazol-2-yl)-2-methylphenyl)-4-hydroxyspiro[cyclohexane-1,3'-indolin]-2'-one;

6'-(2-Methyl-5-(5-methyl-1,2,4-oxadiazol-3-yl)phenyl)spiro[cyclopentane-1,3'-indolin]-2'-one;

6'-(2-Methyl-5-(3-methyl-1,2,4-oxadiazol-5-yl)phenyl)spiro[cyclopentane-1,3'-indolin]-2'-one;

6-[2-Methyl-5-(2-methyl-1H-imidazol-5-yl)phenyl]-2',3',5',6'-tetrahydrospiro[indole-3,4'-pyran]-2(1H)-one; and 6-(2-methyl-5-(2-methyl-1H-imidazol-2-yl)phenyl)-2',3',5',6'-tetrahydrospiro-[indoline-3,4'-pyran]-2-one.

20. A pharmaceutical composition comprising the compound according to claim 1 and a pharmaceutically acceptable diluent or carrier.

21. A composition comprising:
(i) the compound according to claim 1; and
(ii) another compound chosen from (1) antagonists of M3 muscarinic receptors, (2) β2-agonists, (3) PDE4 inhibitors, (4) corticosteroids, (5) leukotriene D4 antagonists, (6) inhibitors of egfr-kinase, (7) antagonists of the A2B adenosine receptor, (8) NK1 receptor agonists, (9) CRTh2 antagonists, (10) syk kinase inhibitors, (11) CCR3 antagonists, (12) VLA-4 antagonists, (13) methotrexate, (14) JAK3 inhibitors, (15) DHODH inhibitors and (16) a disease modifying antirheumatic drug (DMARD).

* * * * *

UNITED STATES PATENT AND TRADEMARK OFFICE
CERTIFICATE OF CORRECTION

PATENT NO. : 8,772,288 B2
APPLICATION NO. : 12/936784
DATED : July 8, 2014
INVENTOR(S) : Eastwood et al.

It is certified that error appears in the above-identified patent and that said Letters Patent is hereby corrected as shown below:

In the Claims

Claim 19, col. 157, line 39,
"oxospiro[cyclohexane-1,3'-indoline]-6-yl)benzamide;" should read
--oxospiro[cyclohexane-1,3'-indoline]-6'-yl)benzamide;--.

Claim 19, col. 158, line 50,
"6'-(2-Methyl-5-(5-methyl-1,4-oxadiazol-2-yl)phenyl)" should read
--6'-(2-Methyl-5-(5-methyl-1,3,4-oxadiazol-2-yl)phenyl)--.

Signed and Sealed this
Eleventh Day of November, 2014

Michelle K. Lee
*Deputy Director of the United States Patent and Trademark Office*